(12) United States Patent
Hersperger et al.

(10) Patent No.: US 7,858,781 B2
(45) Date of Patent: Dec. 28, 2010

(54) CHEMOKINE RECEPTOR ANTAGONISTS

(75) Inventors: René Hersperger, Münchenstein (CH); Philipp Janser, Basel (CH); Emil Pfenninger, Allschwil (CH); Hans Juerg Wuethrich, Kehrsatz (CH); Wolfgang Miltz, Basel (CH)

(73) Assignee: Novartis AG, Basel (CH)

( * ) Notice: Subject to any disclaimer, the term of this patent is extended or adjusted under 35 U.S.C. 154(b) by 1042 days.

(21) Appl. No.: 10/597,753

(22) PCT Filed: Feb. 10, 2005

(86) PCT No.: PCT/EP2005/001362

§ 371 (c)(1),
(2), (4) Date: Sep. 20, 2006

(87) PCT Pub. No.: WO2005/077932

PCT Pub. Date: Aug. 25, 2005

(65) Prior Publication Data

US 2007/0155721 A1   Jul. 5, 2007

(30) Foreign Application Priority Data

Feb. 11, 2004   (GB) .................. 0403038.3

(51) Int. Cl.
*C07D 403/00* (2006.01)
*C07D 209/36* (2006.01)
(52) U.S. Cl. ...................... 540/602; 548/484
(58) Field of Classification Search ................ 546/184; 514/314
See application file for complete search history.

(56) References Cited

U.S. PATENT DOCUMENTS

| 6,166,006 A | 12/2000 | Shiraishi et al. ........ 514/213.01 |
| 6,268,354 B1 | 7/2001 | Nishimura et al. .......... 514/110 |
| 6,465,485 B1* | 10/2002 | Branch et al. .............. 514/307 |
| 6,627,651 B1 | 9/2003 | Shiraishi et al. ............. 514/431 |
| 6,838,585 B2* | 1/2005 | Spivak .......................... 585/25 |
| 7,078,419 B2* | 7/2006 | Cirillo et al. ................. 514/336 |
| 2004/0043995 A1 | 3/2004 | Bignon |

FOREIGN PATENT DOCUMENTS

| EP | 0 416 581 | 3/1991 |
| EP | 656360 | 5/1995 |
| WO | 98/32438 | 7/1998 |
| WO | 99/32100 | 7/1999 |
| WO | 01/87839 | 11/2001 |
| WO | 03/048123 | 6/2003 |
| WO | 2005/019174 | 3/2005 |

OTHER PUBLICATIONS

Sigma-Aldrich On-line Catalog—heteroaryl boronic acid chemistry products, pp. 1-9.*
Patent Abstracts of Japan, vol. 2000, No. 20, Jul. 10, 2001 & JP 2001 058988 A (Takeda Chem Ind Ltd), Mar. 6, 2001 abstract; claim 1.
Mahalingam et al, Chemokines and chemokine receptors in infectious diseases, Immun. And Cell Biology, 1999, 77, 469-475.
Stefan Lober et al., "Click Linker: Efficient and High-Yielding Synthesis of a New Family of SPOS Resins by 1,3-Dipolar Cycloaddition", Organic Letters, vol. 5, No. 10, pp. 1753-1755, (2003).

* cited by examiner

*Primary Examiner*—Rita J Desai
*Assistant Examiner*—John Mabry
(74) *Attorney, Agent, or Firm*—Sophie Binet Cross

(57) ABSTRACT

A compound of formula (I) or a pharmaceutically acceptable salt or prodrug ester thereof, wherein the variants R, R9, Z, X, Q and Y are defined in the specification.

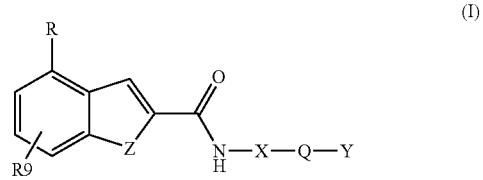

6 Claims, No Drawings

CHEMOKINE RECEPTOR ANTAGONISTS

The invention relates to bicyclic carbonyl amino derivatives which are antagonists of Chemokine Receptor 2 (CCR-2) and Chemokine Receptor 5 (CCR-5), and to their use in the treatment of diseases and disorders which involve migration and activation of monocytes and T-cells, including inflammatory diseases.

Accordingly the invention in a first aspect provides a compound of formula (I), or a pharmaceutically acceptable salt or prodrug ester thereof:

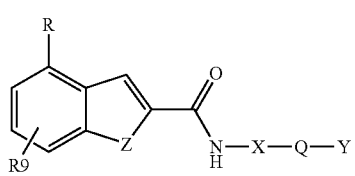

(I)

Wherein:

Z is $CR_1R_2$, $NR_3$, O or S;

R is selected from the group consisting of hydroxy, an optionally substituted $C_1$-$C_7$ alkoxy, $C_2$-$C_7$ alkenoxy, cycloalkyloxy, aryloxy, heteroaryloxy, aryl-$C_1$-$C_7$ alkoxy or heteroaryl-$C_1$-$C_7$ alkoxy, an optionally substituted $C_1$-$C_7$ alkyl or $C_2$-$C_7$ alkenyl, an optionally substituted aryl, heteroaryl or an optionally substituted aryl-$C_1$-$C_7$ alkyl group;

R9 represents one or more ring substituents selected from the group consisting of H, hydroxy, an optionally substituted $C_1$-$C_7$ alkoxy, $C_2$-$C_7$ alkenoxy, cycloalkyloxy, aryloxy, heteroaryloxy, aryl-$C_1$-$C_7$ alkoxy or heteroaryl-$C_1$-$C_7$ alkoxy, an optionally substituted $C_1$-$C_7$ alkyl or $C_2$-$C_7$ alkenyl, an optionally substituted aryl, heteroaryl or an optionally substituted aryl-$C_1$-$C_7$ alkyl group;

$R_1$, $R_2$, and $R_3$ are independently selected from the group consisting of H and $C_1$-$C_7$ alkyl;

X is a $C_3$-$C_{18}$ cycloalkyl, heterocycloalkyl, aryl or heteroaryl each of which may be optionally substituted;

Q is a linker of between 1 and 3 atoms in length;

Y is $C_3$-$C_{18}$ cycloalkyl, heterocycloalkyl, bridged cycloalkyl, bridged heterocycloalkyl, aryl, heteroaryl, fused aryl-heterocycloalkyl, all of which are independently optionally substituted once or more;

The optional substituent or substituents on R and R9 are independently selected from the group consisting of halogen, hydroxy, $C_1$-$C_7$ alkyl, mono or di-lower alkylamino, aminocarbonyl, mono or di-lower alkylaminocarbonyl, amino, carboxy, $C_1$-$C_7$ alkoxy, $C_3$-$C_{12}$ cycloalkyl, $C_3$-$C_{18}$ heterocycloalkyl, $C_1$-$C_7$ alkylcarbonyl, $C_1$-$C_7$ alkoxycarbonyl, nitryl, aryl; all of which, except halogen, are independently optionally substituted by one or more substituents, selected from the group consisting of halogen, hydroxyl, $C_1$-$C_7$ alkyl, mono or di-$C_1$-$C_7$ alkylamino, aminocarbonyl, mono or di-$C_1$-$C_7$ alkylaminocarbonyl, amino, carboxy, $C_1$-$C_7$ alkoxy, $C_3$-$C_{12}$ cycloalkyl, $C_3$-$C_{18}$ heterocycloalkyl, $C_1$-$C_7$ alkylcarbonyl, $C_1$-$C_7$ alkoxycarbonyl, nitryl, aryl.

The optional substituent or substituents on X are independently selected from the group consisting of halogen, hydroxyl, $C_1$-$C_7$ alkyl, mono or di-$C_1$-$C_7$ alkylamino, aminocarbonyl, mono or di-$C_1$-$C_7$ alkylaminocarbonyl, amino, carboxy, $C_1$-$C_7$ alkoxy, $C_3$-$C_{12}$ cycloalkyl, $C_3$-$C_{18}$ heterocycloalkyl, $C_1$-$C_7$ alkylcarbonyl, $C_1$-$C_7$ alkoxycarbonyl, nitryl, aryl; all of which, except halogen, are independently optionally substituted by one or more substituents, selected from the group consisting of halogen, hydroxyl, $C_1$-$C_7$ alkyl, mono or di-$C_1$-$C_7$ alkylamino, aminocarbonyl, mono or di-$C_1$-$C_7$ alkylaminocarbonyl, amino, carboxy, $C_1$-$C_7$ alkoxy, $C_3$-$C_{12}$ cycloalkyl, $C_3$-$C_{18}$ heterocycloalkyl, $C_1$-$C_7$ alkylcarbonyl, $C_1$-$C_7$ alkoxycarbonyl, nitryl, aryl.

The optional substituent or substituents on Y are independently selected from the group consisting of halogen, hydroxyl, $C_1$-$C_7$ alkyl, mono or di-$C_1$-$C_7$ alkylamino, aminocarbonyl, mono or di-$C_1$-$C_7$ alkylaminocarbonyl, amino, carboxy, $C_1$-$C_7$ alkoxy, $C_3$-$C_{12}$ cycloalkyl, $C_3$-$C_{18}$ heterocycloalkyl, $C_1$-$C_7$ alkylcarbonyl, $C_1$-$C_7$ alkoxycarbonyl, nitryl, aryl; all of which, except halogen, are independently optionally substituted by one or more substituents, selected from the group consisting of halogen, hydroxyl, $C_1$-$C_7$ alkyl, mono or di-$C_1$-$C_7$ alkylamino, aminocarbonyl, mono or di-$C_1$-$C_7$ alkylaminocarbonyl, amino, carboxy, $C_1$-$C_7$ alkoxy, $C_3$-$C_{12}$ cycloalkyl, $C_3$-$C_{18}$ heterocycloalkyl, $C_1$-$C_7$ alkylcarbonyl, $C_1$-$C_7$ alkoxycarbonyl, nitryl, aryl.

For the avoidance of doubt, the terms listed below are to be understood to have the following meaning throughout the present description and claims:

The term "lower", when referring to organic radicals or compounds means a compound or radical with may be branched or unbranched with up to and including 7 carbon atoms.

A lower alkyl group may be branched, unbranched or cyclic and contains 1 to 7 carbon atoms, preferably 1 to 4 carbon atoms. Lower alkyl represents, for example: methyl, ethyl, propyl, butyl, isopropyl, isobutyl, tertiary butyl or 2,2-dimethylpropyl.

A lower alkoxy group may be branched or unbranched and contains 1 to 7 carbon atoms, preferably 1 to 6 carbon atoms. Lower alkoxy represents, for example: methoxy, ethoxy, propoxy, butoxy, isopropoxy, isobutoxy or tertiary butoxy. Lower alkoxy includes cycloalkyloxy and cycloalkyl-lower alkyloxy.

A lower alkene, alkenyl or alkenoxy group is branched or unbranched and contains 2 to 7 carbon atoms, preferably 1 to 4 carbon atoms and contains at least one carbon-carbon double bond. Lower alkene, lower alkenyl or lower alkenyloxy represents for example vinyl, prop-1-enyl, allyl, butenyl, isopropenyl or isobutenyl and the oxy equivalents thereof.

In the present application, oxygen containing substituents, e.g. alkoxy, alkenyloxy, alkynyloxy, carbonyl, etc. encompass their sulphur containing homologues, e.g. thioalkoxy, thioalkenyloxy, thioalkynyloxy, thiocarbonyl, sulphone, sulphoxide etc.

Halo or halogen represents chloro, fluoro, bromo or iodo.

Aryl represents carbocyclic aryl, heterocyclic aryl or biaryl.

Carbocyclic aryl is an aromatic cyclic hydrocarbon containing from 6 to 18 ring atoms. It can be monocyclic, bicyclic or tricyclic, for example naphthyl, phenyl, or phenyl mono-, di- or trisubstituted by one, two or three substituents.

Heterocyclic aryl is an aromatic monocyclic or bicyclic hydrocarbon containing from 5 to 18 ring atoms one or more of which are heteroatoms selected from O, N or S. Preferably there are one or two heteroatoms. Heterocyclic aryl represents, for example: pyridyl, indolyl, quinoxalinyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl, thienyl. Heterocyclic aryl also includes such substituted radicals.

Cycloalkyl represents a cyclic hydrocarbon containing from 3 to 12 ring atoms preferably from 3 to 6 ring atoms.

Cycloalkyl represents, for example: cyclopropyl, cyclobutyl, cyclopentyl, or cyclohexyl. The cycloalkyl may optionally be substituted.

Heterocycloalkyl represents a mono-, di- or tricyclic hydrocarbon which may be saturated or unsaturated and which contains one or more, preferably one to three heteroatoms selected from O, N or S. Preferably it contains between three and 18 ring atoms. The term heterocycloalkyl is intended also to include bridged heterocycloalkyl groups such as 3-hydroxy-8-aza-bicyclo[3.2.1]oct-8-yl.

Pharmaceutically acceptable prodrug esters are ester derivatives which are convertible by solvolysis or under physiological conditions to the free carboxylic acid of formula (I). Such esters are for example lower alkyl esters (such as methyl or ethyl esters), carboxy-lower alkyl esters such as the carboxymethyl ester, nitrooxy-lower alkyl esters (such as the 4-nitrooxybutyl ester).

Referring to formula (I), preferably Z is $NH$, $NCH_3$, $CH_2$, S or O.

R is preferably hydroxy, an optionally substituted lower alkoxy, alkenoxy, cycloalkyl-lower alkyloxy, aryloxy, heteroaryloxy, aryl-lower alkyloxy or heteroaryl lower alkyloxy, an optionally substituted aryl, heteroaryl or an optionally substituted aryl-lower alkyl group.

More preferably, R is an oxy group, e.g. $C_1$-$C_7$ alkoxy. Yet more preferably, R is a branched $C_1$-$C_7$ alkoxy or a substituted $C_1$-$C_7$ alkoxy. A preferred substituent for the substituted $C_1$-$C_7$ alkoxy is a furyl or benzofuryl which is optionally substituted.

R9 is preferably hydrogen.

X is preferably selected from the group consisting of:

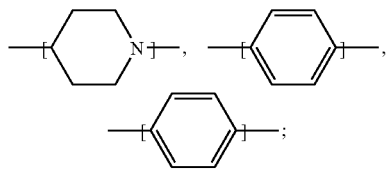

Most preferably, X is

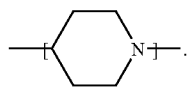

Q is preferably defined by —$CR_4R_5$— or —$CR_4R_5$-$Q_1$- wherein $Q_1$ denotes —$CR_6R_7$— or —$NR_8$—; $R_4$, $R_5$, $R_6$ and $R_7$ and $R_8$ being independently selected from the group consisting of H, an optionally substituted lower alkyl, an optionally substituted lower alkenyl, an optionally substituted aryl or an optionally substituted aryl-lower alkyl group, for example methyl, $(CH_3)_2CH$—$CH_2$—, $CH_3$—C(=$CH_2$)—$CH_2$—, $(CH_3)_3C$—$CH_2$—, benzyl;

Q is more preferably selected from the group consisting of: —$CH_2$—, —$CH_2$—$CH_2$—, —$CH_2$—$CH_2$—$CH_2$—, —$CH(CH_3)$—$CH_2$—, —$CH_2$—$CH(CH_3)$—, —$CH_2$—$NH_2$—, —$CH(CH_3)$—$NH$—, —$CH_2$—$N(CH_3)$—, —$CH_2$—$CH(CH_2OH)$— or —$CH(CH_3)$—$NH(CH_3)$—;

Y is preferably selected from the group consisting of: piperidinyl, azepanyl, azocanyl, phenyl, tetrahydropyranyl, 8-aza-bicyclo[3.2.1]oct-8-yl, tetrahydropyridinyl, octahydroquinolizinyl, hexahydro-pyrrolooxazinyl, octahydropyridooxazinyl each of which is optionally substituted. Preferred optional substituents for Y are: hydroxy, amino, halo, $C_1$-$C_7$ alkyl.

A second aspect of the invention provides a compound of formula (II), or a pharmaceutically acceptable salt, ester or prodrug thereof:

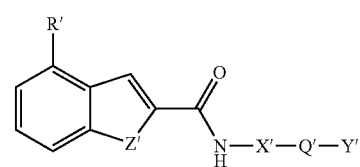

wherein:

Z' is $NH$, $NCH_3$, $CH_2$, S or O.

R' is hydroxy, an optionally substituted $C_1$-$C_7$ alkoxy, cycloalkyl-$C_1$-$C_7$ alkyloxy, aryloxy, heteroaryloxy or aryl-$C_1$-$C_7$ alkyloxy, an optionally substituted aryl, heteroaryl or an optionally substituted aryl-$C_1$-$C_7$ alkyl group;

X' is selected from the group consisting of:

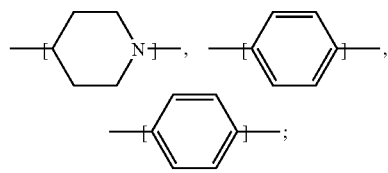

Q' is selected from the group consisting of: —$CH_2$—, —$CH_2$—$CH_2$—, —$CH_2$—$CH_2$—$CH_2$—, —$CH(CH_3)$—$CH_2$—, —$CH_2$—$CH(CH_3)$—, —$CH_2$—$NH_2$—, —$CH(CH_3)$—$NH$—, —$CH_2$—$N(CH_3)$—, —$CH_2$—$CH(CH_2OH)$— or —$CH(CH_3)$—$NH(CH_3)$—;

Y' is $C_3$-$C_{18}$ cycloalkyl, heterocycloalkyl, bridged cycloalkyl, bridged heterocycloalkyl, aryl, heteroaryl, fused aryl-heterocycloalkyl, all of which are independently optionally substituted once or more;

the optional substituent or substituents on R' being independently selected from the group consisting of halogen, hydroxy, $C_1$-$C_7$ alkyl, mono or di-$C_1$-$C_7$ alkylamino, aminocarbonyl, mono or di-$C_1$-$C_7$ alkylaminocarbonyl, amino, carboxy, $C_1$-$C_7$ alkoxy, $C_3$-$C_{12}$ cycloalkyl, $C_3$-$C_{18}$ heterocycloalkyl, $C_1$-$C_7$ alkylcarbonyl, $C_1$-$C_7$ alkoxycarbonyl, nitryl, aryl; all of which, except halogen, are independently optionally substituted by one or more substituents, selected from the group consisting of halogen, hydroxyl, $C_1$-$C_7$ alkyl, mono or di-$C_1$-$C_7$ alkylamino, aminocarbonyl, mono or di-lower alkylaminocarbonyl, amino, carboxy, $C_1$-$C_7$ alkoxy, $C_3$-$C_{12}$ cycloalkyl, $C_3$-$C_{18}$ heterocycloalkyl, $C_1$-$C_7$ alkylcarbonyl, $C_1$-$C_7$ alkoxycarbonyl, nitryl, aryl;

the optional substituent or substituents on Y' being independently selected from the group consisting of halogen, hydroxyl, $C_1$-$C_7$ alkyl, mono or di-$C_1$-$C_7$ alkylamino, aminocarbonyl, mono or di-$C_1$-$C_7$ alkylaminocarbonyl, amino, carboxy, $C_1$-$C_7$ alkoxy, $C_3$-$C_{12}$ cycloalkyl, $C_3$-$C_{18}$ heterocycloalkyl, $C_1$-$C_7$ alkylcarbonyl, $C_1$-$C_7$ alkoxycarbonyl, nitryl, aryl; all of which, except halogen, are independently optionally substituted by one or more substituents, selected from the group consisting of halogen, hydroxyl, $C_1$-$C_7$ alkyl, mono or di-$C_1$-$C_7$ alkylamino, aminocarbonyl, mono or di-$C_1$-$C_7$ alkylaminocarbonyl, amino, carboxy, $C_1$-$C_7$ alkoxy, $C_3$-$C_{12}$ cycloalkyl, $C_3$-$C_{18}$ heterocycloalkyl, $C_1$-$C_7$ alkylcarbonyl, $C_1$-$C_7$ alkoxycarbonyl, nitryl, aryl.

Preferred compounds of formula I are:

4-Methoxy-1H-indole-2-carboxylic acid [1-(2-azepan-1-yl-ethyl)-piperidin-4-yl]-amide 4-Isopropoxy-1H-indole-2-carboxylic acid [1-(2-azepan-1-yl-ethyl)-piperidin-4-yl]-amide 4-Isopropoxy-1H-indole-2-carboxylic acid {1-[2-(4-hydroxy-piperidin-1-yl)-ethyl]-piperidin-4-yl}-amide 4-Cyclopropylmethoxy-1H-indole-2-carboxylic acid [1-(2-azepan-1-yl-ethyl)-piperidin-4-yl]-amide 4-Cyclopropylmethoxy-1H-indole-2-carboxylic acid {1-[2-(4-hydroxy-piperidin-1-yl)-ethyl]-piperidin-4-yl}-amide 4-Cyclopropylmethoxy-1H-indole-2-carboxylic acid {1-[(S)-2-(4-hydroxy-piperidin-1-yl)-propyl]-piperidin-4-yl}-amide 4-Cyclopropylmethoxy-1H-indole-2-carboxylic acid {1-[(S)-2-((3S,4S)-4-hydroxy-3-methyl-piperidin-1-yl)-propyl]-piperidin-4-yl}-amide 4-Isobutoxy-1H-indole-2-carboxylic acid [1-(2-azepan-1-yl-ethyl)-piperidin-4-yl]-amide 4-Isobutoxy-1H-indole-2-carboxylic acid [1-(2-piperidin-1-yl-ethyl)-piperidin-4-yl]-amide 4-Isobutoxy-1H-indole-2-carboxylic acid {1-[2-(RS)-2-methyl-piperidin-1-yl)-ethyl]-piperidin-4-yl}-amide 4-Isobutoxy-1H-indole-2-carboxylic acid {1-[2-(4-methyl-piperidin-1-yl)-ethyl]-piperidin-4-yl}-amide 4-Isobutoxy-1H-indole-2-carboxylic acid {1-[2-((2S,6R)-2,6-dimethyl-piperidin-1-yl)-ethyl]-piperidin-4-yl}-amide 4-Isobutoxy-1H-indole-2-carboxylic acid {1-[2-((R)-3-hydroxy-piperidin-1-yl)-ethyl]-piperidin-4-yl}-amide 4-Isobutoxy-1H-indole-2-carboxylic acid {1-[2-((S)-3-hydroxy-piperidin-1-yl)-ethyl]-piperidin-4-yl}-amide 4-Isobutoxy-1H-indole-2-carboxylic acid {1-[2-(4-hydroxy-piperidin-1-yl)-ethyl]-piperidin-4-yl}-amide 4-Isobutoxy-1H-indole-2-carboxylic acid {1-[2-((1R,3S,5S)-3-hydroxy-8-aza-bicyclo[3.2.1]oct-8-yl)-ethyl]-piperidin-4-yl}-amide 4-Isobutoxy-1H-indole-2-carboxylic acid {1-[(S)-2-(4-hydroxy-piperidin-1-yl)-propyl]-piperidin-4-yl}-amide 4-Isobutoxy-1H-indole-2-carboxylic acid [4-(2-azepan-1-yl-ethyl)-phenyl]-amide 4-Isobutoxy-1H-indole-2-carboxylic acid (4-{[methyl-(tetrahydro-pyran-4-yl)-amino]-methyl}-cyclohexyl)-amide 4-Isobutoxy-1H-indole-2-carboxylic acid (4-{[methyl-(tetrahydro-pyran-4-yl)-amino]-methyl}-phenyl)-amide 4-Isobutoxy-1H-indole-2-carboxylic acid (4-{(R)-1-[methyl-(tetrahydro-pyran-4-yl)-amino]-ethyl}-phenyl)-amide 4-Cyclobutylmethoxy-1H-indole-2-carboxylic acid [1-(2-azepan-1-yl-ethyl)-piperidin-4-yl]-amide 4-Cyclobutylmethoxy-1H-indole-2-carboxylic acid {1-[2-(3-(R)-hydroxy-piperidin-1-yl)-ethyl]-piperidin-4-yl}-amide 4-Cyclobutylmethoxy-1H-indole-2-carboxylic acid {1-[2-(4-hydroxy-piperidin-1-yl)-ethyl]-piperidin-4-yl}-amide 4-Cyclobutylmethoxy-1H-indole-2-carboxylic acid {1-[2-((3S,4S)-4-hydroxy-3-methyl-piperidin-1-yl)-ethyl]-piperidin-4-yl}-amide 4-Cyclobutylmethoxy-1H-indole-2-carboxylic acid {1-[2-((1R,3S,5S)-3-hydroxy-8-aza-bicyclo[3.2.1]oct-8-yl)-ethyl]-piperidin-4-yl}-amide 4-Cyclobutylmethoxy-1H-indole-2-carboxylic acid {1-[(S)-2-(4-hydroxy-piperidin-1-yl)-propyl]-piperidin-4-yl}-amide 4-Cyclobutylmethoxy-1H-indole-2-carboxylic acid {1-[(S)-2-((3S,4S)-4-hydroxy-3-methyl-piperidin-1-yl)-propyl]-piperidin-4-yl}-amide 4-(3-Methyl-butyloxy)-1H-indole-2-carboxylic acid {1-[2-(4-hydroxy-piperidin-1-yl)-ethyl]-piperidin-4-yl}-amide dihydrochloride 4-Cyclopentylmethoxy-1H-indole-2-carboxylic acid {1-[2-(4-hydroxy-piperidin-1-yl)-ethyl]-piperidin-4-yl}-amide 4-(1,2-Dimethyl-propoxy)-1H-indole-2-carboxylic acid [1-(2-azepan-1-yl-ethyl)-piperidin-4-yl]-amide 4-(2,2-Dimethyl-propoxy)-1H-indole-2-carboxylic acid [1-(2-azepan-1-yl-ethyl)-piperidin-4-yl]-amide 4-(4-Methyl-pentyloxy)-1H-indole-2-carboxylic acid {1-[2-(4-hydroxy-piperidin-1-yl)-ethyl]-piperidin-4-yl}-amide dihydrochloride 4-(3,3-Dimethyl-butoxy)-1H-indole-2-carboxylic acid {1-[2-(4-hydroxy-piperidin-1-yl)-ethyl]-piperidin-4-yl}-amide dihydrochloride 4-(Furan-2-ylmethoxy)-1H-indole-2-carboxylic acid [1-(2-azepan-1-yl-ethyl)-piperidin-4-yl]-amide 4-(Furan-3-ylmethoxy)-1H-indole-2-carboxylic acid [1-(2-azepan-1-yl-ethyl)-piperidin-4-yl]-amide 4-(Furan-3-ylmethoxy)-1H-indole-2-carboxylic acid {1-[2-(4-hydroxy-piperidin-1-yl)-ethyl]-piperidin-4-yl}-amide 4-(Furan-3-ylmethoxy)-1H-indole-2-carboxylic acid {1-[2-((3S,4S)-4-hydroxy-3-methyl-piperidin-1-yl)-ethyl]-piperidin-4-yl}-amide 4-(Furan-3-ylmethoxy)-1H-indole-2-carboxylic acid {1-[(S)-2-(4-hydroxy-piperidin-1-yl)-propyl]-piperidin-4-yl}-amide 4-(Furan-3-ylmethoxy)-1H-indole-2-carboxylic acid {1-[(S)-2-((3S,4S)-4-hydroxy-3-methyl-piperidin-1-yl)-propyl]-piperidin-4-yl}-amide 4-Benzyloxy-1H-indole-2-carboxylic acid [1-(2-azepan-1-yl-ethyl)-piperidin-4-yl]-amide 4-(5-chloro-benzofuran-3-ylmethoxy)-1H-indole-2-carboxylic acid {1-[(1S 9aR)-1-(octahydro-quinolizin-1-yl)methyl]-piperidin-4-yl}-amide dihydrochloride 4-(5-Chloro-benzofuran-3-ylmethoxy)-1H-indole-2-carboxylic acid [1-(2-azepan-1-yl-ethyl)-piperidin-4-yl]-amide 4-(5-Chloro-benzofuran-3-ylmethoxy)-1H-indole-2-carboxylic acid {1-[2-(4-hydroxy-piperidin-1-yl)-ethyl]-piperidin-4-yl}-amide 4-(5-Chloro-benzofuran-3-ylmethoxy)-1H-indole-2-carboxylic acid {1-[2-((3S,4S)-4-hydroxy-3-methyl-piperidin-1-yl)-ethyl]-piperidin-4-yl}-amide 4-(5-Chloro-benzofuran-3-ylmethoxy)-1H-indole-2-carboxylic acid {1-[(S)-2-(4-hydroxy-piperidin-1-yl)-propyl]-piperidin-4-yl}-amide dihydrochloride 4-(5-Chloro-benzofuran-3-ylmethoxy)-1H-indole-2-carboxylic acid {1-[(S)-2-((3S,4S)-4-hydroxy-3-methyl-piperidin-1-yl)-propyl]-piperidin-4-yl}-amide dihydrochloride 4-(4-Fluoro-benzofuran-3-ylmethoxy)-1H-indole-2-carboxylic acid {1-[(1S,9aR)-1-(octahydro-quinolizin-1-yl)methyl]-piperidin-4-yl}-amide dihydrochloride 4-(4-Fluoro-benzofuran-3-ylmethoxy)-1H-indole-2-carboxylic acid {1-[2-(4-hydroxy-piperidin-1-yl)-ethyl]-piperidin-4-yl}-amide dihydrochloride 4-(Benzofuran-3-ylmethoxy)-1H-indole-2-carboxylic acid {1-[(1S,9aR)-1-(octahydro-quinolizin-1-yl)methyl]-piperidin-4-yl}-amide dihydrochloride 4-(Benzofuran-3-ylmethoxy)-1H-indole-2-carboxylic acid {1-[2-(4-hydroxy-piperidin-1-yl)-ethyl]-piperidin-4-yl}-amide 4-(Benzofuran-3-ylmethoxy)-1H-indole-2-carboxylic acid {1-[2-((3S,4S)-4-hydroxy-3-methyl-piperidin-1-yl)-ethyl]-piperidin-4-yl}-amide 4-(Benzofuran-3-ylmethoxy)-1H-indole-2-carboxylic acid {1-[(S)-2-(4-hydroxy-piperidin-1-yl)-propyl]-piperidin-4-yl}-amide 4-(Benzofuran-3-ylmethoxy)-1H-indole-2-carboxylic acid {1-[(S)-2-((3S,4S)-4-hydroxy-3-methyl-piperidin-1-yl)-propyl]-piperidin-4-yl}-amide 4-(6-Fluoro-benzofuran-3-ylmethoxy)-1H-indole-2-carboxylic acid {1-[(1S,9aR)-1-(octahydro-quinolizin-1-yl)methyl]-piperidin-4-yl}-amide dihydrochloride 4-(6-Fluoro-benzofuran-3-ylmethoxy)-1H-indole-2-carboxylic acid {1-[2-(4-hydroxy-piperidin-1-yl)-ethyl]-piperidin-4-yl}-amide dihydrochloride 4-(6-Fluoro-benzofuran-3-ylmethoxy)-1H-indole-2-carboxylic acid {1-[2-((3S,4S)-4-hydroxy-3-methyl-piperidin-1-yl)-ethyl]-piperidin-4-yl}-amide dihydrochloride 4-(6-Fluoro-benzofuran-3-ylmethoxy)-1H-indole-2-carboxylic acid {1-[(S)-2-(4-hydroxy-piperidin-1-yl)-propyl]-piperidin-4-yl}-amide dihydrochloride 4-(6-Fluoro-benzofuran-3-ylmethoxy)-1H-indole-2-carboxylic acid {1-[(S)-2-((3S,4S)-4-hydroxy-3-methyl-piperidin-1-yl)-propyl]-piperidin-4-yl}-amide 4-(5-Fluoro-benzofuran-3-ylmethoxy)-1H-indole-2-carboxylic acid {1-[(1S,9aR)-1-(octahydro-quinolizin-1-yl)methyl]-piperidin-4-yl}-amide 4-(5-Fluoro-benzofuran-3-ylmethoxy)-1H-indole-2-carboxylic acid {1-[2-(4-hydroxy-piperidin-1-yl)-ethyl]-piperidin-4-yl}-amide dihydrochloride 4-(5-Fluoro-benzofuran-3-ylmethoxy)-1H-indole-2-carboxylic acid {1-[2-((3R,4R,5S)-4-hydroxy-3,5-dimethyl-piperidin-1-yl)-ethyl]-piperidin-4-yl}-amide dihydrochloride 4-(5-Fluoro-benzofuran-3-ylmethoxy)-1H-indole-2-carboxylic acid {1-[(S)-2-(4-hydroxy-piperidin-1-yl)-propyl]-piperidin-4-yl}-amide dihydrochloride 4-(5-Fluoro-benzofuran-3-ylmethoxy)-1H-indole-2-carboxylic acid {1-[(S)-2-((3S,4S)-4-hydroxy-3-methyl-piperidin-1-yl)-propyl]-piperidin-4-yl}-amide 4-(7-Fluoro-benzofuran-3-ylmethoxy)-1H-indole-2-carboxylic acid {1-[(1S,9aR)-1-(octahydro-quinolizin-1-yl)methyl]-piperidin-4-yl}-amide dihydrochloride 4-(4,6-Difluoro-benzofuran-3-ylmethoxy)-1H-indole-2-carboxylic acid {1-[(1S,9aR)-1-(octahydro-quinolizin-1-yl)methyl]-piperidin-4-yl}-amide dihydrochloride 4-(4,6-Difluoro-benzofuran-3-ylmethoxy)-1H-indole-2-carboxylic acid {1-[2-(4-hydroxy-piperidin-1-yl)-ethyl]-piperidin-4-yl}-amide dihydrochloride 4-(4,6-Difluoro-benzofuran-3-ylmethoxy)-1H-indole-2-carboxylic acid {1-[2-((3S,4S)-4-hydroxy-3-methyl-piperidin-1-yl)-ethyl]-piperidin-4-yl}-amide dihydrochloride 4-(4,6-Difluoro-benzofuran-3-ylmethoxy)-1H-indole-2-carboxylic acid {1-[(S)-2-(4-hydroxy-piperidin-1-yl)-propyl]-piperidin-4-yl}-amide dihydrochloride 4-(4,6-Difluoro-benzofuran-3-ylmethoxy)-1H-indole-2-carboxylic acid {1-[(S)-2-((3S,4S)-4-hydroxy-3-methyl-piperidin-1-yl)-propyl]-piperidin-4-yl}-amide dihydrochloride 4-(7-Chloro-benzofuran-3-ylmethoxy)-1H-indole-2-carboxylic acid {1-[(1S,9aR)-1-(octahydro-quinolizin-1-yl)methyl]-piperidin-4-yl}-amide dihydrochloride 4-(6-Chloro-benzofuran-3-ylmethoxy)-1H-indole-2-carboxylic acid {1-[(1S,9aR)-1-(octahydro-quinolizin-1-yl)methyl]-piperidin-4-yl}-amide dihydrochloride 4-(6-Chloro-benzofuran-3-ylmethoxy)-1H-indole-2-carboxylic acid {1-[2-(4-hydroxy-piperidin-1-yl)-ethyl]-piperidin-4-yl}-amide 4-(6-Chloro-benzofuran-3-ylmethoxy)-1H-indole-2-carboxylic acid {1-[2-((3S,4S)-4-hydroxy-3-methyl-piperidin-1-yl)-ethyl]-piperidin-4-yl}-amide 4-(6-Chloro-benzofuran-3-ylmethoxy)-1H-indole-2-carboxylic acid {1-[(S)-2-(4-hydroxy-piperidin-1-yl)-propyl]-piperidin-4-yl}-amide dihydrochloride 4-(4-Chloro-benzofuran-3-ylmethoxy)-1H-indole-2-carboxylic acid {1-[(1S,9aR)-1-(octahydro-quinolizin-1-yl)methyl]-piperidin-4-yl}-amide dihydrochloride 4-(4-Chloro-benzofuran-3-ylmethoxy)-1H-indole-2-carboxylic acid {1-[2-(4-hydroxy-piperidin-1-yl)-ethyl]-piperidin-4-yl}-amide dihydrochloride 4-(4-Chloro-benzofuran-3-ylmethoxy)-1H-indole-2-carboxylic acid {1-[2-((3R,4R,5S)-4-hydroxy-3,5-dimethyl-piperidin-1-yl)-ethyl]-piperidin-4-yl}-amide dihydrochloride 4-(4-Chloro-benzofuran-3-ylmethoxy)-1H-indole-2-carboxylic acid {1-[(S)-2-(4-hydroxy-piperidin-1-yl)-propyl]-piperidin-4-yl}-amide 4-(7-Methoxy-benzofuran-3-ylmethoxy)-1H-indole-2-carboxylic acid {1-[(1S,9aR)-1-(octahydro-quinolizin-1-yl)methyl]-piperidin-4-yl}-amide dihydrochloride 4-(7-Methoxy-benzofuran-3-ylmethoxy)-1H-indole-2-carboxylic acid [1-(2-piperidin-1-yl-ethyl)-piperidin-4-yl]-amide 4-(7-Methoxy-benzofuran-3-ylmethoxy)-1H-indole-2-carboxylic acid {1-[2-(4-hydroxy-piperidin-1-yl)-ethyl]-piperidin-4-yl}-amide dihydrochloride 4-(7-Methoxy-benzofuran-3-ylmethoxy)-1H-indole-2-carboxylic acid {1-[2-((3S,4S)-4-hydroxy-3-methyl-piperidin-1-yl)-ethyl]-piperidin-4-yl}-amide dihydrochloride 4-(7-Methoxy-benzofuran-3-ylmethoxy)-1H-indole-2-carboxylic acid {1-[(S)-2-(4-hydroxy-piperidin-1-yl)-propyl]-piperidin-4-yl}-amide dihydrochloride 4-(7-Methoxy-benzofuran-3-ylmethoxy)-1H-indole-2-carboxylic acid {1-[(S)-2-((3S,4S)-4-hydroxy-3-methyl-piperidin-1-yl)-propyl]-piperidin-4-yl}-amide 4-(6-Methoxy-benzofuran-3-ylmethoxy)-1H-indole-2-carboxylic acid {1-[(1S,9aR)-1-(octahydro-quinolizin-1-yl)methyl]-piperidin-4-yl}-amide 4-(6-Methoxy-benzofuran-3-ylmethoxy)-1H-indole-2-carboxylic acid [1-(2-azepan-1-yl-ethyl)-piperidin-4-yl]-amide 4-(6-Methoxy-benzofuran-3-ylmethoxy)-1H-indole-2-carboxylic acid {1-[2-(4-hydroxy-piperidin-1-yl)-ethyl]-piperidin-4-yl}-amide 4-(6-Methoxy-benzofuran-3-ylmethoxy)-1H-indole-2-carboxylic acid {1-[2-((3S,4S)-4-hydroxy-3-methyl-piperidin-1-yl)-ethyl]-piperidin-4-yl}-amide dihydrochloride 4-(6-Methoxy-benzofuran-3-ylmethoxy)-1H-indole-2-carboxylic acid {1-[(S)-2-(4-hydroxy-piperidin-1-yl)-propyl]-piperidin-4-yl}-amide 4-(6-Methoxy-benzofuran-3-ylmethoxy)-1H-indole-2-carboxylic acid {1-[(S)-2-((3S,4S)-4-hydroxy-3-methyl-piperidin-1-yl)-propyl]-piperidin-4-yl}-amide 4-(5-Methoxy-benzofuran-3-ylmethoxy)-1H-indole-2-carboxylic acid [1-(2-azepan-1-yl-ethyl)-piperidin-4-yl]-amide 4-(5-Methoxy-benzofuran-3-ylmethoxy)-1H-indole-2-carboxylic acid {1-[2-(4-hydroxy-piperidin-1-yl)-ethyl]-piperidin-4-yl}-amide 4-(4-Methoxy-benzofuran-3-ylmethoxy)-1H-indole-2-carboxylic acid {1-[(1S,9aR)-1-(octahydro-quinolizin-1-yl)methyl]-piperidin-4-yl}-amide 4-(4-Methoxy-benzofuran-3-ylmethoxy)-1H-indole-2-carboxylic acid {1-[2-(4-hydroxy-piperidin-1-yl)-ethyl]-piperidin-4-yl}-amide
4-(4-Methoxy-benzofuran-3-ylmethoxy)-1H-indole-2-carboxylic acid {1-[2-((3S,4S)-4-hydroxy-3-methyl-piperidin-1-yl)-ethyl]-piperidin-4-yl}-amide
4-(4-Methoxy-benzofuran-3-ylmethoxy)-1H-indole-2-carboxylic acid {1-[(S)-2-(4-hydroxy-piperidin-1-yl)-propyl]-piperidin-4-yl}-amide
4-(4-Methoxy-benzofuran-3-ylmethoxy)-1H-indole-2-carboxylic acid {1-[(S)-2-((3S,4S)-4-hydroxy-3-methyl-piperidin-1-yl)-propyl]-piperidin-4-yl}-amide
4-(4,6-dimethoxy-benzofuran-3-ylmethoxy)-1H-indole-2-carboxylic acid {1-[(1S,9aR)-1-(octahydro-quinolizin-1-yl)methyl]-piperidin-4-yl}-amide dihydrochloride
4-(4,6-Dimethoxy-benzofuran-3-ylmethoxy)-1H-indole-2-carboxylic acid {1-[2-(4-hydroxy-piperidin-1-yl)-ethyl]-piperidin-4-yl}-amide
4-(4,6-Dimethoxy-benzofuran-3-ylmethoxy)-1H-indole-2-carboxylic acid {1-[2-((3S,4S)-4-hydroxy-3-methyl-piperidin-1-yl)-ethyl]-piperidin-4-yl}-amide dihydrochloride
4-(4,6-Dimethoxy-benzofuran-3-ylmethoxy)-1H-indole-2-carboxylic acid {1-[(S)-2-(4-hydroxy-piperidin-1-yl)-propyl]-piperidin-4-yl}-amide
4-(4,6-Dimethoxy-benzofuran-3-ylmethoxy)-1H-indole-2-carboxylic acid {1-[(S)-2-((3S,4S)-4-hydroxy-3-methyl-piperidin-1-yl)-propyl]-piperidin-4-yl}-amide
4-(5,6-dimethyl-benzofuran-3-ylmethoxy)-1H-indole-2-carboxylic acid {1-[(1S,9aR)-1-(octahydro-quinolizin-1-yl)methyl]-piperidin-4-yl}-amide dihydrochloride
4-(5,6-Dimethyl-benzofuran-3-ylmethoxy)-1H-indole-2-carboxylic acid {1-[2-(4-hydroxy-piperidin-1-yl)-ethyl]-piperidin-4-yl}-amide
4-(5,6-Dimethyl-benzofuran-3-ylmethoxy)-1H-indole-2-carboxylic acid {1-[2-((3S,4S)-4-hydroxy-3-methyl-piperidin-1-yl)-ethyl]-piperidin-4-yl}-amide dihydrochloride
4-(5,6-Dimethyl-benzofuran-3-ylmethoxy)-1H-indole-2-carboxylic acid {1-[(S)-2-(4-hydroxy-piperidin-1-yl)-propyl]-piperidin-4-yl}-amide dihydrochloride
4-(5,6-Dimethyl-benzofuran-3-ylmethoxy)-1H-indole-2-carboxylic acid {1-[(S)-2-((3S,4S)-4-hydroxy-3-methyl-piperidin-1-yl)-propyl]-piperidin-4-yl}-amide dihydrochloride
4-(4-Ethoxy-phenyl)-1H-indole-2-carboxylic acid {1-[(S)-2-(4-hydroxy-piperidin-1-yl)-propyl]-piperidin-4-yl}-amide
4-(4-Methoxy-phenyl)-1H-indole-2-carboxylic acid {1-[(S)-2-(4-hydroxy-piperidin-1-yl)-propyl]-piperidin-4-yl}-amide
4-Phenoxy-1H-indole-2-carboxylic acid [1-(2-azepan-1-yl-ethyl)-piperidin-4-yl]-amide
4-m-Tolyloxy-1H-indole-2-carboxylic acid [1-(2-azepan-1-yl-ethyl)-piperidin-4-yl]-amide
4-m-Tolyloxy-1H-indole-2-carboxylic acid {1-[2-(3-(RS)-hydroxy-piperidin-1-yl)-ethyl]-piperidin-4-yl}-amide
4-m-Tolyloxy-1H-indole-2-carboxylic acid {1-[2-(4-hydroxy-piperidin-1-yl)-ethyl]-piperidin-4-yl}-amide
4-p-Tolyloxy-1H-indole-2-carboxylic acid [1-(2-azepan-1-yl-ethyl)-piperidin-4-yl]-amide
4-p-Tolyloxy-1H-indole-2-carboxylic acid {1-[2-(3-(RS)-hydroxy-piperidin-1-yl)-ethyl]-piperidin-4-yl}-amide
4-p-Tolyloxy-1H-indole-2-carboxylic acid {1-[2-(4-hydroxy-piperidin-1-yl)-ethyl]-piperidin-4-yl}-amide
4-(3-Fluoro-phenoxy)-1H-indole-2-carboxylic acid [1-(2-azepan-1-yl-ethyl)-piperidin-4-yl]-amide
4-(3-Fluoro-phenoxy)-1H-indole-2-carboxylic acid {1-[2-(4-hydroxy-piperidin-1-yl)-ethyl]-piperidin-4-yl}-amide
4-(4-Fluoro-phenoxy)-1H-indole-2-carboxylic acid [1-(2-azepan-1-yl-ethyl)-piperidin-4-yl]-amide
4-(4-Fluoro-phenoxy)-1H-indole-2-carboxylic acid {1-[2-(4-hydroxy-piperidin-1-yl)-ethyl]-piperidin-4-yl}-amide
4-(3,4-Difluoro-phenoxy)-1H-indole-2-carboxylic acid [1-(2-azepan-1-yl-ethyl)-piperidin-4-yl]-amide
4-(3,5-Difluoro-phenoxy)-1H-indole-2-carboxylic acid [1-(2-azepan-1-yl-ethyl)-piperidin-4-yl]-amide
4-(3,5-Difluoro-phenoxy)-1H-indole-2-carboxylic acid {1-[2-(3-RS-hydroxy-piperidin-1-yl)-ethyl]-piperidin-4-yl}-amide
4-(3,5-Difluoro-phenoxy)-1H-indole-2-carboxylic acid {1-[2-(4-hydroxy-piperidin-1-yl)-ethyl]-piperidin-4-yl}-amide
4-(6-Chloro-pyridin-2-yloxy)-1H-indole-2-carboxylic acid [1-(2-azepan-1-yl-ethyl)-piperidin-4-yl]-amide
4-Isobutoxy-1H-indole-2-carboxylic acid [1-(octahydro-quinolizin-1-ylmethyl)-piperidin-4-yl]-amide dihydrochloride
4-Isobutoxy-1H-indole-2-carboxylic acid [1-(1-methyl-piperidin-3-ylmethyl)-piperidin-4-yl]-amide
4-Cyclobutylmethoxy-1H-indole-2-carboxylic acid {1-[(1S,9aR)-1-(octahydro-quinolizin-1-yl)methyl]-piperidin-4-yl}-amide
4-Cyclobutylmethoxy-1H-indole-2-carboxylic acid {1-[(S)-2-((3R,4R)-4-hydroxy-3-methyl-piperidin-1-yl)-propyl]-piperidin-4-yl}-amide
4-Cyclobutylmethoxy-1H-indole-2-carboxylic acid {1-[(S)-2-((3S,4R,5S)-3,4-dihydroxy-5-methyl-piperidin-1-yl)-propyl]-piperidin-4-yl}-amide
4-Cyclobutylmethoxy-1H-indole-2-carboxylic acid {1-[(R)-3-hydroxy-2-((3S,4S)-4-hydroxy-3-methyl-piperidin-1-yl)-propyl]-piperidin-4-yl}-amide
4-(Furan-3-ylmethoxy)-1H-indole-2-carboxylic acid {1-[(1S,9aR)-1-(octahydro-quinolizin-1-yl)methyl]-piperidin-4-yl}-amide
4-(Furan-3-ylmethoxy)-1H-indole-2-carboxylic acid {1-[(S)-2-((3R,4R)-4-hydroxy-3-methyl-piperidin-1-yl)-propyl]-piperidin-4-yl}-amide
4-(2-Methyl-thiazol-4-ylmethoxy)-1H-indole-2-carboxylic acid [1-(octahydro-quinolizin-1-ylmethyl)-piperidin-4-yl]-amide
4-(Benzofuran-3-ylmethoxy)-1H-indole-2-carboxylic acid {1-[2-(3,4-dihydroxy-5-methyl-piperidin-1-yl)-propyl]-piperidin-4-yl}-amide
4-(5-Fluoro-benzofuran-3-ylmethoxy)-1H-indole-2-carboxylic acid {1-[(S)-2-((3RS,4SR)-3,4-dihydroxy-piperidin-1-yl)-propyl]-piperidin-4-yl}-amide
4-(5-Chloro-benzofuran-3-ylmethoxy)-1H-indole-2-carboxylic acid {1-[(S)-2-((3RS,4SR)-3,4-dihydroxy-piperidin-1-yl)-propyl]-piperidin-4-yl}-amide
4-(5-Chloro-benzofuran-3-ylmethoxy)-1H-indole-2-carboxylic acid {1-[(9S,9aS)-1-(octahydro-pyrido[2,1-c][1,4]oxazin-9-yl)methyl]-piperidin-4-yl}-amide
4-(5-Chloro-benzofuran-3-ylmethoxy)-1H-indole-2-carboxylic acid {1-[(8S,8aS)-1-(hexahydro-pyrrolo[2,1-c][1,4]oxazin-8-yl)methyl]-piperidin-4-yl}-amide
4-(4-Methoxy-phenyl)-1H-indole-2-carboxylic acid {1-[(1S,9aR)-1-(octahydro-quinolizin-1-yl)methyl]-piperidin-4-yl}-amide
4-(4-Ethoxy-phenyl)-1H-indole-2-carboxylic acid {1-[(1S,9aR)-1-(octahydro-quinolizin-1-yl)methyl]-piperidin-4-yl}-amide
4-(6-Methoxy-pyridin-3-yl)-1H-indole-2-carboxylic acid {1-[(S)-2-((3S,4S)-4-hydroxy-3-methyl-piperidin-1-yl)-propyl]-piperidin-4-yl}-amide 4-(6-Methoxy-pyridin-3-yl)-1H-indole-2-carboxylic acid {1-[2-((3S,4S)-4-hydroxy-3-methyl-piperidin-1-yl)-ethyl]-piperidin-4-yl}-amide
4-p-Tolyloxy-1H-indole-2-carboxylic acid {1-[(1S,9aR)-1-(octahydro-quinolizin-1-yl)methyl]-piperidin-4-yl}-amide
4-Isobutoxy-1H-indole-2-carboxylic acid [1-(2-azepan-1-yl-1S-methyl-ethyl)-piperidin-4-yl]-amide
4-Isobutoxy-1H-indole-2-carboxylic acid [1-(2-azepan-1-yl-1R-methyl-ethyl)-piperidin-4-yl]-amide
4-(Furan-3-ylmethoxy)-1H-indole-2-carboxylic acid [1-(2S-azepan-1-yl-propyl)-piperidin-4-yl]-amide
4-(Furan-3-ylmethoxy)-1H-indole-2-carboxylic acid [1-(2R-azepan-1-yl-propyl)-piperidin-4-yl]-amide
4-Isobutoxy-1H-indole-2-carboxylic acid {1-[2-(3,6-dihydro-2H-pyridin-1-yl)-ethyl]-piperidin-4-yl}-amide
4-Isobutoxy-1H-indole-2-carboxylic acid {1-[2-(4-hydroxy-azepan-1-yl)-ethyl]-piperidin-4-yl}-amide
4-Isobutoxy-1H-indole-2-carboxylic acid {1-[2-(3-amino-azepan-1-yl)-ethyl]-piperidin-4-yl}-amide
4-Isobutoxy-1H-indole-2-carboxylic acid {1-[2-(3-fluoro-piperidin-1-yl)-ethyl]-piperidin-4-yl}-amide
4-(5-Chloro-benzofuran-3-ylmethoxy)-1H-indole-2-carboxylic acid [4-(2-piperidin-1-yl-ethyl)-phenyl]-amide
4-(5-Chloro-benzofuran-3-ylmethoxy)-1H-indole-2-carboxylic acid {4-[2-(4-hydroxy-piperidin-1-yl)-ethyl]-phenyl}-amide
4-Phenyl-1H-indole-2-carboxylic acid [1-(2-azepan-1-yl-ethyl)-piperidin-4-yl]-amide
4-(4-Trifluoromethyl-phenyl)-1H-indole-2-carboxylic acid [1-(2-azepan-1-yl-ethyl)-piperidin-4-yl]-amide
4-p-Tolyl-1H-indole-2-carboxylic acid [1-(2-azepan-1-yl-ethyl)-piperidin-4-yl]-amide
4-(4-Dimethylamino-phenyl)-1H-indole-2-carboxylic acid [1-(2-azepan-1-yl-ethyl)-piperidin-4-yl]-amide
4-Benzo[1,2,5]oxadiazol-5-yl-1H-indole-2-carboxylic acid [1-(2-azepan-1-yl-ethyl)-piperidin-4-yl]-amide
4-(4-Methoxy-phenyl)-1H-indole-2-carboxylic acid [1-(2-azepan-1-yl-ethyl)-piperidin-4-yl]-amide
4-(3-Cyano-phenyl)-1H-indole-2-carboxylic acid [1-(2-azepan-1-yl-ethyl)-piperidin-4-yl]-amide
4-(4-Ethoxy-phenyl)-1H-indole-2-carboxylic acid [1-(2-azepan-1-yl-ethyl)-piperidin-4-yl]-amide
4-[3-(3-Methoxy-propoxy)-phenyl]-1H-indole-2-carboxylic acid [1-(2-azepan-1-yl-ethyl)-piperidin-4-yl]-amide
4-(4-Trifluoromethoxy-phenyl)-1H-indole-2-carboxylic acid [1-(2-azepan-1-yl-ethyl)-piperidin-4-yl]-amide
4-(2,4-Dimethoxy-phenyl)-1H-indole-2-carboxylic acid [1-(2-azepan-1-yl-ethyl)-piperidin-4-yl]-amide
4-(3,4-Dimethoxy-phenyl)-1H-indole-2-carboxylic acid [1-(2-azepan-1-yl-ethyl)-piperidin-4-yl]-amide
4-Benzo[1,3]dioxol-5-yl-1H-indole-2-carboxylic acid [1-(2-azepan-1-yl-ethyl)-piperidin-4-yl]-amide
4-Pyridin-4-yl-1H-indole-2-carboxylic acid [1-(2-azepan-1-yl-ethyl)-piperidin-4-yl]-amide
4-(6-Methoxy-pyridin-3-yl)-1H-indole-2-carboxylic acid [1-(2-azepan-1-yl-ethyl)-piperidin-4-yl]-amide
4-(4-Ethoxy-phenyl)-1H-indole-2-carboxylic acid [1-(2-piperidin-1-yl-ethyl)-piperidin-4-yl]-amide
4-(4-Methoxy-phenyl)-1H-indole-2-carboxylic acid {1-[2-(4-hydroxy-piperidin-1-yl)-ethyl]-piperidin-4-yl}-amide
4-(4-Ethoxy-phenyl)-1H-indole-2-carboxylic acid {1-[2-(4-hydroxy-piperidin-1-yl)-ethyl]-piperidin-4-yl}-amide
4-(6-Methoxy-pyridin-3-yl)-1H-indole-2-carboxylic acid {1-[2-(4-hydroxy-piperidin-1-yl)-ethyl]-piperidin-4-yl}-amide
4-(4-Methoxy-phenyl)-1H-indole-2-carboxylic acid {1-[2-(3-hydroxy-8-aza-bicyclo[3.2.1]oct-8-yl)-ethyl]-piperidin-4-yl}-amide
4-(6-Methoxy-pyridin-3-yl)-1H-indole-2-carboxylic acid {1-[2-(3-hydroxy-8-aza-bicyclo[3.2.1]oct-8-yl)-ethyl]-piperidin-4-yl}-amide
4-Hydroxy-1H-indole-2-carboxylic acid [1-(2-azepan-1-yl-ethyl)-piperidin-4-yl]-amide
4-Methoxy-benzo[b]thiophene-2-carboxylic acid [1-(2-azepan-1-yl-ethyl)-piperidin-4-yl]-amide
4-Isobutoxy-benzo[b]thiophene-2-carboxylic acid [1-(2-azepan-1-yl-ethyl)-piperidin-4-yl]-amide
4-Isobutoxy-benzo[b]thiophene-2-carboxylic acid [1-(2-piperidin-1-yl-ethyl)-piperidin-4-yl]-amide
4-Methoxy-benzofuran-2-carboxylic acid [1-(2-azepan-1-yl-ethyl)-piperidin-4-yl]-amide According to a third aspect of the invention there is provided a compound of formula (I) for use as a pharmaceutical for the prevention, amelioration or treatment of an autoimmune or inflammatory disease or condition.

According to a fourth aspect of the invention there is provided a process for the preparation of a compound of formula (I) comprising:

(a) reacting a compound of formula (III):

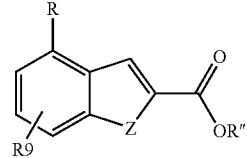

(III)

wherein R" is H or a lower alkyl group, with a compound of formula NH$_2$—X-Q-Y, the groups R, R9, Z, X, Q and Y being defined above; or (b) for the preparation of compounds of formula (I) wherein X is piperidin-4-yl and Q is —CH$_2$—CH$_2$—, and Y is a group having the formula —NR$_7$R$_8$ wherein N, R$_7$ and R$_8$ are linked to define collectively a heterocycloalkyl, bridged cycloalkyl, bridged heterocycloalkyl, heteroaryl, or fused aryl-heterocycloalkyl, reacting a compound of formula (IV):

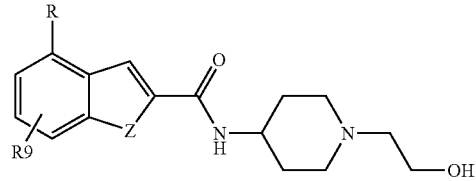

(IV)

with a compound of formula NHR$_7$R$_8$, wherein R$_7$ and R$_8$ are as defined above, and R, R9 and Z are as defined earlier; or (c) for the preparation of compounds of formula (I) wherein X is piperidin-4-yl and Q is CH$_2$—, reacting a compound of formula (V):

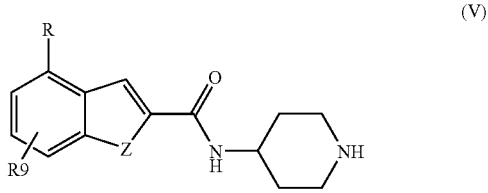

(V)

in which R, R9 and Z are as defined above, with a compound of formula HO—CH$_2$—Y, in which Y is as defined earlier; or (d) for the preparation of compounds of formula (I) wherein R is an optionally substituted aryl group, appropriately substituting the Br group in a compound of formula (VI) for said substituted aryl group:

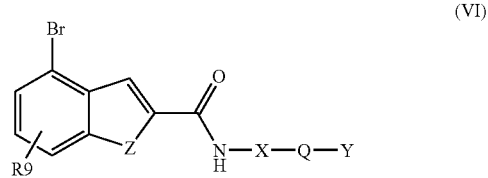

(VI)

wherein Z, R9, X, Q and Y are as earlier defined;

and recovering the resultant compounds of formula (I) in free or salt form.

The process of the invention is effected in conventional manner.

Process variant (a) is a condensation reaction between acid or ester and amine. It is conveniently effected by reacting the acid with the amine in the presence of coupling agents, for example TBTU/DIEA in a solvent such as DMF, or by reacting the ester with the amine in the presence of a coupling agent such as HOBT/EDC.

Process variant (b) is a condensation reaction which is conveniently carried out using a reagent such as cyanomethyl-triphenyl phosphonium iodide and Hunig's base.

Process variant (c) is a condensation reaction is also a condensation reaction which is conveniently carried out using a reagent such as cyanomethyl-triphenyl phosphonium iodide and Hunig's base.

Process variant (d) is a substitution reaction and is conveniently effected using the appropriate aryl-boronic acid and triphenylphosphine in the presence of lead (II) acetate.

The compounds of the invention can be recovered from the reaction mixture and purified in conventional manner. Isomers, such as enantiomers, may be obtained in conventional manner, e.g. by fractional crystallization or asymmetric synthesis from corresponding asymmetrically substituted, e.g. optically active, starting materials.

The starting materials and intermediates are either known or can be prepared according to known methods or analogously as described in the Examples.

According to a fifth aspect of the invention there is provided compound obtainable by any one of the above mentioned processes.

According to a sixth aspect of the invention there is provided a pharmaceutical composition comprising a compound of formula (I) in association with a pharmaceutically acceptable diluent or carrier.

According to a seventh aspect of the invention there is provided the use of a compound of formula (I) in the manufacture of a medicament for use in the treatment of an autoimmune or inflammatory disease or condition.

According to an eighth aspect of the invention there is provided a method of inhibiting chemokine receptors or macrophage proteins or of reducing inflammation in a subject in need of such treatment, which method comprises administering to said subject an effective amount of a compound of formula (I).

According to a ninth aspect of the invention there is provided a method of treating an inflammatory or autoimmune disease or condition, comprising administering to said subject an effective amount of a compound of formula (I).

Agents of the invention may be prepared by processes described below:

EXPERIMENTAL SECTION

| Abbreviations: | |
|---|---|
| BOC: | t-Butyloxycarbonyl |
| Boc2O: | Di-t-butyl dicarbonate |
| DCC: | Dicyclohexyl-carbodiimide |
| DCE: | Dichloroethane |
| DCM: | Dichloromethane |
| DEAD: | Diethyl azadicarboxylate |
| DIEA: | Ethyl-diisopropyl-amine |
| DMAP: | Dimethyl-pyridin-4-yl-amine |
| DME: | 1,2-Dimethoxy-ethane |
| DMF: | N,N-Dimethyl formamide |
| EDC: | (3-Dimethylamino-propyl)-ethyl-carbodiimide hydrochloride |
| Ether: | Ethoxy-ethane |
| EtOH: | Ethanol |
| EtOAc: | Acetic acid ethyl ester |
| HCl: | Hydrochloric acid |
| HOBT: | Benzotriazol-1-ol |
| LAH: | Lithium aluminumhydride |
| LDA: | Lithium diisopropylamine |
| MeOH: | Methanol |
| NaOH: | Sodium hydroxide |
| NMP: | 1-Methyl-pyrrolidin-2-one |
| Pd/C: | Palladium on carbon |
| TBAF: | Tetrabutylammonium fluoride |
| TBME: | t-Butyl-methyl ether |
| TBDMS: | t-Butyl-dimethyl-silyl |
| TBTU: | O-(1H-benzotriazol-1-yl)-N,N,N',N'-tetramethyluronium tetrafluoroborate |
| t-BuOH: | 2-Methyl-propan-2-ol |
| TFA: | Trifluoro-acetic acid |
| THF: | Tetrahydrofuran |

1H-NMR spectra are recorded on a Varian Gemini 400 MHz NMR spectrometer. Significant peaks are tabulated in the order: multiplicity (s, singlet; d, doublet; t, triplet; q, quartet; m, multiplet; br, broad) and number of protons. Electron Spray Ionization (ESI) mass spectra are recorded on a Hewlett Packard 5989A mass spectrometer. Mass spectrometry results are reported as the ratio of mass over charge. Preparative HPLC purifications are performed with XTerra™ RP18 19×150 mm columns, using acetonitrile/water or MeOH/water as eluent systems. All reagents, starting materials and intermediates utilized in these examples are available from commercial sources or are readily prepared by methods known to those skilled in the art.
Synthesis of the Amine Building Blocks
The amines 1, 5, 7, 10, 12, 14, 17, 20, 21, 24, 27, 30, 35, 41, 50, 56, 60, 61, 63, 67, 70 and 72 are prepared according the reaction schemes outlined below,
Reaction Scheme 1:
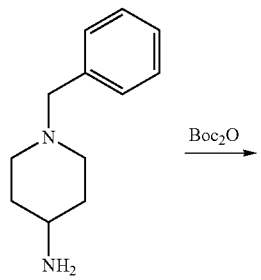
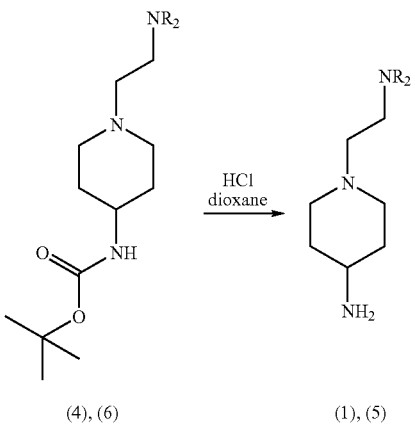
Reaction Scheme 2:
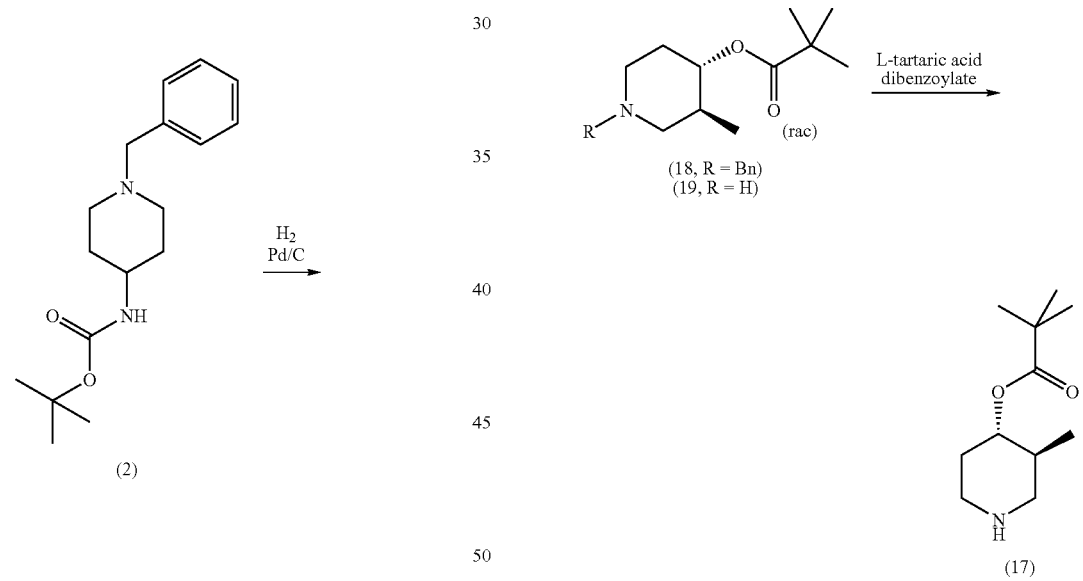
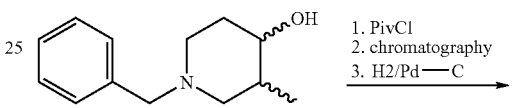
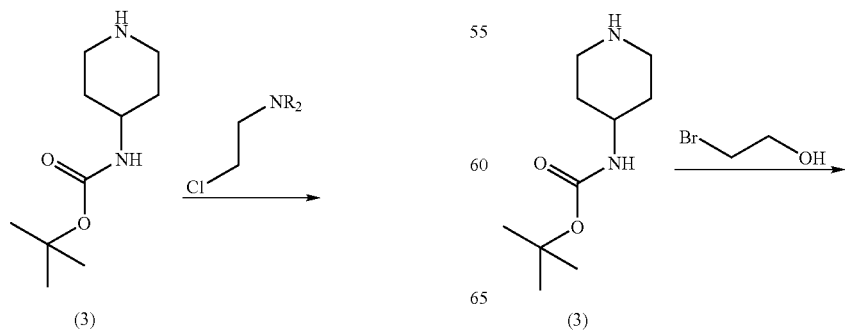

-continued
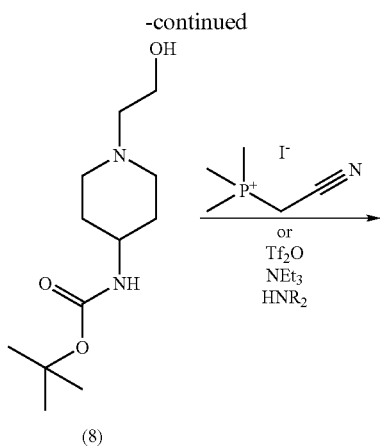
(8)
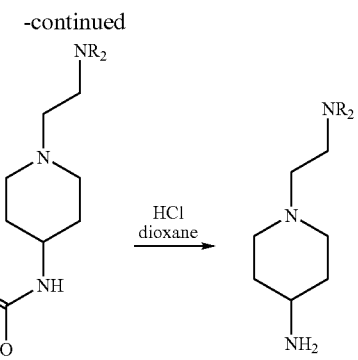
(28), (26), (29) → (21), (24), (27)
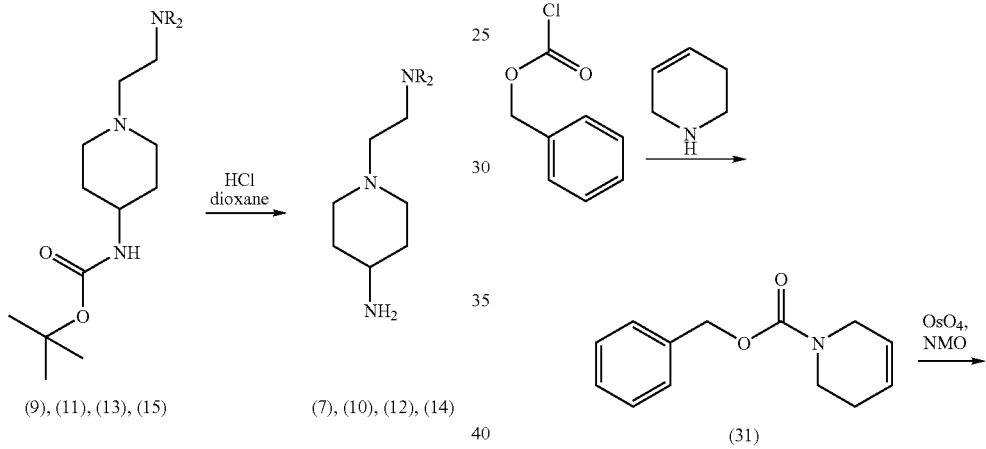
Reaction Scheme 4:
(31)
(rac) (32)
(33) (1 enantiomer)
(34)
Reaction Scheme 3:
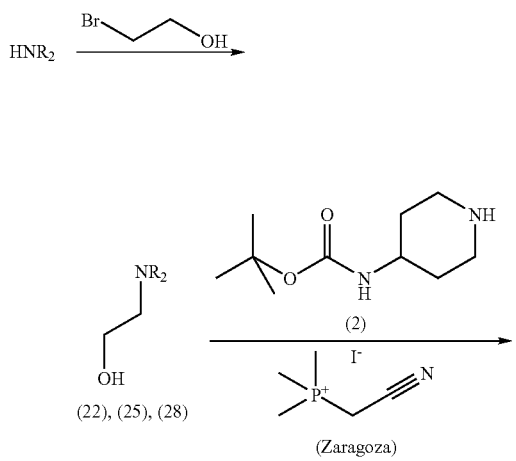
(22), (25), (28)
(Zaragoza)

-continued
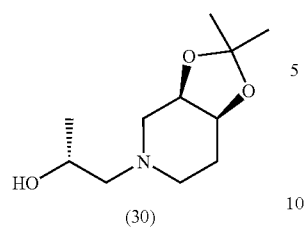
(30)
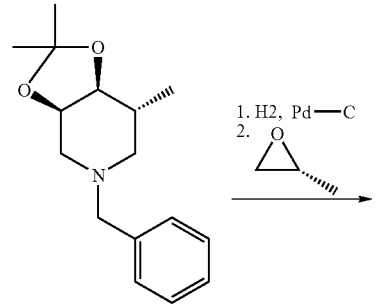
1. H2, Pd—C
2.
(39)
Reaction Scheme 5:
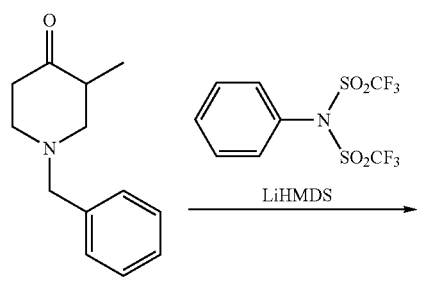
LiHMDS
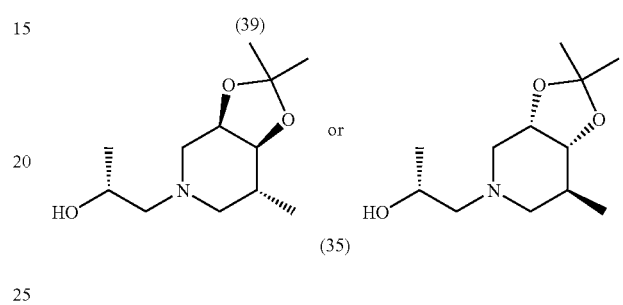
(35)
Reaction Scheme 6:
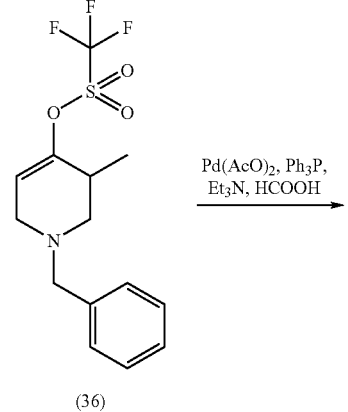
Pd(AcO)$_2$, Ph$_3$P, Et$_3$N, HCOOH
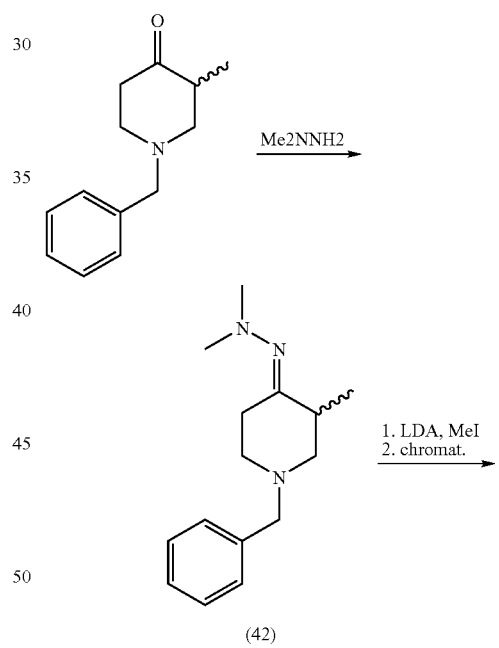
Me2NNH2
(36)
1. LDA, MeI
2. chromat.
OsO$_4$, NMO
(37)
(42)
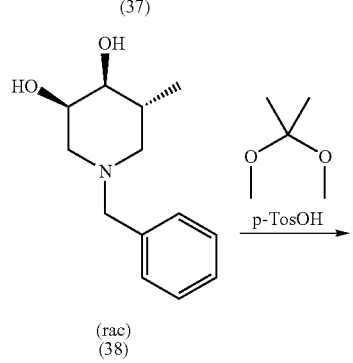
p-TosOH
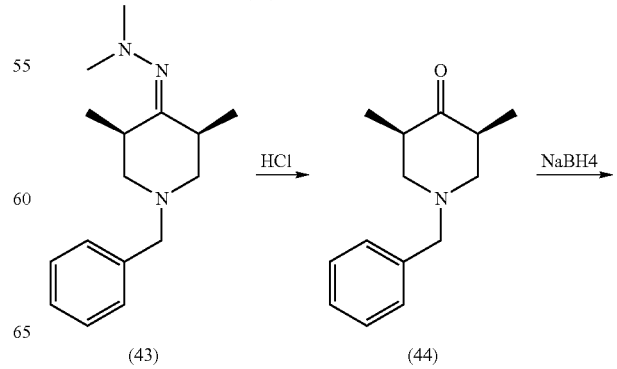
HCl
NaBH4
(rac)
(38)
(43)  (44)

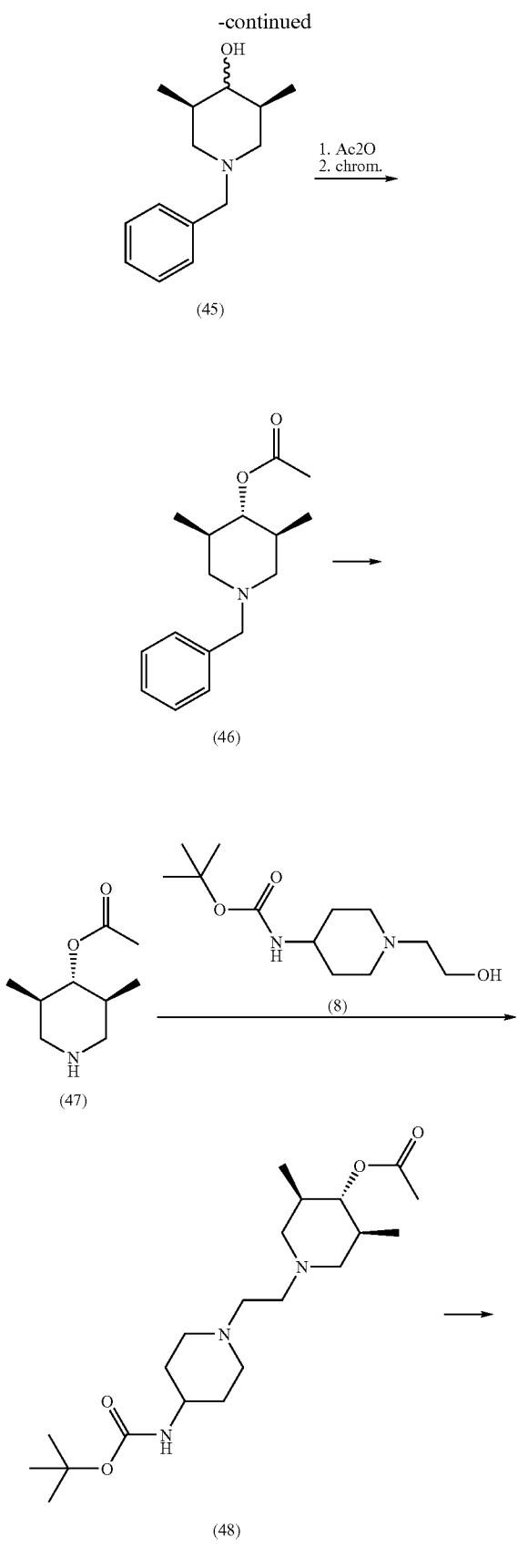
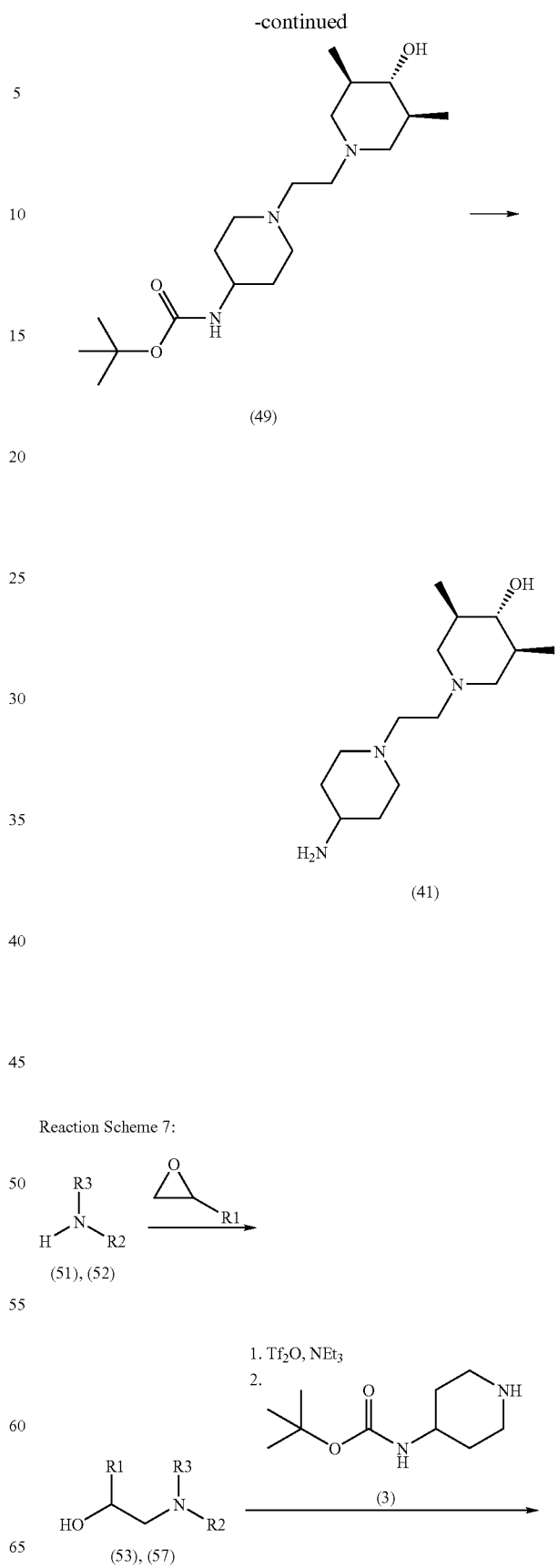

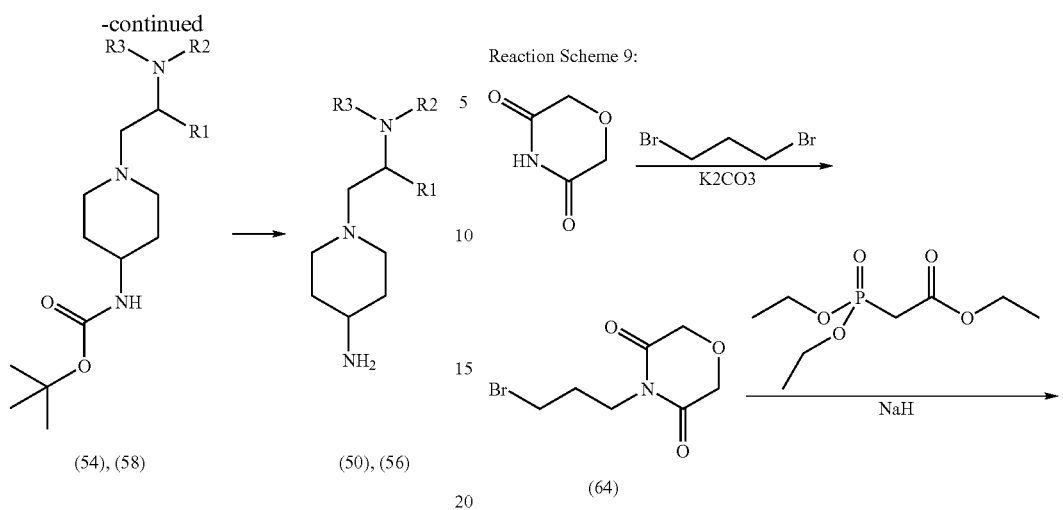
(54), (58) → (50), (56)
Reaction Scheme 8:
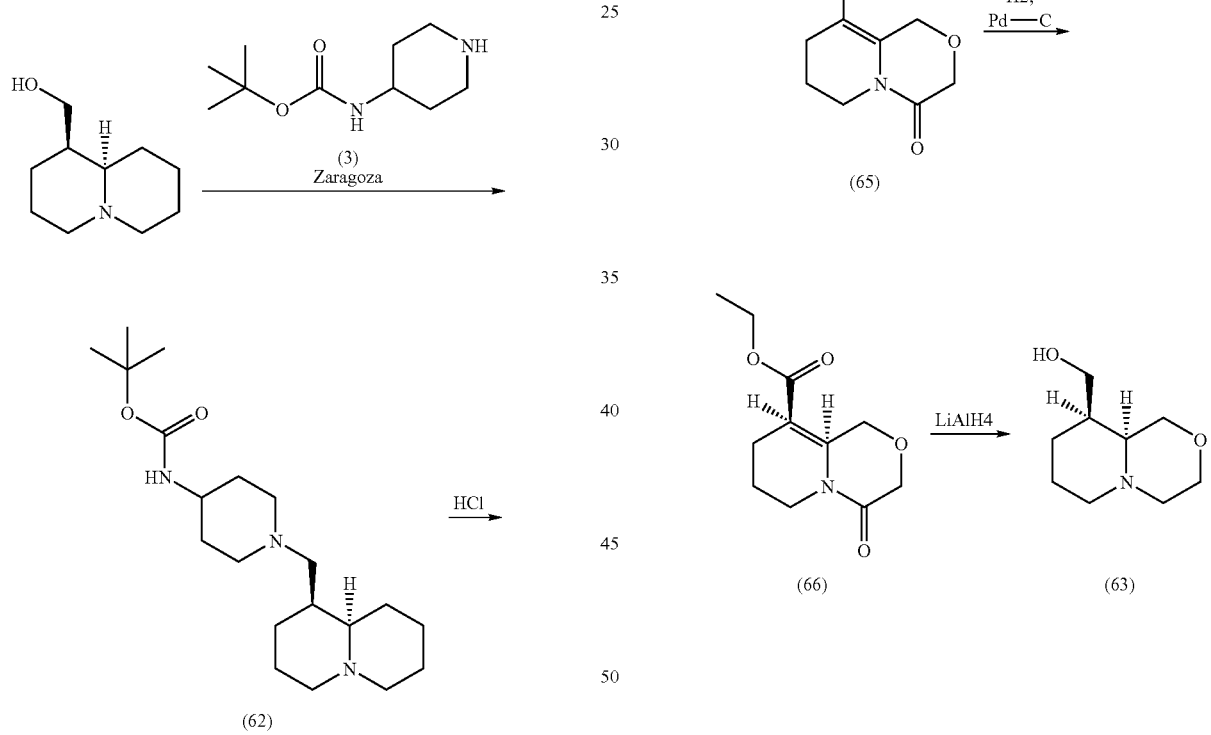
Reaction Scheme 9:
Reaction Scheme 10:
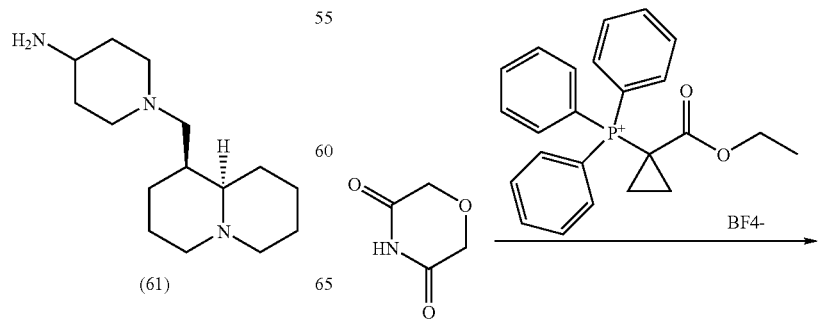

-continued

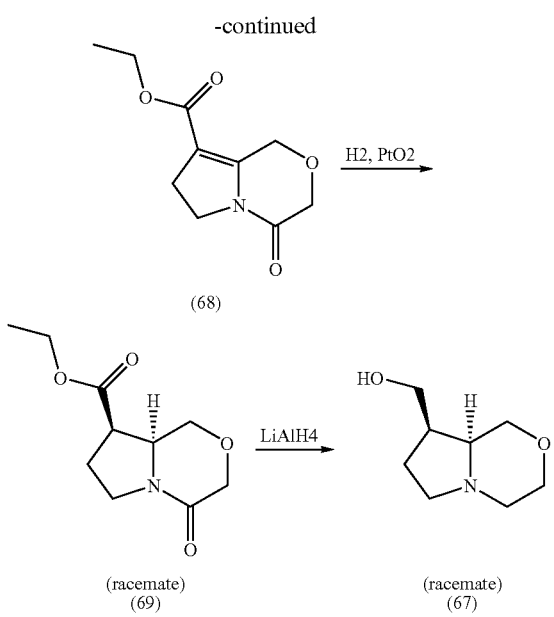

(68)

(racemate)
(69)

(racemate)
(67)

Reaction Scheme 11:

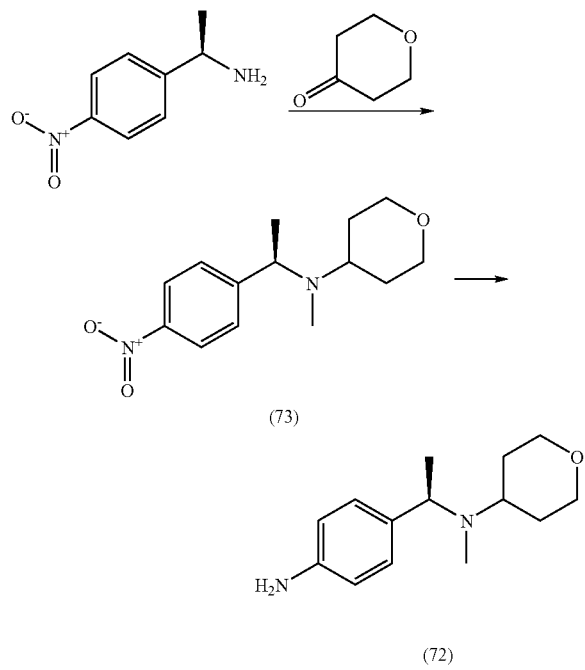

(73)

(72)

Synthesis of 1-(2-Piperidin-1-yl-ethyl)-piperidin-4-ylamine tri-hydrochloride (1) (reaction scheme 1)

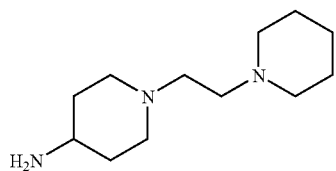

(1) (1-Benzyl-piperidin-4-yl)-carbamic acid tert-butyl ester (2)

1-Benzyl-piperidin-4-ylamine (50 g, 262.76 mmol) is dissolved in a mixture of 200 ml of water, 145 ml of 2 molar aqueous sodium hydroxide and 350 ml of t-BuOH at 0° C. A solution of Boc2O (63.1 g, 1.1 equivalents) in 150 ml of t-BuOH is added dropwise within one hour at 0° C. A white suspension is formed which is allowed to stir overnight at room temperature. The reaction mixture is diluted with ether and washed with water. The organic layers are dried over anhydrous sodium sulfate and evaporated under reduced pressure.

Yield: 71.5 g of a pale yellow solid (93%). MS (ESI): 291 [M+H]$^+$, 1H-NMR (DMSO-d$_6$): δ (ppm) 7.2-7.35 (m, 5H), 6.77 (br d, 1H), 3.44 (s, 2H), 3.22 (br m, 1H), 2.75 (m, 2H), 1.95 (dt, 2H), 1.68 (m, 2H), 1.38 (s, 9H), 1.36 (dt 2H).

(2) Piperidin-4-yl-carbamic acid tert-butyl ester (3)

A solution of the ester 2 from above (66 g, 227.27 mmol) in 1 l of ethanol is hydrogenated under normal pressure with 10 g of Pd/C (10%) for 16 hours at room temperature. The mixture is filtered over celite and evaporated under reduced pressure. Recrystallisation from ether gave 34.5 g (76%) of white crystals.

MS (ESI): 201 [M+H]$^+$, 401 [2M+H]+, 1H-NMR (DMSO-d$_6$): δ (ppm) 6.7 (br d, NH), 3.22 (br m, 1H), 2.88 (dt, 2H), 2.39 (dt, 2H), 1.8 (brs, NH), 1.6 (dt, 2H), 1.35 (s, 9H), 1.18 (dt, 2H).

(3) 1-(2-Piperidin-1-yl-ethyl)-piperidin-4-yl]-carbamic acid tert-butyl ester (4)

Piperidin-4-yl-carbamic acid tert-butyl ester (3) (4.8 g, 23.72 mmol), 1-(2-Chloro-ethyl)-piperidine hydrochloride (5.3 g, 26.09 mmol) and DIEA (8.9 ml, 52.18 mmol) are dissolved in 150 ml of chloroform and refluxed for 18 hours. After addition of more 1-(2-Chloro-ethyl)-piperidine hydrochloride (2.65 g, 13.05 mmol) and DIEA (4.4 ml, 26.09 mmol) the reaction mixture is refluxed for another 4 hours. After cooling to room temperature, the mixture is diluted with DCM and washed with water and 5% aqueous sodium hydrogen carbonate solution. Evaporation gave 7.3 g of brownish crystals which are recrystallized from ether/hexane.

Yield: 5.3 g (72%) of beige crystals. MS (ESI): 312 [M+H]$^+$, 1H-NMR (DMSO-d$_6$): δ (ppm) 6.75 (br d, NH), 3.18 (br m, 1H), 2.8 (m, 2H), 2.3-2.4 (m, 8H), 1.92 (dt, 2H), 1.65 (m, 2H), 1.48 (m, 4H), 1.38 (s, 9H), 1.3-1.4 (m, 4H).

(4) 1-(2-Piperidin-1-yl-ethyl)-piperidin-4-ylamine tri-hydrochloride (1)

Ester 4 from above (5.2 g, 16.7 mmol) is suspended at 0° C. in 60 ml of a 4M solution of HCl in dioxane and stirred at room temperature for 3 hours. After evaporation under reduced pressure the crude product is dried at high vacuum.

Yield: 5.3 g (99%) of light beige crystals. MS (ESI): 212 [M+H]$^+$, 1H-NMR (D2O): δ (ppm) 4.14 (m, 2H), 4.04 (br m, 5H), 3.8 (m, 4H), 3.65 (dt, 2H), 2.85 (d, 2H), 2.45 (m, 2H), 2.35 (m, 4H), 2.15 (m, 2H).

Synthesis of 1-(2-Azepan-1-yl-ethyl)-piperidin-4-ylamine tri-hydrochloride (5) (reaction scheme 1)

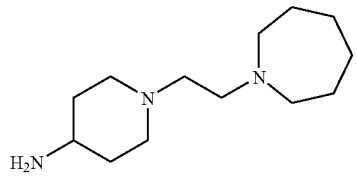

(1) [1-(2-Azepan-1-yl-ethyl)-piperidin-4-yl]-carbamic acid tert-butyl ester (6)

It is synthesized analogously to ester 4 starting from 2-(hexamethyleneimino)ethyl chloride (13.8 g) and ester 3 (12.4 g).

Yield: 14 g of a colorless solid (63%). MS (ESI): 326 [M+H]$^+$, 1H-NMR (DMSO-$d_6$): δ (ppm) 6.75 (br d, NH), 3.18 (br m, 1H), 2.8 (m, 2H), 2.3-2.6 (m, 8H), 1.95 (dt, 2H), 1.65 (m, 2H), 1.55 (m, 6H), 1.38 (s, 9H), 1.3-1.4 (m, 4H).

(2) 1-(2-Azepan-1-yl-ethyl)-piperidin-4-ylamine tri-hydrochloride (5)

It is prepared analogously to 1 starting from ester 6 (14 g).

Yield: 13 g (90%) of a colorless solid. MS (ESI): 226 [M+H]$^+$, 1H-NMR (120° C., DMSO-$d_6$): δ (ppm) 8.5 (br, NH3+), 3.5 (m, 5H), 3.4 (m, 2H), 3.3 (m, 4H), 2.97 (m, 2H), 2.18 (m, 2H), 2.05 (m, 2H), 1.9 (m, 4H), 1.7 (m, 4H).

Synthesis of 1-[2-(4-Methyl-piperidin-1-yl)-ethyl]-piperidin-4-ylamine tri-hydrochloride (7) (reaction scheme 2)

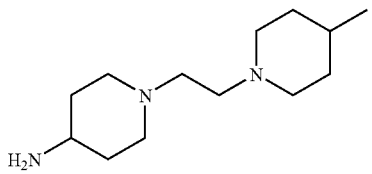

(1) [1-(2-Hydroxy-ethyl)-piperidin-4-yl]-carbamic acid tert-butyl ester (8)

To a solution of piperidin-4-yl-carbamic acid tert-butyl ester 3 (10 g, 50 mmol) in 100 ml of methanol are added sodium carbonate (21.2 g, 200 mmol) and 2-bromoethanol (7.1 ml, 100 mmol). The mixture is stirred over night. The solvents are then evaporated and the residue is triturated with DCM, filtered and evaporated again. The crude product is purified by chromatography using EtOAc/MeOH (saturated with ammonia): 9/1.

Yield: 8.07 g (66%). MS (ESI): 245.2 [M+H]$^+$, 1H-NMR (DMSO-$d_6$): δ (ppm) 6.75 (br d, 1H), 4.34 (t, 1H), 3.46 (q, 2H), 3.19 (br m, 1H), 2.8 (m, 2H), 2.35 (t, 2H), 1.95 (m, 2H), 1.66 (m, 2H), 1.39 (s, 9H), 1.35 (m, 2H).

(2) {1-[2-(4-Methyl-piperidin-1-yl)-ethyl]-piperidin-4-yl}-carbamic acid tert-butyl ester (9)

A mixture of ester 8 (3 g, 12.28 mmol), 4-methyl piperidine (1.46 ml, 12.28 mmol) and DIEA (2.7 ml, 15.96 mmol) in 30 ml of propionitrile is treated with solid cyanomethyl-trimethyl-phosphonium iodide (3.58 g, 14.74 mmol) and heated at reflux for 3 hours. After cooling to room temperature, a 2M-K2CO3 solution is added until basic and the mixture is extracted twice with DCM. The organic layers are washed with brine, dried over anhydrous sodium sulfate and evaporated. The crude material is purified by chromatography using EtOAc/MeOH (saturated with ammonia): 9/1.

Yield: 2 g (50%). MS (ESI): 326.3 [M+H]$^+$, 1H-NMR (DMSO-$d_6$): δ (ppm) 6.74 (br d, 1H), 3.16 (m, 1H), 2.78 (m, 4H), 2.33 (br s, 4H), 1.86 (m, 4H), 1.64 (m, 2H), 1.53 (m, 2H), 1.36 (s, 9H), 1.32 (m, 3H), 1.08 (m, 2H), 0.86 (d, 3H).

(3) 1-[2-(4-Methyl-piperidin-1-yl)-ethyl]-piperidin-4-ylamine tri-hydrochloride (7)

The tert-butyl ester 9 (2 g, 6.14 mmol) is suspended in 10 ml of dioxane. DCM is then added until the solid dissolved. To this mixture, 4M-HCl in dioxane (12.3 ml, 49.2 mmol) is added. After stirring over night the solvents are evaporated to leave a white solid product.

Yield: 2.06 g (100%). MS (ESI): 226.2 [M+H]$^+$

Synthesis of 1-[2-((RS)-2-Methyl-piperidin-1-yl)-ethyl]-piperidin-4-ylamine tri-hydrochloride (10) (reaction scheme 2)

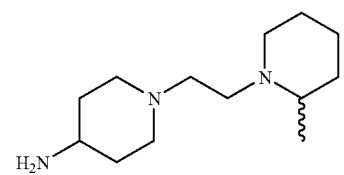

(1) {1-[2-((S)-2-Methyl-piperidin-1-yl)-ethyl]-piperidin-4-yl}-carbamic acid tert-butyl ester (11)

It is prepared analogously to 9 starting from tert-butyl ester 8 (2 g, 8.19 mmol), (S)-2-methyl-piperidine (0.985 ml, 8.19 mmol), DIEA (1.8 ml, 10.65 mmol) and cyanomethyl-trimethyl-phosphonium iodide (2.39 g, 9.83 mmol).

Yield: 1.35 g (51%). MS (ESI): 326.3 [M+H]$^+$, 1H-NMR (CDCl$_3$): δ (ppm) 4.42 (br d, 1H), 3.47 (m, 1H), 2.84 (m, 4H), 2.47 (m, 3H), 2.15-2.35 (m, 2H), 2.1 (m, 2H), 1.92 (m, 2H), 1.2-1.75 (m, 8H), 1.44 (s, 9H), 1.08 (d, 3H).

(2) 1-[2-((RS)-2-Methyl-piperidin-1-yl)-ethyl]-piperidin-4-ylamine tri-hydrochloride (10)

It is prepared by BOC-cleavage of tert-butyl ester 11 (1.3 g, 3.99 mmol) with 4M-HCl in dioxane (8 ml, 32 mmol) as described for amine 7.

Yield: 1.3 g (97%). MS (ESI): 226.2 [M+H]$^+$

Synthesis of (R)-1-[2-(4-Amino-piperidin-1-yl)-ethyl]-piperidin-3-ol tri-hydrochloride (12) (reaction scheme 2)

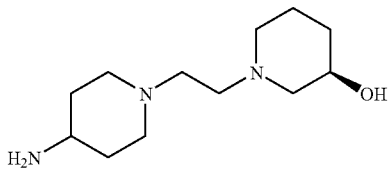

(1) {1-[2-((R)-3-Hydroxy-piperidin-1-yl)-ethyl]-piperidin-4-yl}-carbamic acid tert-butyl ester (13)

It is prepared analogously to 9 starting from tert-butyl ester 8 (3.52 g, 14.41 mmol), (R)-3-hydroxy-piperidine hydrochloride (2.18 g, 15.85 mmol), DIEA (5.6 ml, 33.14 mmol) and cyanomethyl-trimethyl-phosphonium iodide (4.2 g, 17.29 mmol).

Yield: 1.71 g (36%). MS (ESI): 328.2 [M+H]$^+$, 1H-NMR (CDCl$_3$): δ (ppm) 4.61 (br d, 1H), 3.89 (m, 3H), 3.53 (m, 1H), 3.03 (m, 2H), 2.55-2.73 (m, 6H), 2.44 (m, 1H), 2.3 (m, 2H), 1.83-2.02 (m, 3H), 1.5-1.7 (m, 4H), 1.44 (s, 9H).

(2) (R)-1-[2-(4-Amino-piperidin-1-yl)-ethyl]-piperidin-3-ol tri-hydrochloride (12)

It is prepared by BOC-cleavage of tert-butyl ester 13 (1.7 g, 5.19 mmol) with 4M-HCl in dioxane (10.4 ml, 41.52 mmol) as described for amine 7.

Yield: 1.69 g (96%). MS (ESI): 228.3 [M+H]$^+$

Synthesis of (3S,4S)-1-[2-(4-Amino-piperidin-1-yl)-ethyl]-3-methyl-piperidin-4-ol tri-hydrochloride (14)

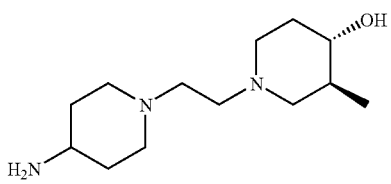

(1) 2,2-Dimethyl-propionic acid (3S,4S)-1-[2-(4-tert-butoxycarbonylamino-piperidin-1-yl)-ethyl]-3-methyl-piperidin-4-yl ester (15)

A solution of tert-butyl ester 8 (4.8 g, 19.65 mmol) and triethylamine (4.1 ml, 29.47 mmol) in 150 ml of DCM is cooled to −78C. Triflic anhydride (4.3 ml, 25.54 mmol) is slowly added and stirring continued for 1 hour. The mixture is then allowed to warm up to 0 C and a solution of 2,2-dimethyl-propionic acid 3S-methyl-piperidin-4S-yl ester, 17, preparation see below, (3.72 g, 18.66 mmol) in 20 ml of DCM is added at 0 C. Stirring is continued at room temperature for 1 hour. The mixture is washed twice with water, dried over sodium sulphate, filtered and evaporated.

Yield: 9.3 g (>100%, contained some triethylamine). MS (ESI): 426.3 [M+H]$^+$.

(2) {1-[2-((3S,4S)-4-Hydroxy-3-methyl-piperidin-1-yl)-ethyl]-piperidin-4-yl}-carbamic acid tert-butyl ester (16)

Crude 15 (8.2 g, 19.27 mmol) is treated with NaOMe (0.5M in methanol, 77 ml, 38.5 mmol) and heated under reflux for 24 hours. The solvent is then evaporated, the residue taken up in DCM and extracted with 1N—NaOH and brine. Drying and evaporation gave a brown oil which is purified by chromatography on silicagel using DCM (saturated with ammonia) and MeOH (from 1% to 5%).

Yield: 3.07 g (46%). MS (ESI): 342.3 [M+H]$^+$, 1H-NMR (CDCl$_3$): δ (ppm) 4.51 (br d, 1H), 3.5 (br m, 1H), 3.17 (td, 1H), 2.85-3.08 (m, 4H), 2.63 (m, 4H), 2.1-2.35 (m, 3H), 1.48-2.04 (m, 9H), 1.42 (s, 9H), 0.99 (d, 3H).

(3) (3S,4S)-1-[2-(4-Amino-piperidin-1-yl)-ethyl]-3-methyl-piperidin-4-ol tri-hydrochloride (14)

It is prepared by BOC-cleavage of tert-butyl ester 16 (3.07 g, 8.98 mmol) with 4M-HCl in dioxane (11.2 ml, 44.8 mmol) as described for amine 7.

Yield: 3.1 g (98%). MS (ESI): 328.2 [M+H]$^+$, 1H-NMR (CDCl$_3$): δ (ppm) 4.61 (br d, 1H), 3.89 (m, 3H), 3.53 (m, 1H), 3.03 (m, 2H), 2.55-2.73 (m, 6H), 2.44 (m, 1H), 2.3 (m, 2H), 1.83-2.02 (m, 3H), 1.5-1.7 (m, 4H), 1.44 (s, 9H).

Synthesis of 2,2-Dimethyl-propionic acid (3S,4S)-3-methyl-piperidin-4-yl ester (17) (reaction scheme 2)

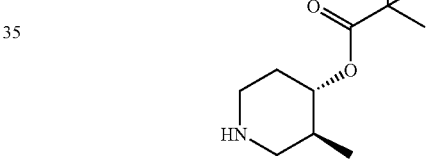

(1) Step A: trans-2,2-Dimethyl-propionic acid 1-benzyl-3-methyl-piperidin-4-yl ester (18)

To a cis/trans mixture of 1-benzyl-3-methyl-piperidin-4-ol (50 g, 243 mmol, prepared as described in *Can. J. Chem.* (1972) 50, 803) in THF is added triethylamine (51 ml, 365 mmol) followed by 2,2-dimethyl-propionyl chloride (45 ml, 365 mmol). The reaction is exothermic and a precipitate is formed. The mixture is heated under reflux for 18 hours, cooled, filtered and washed with ether. The organic layers are washed with 1N—NaOH and brine, dried and evaporated. The crude is purified by chromatography on silicagel using hexane and EtOAc (5%) to give pure trans-isomer as a colourless oil.

Yield: 38 g (54%). MS (ESI): 290.1 [M+H]$^+$, 1H-NMR (DMSO-d$_6$): δ (ppm) 7.3 (m, 5H), 4.29 (td, 1H), 3.45 (d, 2H), 2.74 (d, 2H), 2.05 (td, 1H), 1.8 (m, 3H), 1.46 (m, 1H), 1.14 (s, 9H), 0.8 (d, 3H).

(2) Step B: trans-2,2-dimethyl-propionic acid 3-methyl-piperidin-4-yl ester (19)

The trans-ester 18 (104 g, 359 mmol) is hydrogenated in methanol (1700 ml) with Pd/C in the presence of one equivalent of HCl (431 ml, 359 mmol, 1.25M in MeOH). The mixture is filtered and evaporated. The residue is redissolved in ether and extracted with 1N—NaOH and brine. Evaporation gives a colourless oil.

Yield: 62.7 g (87%). MS (ESI): 200.2 [M+H]$^+$, 1H-NMR (CDCl$_3$): δ (ppm) 4.46 (td, 1H), 3.06 (m, 2H), 2.68 (td, 1H), 2.35 (m, 1H), 1.94 (m, 1H), 1.68 (m, 2H), 1.34-1.46 (m, 1H), 1.2 (s, 9H), 0.96 (d, 3H).

(3) Step C: 2,2-Dimethyl-propionic acid (3S,4S)-3-methyl-piperidin-4-yl ester (17)

Racemic 19 (62.7 g, 314.4 mmol) is dissolved in EtOAc (300 ml) and a solution of L-(−)-O,O'-Dibenzoyl tartaric acid (56.3 g, 157.2 mmol) in EtOAc (450 ml) is added. The formed solid is filtered off, washed with cold EtOAc and dried. It is then re-crystallized from hot methanol (400 ml). The crystals are collected and the free base is liberated by treatment with 1N—NaOH and extraction with ether.

Yield: 13 g (21%). MS and 1H-NMR are identical to racemic 19. [α]$_D$=65.1 (c=1 in MeOH).

Synthesis 2,2-Dimethyl-propionic acid (3R,4R)-3-methyl-piperidin-4-yl ester (20)

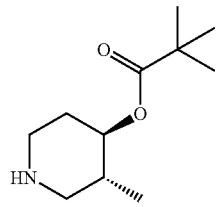

The mother liquor of 17 from above is treated with 1N—NaOH to obtain the free base which is then crystallized with D-(+)-O,O'-Dibenzoyl tartaric acid as described above to give the antipode 20.

Yield: 16 g (25%). MS and 1H-NMR are identical to racemic 19. [α]$_D$=−64.7 (c=1 in MeOH)

Synthesis of 1-[2-(4-Amino-piperidin-1-yl)-ethyl]-piperidin-4-ol tri-hydrochloride (21) (reaction scheme 3)

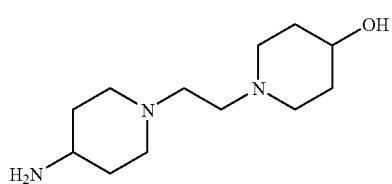

(1) 1-(2-Hydroxy-ethyl)-piperidin-4-ol (22)

Piperidin-4-ol (5 g, 49.4 mmol) is dissolved in 200 ml of ethanol and anhydrous sodium carbonate (21 g, 197.6 mmol) is added. 2-Bromo-ethanol (6.9 ml, 98.8 mmol) is added dropwise and the reaction mixture is refluxed for 16 hours. After evaporation under reduced pressure the mixture is stirred with 200 ml of DCM and filtered. The clear filtrate is evaporated under reduced pressure and dried at high vacuum.

Yield: 4.3 g (60%) of a colorless oil. MS (ESI): 146 [M+H]$^+$, 1H-NMR (DMSO-d$_6$): δ (ppm) 4.52 (d, 1H), 4.32 (t, 1H), 3.48 (dt, 2H), 3.4 (m, 1H), 2.7 (m, 2H), 2.35 (t, 2H), 2.05 (m, 2H), 1.68 (m, 2H), 1.3-1.4 (m, 2H).

(2) {1-[2-(4-Hydroxy-piperidin-1-yl)-ethyl]-piperidin-4-yl}-carbamic acid tert-butyl ester (23)

Piperidin-4-yl-carbamic acid tert-butyl ester 3 (5 g, 25 mmol), 1-(2-Hydroxy-ethyl)-piperidin-4-ol 22 (4 g, 27.5 mmol) and DIEA (5.6 ml, 32.5 mmol) are suspended in 25 ml of propionitril. Cyanomethyl-trimethyl-phosphonium iodide (4 g, 30 mmol) is added and the reaction mixture is refluxed. Additional portions of cyanomethyl-trimethyl-phosphonium iodide (1.5 g, 11.25 mmol) are added after 90 minutes and after 3 hours. After cooling to room temperature, a solution of potassium carbonate (4 g) in 250 ml of water is added and the product is isolated by extraction with DCM. Evaporation under reduced pressure gave 6.9 g of a red oil which could be crystallized from ether.

Yield: 2.2 g (27%) of colorless crystals. MS (ESI): 328 [M+H]$^+$, 1H-NMR (DMSO-d$_6$): δ (ppm) 6.72 (br d, 1H), 4.5 (d, 1H), 3.42 (m, 1H), 3.2 (m, 1H), 2.8 (m, 2H), 2.7 (m, 2H), 2.35 (m, 4H), 2.0 (dt, 2H), 1.9 (dt, 2H), 1.68 (m, 4H), 1.4 (s, 9H), 1.35 (m, 4H).

(3) 1-[2-(4-Amino-piperidin-1-yl)-ethyl]-piperidin-4-ol tri-hydrochloride (21)

Ester 23 (2.2 g, 6.72 mmol) is dissolved in 4M HCl in dioxane at 0° C. and stirred at room temperature for 3 hours. After evaporation of the solvent the product is dried at high vacuum.

Yield: 2.3 g (100%) of a white solid. MS (ESI): 228 [M+H]$^+$, 1H-NMR (DMSO-d$_6$): δ (ppm) 5 (m, 1H), 3.4 (m, 4H), 2.7 (m, 4H), 2.4 (m, 2H), 1.85-2.0 (m, 4H), 1.65 (m, 4H), 1.35 (m, 4H), 1.2 (m, 2H).

Synthesis of 8-[2-(4-Amino-piperidin-1-yl)-ethyl]-8-aza-bicyclo[3.2.1]octan-3-ol tri-hydrochloride (24) (reaction scheme 3)

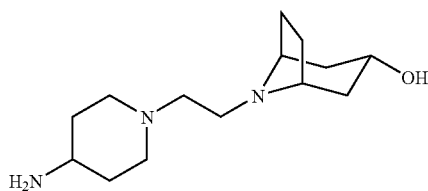

(1) 8-(2-Hydroxy-ethyl)-8-aza-bicyclo[3.2.1]octan-3-ol (25)

8-Aza-bicyclo[3.2.1]octan-3-ol hydrochloride (5.1 g, 31.45 mmol)) and sodium carbonate (13.3 g, 125.8 mmol) are suspended in 150 ml of ethanol at room temperature. 2-Bromo-ethanol (4.4 ml, 62.9 mmol) is added dropwise within 20 minutes and the reaction mixture is refluxed for 15 hours. After cooling to room temperature the reaction mixture is evaporated under reduced pressure. The mixture is stirred with 200 ml of DCM and filtered. The clear filtrate is dried over anhydrous sodium sulfate, filtered, evaporated under reduced pressure and dried at high vacuum.

(2) {1-[2-(3-Hydroxy-8-aza-bicyclo[3.2.1]oct-8-yl)-ethyl]-piperidin-4-yl}-carbamic acid tert-butyl ester (26)

Yield: 5.4 g (100%) of a colorless oil. MS (ESI): 172 [M+H]+, 1H-NMR (DMSO-d6): δ (ppm) 4.25 (d, 2H), 3.78 (t, 1H), 3.42 (t, 2H), 3.06 (m, 2H), 2.36 (t, 2H), 2.03 (m, 2H), 1.85 (m, 2H), 1.75 (m, 2H), 1.55 (d, 2H).

Piperidin-4-yl-carbamic acid tert-butyl ester 3 (1 g, 5 mmol), 8-(2-hydroxy-ethyl)-8-aza-bicyclo[3.2.1]octan-3-ol 25 (1 g, 5.5 mmol) and DIEA (1.1 ml, 6.5 mmol) are dissolved in 5 ml of propionitril. Cyanomethyl-trimethyl-phosphonium iodide (792 mg, 6 mmol) is added under stirring and the reaction mixture is refluxed and followed by TLC. Additional cyanomethyl-trimethyl-phosphonium iodide (400 mg) is added after 2 hours and the mixture is refluxed for another hour. After cooling to room temperature, DCM. The combined organic layers are washed with brine, dried over anhydrous a solution of potassium carbonate (4 g) in 250 ml of water is added and the product is isolated by extraction with sodium sulfate, filtered and evaporated under reduced pressure. The crude product (1.9 g) is crystallized from ether.

Yield: 940 mg (53%) of light beige crystals. MS (ESI): 354 [M+H]+, 1H-NMR (DMSO-d6): δ (ppm) 6.73 (br d, 1H), 4.25 (d, OH), 3.8 (m, 1H), 3.17 (m, 1H), 3.08 (m, 2H), 2.8 (m, 2H), 2.35 (m, 4H), 2.0 (m, 2H), 1.92 (m, 2H), 1.85 (dt, 2H), 1.78 (m, 2H), 1.65 (m, 2H), 1.53 (m, 2H), 1.38 (s, 9H), 1.33 (m, 2H).

(3) 8-[2-(4-Amino-piperidin-1-yl)-ethyl]-8-aza-bicyclo[3.2.1]octan-3-ol tri-hydrochloride (24)

Ester 26 (4.5 g, 12.73 mmol) is dissolved in 4M HCl in dioxane at 0° C. and stirred at room temperature for 3 hours. After evaporation of the solvent the product is dried at high vacuum.

Yield: 4.6 g (100%) of a white solid. MS (ESI): 254 [M+H]+.

Synthesis of 1-[2-((2S,6R)-2,6-Dimethyl-piperidin-1-yl)-ethyl]-piperidin-4-ylamine tri-hydrochloride (27) (reaction scheme 3)

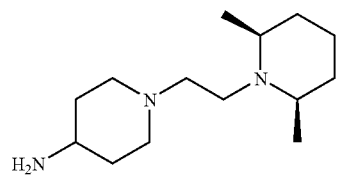

(1) {1-[2-(2,6-Dimethyl-piperidin-1-yl)-ethyl]-piperidin-4-yl}-carbamic acid tert-butyl ester (28)

Compound 28 is prepared analogously to 25 starting from cis-2,6-dimethylpiperidin (6.4 ml, 44.17 mmol) and bromethanol (6.1 ml, 88.33 mmol).

Yield: 3.9 g (56%) of a yellow oil. MS (ESI): 158.1 [M+H]+]+, 1H-NMR (DMSO-d6): δ (ppm) 4.48 (br, 1H), 3.4 (t, 2H), 2.6 (t, 2H), 2.4 (m, 2H), 1.1-1.6 (m, 6H), 1.03 (d, 6H).

(2) {1-[2-(2,6-Dimethyl-piperidin-1-yl)-ethyl]-piperidin-4-yl}-carbamic acid tert-butyl ester (29)

Compound 29 is prepared analogously to 26 starting from compound 28 (3.85 g, 24.48 mmol) and piperidin-4-yl-carbamic acid tert-butyl ester 3 (4.46 g, 22.25 mmol).

Yield: 6.16 g (82%) of a yellow oil. MS (ESI): 340.4 [M+H]+, 1H-NMR (DMSO-d6): δ (ppm) 6.73 (br d, 1H), 3.18 (m, 1H), 2.75 (m, 2H), 2.65 (m, 2H), 2.35 (m, 2H), 2.25 (m, 2H), 1.92 (m, 2H), 1.65 (m, 2H), 1.57 (m, 2H), 1.49 (m, 2H), 1.38 (s, 9H), 1.35 (m, 2H), 1.12 (m, 2H), 1.03 (d, 6H).

(3) 1-[2-((2S,6R)-2,6-Dimethyl-piperidin-1-yl)-ethyl]-piperidin-4-ylamine tri-hydrochloride (27)

Compound 27 is prepared analogously to 24 starting from the BOC protected derivative 29 (6.16 g, 18.14 mmol).

Yield: 6.3 g (100%) of a white solid. MS (ESI): 240.3 [M+H]+.

Synthesis of (R)-1-((3a,7a)-2,2-Dimethyl-tetrahydro-[1,3]dioxolo[4,5-c]pyridin-5-yl)-propan-2-ol (30) (reaction scheme 4)

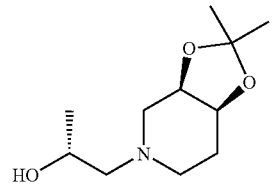

(1) 3,6-Dihydro-2H-pyridine-1-carboxylic acid benzyl ester (31)

1,2,3,6-Tetrahydro-pyridine (3 g, 36.1 mmol) are treated with 10% aqueous sodium carbonate (2.1 ml) and cooled to 0° C. Within 1 h, benzyl chloroformate (Z-chloride, 5.1 ml, 36 mmol) is added dropwise within 1 h. After additional stirring for 2 h, the mixture is treated with 30 ml of brine and extracted four times with diethyl ether. The organic layers are dried over sodium sulphate and evaporated. The crude product, 7 g of a colorless oil, is purified by Flash-chromatography (silica gel, cyclohexane/ethyl acetate 9:1).

Yield: 3.63 g (46%) of a colorless oil. MS (ESI): 218 [M+H]+, 1H-NMR (CDCl3): δ (ppm) 7.28-7.4 (m, 5H), 5.83 (m, 1H), 5.66 (m, 1H), 5.15 (s, 2H), 3.95 (m, 2H), 3.58 (t, 2H), 2.15 (m, 2H).

(2) 3,4-Dihydroxy-piperidine-1-carboxylic acid benzyl ester (32)

31 (3.63 g, 16.7 mmol) is dissolved in 16 ml of a 1:1 mixture of water and acetone. After addition of N-methyl-morpholine-N-oxide (2.9 g, 24.8 mmol), a 1% solution of osmium tetroxide in tert. Butanol (7.23 ml, 0.28 mmol) is added. The mixture is stirred at room temperature for 20 h. Then 70 ml of a saturated sodium bisulfite solution is added. After 15 min stirring at room temperature, the reaction mixture is extracted with ethyl acetate. The organic layers are dried over sodium sulphate and evaporated. The crude product, 4.7 g of a yellow oil, is purified by Flash-chromatography (silica gel, ethyl acetate).

Yield: 3.83 g (91%). MS (ESI): 252 [M+H]+, 1H-NMR (CDCl3): δ (ppm) 7.27-7.4 (m, 5H), 5.13 (s, 2H), 3.88 (m, 1H), 3.79 (m, 2H), 3.66 (m, 2H), 3.5 (dd, 1H), 3.34 (m, 1H), 2.13 (m, 2H), 1.82 (m, 1H), 1.7 (m, 1H).

(3) 2,2-Dimethyl-tetrahydro-[1,3]dioxolo[4,5-c]pyridine-5-carboxylic acid benzyl ester (33)

32 from above (3.72 g, 14.8 mmol) is dissolved in 20 ml of dichloromethane. After addition of 2,2-dimethoxypropane (3.6 ml, 30 mmol) and p-toluene sulfonic acid (141 mg, 0.7 mmol) the mixture is stirred at room temperature for 4 h. Then the mixture is diluted with 30 ml of dichloromethane, washed subsequently with 1N NaOH and brine, dried over sodium sulphate and evaporated. The crude racemic product, 4.32 g of a yellow oil, is separated into its enantiomers by chiral HPLC (chiralcel, OJ, 20 um, hexane/isopropanol 9:1).

Yield: 810 mg peak 1 and 942 mg (peak2) (40%) MS (ESI): 292.2 [M+H]+, 1H-NMR (CDCl3): δ (ppm) 7.25-7.4 (m, 5H), 5.14 (s, 2H), 4.18-4.4 (m, 2H), 3.7-3.82 (m, 1H), 3.38-3.58 (m, 3H), 1.74-2.0 (m, 2H), 1.44 (s, 3H), 1.35 (s, 3H).

(4) 2,2-Dimethyl-hexahydro-[1,3]dioxolo[4,5-c]pyridine (34)(single cis-enantiomer, absolute configuration unknown)

33 (peak 1 from above) (450 mg, 1.54 mmol) is dissolved in 10 ml of methanol. After addition of 10% palladium on carbon (45 mg) the mixture is hydrogenated at room temperature for 20 h. Then the mixture is filtrated over celite. Evaporation gave 240 mg (99%) of a colorless oil.

MS (ESI): 158.2 [M+H]+, 1H-NMR (CDCl3): δ (ppm) 4.25 (m, 1H), 4.12 (m, 1H), 2.9-3.1 (m, 3H), 2.78 (m, 1H), 1.85-2.40 (m, 3H), 1.52 (s, 3H), 1.38 (s, 3H).

(5) 1-(2,2-Dimethyl-tetrahydro-[1,3]dioxolo[4,5-c]pyridin-5-yl)-propan-2-ol (30)(single enantiomer, absolute configuration of dioxol unknown)

34 (90 mg, 0.57 mmol), (R)-(+)-propylenoxide (166 mg, 2.8 mmol), and triethylamine (160 ul, 1.1 mmol) are dissolved in 2 ml of ethanol and stirred at room temperature for 4 h. The reaction mixture is diluted with 20 ml of ethyl acetate, washed subsequently with 1N NaOH and brine, dried over sodium sulphate and evaporated. The crude product, 100 mg of a yellow oil, is purified by Flash-chromatography (silica gel, dichloromethane/methanol/ammonia 95:5:0.5).

Yield: 70 mg (57%). MS (ESI): 216.2 [M+H]+, 1H-NMR (CDCl3): δ (ppm) 4.03-4.28 (m, 2H), 3.9 (m, 1H), 2.2-3.08 (m, 6H), 1.36-2.13 (m, 3H), 1.51 (s, 3H), 1.38 (s, 3H), 1.12-1.22 (dd, 3H).

Synthesis of (R)-1-(2,2,7-trimethyl-tetrahydro-[1,3]dioxolo[4,5-c]pyridin-5-yl)-propan-2-ol (35) (reaction scheme 5)

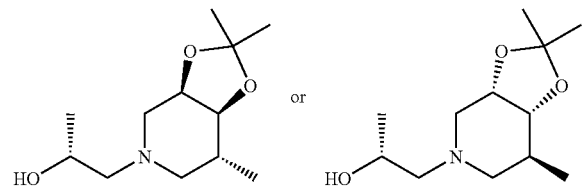

(1) Trifluoro-methanesulfonic acid 1-benzyl-3-(R,S)-methyl-1,2,3,6-tetrahydro-pyridin-4-yl ester (36)

1M lithium-bis-(trimethylsilyl)-amid solution in THF (540 ul, 0.54 mmol) is diluted with 1 ml of THF and cooled to −78° C. A solution of 1-benzyl-3-methyl-4-piperidone (100 mg, 0.49 mmol) in 0.5 ml THF is added via syringe within 5 min. After stirring for 2 h at this temperature, a solution of N-phenyl-trifluoromethansulfonimid (188 mg, 0.52 mmol) in 1 ml of THF is added within 10 min. The beige suspension is stirred for another 4 h at 0° C. The yellow solution is quenched with 1 ml of saturated ammonium chloride solution, diluted with ice-cold water and three times extracted with ethyl acetate. The organic layers are washed with brine, dried over sodium sulphate and evaporated. The crude product, 311 mg of a yellow oil, is purified by Flash-chromatography (silica gel, cyclohexane/ethyl acetate 4:1).

Yield: 127 mg (77%) of a colorless oil. MS (ESI): 336 [M+H]+, 1H-NMR (DMSO-d6): δ (ppm) 7.22-7.36 (m, 5H), 5.89 (dd, 1H), 3.54-3.65 (m, 2H), 3.05 (br s, 2H), 2.75 (m, 1H), 2.59 (m, 1H), 2.32 (m, 1H), 1.06 (d, 3H).

(2) 1-Benzyl-3-(R,S)-methyl-1,2,3,6-tetrahydropyridine (37)

36 from above (100 mg, 0.3 mmol), palladium-(II)-acetate (1.34 mg, 6 umol), triphenylphosphin (3.1 mg, 12 umol) and triethylamine (125 ul, 0.9 mmol) are dissolved in 1 ml of DMF. After addition of formic acid (22.5 ul, 0.6 mmol) the mixture is stirred for 1 h at 60° C. The reaction mixture is diluted with ethyl acetate, washed subsequently with 1N NaOH and brine, dried over sodium sulphate and evaporated. The crude product, 78 mg of a yellow oil, is purified by Flash-chromatography (silica gel, cyclohexane/ethyl acetate 3:1).

Yield: 42 mg (75%) of a yellow oil. MS (ESI): 188.2 [M+H]+, 1H-NMR (CDCl3): δ (ppm) 7.23-7.41 (m, 5H), 5.62 (s, 2H), 3.63 (br s, 2H), 3.12 (d, 1H), 2.83 (m, 2H), 2.48 (m, 1H), 2.02 (br s, 1H), 0.96 (d, 3H).

(3) (3RS,4SR,5RS)-1-Benzyl-5-methyl-piperidine-3,4-diol (racemic) (38)

37 (570 mg, 3 mmol) is dissolved in 10 ml of a 1:1 mixture of water and acetone. After addition of N-methyl-morpholine-N-oxide (529 mg, 4.5 mmol), a 2.5% solution of osmium tetroxide in tert. Butanol (527 ul, 52 umol) is added. The mixture is stirred at room temperature for 24 h. Then 10 ml of a saturated sodium bisulfite solution is added. After 15 min stirring at room temperature, the reaction mixture is extracted with ethyl acetate. The organic layers are washed subsequently with 1N NaOH and brine, dried over sodium sulphate and evaporated. The crude product, 460 mg of a dark brown oil, is purified by Flash-chromatography (silica gel, dichloromethane/methanol/ammonia 95:5:0.5).

Yield: 290 mg (43%) of the cis diol, trans to the methyl group and 20 mg (3%) of the all-cis derivative. MS (ESI): 222 [M+H]+, 1H-NMR (DMSO-d6): δ (ppm) 7.17-7.32 (m, 5H), 4.21 (d, 1H), 4.04 (br d, 1H), 3.58 (m, 3H), 3.41 (dd, 2H), 3.02 (m, 1H), 2.62 (m, 1H), 2.56 (br d, 1H), 2.12 (br d, 1H), 1.69-1.88 (m, 2H), 0.86 (d, 3H).

(4) (3aRS,7RS,7aSR)-5-Benzyl-2,2,7-trimethyl-hexahydro-[1,3]dioxolo[4,5-c]pyridine (racemic) (39)

38 from above (290 mg, 1.3 mmol) is dissolved in 4 ml of dichloromethane. After portionwise addition of 2,2-dimethoxypropane (1.6 ml, 13 mmol) and p-toluene sulfonic acid (300 mg, 1.6 mmol) the mixture is stirred at room temperature for 16 h. Then the mixture is diluted with dichloromethane, washed subsequently with 1N NaOH and brine, dried over sodium sulphate and evaporated. The crude product, 333 mg of a yellow oil, is purified by Flash-chromatography (silica gel, cyclohexane/ethyl acetate 3:1).

Yield: 303 mg (89%) MS (ESI): 262.2 [M+H]$^+$, 1H-NMR (CDCl$_3$): δ (ppm) 7.20-7.40 (m, 5H), 4.19 (br s, 1H), 3.69 (br s, 1H), 3.43-3.63 (m, 2H), 2.89 (m, 1H), 2.53 (m, 2H), 2.02 (m, 1H), 1.88 (m, 1H), 1.53 (s, 3H), 1.37 (s, 3H), 1.00 (d, 3H).

(5) (3aRS,7RS,7aSR)-5-Benzyl-2,2,7-trimethyl-hexahydro-[1,3]dioxolo[4,5-c]pyridine (racemic) (40)

39 from above (250 mg, 0.96 mmol) is dissolved in 5 ml of isopropanol. After addition of 10% palladium on carbon (25 mg) the mixture is hydrogenated at room temperature for 16 h. Then the mixture is filtrated over celite. Evaporation gave 170 mg (100%) of a colorless oil.

MS (ESI): 172.2 [M+H]$^+$, 1H-NMR (CDCl$_3$): δ (ppm) 4.05 (m, 1H), 3.67 (dd, 1H), 3.39 (d, 1H), 2.98 (m, 2H), 2.21 (t, 1H), 2.05 (m, 1H), 1.73 (m, 1H), 1.52 (s, 3H), 1.37 (s, 3H), 0.98 (d, 3H).

(6) 1-(2,2,7-Trimethyl-tetrahydro-[1,3]dioxolo[4,5-c]pyridin-5-yl)-propan-2-ol (35) (mixture of diastereomers)

40 (175 mg, 1 mmol), (R)-(+)-propylenoxide (297 mg, 5.1 mmol), and triethylamine (285 ul, 2 mmol) are dissolved in 3 ml of ethanol and stirred at room temperature for 5 h. After evaporation the residue is dissolved in ethyl acetate, washed subsequently with 1N NaOH and brine, dried over sodium sulphate and evaporated. The crude product, 214 mg of a yellow oil, is purified by Flash-chromatography (silica gel, dichloromethane/methanol/ammonia 95:5:0.5).

Yield: 140 mg (60%). MS (ESI): 172.2 [M+H]$^+$, 1H-NMR (CDCl$_3$): δ (ppm) 4.05 (m, 1H), 3.67 (dd, 1H), 3.39 (d, 1H), 2.98 (m, 2H), 2.21 (t, 1H), 2.05 (m, 1H), 1.73 (m, 1H), 1.52 (s, 3H), 1.37 (s, 3H), 0.98 (d, 3H).

Synthesis of (3R,4R,5S)-1-[2-(4-Amino-piperidin-1-yl)-ethyl]-3,5-dimethyl-piperidin-4-ol tri-hydrochloride (41) (reaction scheme 6)

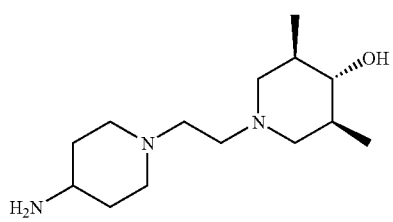

(1) N'-[1-Benzyl-3-methyl-piperidin-(4E)-ylidene]-N,N-dimethyl-hydrazine (42)

N,N-dimethylhydrazine (3 ml, 39.3 mmol) and 1-benzyl-3-methyl-piperidin-4-one (4 g, 19.7 mmol) are dissolved in 50 ml of ethanol and refluxed for 18 hours. The reaction mixture is evaporated under reduced pressure and dried at high vacuum.

Yield: 4.8 g g of a pale oil (99%). MS (ESI): 246 [M+H]$^+$, 1H-NMR (DMSO-d$_6$): δ (ppm) 7.29 (m, 4H), 7.23 (m, 1H), 3.48 (m, 2H), 2.8 (m, 1H), 2.65 (m, 1H), 2.35-2.55 (m, 2H), 2.29 (s, 6H), 2.25 (m, 1H), 1.9-2.1 (m, 1H), 1.00 (d, 3H).

(2) N'-(1-Benzyl-3,5-dimethyl-piperidin-4-ylidene)-N,N-dimethyl-hydrazine (43)

Diisopropylamine (3.3 ml, 23.5 mmol) is dissolved in 20 ml of THF and cooled to −5° C. A 1.6M solution of n-butyl-lithium in THF (14.7 ml, 23.5 mmol) is added dropwise within 10 min. After additional 10 min at −5° C., a solution of 42 (4.8 g, 19.6 mmol) in 30 ml of THF is added within 20 min (the color of the reaction mixture changed to red). Now, the solution is cooled to −78 C. Methyliodide (1.33 ml, 21.5 mmol) is added dropwise within 15 min and the mixture is allowed to warm to room temperature over night. Dichloromethane is added and the solution is washed with water. Evaporation gave 5 g of a colorless oil, which is further purified by flash-chromatography (silicagel, ethyl acetate/hexanes 1:1)

Yield: 1.7 g g of a white solid (33%). MS (ESI): 260 [M+H]$^+$, 1H-NMR (DMSO-d$_6$): δ (ppm) 7.33 (m, 4H), 7.22 (m, 1H), 3.48 (m, 2H), 3.37 (m, 1H), 2.68 (m, 1H), 2.59 (m, 1H), 2.43 (m, 1H), 2.43 (m, 1H), 2.29 (s, 6H), 2.15 (m, 1H), 2.0 (m, 1H), 1.23 (d, 6H).

(3) 1-Benzyl-3,5-dimethyl-piperidin-4-one (44)

43 (1.7 g, 6.5 mmol) is dissolved in a 1.25M solution of HCl in methanol (20 ml, 25 mmol) and refluxed for 1.5 h The reaction mixture is evaporated under reduced pressure and dried at high vacuum. The residue (1.7 g of a colorless oil) is dissolved in ethyl acetate and treated with 5M NaOH. The organic layers are evaporated under reduced pressure.

Yield: 1.4 g g of a colorless oil (84%). MS (ESI): 218 [M+H]$^+$, 1H-NMR (DMSO-d$_6$): δ (ppm) 7.3 (m, 4H), 7.25 (m, 1H), 3.58 (m, 2H), 3.07 (m, 2H), 2.68 (m, 2H), 1.97 (dd, 2H), 0.82 (d, 6H).

(4) 1-Benzyl-3,5-dimethyl-piperidin-4-ol (45)

Sodiumboronhydride (121 mg, 3.2 mmol) is added to a solution of 44 (1.4 g, 6.4 mmol) in 15 ml of methanol and the mixture is stirred at room temperature for 30 min. The mixture is evaporated, and the residue is dissolved in ethyl acetate and washed with water.

Yield: 1.4 g g of a colorless oil (99%). MS (ESI): 220 [M+H]$^+$.

(5) Acetic acid (3S,4R,5R)-1-benzyl-3,5-dimethyl-piperidin-4-yl ester (46)

DMAP (40 mg, 0.3 mmol) is added to a solution of 45 (1.4 g, 6.4 mmol) in 10 ml of pyridine. After addition of acetic anhydride (0.9 ml, 9.5 mmol) the mixture is stirred at 110° C. for 2 h. The mixture is evaporated, and the residue is dissolved in dichloromethane and washed with water. Evaporation gave 1.6 g of a colorless oil, which is further purified by flash-chromatography (silicagel, ethyl acetate/hexanes 1:9)

Yield: 0.7 g of a colorless oil (42%, fraction 1). MS (ESI): 262 [M+H]+, 1H-NMR (DMSO-d$_6$): δ (ppm) 7.2-7.3 (m, 5H), 4.18 (dd, 1H), 3.42 (s, 2H), 2.8 (m, 2H), 2.05 (s, 3H), 1.7-1.8 (m, 4H), 0.72 (d, 6H).

(6) Acetic acid (3R,4R,5S)-3,5-dimethyl-piperidin-4-yl ester (47)

Palladium hydroxide on carbon (20%, 300 mg) is placed into a flask filled with argon and carefully covered with 25 ml of methanol. A solution of 46 (0.7 g, 2.7 mmol) in methanol is added and the mixture is hydrogenated at room temperature for 15 h. After filtration over celite, the filtrate is evaporated and dried under high vacuum.

Yield: 0.41 g of a colorless oil (89%). MS (ESI): 172 [M+H]+, 1H-NMR (DMSO-d$_6$): δ (ppm) 4.22 (dd, 1H), 2.8 (dd, 2H), 2.15 (dd, 2H), 2.05 (s, 3H), 1.5 (m, 2H), 0.7 (d, 6H).

(7) Acetic acid (3S,4R,5R)-1-[2-(4-tert-butoxycarbonylamino-piperidin-1-yl)-ethyl]-3,5-dimethyl-piperidin-4-y ester (48)

47 (2.3 g, 13.4 mmol) is dissolved in 5 ml of propionitril and after addition of 8 (3.3 g, 13.4 mmol), cyanomethyl-trimethyl-phosphonium iodide (4.4 g, 33.6 mmol) and N-ethyldiisopropylamine (11.5 ml, 67.1 mmol) the mixture is refluxed for 24 h (TLC control). Then the mixture is evaporated under reduced pressure. The residue is diluted with ethyl acetate, washed 10% K2CO3- and NaCl-solution, and dried over Na2SO4.

Yield: 3.3 g of a brown oil (62%). MS (ESI): 398 [M+H]+.

(8) {1-[2-((3S,4R,5R)-4-Hydroxy-3,5-dimethyl-piperidin-1-yl)-ethyl]-piperidin-4-yl}-carbamic acid tert-butyl ester (49)

48 (3.3 g, 8.3 mmol) is dissolved in 100 ml of methanol and after addition of NaOMe powder (2.2 g, 41.5 mmol) the mixture is refluxed for 6 h (TLC control). Then the mixture is evaporated under reduced pressure. The residue is diluted with ethyl acetate, washed with water, and dried over Na2SO4. Evaporation gave 3.1 g of a brown oil. The crude product is purified by recrystallization from ether.

Yield: 800 mg of a colorless solid (27%). MS (ESI): 356 [M+H]+, 1H-NMR (DMSO-d$_6$): δ (ppm) 6.7 (br d, 1H), 4.4 (d, 1H), 3.15 (br m, 1H), 2.75 (m, 4H), 2.4 (m, 1H), 2.3 (m, 4H), 1.9 (m, 2H), 1.3-1.7 (m, 8H), 1.38 (s, 9H), 0.85 (d, 6H).

(9) 3R,4R,5S)-1-[2-(4-Amino-piperidin-1-yl)-ethyl]-3,5-dimethyl-piperidin-4-ol tri-hydrochloride (41)

49 is dissolved in a 4M solution of HCl in dioxane (20 ml) and stirred for 4 h (TLC control) at room temperature. Then the mixture is cooled down to 0 C and filtrated. The residue is washed with ether. Evaporation gave 510 mg (89%) of grey crystals.

MS (ESI): 256 [M+H]+.

Synthesis of 1-[(S)-2-(4-Amino-piperidin-1-yl)-1-methyl-ethyl]-piperidin-4-ol tri-hydrochloride (50)
(reaction scheme 7)

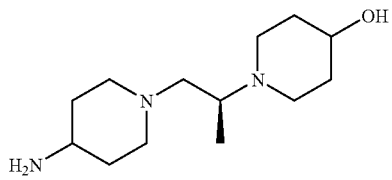

(1) 2,2-Dimethyl-propionic acid 1-benzyl-piperidin-4-yl ester (51)

A solution of 1-benzyl-piperidin-4-ol (25 g, 130.7 mmol) and triethylamine (36.1 ml, 261.4 mmol) in 250 ml of THF is treated with 2,2-dimethyl-propionyl chloride (32.2 ml, 261.4 mmol). The suspension is heated under reflux over night. The solvent is evaporated, the residue taken up in DCM and washed with saturated sodium bicarbonate solution and brine. Drying and evaporation gave an orange oil.

Yield: 38.3 g (100% crude). MS (ESI): 276 [M+H]+, 1H-NMR (CDCl$_3$): δ (ppm) 7.31 (m, 4H), 7.25 (m, 1H), 4.79 (m, 1H), 3.5 (s, 2H), 2.61 (m, 2H), 2.32 (m, 2H), 1.86 (m, 2H), 1.69 (m, 2H), 1.18 (s, 9H).

(2) 2,2-Dimethyl-propionic acid piperidin-4-yl ester (52)

A solution of piperidine 51 (35.99 g, 130.7 mmol) in methanol is hydrogenated with Pd/C in the presence of one equivalent of HCl (104.5 ml, 130.7 mmol, 1.25M in MeOH). After filtration and evaporation, the crude is taken up in ether and washed with 1N—NaOH and brine. Drying, evaporation and distillation (0.08 mbar, 75-90 C) gave a colourless oil.

Yield: 17.98 g (74%).

MS (ESI): 186 [M+H]+, 1H-NMR (DMSO-d$_6$): δ (ppm) 9.22 (br s, 1H), 4.89 (m, 1H), 3.08 (m, 4H), 1.99 (m, 2H), 1.78 (m, 2H), 1.15 (s, 9H).

(3) 2,2-Dimethyl-propionic acid 1-((R)-2-hydroxy-propyl)-piperidin-4-yl ester (53)

A solution of piperidine 52 (2 g, 10.8 mmol) and (R)-2-Methyl-oxirane (3.78 ml, 54 mmol) in 2 ml of ethanol is stirred for 24 hours in a closed flask. The solvent is evaporated and the residue distilled in a Kugelrohr apparatus (0.08 mbar, 75-90 C).

Yield: 2.58 g (98%). MS (ESI): 244.2 [M+H]+, 1H-NMR (CDCl$_3$): δ (ppm) 4.65 (m, 1H), 4.1 (br s, 1H), 3.72 (m, 1H), 2.55 (m, 2H), 2.31 (m, 2H), 2.23 (m, 1H), 2.14 (m, 1H), 1.75 (m, 2H), 1.55 (m, 2H), 1.14 (s, 9H), 1.03 (d, 3H), [α]$_D$=−23.1 (c=1 in MeOH)

(4) 2,2-Dimethyl-propionic acid 1-[(S)-2-(4-tert-butoxycarbonylamino-piperidin-1-yl)-1-methyl-ethyl]-piperidin-4-yl ester (54)

A solution of alcohol 53 (1.26 g, 5.16 mmol) and triethylamine (1.43 ml, 10.32 mmol) in 80 ml of DCM is cooled to −78 C. Triflic anhydride (0.85 ml, 5.16 mmol) is slowly added and stirring continued for 1 hour. The mixture is then allowed to warm up to 0 C and cooled back to −78 C after 15 minutes.

A solution of piperidin-4-yl-carbamic acid tert-butyl ester, 3, (1.03 g, 5.16 mmol) in 40 ml of DCM is slowly added at −78 C. After complete addition, the cooling bath is removed and the dark solution is allowed to warm up to room temperature. The mixture is washed twice with water, dried over sodium sulphate, filtered and evaporated. The crude is purified by chromatography on silicagel using DCM (saturated with ammonia) and MeOH (1%).

Yield: 1.7 g (77%).

MS (ESI): 426.3 [M+H]$^+$, 1H-NMR (CDCl$_3$): δ (ppm) 4.74 (m, 1H), 4.43 (m, 1H), 3.43 (br m, 1H), 2.89 (m, 1H), 1.97-2.82 (m, 11H), 1.87 (m, 4H), 1.64 (m, 2H), 1.43 (s, 9H), 1.38 (m, 1H), 1.19 (s, 9H), 1.0 (d, 3H). [α]$_D$=−9.3 (c=1 in MeOH)

(5) {1-[(S)-2-(4-Hydroxy-piperidin-1-yl)-propyl]-piperidin-4-yl}-carbamic acid tert-butyl ester (55)

Ester 54 from above (1.7 g, 3.52 mmol) is treated with NaOMe (0.5M in methanol, 21 ml, 10.5 mmol) and heated under reflux for 24 hours. The solvent is then evaporated, the residue taken up in DCM and extracted with 1N—NaOH and brine. After drying and evaporation the crued is purified by chromatography on silicagel using DCM (saturated with ammonia) and MeOH (from 1% to 3%) to give a white powder.

Yield: 0.77 g (56%). MS (ESI): 342.3 [M+H]$^+$, 1H-NMR (CDCl$_3$): δ (ppm) 4.43 (m, 1H), 3.64 (m, 1H), 3.43 (m, 1H), 2.88 (m, 1H), 2.75 (m, 4H), 1.8-2.45 (m, 10H), 1.3-1.65 (m, 5H), 1.44 (s, 9H), 0.99 (d, 3H). [α]$_D$=−15.3 (c=1 in MeOH).

(6) 1-[(S)-2-(4-Amino-piperidin-1-yl)-1-methyl-ethyl]-piperidin-4-ol tri-hydrochloride (50)

It is prepared by BOC-cleavage of tert-butyl ester 55 (0.666 g, 1.95 mmol) with 4M-HCl in dioxane (2.93 ml, 11.72 mmol) as described for amine 7.

Yield: 0.64 g (93%). MS (ESI): 242.3 [M+H]$^+$, 1H-NMR (DMSO-d$_6$): δ (ppm) 10.5-10.85 (br m, 2H), 8.3-8.8 (br m, 3H), 2.75-4.15 (br m, 15H), 1.6-2.3 (br m, 7H), 1.39 (d, 3H). [α]$_D$=+13.2 (c=1 in MeOH)

Synthesis of (3S,4S)-1-[(S)-2-(4-Amino-piperidin-1-yl)-1-methyl-ethyl]-3-methyl-piperidin-4-ol tri-hydrochloride (56) (reaction scheme 7)

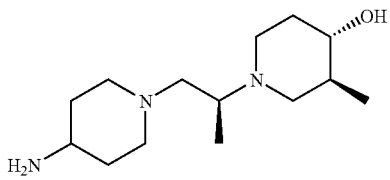

(1) 2,2-Dimethyl-propionic acid (3S,4S)-1-((R)-2-hydroxy-propyl)-3-methyl-piperidin-4-yl ester (57)

A solution of piperidine 17 (2 g, 10.8 mmol) and (R)-2-Methyl-oxirane (3.78 ml, 54 mmol) in 2 ml of ethanol is stirred for 24 hours in a closed flask. The solvent is evaporated and the residue distilled in a Kugelrohr apparatus (0.08 mbar, 75-90 C).

Yield: 2.58 g (98%). MS (ESI): 258.2 [M+H]$^+$, 1H-NMR (CD$_3$OD): δ (ppm) 4.39 (td, 1H), 3.82 (m, 1H), 2.95 (m, 1H), 2.76 (m, 1H), 2.42 (td, 1H), 2.17-2.33 (m, 2H), 1.96 (m, 1H), 1.75-1.9 (m, 2H), 1.62 (m, 1H), 1.2 (s, 9H), 1.13 (d, 3H), 0.89 (d, 3H). [α]$_D$=−23.1 (c=1 in MeOH)

(2) 2,2-Dimethyl-propionic acid (3S,4S)-1-[(S)-2-(4-tert-butoxycarbonylamino-piperidin-1-yl)-1-methyl-ethyl]-3-methyl-piperidin-4-yl ester (58)

A solution of alcohol 57 (1.26 g, 5.16 mmol) and triethylamine (1.43 ml, 10.32 mmol) in 80 ml of DCM is cooled to −78 C. Triflic anhydride (0.85 ml, 5.16 mmol) is slowly added and stirring continued for 1 hour. The mixture is then allowed to warm up to 0 C and cooled back to −78 C after 15 minutes. A solution of piperidin-4-yl-carbamic acid tert-butyl ester, 3, (1.03 g, 5.16 mmol) in 40 ml of DCM is slowly added at −78 C. After complete addition, the cooling bath is removed and the dark solution is allowed to warm up to room temperature. The mixture is washed twice with water, dried over sodium sulphate, filtered and evaporated. The crude is purified by chromatography on silicagel using DCM (saturated with ammonia) and MeOH (1%)

Yield: 1.7 g (77%). MS (ESI): 440.3 [M+H]$^+$, 1H-NMR (CD$_3$OD): δ (ppm) 4.3 (td, 1H), 3.34 (m, 1H), 3.01 (m, 1H), 2.78-2.91 (m, 4H), 2.52 (dd, 1H), 2.42 (td, 1H), 2.02-2.3 (m, 4H), 1.94 (m, 1H), 1.84 (m, 3H), 1.5 (m, 3H), 1.45 (s, 9H), 1.21 (s, 9H), 1.04 (d, 3H), 0.9 (d, 3H). [α]$_D$=−9.3 (c=1 in MeOH)

(3) {1-[(S)-2-((3S,4S)-4-Hydroxy-3-methyl-piperidin-1-yl)-propyl]-piperidin-4-yl}-carbamic acid tert-butyl ester (59)

Ester 58 from above (1.7 g, 3.52 mmol) is treated with NaOMe (0.5M in methanol, 21 ml, 10.5 mmol) and heated under reflux for 24 hours. The solvent is then evaporated, the residue taken up in DCM and extracted with 1N—NaOH and brine. After drying and evaporation the crued is purified by chromatography on silicagel using DCM (saturated with ammonia) and MeOH (from 1% to 3%) to give a white powder.

Yield: 0.77 g (56%). MS (ESI): 356.3 [M+H]$^+$, 1H-NMR (CD$_3$OD): δ (ppm) 4.86 (s, 1H), 3.32 (m, 1H), 2.94-3.06 (m, 2H), 2.72-2.87 (m, 3H), 2.49 (dd, 1H), 2.34 (td, 1H), 2.14-2.28 (m, 2H), 1.97-2.1 (m, 2H), 1.75-1.93 (m, 3H), 1.53 (m, 4H), 1.44 (s, 9H), 1.04 (d, 3H), 0.97 (d, 3H). [α]$_D$=−15.3 (c=1 in MeOH)

(4) (3S,4S)-1-[(S)-2-(4-Amino-piperidin-1-yl)-1-methyl-ethyl]-3-methyl-piperidin-4-ol tri-hydrochloride (56)

It is prepared by BOC-cleavage of tert-butyl ester 59 (0.666 g, 1.95 mmol) with 4M-HCl in dioxane (2.93 ml, 11.72 mmol) as described for amine 7.

Yield: 0.64 g (93%). MS (ESI): 256.2 [M+H]$^+$, 1H-NMR (CD$_3$OD): δ (ppm) 4.25 (br m, 1H), 4.03 (br m, 3H), 3.05-3.9 (m, 9H), 1.95-2.55 (m, 7H), 1.54 (d, 3H), 1.1 (d, 3H). [α]$_D$=+13.2 (c=1 in MeOH)

Synthesis 2,2-Dimethyl-propionic acid (3S,4S)-1-((S)-2-hydroxy-3-trityioxy-propyl)-3-methyl-piperidin-4-yl ester (60)

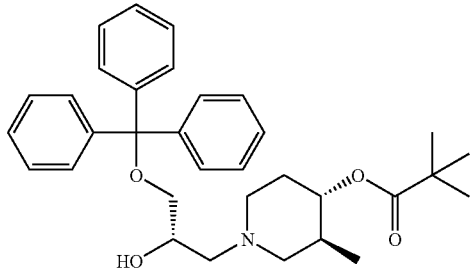

(S)-2-Trityloxymethyl-oxirane (636 mg, 2 mmol) and 2,2-dimethyl-propionic acid (3S,4S)-3-methyl-piperidin-4-yl ester (17, 400 mg, 2 mmol) are dissolved in 7 ml of ethanol and stirred at room temperature for 23 h. The white suspension is heated to 40° C. and stirred for additional 2 h. The reaction mixture is evaporated under reduced pressure and the crude product is purified by Flash-chromatography. (silica gel, 20% ethyl acetate in cyclohexane).

Yield: 681 mg (66%) of a white foam. MS (ESI): 516.4 [M+H]$^+$, 1H-NMR (CDCl$_3$): δ (ppm) 7.4 (d, 6H), 7.31 (dd, 6H), 7.23 (dd, 3H), 4.62 (d, 1H), 4.22 (m, 1H), 3.74 (m, 1H), 2.95 (d, 2H), 2.72 (m, 2H), 2.22-2.41 (m, 2H), 2.07 (m, 1H), 1.58-1.84 (m, 3H), 1.14 (s, 9H), 0.76 (d, 3H).

Synthesis of (1-[(1S,9aR)-1-(Octahydro-quinolizin-1-yl)methyl]-piperidin-4-ylamine tri-hydrochloride (61) (reaction scheme 8)

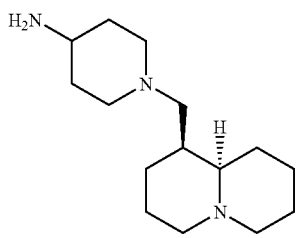

(1) {1-[(1S,9aR)-1-(Octahydro-quinolizin-1-yl)methyl]-piperidin-4-yl}-carbamic acid tert-butyl ester (62)

3 (3 g, 15 mmol) is dissolved in 150 ml of propionitril. Ethyldiisopropylamine (10.2 ml, 60 mmol), (−)-lupinine (2.5 g, 15 mmol) and cyanomethyl-trimethyl-phosphonium iodide (Zaragoza reagent, 7.3 g, 30 mmol) are added. The reaction mixture is heated to 120° C. and stirred for 22 hours. Then the mixture is evaporated under reduced pressure. The residue is dissolved with ethyl acetate, washed 10% K2CO3- and NaCl-solution, and dried over Na2SO4. Evaporation gave 5.7 g of a brown oil. The crude product is purified by Flash-chromatography (ethyl acetate, then methanol/ethyl acetate (4:6), silicagel).

Yield: 4.3 g (81.7%) of a brown oil. MS (ESI): 352 [M+H]$^+$, 1H-NMR (DMSO-d$_6$): δ (ppm) 6.7 (br d, 1H), 3.2 (m, 1H), 2.7-2.75 (m, 4H), 2.4 (dd, 1H), 2.2 (dd, 1H), 1.38 (s, 9H), 1.15-2.0 (m, 20H).

(2) 1-[(1S,9aR)-1-(Octahydro-quinolizin-1-yl)methyl]-piperidin-4-ylamine tri-hydrochloride (61)

The ester 62 (3.8 g, 10.8 mmol) is dissolved in 15 ml of dioxane and after addition of 70 ml of a 4M solution of HCl in dn of HCl in dioxan the mixture is stirred for 4 hours at RT. The product is filtered off and is used in the next step without further purification.

Yield: 3.9 g (100%). MS (ESI): 252 [M+H]$^+$.

Synthesis of (9R,9aS)-1-(Octahydro-pyrido[2,1-c][1,4]oxazin-9-yl)-methanol (racemate) (63) (reaction scheme 9)

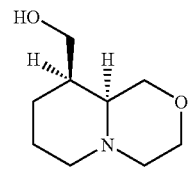

(1) 4-(3-Bromo-propyl)-morpholine-3,5-dione (64)

A pale yellow suspension of morpholine-3,5-dione (1.2 g, 10 mmol), of 1,3-dibromopropane (3.4 ml, 33 mmol), and potassium carbonate (2.7 g, 19 mmol) in 23 ml of 2-butanone is refluxed under an argon athmosphere for 22 hours. After cooling, the suspension is concentrated on a rotary evaporator, poured into ice/water, and extracted twice with ethyl acetate. The combined organic phases are washed with brine, dried over anhydrous sodium sulphate, and evaporated. The residual yellow oil (2.06 g) is purified by chromatography (Biotage 40Mi, I=15 cm, cyclohexane/ethyl acetate 3:1).

Yield: 1.24 g (52.5%) of a colorless oil. MS (EI): 235 [M]$^+$, 1H-NMR (CDCl$_3$): δ (ppm) 4.37 (s, 4H), 3.95 (t, 2H), 3.39 (t, 2H), 2.18 (m, 2H).

(2) 4-Oxo-1,3,4,6,7,8-hexahydro-pyrido[2,1-c][1,4]oxazine-9-carboxylic acid ethyl ester (65)

To an ice-cold suspension of sodium hydride (150 mg, 60% in mineral oil 3.75 mmol) in 26 ml of anhydrous THF under argon is added a solution of triethyl phosphonoacetate (0.31 ml, 1.5 mmol) in 6 ml of anhydrous THF. The suspension is stirred at RT for 2 hrs, then 64 (354 mg, 1.5) in 6 ml of THF is added, and the resulting mixture is refluxed for 10 hours. After cooling, the suspension is concentrated on a rotary evaporator, poured onto ice/sat. aqueous ammonium chloride solution, and extracted twice with ethyl acetate. The combined organic phases are washed with brine, dried over anhydrous sodium sulphate, and evaporated. The residual yellow oil (339 mg) is purified by chromatography (Biotage 12Mi, I=15.5 cm, cyclohexane/ethyl acetate 3:1).

Yield: 60.3 mg (17.8%) of a colorless oil. MS (ESI): 226 [M+H]$^+$, 1H-NMR (CDCl$_3$): δ (ppm) 4.94 (s, 2H), 4.27 (s, 2H), 4.20 (q, 2H), 3.75 (dd, 2H), 2.45 (m, 2H), 1.88 (m, 2H), 1.30 (t, 3H)

(3) (9RS,9aSR)-4-Oxo-octahydro-pyrido[2,1-c][1,4]oxazine-9-carboxylic acid ethyl ester (racemate) (66)

A solution of 65 (225 mg, 1.0 mmol) in 5 ml of acetic acid is hydrogenated over 225 mg of platinum dioxide at RT and normal pressure for 18 hours. Another 225 mg of platinum dioxide is added and hydrogenation continued for 24 hours.

The black suspension is diluted with 10 ml of DCM and filtered through a pad of celite. The filtrate is evaporated to give 268 mg of a yellow oil which is purified by chromatography (Biotage 12Si, I=7.5 cm, ethyl acetate/ethanol 9:1).

Yield: 144 mg (63.3%) of a yellow oil. MS (ESI): 228 [M+H]+, 1H-NMR (DMSO-$d_6$): δ (ppm) 4.45 (m, 1H), 4.00 (m, 2H), 3.9-3.75 (m, 4H), 3.60 (m, 1H), 2.65 (m, 1H), 2.55 (m, 1H), 1.90 (m, 2H), 1.75 (m, 1H), 1.45 (m, 1H), 1.16 (t, 3H).

(4) (9RS,9aSR)-1-(Octahydro-pyrido[2,1-c][1,4]oxazin-9-yl)-methanol (racemate) (63)

To a solution of 66 (114 mg, 0.5 mmol) in 5 ml of anhydrous THF is added LAH (40 mg, 1.0 mmol) and the mixture refluxed for 9 hours. The mixture is cooled to 0° C. and treated successively with 0.04 ml of water, 3N aqueous sodium hydroxide (0.04 ml, 0.12), and 0.12 ml of water. The mixture is stirred for 15 min. and then extracted three times with DCM. The combined organic phases are dried over anhydrous sodium sulphate and evaporated under educed pressure. The residual pale yellow oil (75 mg) is purified by chromatography (Biotage 12Si, I=7.5 cm, DCM/MeOH/conc. Ammonia 95:4.5:0.5).

Yield: 35.1 mg (41.0%) of a pale yellow oil. MS (ESI): 172 [M+H]+, 1H-NMR (DMSO-$d_6$): δ (ppm) 4.30 (br s, 1H), 3.65-3.55 (m, 4H), 3.50-3.35 (m, 2H), 2.70 (br d, 1H), 2.55 (br d, 1H), 2.10-1.95 (m, 2H), 1.85-1.60 (m, 2H), 1.60-1.50 (m, 2H), 1.35-1.20 (m, 2H).

Synthesis of (8R,8aS)-1-(hexahydro-pyrrolo[2,1-c][1,4]oxazin-8-yl)-methanol (racemate) (67) (reaction scheme 10)

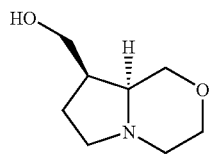

(1) 4-Oxo-3,4,6,7-tetrahydro-1H-pyrrolo[2,1-c][1,4]oxazine-8-carboxylic acid ethyl ester (68)

To a suspension of sodium hydride (480 mg, 60% in mineral oil, 12 mmol) in 10 ml of anhydrous THF is added morpholine-3,5-dione (1.2 g, 10 mmol) in 20 ml of THF under an argon athmosphere. After 10 min., 1-carbethoxycyclopropyltriphenylphosphonium tetrafluoroborate (Fuchs' reagent, 6.8 g, 11 mmol)) in 20 ml of THF are added and the mixture is refluxed for 21 hours. After cooling, the suspension is concentrated on a rotary evaporator, poured onto ice/sat. sodium bicarbonate solution, and extracted three times with ether. The combined organic phases are washed with brine, dried over anhydrous sodium sulphate, and evaporated. The residual yellow oil (3.04 g) is purified by chromatography (Silica gel 60, 0.063-0.2 mesh, cyclohexane/ethyl acetate 1:1).

Yield: 1.08 g (51.2%) of a colorless solid. MS (EI): 211 [M]+, 1H-NMR (DMSO-$d_6$): δ (ppm) 4.77 (s, 2H), 4.17 (s, 2H), 4.11 (q, 2H), 3.82 (m, 2H), 2.70 (m, 2H), 1.22 (t, 3H).

(2) (8RS,8aSR)-4-Oxo-hexahydro-pyrrolo[2,1-c][1,4]oxazine-8-carboxylic acid ethyl ester (racemate) (69)

A solution of 68 (1.056 g, 5.0 mmol) in 25 ml of acetic acid is hydrogenated over 1.056 g of platinum dioxide at RT and normal pressure for 18 hours. The black suspension is diluted with 20 ml of DCM and filtered through a pad of celite. The filtrate is evaporated to give 1.09 g of a yellow oil which is purified by chromatography (Silica gel 60, 0.063-0.2 mesh, ethyl acetate/ethanol 9:1).

Yield: 809 mg (75.7%) of a yellow oil. MS (ESI): 214 [M+H]+, 1H-NMR (DMSO-$d_6$): δ (ppm) 4.15-3.80 (m, 6H), 3.70-3.05 (m, 4H), 2.70-1.90 (m, 2H), 1.18 (t, 3H).

(3) (8RS,8aSR)-1-(Hexahydro-pyrrolo[2,1-c][1,4]oxazin-8-yl)-methanol (racemate) (67)

To a solution of 69 (1.1 g, 5.0 mmol) in 50 ml of anhydrous THF are added LAH (400 mg, 10 mmol) and the mixture refluxed for 18 hours. The mixture is cooled to 0° C. and treated successively with 0.4 ml of water, 0.4 ml of 3N aq. sodium hydroxide, and 1.2 ml of water. The mixture is stirred for 15 min. and then extracred three times with DCM. The combined organic phases are dried over anhydrous sodium sulphate and evaporated. The residual yellow oil (880 mg) is purified by chromatography (Silica gel 60, 0.063-0.2 mesh, DCM/MeOH/conc. ammonia 90:9:1).

Yield: 552 mg (70.2%) of a pink oil. MS (ESI): 158 [M+H]+, 1H-NMR (DMSO-$d_6$): δ (ppm) 4.42 (br s, 1H), 3.85 (m, 1H), 3.65 (m, 1H), 3.35 (m, 2H), 3.15 (m, 1H), 2.95 (m, 1H), 2.85 (m, 1H), 2.15-1.90 (m, 5H), 1.75 (m, 1H), 1.20 (m, 1H).

Synthesis of 4-(2-Azepan-1-yl-ethyl)-phenylamine di-hydrochloride (70)

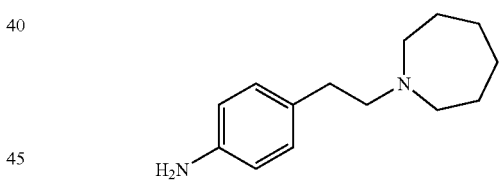

(1) 1-[2-(4-Nitro-phenyl)-ethyl]-azepane (71)

1-(2-Bromo-ethyl)-4-nitro-benzene (10 g, 43.47 mmol) is added under argon to a mixture of azepane (4.9 ml, 43.47 mmol) and potassium carbonate (6 g, 43.47 mmol) in 100 ml of DMF. After stirring over night at room temperature, the mixture is filtered and evaporated under high vacuum. The residue is dissolved in ethyl acetate, washed with water and brine and dried over sodium sulfate. Evaporation gave 9.1 g (84%) of a yellow oil.

MS (ESI): 247.2 [M+H]+, 1H-NMR (CDCl$_3$): δ (ppm) 8.15 (d, 2H), 7.55 (d, 2H), 2.87 (t, 2H), 2.73 (t, 2H), 2.65 (t, 4H), 1.5-1.6 (m, 8H).

(2) 4-(2-Azepan-1-yl-ethyl)-phenylamine di-hydrochloride (70)

Compound 71 (9.1 g, 36.65 mmol) is hydrogenated for 3 h at room temperature with palladium on carbon in 150 ml of ethanol and 18.3 ml of 4M aqueous hydrochloric acid. The mixture is filtered over celite and evaporated.

Yield: 10.7 g (100%) of a beige solid. MS (ESI): 219 [M+H]+, 1H-NMR (CDCl3): δ (ppm) 10.85 (br, 1H), 9.8 (br, 3H), 7.3 (m, 2H), 7.2 (m, 2H), 3.42 (m, 2H), 3.25 (m, 2H), 3.18 (m, 2H), 3.08 (m, 2H), 1.85 (m, 4H), 1.68 (m, 2H), 1.58 (m, 2H).

Synthesis of [(R)-1-(4-Amino-phenyl)-ethyl]-methyl-(tetrahydro-pyran-4-yl)-amine di-hydrochloride (72) (reaction scheme 11)

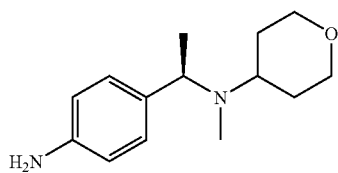

(1) Methyl-[(R)-1-(4-nitro-phenyl)-ethyl]-(tetrahydro-pyran-4-yl)-amine (73)

(R)-α-Methyl-4-nitro-benzylammonium hydrochloride (Aldrich, 3 g, 15 mmol), tetrahydropyridon (1.5 g, 15 mmol), pyridine (1.2 ml, 15 mmol) are dissolved in 100 ml DCE. Sodium triacetoxyborohydride (4 g, 19 mmol, 95%) is added under stirring at room temperature; after 18 hours reaction time formaldehyde (2.4 ml, 30% in water) is added followed by sodium triacetoxyborohydride (3 g, 14 mmol, 95%) and the mixture is again stirred for 18 hours at room temperature. After addition of 2 m HCl the product is isolated by distribution between aqueous ammonia and EtOAc. The combined organic layers are washed with brine, dried over anhydrous sodium sulfate, filtered and evaporated under reduced pressure. The crude product (3.2 g, 82%) is used without further purification.

MS (ESI): 265 [M+H]+, 1H-NMR (CDCl3): δ (ppm) 8.20 (d, 2H), 7.55 (d, 2H), 4.0 (br m, 2H), 3.95 (br m, 1H), 3.3 (br m, 2H), 2.7 (br m, 1H), 2.20 (s, 3H), 1.7 (br m, 4H), 1.40 (d, 3H)

(2) [(R)-1-(4-Amino-phenyl)-ethyl]-methyl-(tetrahydro-pyran-4-yl)-amine di-hydrochloride (72)

Methyl-[(R)-1-(4-nitro-phenyl)-ethyl]-(tetrahydro-pyran-4-yl)-amine 73 from above (3.2 g, 12 mmol) is stirred with RaNi (1 g) in 100 ml of MeOH. Hydrazine monohydrate (3.2 ml) is added dropwise at room temperature and the reaction mixture is stirred for further 3 hours. After filtration and evaporation under reduced pressure the product is isolated by distribution between Et2O and brine, drying the organic phase with sodium sulfate, filtration and evaporation as yellow oil (2.6 g, 92%).

MS (ESI): 235 [M+H]+, 1H-NMR (CDCl3): δ (ppm) 7.15 (d, 2H), 6.65 (d, 2H), 4.0 (br m, 2H), 3.7 (br m, 1H), 3.6 (NH2), 3.3 (br m, 2H), 2.7 (br m, 1H), 2.20 (s, 3H), 1.7 (br m, 4H), 1.30 (d, 3H)

Synthesis of the indole-2-carboxamides

The indole-2-carboxamides are generally prepared by a TBTU-mediated coupling of appropriately substituted indole-2-carboxylic acids with the corresponding amines in the presence of Hünig's base (reaction scheme 12).

Reaction Scheme 12:

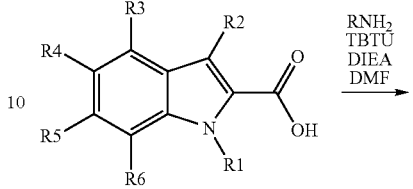

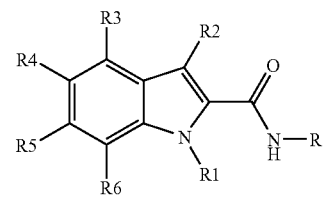

An illustrative example is given below.

Example 1

4-Methoxy-1H-indole-2-carboxylic acid [1-(2-azepan-1-yl-ethyl)-piperidin-4-yl]-amide

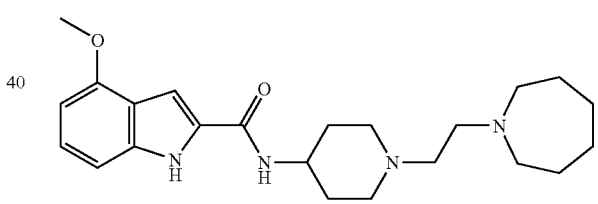

A solution of 4-Methoxy-1H-indole-2-carboxylic acid (930 mg, 4.86 mmol), amine 5 (1.63 g, 4.86 mmol) and DIEA (2.5 ml, 14.58 mmol) in 20 ml of DMF is treated with solid TBTU (1.56 g, 4.86 mmol). The mixture is stirred over night and then evaporated. The crude residue is dissolved in EtOAc and washed twice with sodium bicarbonate (10%). The aqueous layers are re-extracted with DCM, the combined organic layers are washed with brine and dried over sodium sulfate. The crude product is then purified by chromatography on silicagel using DCM (saturated with ammonia) and MeOH (from 0% to 2%).

Yield: 0.975 g (50%) of beige powder. MS (ESI): 399.3 [M+H]+, 1H-NMR (DMSO-d6): δ (ppm) 11.65 (s, 1H), 8.24 (d, 1H), 7.28 (s, 1H), 7.09 (t, 1H), 7.0 (d, 1H), 6.5 (d, 1H), 3.75-3.9 (m, 4H), 2.92-3.25 (m, 8H), 2.73 (m, 2H), 2.27 (m, 2H), 1.52-1.9 (m, 12H).

The formation of the dihydrochlorides can be achieved by treatment of a solution of the free base in DCM or acetone with 2M HCl in ether at 0° C.

Example 2

4-Isopropoxy-1H-indole-2-carboxylic acid [1-(2-azepan-1-yl-ethyl)-piperidin-4-yl]-amide

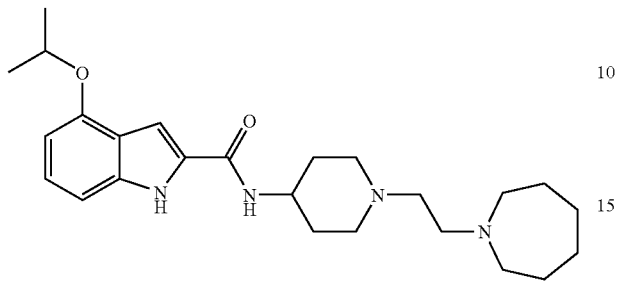

This compound is synthesized analogously to Example 1 from 4-Isopropoxy-1H-indole-2-carboxylic acid 74 (preparation see below) and amine 5.

MS (ESI): 427.3 [M+H]$^+$, 1H-NMR (DMSO-d$_6$): δ (ppm) 8.24 (d, 1H), 7.22 (d, 1H), 7.06 (t, 1H), 6.98 (d, 1H), 6.51 (d, 1H), 4.75 (m, 1H), 3.75 (m, 1H), 2.99 (m, 2H), 2.53-2.64 (m, 6H), 2.39 (m, 2H), 2.02 (m, 2H), 1.77 (m, 2H), 1.49-1.63 (m, 10H), 1.35 (d, 6H).

Synthesis of 4-Isopropoxy-1H-indole-2-carboxylic acid (74)

(1) Step A: 4-Hydroxy-1H-indole-2-carboxylic acid methyl ester (75)

To an ice cold solution of 4-Methyloxy-1H-indole-2-carboxylic acid methyl ester (1 g, 4.87 mmol) in DCM (10 ml) is added BBr3 (1M in DCM, 4.9 ml, 4.9 mmol). It is stirred for 1 hour and another equivalent (4.9 ml) of BBr3 is added. After another hour, the mixture is poured on ice and the pH is adjusted to 7 with sodium bicarbonate. Extraction with DCM gave a yellow powder.

Yield: 0.82 g (88%). MS (ESI): 192.0 [M+H]$^+$, 1H-NMR (DMSO-d$_6$): δ (ppm) 11.78 (br s, 1H), 9.73 (s, 1H), 7.21 (d, 1H), 7.05 (dd, 1H), 6.89 (d, 1H), 6.4 (d, 1H), 3.86 (s, 3H).

(2) Step B: 4-Isopropoxy-1H-indole-2-carboxylic acid methyl ester (76)

DEAD (0.227 ml, 1.47 mmol) is slowly added to a solution of 4-Hydroxy-1H-indole-2-carboxylic acid methyl ester 75 (200 mg, 1.05 mmol), triphenylphosphine (384 mg, 1.47 mmol) and isopropanol (0.108 ml, 1.43 mmol) in 2 ml of THF. Stirring is continued for 20 minutes and the solvent is then evaporated. The crude mixture is purified by chromatography on silicagel using cyclohexane/EtOAc (9/1).

Yield: 89 mg (37%). MS (ESI): 234.0 [M+H]$^+$, 1H-NMR (DMSO-d$_6$): δ (ppm) 11.89 (s, 1H), 7.26 (t, 1H), 7.07 (s, 1H), 6.98 (d, 1H), 6.54 (d, 1H), 4.72 (m, 1H), 3.85 (s, 3H), 1.33 (d, 6H).

(3) Step C: 4-Isopropoxy-1H-indole-2-carboxylic acid (74)

4-Isopropoxy-1H-indole-2-carboxylic acid methyl ester 76 (114 mg, 0.49 mmol) is dissolved in 5 ml of THF. A 2M-solution of LiOH in water (2.5 ml, 5 mmol) is added and the mixture is stirred for 48 hours. The solvent is then evaporated and the residue is partitioned between water and EtOAc. The water layer is acidified with HCl and extracted twice with EtOAc. The combined organic layers are washed with brine, dried over anhydrous sodium sulfate, filtered and evaporated to give a yellow powder.

Yield: 95 mg (89%). MS (ESI): 219.9 [M+H]$^+$, 1H-NMR (DMSO-d$_6$): δ (ppm) 11.72 (br s, 1H), 7.14 (dd, 1H), 7.0 (m, 2H), 6.55 (d, 1H), 4.72 (m, 1H), 1.33 (d, 6H).

Example 3b

4-Isopropoxy-1H-indole-2-carboxylic acid {1-[2-(4-hydroxy-piperidin-1-yl)-ethyl]-piperidin-4-yl}-amide

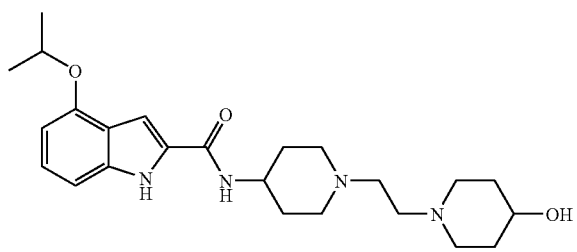

This compound is synthesized analogously to Example 1 from 4-isopropoxy-1H-indole-2-carboxylic acid 74 (preparation see Example 2) and amine 21.

MS (ESI): 429.3 [M+H]$^+$, 1H-NMR (DMSO-d$_6$): δ (ppm) 11.42 (s, 1H), 8.2 (d, 1H), 7.19 (s, 1H), 7.02 (t, 1H), 6.94 (d, 1H), 6.48 (d, 1H), 4.72 (m, 1H), 4.5 (br. s, 1H), 3.74 (m, 1H), 3.25-3.45 (m, 3H), 2.86 (m, 2H), 2.71 (m, 2H), 2.37 (br. s, 4H), 2.0 (m, 4H), 1.73 (m, 4H), 1.54 (m, 2H), 1.33 (d, 6H).

Example 4

4-Cyclopropylmethoxy-1H-indole-2-carboxylic acid [1-(2-azepan-1-yl-ethyl)-piperidin-4-yl]-amide

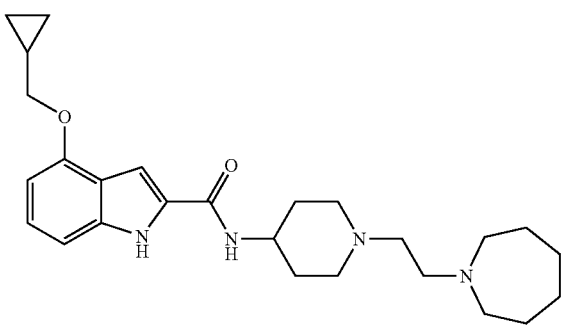

This compound is synthesized analogously to Example 1 from 4-Cyclopropylmethoxy-1H-indole-2-carboxylic acid 77 (preparation see below) and amine 5.

MS (ESI): 439.3 [M+H]$^+$, 1H-NMR (DMSO-d$_6$): δ (ppm) 11.43 (s, 1H), 8.2 (d, 1H), 7.27 (s, 1H), 7.01 (t, 1H), 6.96 (d, 1H), 6.42 (d, 1H), 3.9 (d, 2H), 3.72 (m, 1H), 2.87 (m, 2H), 2.52-2.62 (m, 6H), 2.37 (m, 2H), 2.0 (m, 2H), 1.76 (m, 2H) 1.47-1.63 (m, 10H), 1.3 (m, 1H), 0.61 (m, 2H), 0.37 (m, 2H).

Synthesis of 4-Cyclopropylmethoxy-1H-indole-2-carboxylic acid (77)

(1) Step A: 4-Cyclopropylmethoxy-1H-indole-2-carboxylic acid (78)

DEAD (2.1 ml, 13.65 mmol) is slowly added to a solution of 4-hydroxy-1H-indole-2-carboxylic acid ethyl ester 79 (2 g, 9.75 mmol), triphenylphosphine (3.58 g, 13.65 mmol) and cyclopropyl-methanol (1.05 ml, 12.26 mmol) in 20 ml of THF, so that the temperature always remained below 30° C. Stirring is continued for 2 hours and the solvent is then evaporated. The crude residue is purified by chromatography (cyclohexane:EtOAc/95:5). Yield: 1.17 g (46%).

MS (ESI): 260.1 [M+H]$^+$, 1H-NMR (CDCl$_3$): δ (ppm) 8.85 (s, 1H), 7.4 (s, 1H), 7.19 (t, 1H), 6.99 (d, 1H), 6.45 (d, 1H), 4.4 (q, 2H), 3.95 (d, 2H), 1.41 (t, 3H), 1.34 (m, 1H), 0.66 (m, 2H), 0.4 (m, 2H).

(2) Step B: 4-Cyclopropylmethoxy-1H-indole-2-carboxylic acid (77)

The 4-cyclobutylmethoxy-1H-indole-2-carboxylic acid ethyl ester 78 obtained above is mixed with a 2M-solution of KOH in EtOH (16.9 ml, 33.8 mmol) and stirred for 24 hours. The solvent is then evaporated and the residue is partitioned between water and DCM. The water layer is acidified with HCl and extracted twice with EtOAc. The combined organic layers are washed with brine, dried over anhydrous sodium sulfate, filtered and evaporated to give a white powder.

Yield: 1.02 g (99%).

MS (ESI): 232.2 [M+H]$^+$, 1H-NMR (CDCl$_3$): δ (ppm) 8.84 (s, 1H), 7.55 (s, 1H), 7.26 (t, 1H), 7.01 (d, 1H), 6.48 (d, 1H), 3.97 (d, 2H), 1.36 (m, 1H), 0.66 (m, 2H), 0.41 (m, 2H).

Example 5

4-Cyclopropylmethoxy-1H-indole-2-carboxylic acid {1-[2-(4-hydroxy-piperidin-1-yl)-ethyl]-piperidin-4-yl}-amide

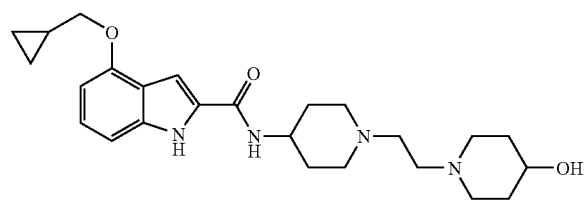

This compound is synthesized analogously to Example 1 from 4-Cyclopropylmethoxy-1H-indole-2-carboxylic acid 77 (preparation see Example 4) and amine 21.

MS (ESI): 441.3 [M+H]$^+$, 1H-NMR (DMSO-d$_6$): δ (ppm) 11.43 (s, 1H), 8.2 (d, 1H), 7.27 (s, 1H), 7.01 (t, 1H), 6.96 (d, 1H), 6.42 (d, 1H), 4.49 (d, 1H), 3.91 (d, 2H), 3.72 (m, 1H), 3.4 (m, 1H), 2.86 (m, 2H), 2.71 (m, 2H), 2.38 (br. s, 4H) 1.99 (m, 4H), 1.75 (m, 2H), 1.68 (m, 2H), 1.54 (m, 2H), 1.22-1.42 (m, 3H), 0.61 (m, 2H), 0.37 (m, 2H).

Example 6

4-Cyclopropylmethoxy-1H-indole-2-carboxylic acid {1-[(S)-2-(4-hydroxy-piperidin-1-yl)-propyl]-piperidin-4-yl}-amide

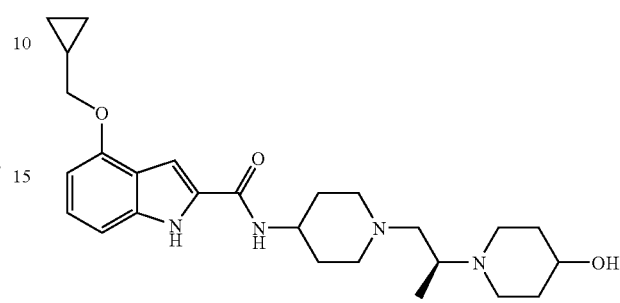

This compound is synthesized analogously to example 1 from 4-cyclopropylmethoxy-1H-indole-2-carboxylic acid, 77 (see example 4) and amine 50.

MS (ESI): 455.4 [M+H]$^+$, 1H-NMR (CD$_3$OD): δ (ppm) 7.14 (s, 1H), 6.98 (t, 1H), 6.89 (d, 1H), 6.33 (d, 1H), 3.83 (d, 2H), 3.75 (m, 1H), 3.45 (m, 1H), 2.93 (m, 1H), 2.77 (m, 1H), 2.68 (m, 3H), 2.39 (m, 1H), 2.26 (m, 2H), 2.11 (m, 2H), 1.95 (m, 1H), 1.79 (m, 2H), 1.73 (m, 2H), 1.55 (m, 2H) 1.42 (m, 2H), 1.21 (m, 1H), 0.93 (d, 3H), 0.51 (m, 2H), 0.28 (m, 2H).

Example 7

4-Cyclopropylmethoxy-1H-indole-2-carboxylic acid {1-[(S)-2-((3S,4S)-4-hydroxy-3-methyl-piperidin-1-yl)-propyl]-piperidin-4-yl}-amide

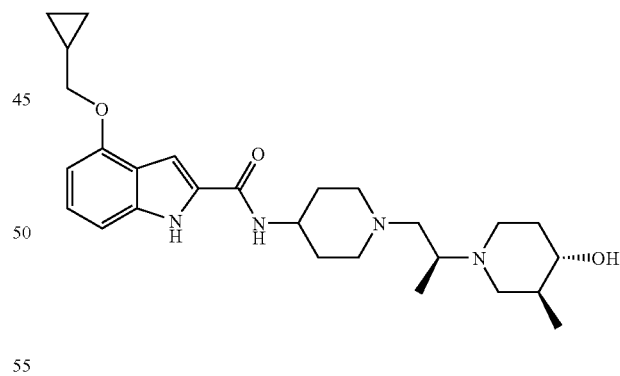

This compound is synthesized analogously to example 1 from 4-cyclopropylmethoxy-1H-indole-2-carboxylic acid, 77 (see example 4) and amine 56.

MS (ESI): 469.2 [M+H]$^+$, 1H-NMR (DMSO-d$_6$): δ (ppm) 11.44 (s, 1H), 8.2 (d, 1H), 7.27 (s, 1H), 7.01 (t, 1H), 6.95 (d, 1H), 6.41 (d, 1H), 4.44 (d, 1H), 3.91 (d, 2H), 3.74 (m, 1H), 2.61-2.95 (m, 6H), 2.04-2.38 (m, 4H), 1.85-1.97 (m, 2H), 1.66-1.81 (m, 3H), 1.45-1.63 (m, 2H), 1.2-1.43 (m, 3H), 0.91 (d, 3H), 0.87 (d, 3H), 0.61 (m, 2H), 0.37 (m, 2H).

Example 8

4-Isobutoxy-1H-indole-2-carboxylic acid [1-(2-azepan-1-yl-ethyl)-piperidin-4-yl]-amide

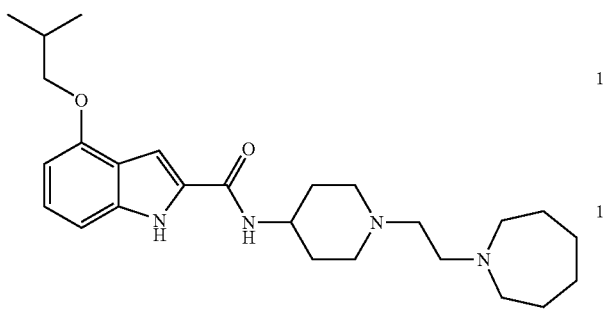

This compound is synthesized analogously to Example 1 from 4-Isobutoxy-1H-indole-2-carboxylic acid 80 (preparation see below) and amine 5.

MS (ESI): 441.3 [M+H]$^+$, 1H-NMR (DMSO-d$_6$): δ (ppm) 11.45 (s, 1H), 8.21 (d, 1H), 7.23 (d, 1H), 7.03 (t, 1H), 6.97 (d, 1H), 6.46 (d, 1H), 3.84 (d, 2H), 3.75 (m, 1H), 2.99 (m, 1H), 2.53-2.67 (m, 6H), 2.41 (m, 2H), 2.1 (m, 1H), 2.02 (m, 2H) 1.78 (m, 2H), 1.48-1.62 (m, 8H), 1.06 (d, 6H).

Synthesis of 4-Isobutoxy-1H-indole-2-carboxylic acid (80)

(1) Step A: 4-Hydroxy-1H-indole-2-carboxylic acid ethyl ester (79)

To a solution of 4-Benzyloxy-1H-indole-2-carboxylic acid ethyl ester (29 g, 98.2 mmol) in a mixture of MeOH (750 ml) and DCM (500 ml) is added 1 gram of Pd/C (10%). It is hydrogenated under normal pressure for 24 hours. After filtration and evaporation a white powder is obtained.

Yield: 19.63 g (97%). MS (ESI): 206.0 [M+H]$^+$, 1H-NMR (DMSO-d$_6$): δ (ppm) 11.72 (brs, 1H), 9.69 (s, 1H), 7.2 (s, 1H), 7.05 (t, 1H), 6.98 (d, 1H), 6.38 (d, 1H), 4.33 (q, 2H), 1.32 (t, 3H).

(2) Step B: 4-Isobutoxy-1H-indole-2-carboxylic acid ethyl ester (81)

DEAD (10.2 ml, 65.28 mmol) is slowly added to a solution of 4-Hydroxy-1H-indole-2-carboxylic acid ethyl ester 79 (9.57 g, 46.63 mmol), triphenylphosphine (17.12 g, 65.28 mmol) and isobutanol (5.9 ml, 63.42 mmol) in 100 ml of THF, so that the temperature always remained below 30° C. Stirring is continued for 3 hours and the solvent is then evaporated. The crude mixture is purified by chromatography on silicagel using first cyclohexane as eluent, then increasing amounts of EtOAc (from 5% to 50%).

Yield: 8 g (65%). MS (ESI): 260.0 [M+H]$^+$, 1H-NMR (DMSO-d$_6$): δ (ppm) 8.86 (s, 1H), 7.36 (s, 1H), 7.22 (t, 1H), 6.99 (d, 1H), 6.48 (d, 1H), 4.4 (q, 2H), 3.86 (d, 2H), 2.2 (m, 1H), 1.42 (t, 3H), 1.09 (d, 6H).

(3) Step C: 4-Isobutoxy-1H-indole-2-carboxylic acid (80)

4-Isobutoxy-1H-indole-2-carboxylic acid ethyl ester 81 (5.2 g, 19.9 mmol) is mixed with a 1M-solution of KOH in EtOH (99.5 ml, 99.5 mmol) and stirred for 24 hours. The solvent is then evaporated and the residue is partitioned between water and ether. The water layer is acidified with HCl and extracted twice with ether. The combined organic layers are washed with brine, dried over anhydrous sodium sulfate, filtered and evaporated to give a beige powder.

Yield: 4.32 g (93%). MS (ESI): 234.2 [M+H]$^+$, 1H-NMR (DMSO-d$_6$): δ (ppm) 11.74 (br s, 1H), 7.13 (dd, 1H), 7.06 (s, 1H), 7.0 (d, 1H), 6.49 (d, 1H), 3.85 (d, 2H), 3.35 (br s, 1H), 2.1 (m, 1H), 1.03 (d, 6H).

Example 9

4-Isobutoxy-1H-indole-2-carboxylic acid [1-(2-piperidin-1-yl-ethyl)-piperidin-4-yl]-amide

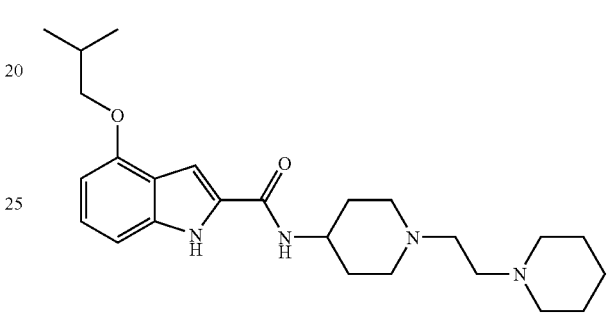

This compound is synthesized analogously to Example 1 from 4-Isobutoxy-1H-indole-2-carboxylic acid 80 (preparation see Example 8) and amine 1.

MS (ESI): 427.3 [M+H]$^+$, 1H-NMR (DMSO-d$_6$): δ (ppm) 11.45 (s, 1H), 8.21 (d, 1H), 7.23 (d, 1H), 7.03 (t, 1H), 6.96 (d, 1H), 3.84 (d, 2H), 3.75 (m, 1H), 2.88 (m, 2H), 2.38 (m, 8H), 2.1 (m, 1H), 2.02 (m, 2H), 1.78 (m, 2H), 1.32-1.63 (m, 9H), 1.07 (d, 6H).

Example 10

4-Isobutoxy-1H-indole-2-carboxylic acid {1-[2-(RS)-2-methyl-piperidin-1-yl)-ethyl]-piperidin-4-yl}-amide

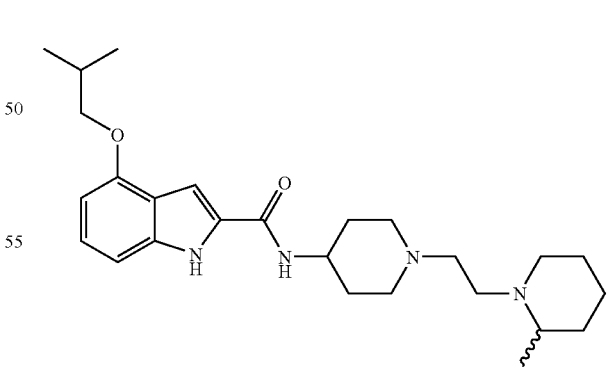

This compound is synthesized analogously to Example 1 from 4-Isobutoxy-1H-indole-2-carboxylic acid 80 (preparation see Example 8) and amine 10.

MS (ESI): 441.3 [M+H]$^+$, 1H-NMR (DMSO-d$_6$): δ (ppm) 11.43 (s, 1H), 8.19 (d, 1H), 7.22 (d, 1H), 7.03 (t, 1H), 6.97 (d, 1H), 6.45 (d, 1H), 3.85 (d, 2H), 3.75 (m, 1H), 2.65-2.93 (m, 7H), 2.05-2.43 (m, 5H), 2.01 (m, 2H), 1.78 (m, 2H), 1.1-1.62 (m, 6H), 1.06 (d, 6H), 1.01 (d, 3H).

Example 11

4-Isobutoxy-1H-indole-2-carboxylic acid {1-[2-(4-methyl-piperidin-1-yl)-ethyl]-piperidin-4-yl}-amide

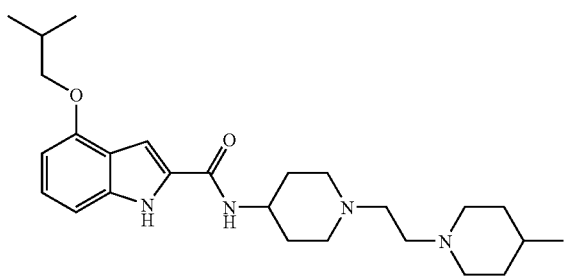

This compound is synthesized analogously to Example 1 from 4-Isobutoxy-1H-indole-2-carboxylic acid 80 (preparation see Example 8) and amine 7.

MS (ESI): 441.3 [M+H]$^+$, 1H-NMR (DMSO-d$_6$): δ (ppm) 11.44 (s, 1H), 8.2 (d, 1H), 7.22 (d, 1H), 7.02 (t, 1H), 6.96 (d, 1H), 6.46 (d, 1H), 3.86 (d, 2H), 3.75 (m, 1H), 2.86 (m, 4H), 2.4 (br s, 4H), 2.11 (m, 1H), 2.02 (m, 2H), 1.9 (m, 2H), 1.79 (m, 2H), 1.55 (m, 4H), 1.3 (m, 1H), 1.11 (m, 2H), 1.06 (d, 6H), 0.88 (d, 3H).

Example 12

4-isobutoxy-1H-indole-2-carboxylic acid {1-[2-(2,6-dimethyl-piperidin-1-yl)-ethyl]-piperidin-4-yl}-amide

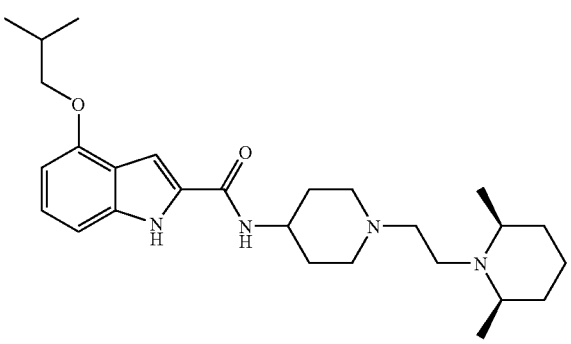

This compound is synthesized analogously to Example 1 from 4-Isobutoxy-1H-indole-2-carboxylic acid 80 (preparation see Example 8) and amine 27.

MS (ESI): 455.3 [M+H]$^+$, 1H-NMR (DMSO-d$_6$): δ (ppm) 8.2 (d, 1H), 7.22 (d, 1H), 7.04 (t, 1H), 6.96 (d, 1H), 6.45 (d, 1H), 3.85 (d, 2H), 3.75 (m, 1H), 2.87 (m, 2H), 2.7 (m, 2H), 2.43 (m, 2H), 2.32 (m, 2H), 2.1 (m, 2H), 2.03 (m, 2H), 1.78 (m, 2H), 1.45-1.65 (m, 5H), 1.0-1.35 (m, 16H).

Example 13

4-Isobutoxy-1H-indole-2-carboxylic acid {1-[2-((R)-3-hydroxy-piperidin-1-yl)-ethyl]-piperidin-4-yl}-amide

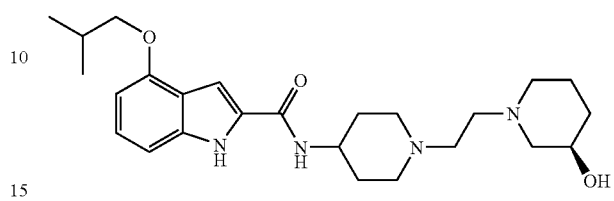

This compound is synthesized analogously to Example 1 from 4-Isobutoxy-1H-indole-2-carboxylic acid 80 (preparation see Example 8) and amine 12.

MS (ESI): 443.3 [M+H]$^+$, 1H-NMR (DMSO-d$_6$): δ (ppm) 11.45 (s, 1H), 8.21 (d, 1H), 7.23 (s, 1H), 7.04 (t, 1H), 6.97 (d, 1H), 6.45 (d, 1H), 4.54 (d, 1H), 3.84 (d, 1H), 3.75 (m, 1H), 3.42 (m, 1H), 2.62-2.93 (m, 2H), 2.49 (br s, 4H), 2.1 (m, 1H), 2.0 (m, 2H), 1.3-1.9 (m, 11H), 1.06 (d, 6H).

Example 14

4-Isobutoxy-1H-indole-2-carboxylic acid {1-[2-((S)-3-hydroxy-piperidin-1-yl)-ethyl]-piperidin-4-yl}-amide

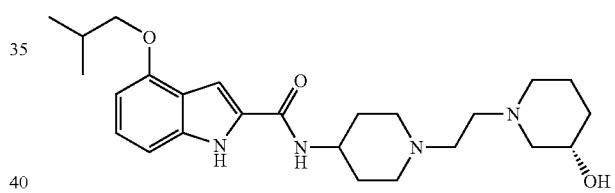

This compound is obtained by preparative separation of racemic material using a chiral HPLC stationary phase (CHIRALCEL OJ-H 1170). The absolute stereochemistry is assigned by comparison with the enantiomerically defined (R)-isomer of example 13.

Example 15

4-Isobutoxy-1H-indole-2-carboxylic acid {1-[2-(4-hydroxy-piperidin-1-yl)-ethyl]-piperidin-4-yl}-amide

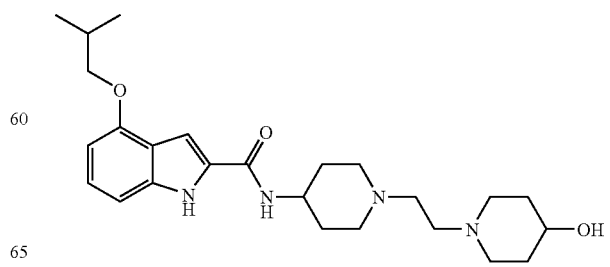

This compound is synthesized analogously to Example 1 from 4-Isobutoxy-1H-indole-2-carboxylic acid 80 (preparation see Example 8) and amine 21.

MS (ESI): 443.3 [M+H]$^+$, 1H-NMR (DMSO-d$_6$): δ (ppm) 11.45 (s, 1H), 8.2 (d, 1H), 7.23 (d, 1H), 7.04 (t, 1H), 6.97 (d, 1H), 6.45 (d, 1H), 4.5 (d, 1H), 3.85 (d, 2H) 3.74 (m, 1H), 3.41 (m, 1H), 2.88 (m, 2H), 2.71 (m, 2H), 2.38 (m, 4H), 2.1 (m, 1H), 2.0 (m, 4H), 1.76 (m, 2H), 1.68 (m, 2H), 1.55 (m, 2H), 1.35 (m, 2H), 1.06 (d, 6H).

Example 16

4-Isobutoxy-1H-indole-2-carboxylic acid {1-[2-(3-hydroxy-8-aza-bicyclo[3.2.1]oct-8-yl)-ethyl]-piperidin-4-yl}-amide

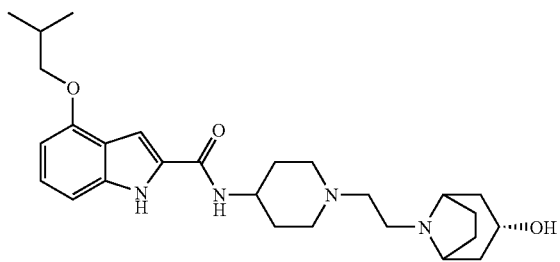

This compound is synthesized analogously to Example 1 from 4-Isobutoxy-1H-indole-2-carboxylic acid 80 (preparation see Example 8) and amine 24.

MS (ESI): 469.3 [M+H]$^+$, 1H-NMR (DMSO-d$_6$): δ (ppm) 8.23 (d, 1H), 7.72 (s, 1H), 6.9-7.1 (m, 2H), 6.46 (d, 1H), 4.57 (br s, 1H), 3.85 (d, 2H), 3.77 (m, 1H), 3.2-3.7 (br m, 4H), 2.94 (m, 2H), 2.75 (m, 2H), 2.56 (m, 2H), 1.5-2.25 (m, 15H), 1.06 (d, 6H).

Example 17

4-Isobutoxy-1H-indole-2-carboxylic acid {1-[(S)-2-(4-hydroxy-piperidin-1-yl)-propyl]-piperidin-4-yl}-amide

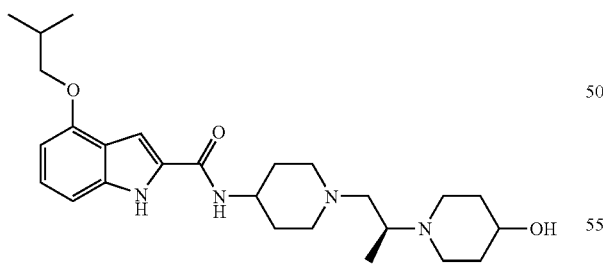

This compound is synthesized analogously to example 1 from 4-isobutoxy-1H-indole-2-carboxylic acid, 80 (see example 8) and amine 50.

MS (ESI): 457.2 [M+H]$^+$, 1H-NMR (DMSO-d$_6$): δ (ppm) 11.43 (s, 1H), 8.19 (d, 1H), 7.22 (d, 1H), 7.02 (t, 1H), 6.96 (d, 1H), 6.44 (d, 1H), 4.47 (d, 1H), 3.84 (d, 2H), 3.73 (m, 1H), 3.37 (m, 1H), 2.6-2.95 (m, 5H), 2.05-2.38 (m, 6H), 1.92 (m, 1H), 1.76 (m, 2H), 1.69 (m, 2H), 1.2-1.65 (m, 4H), 1.05 (d, 6H), 0.92 (d, 3H).

Example 18

4-Isobutoxy-1H-indole-2-carboxylic acid [4-(2-azepan-1-yl-ethyl)-phenyl]-amide

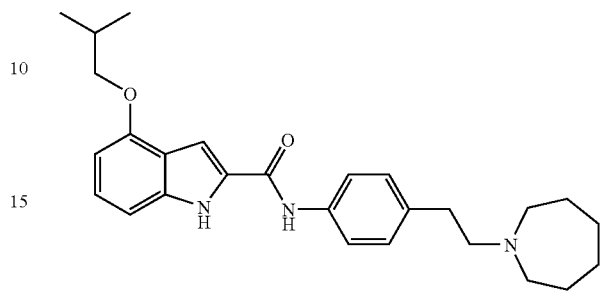

This compound is synthesized analogously to Example 1 from 4-Isobutoxy-1H-indole-2-carboxylic acid 80 (preparation see Example 8) and amine 70.

MS (ESI): 434.3 [M+H]$^+$, 1H-NMR (DMSO-d$_6$): δ (ppm) 11.65 (s, 1H), 10.07 (s, 1H), 7.67 (d, 2H), 7.48 (d, 1H), 7.18 (d, 2H), 7.08 (t, 1H), 7.01 (d, 1H), 6.49 (d, 1H), 3.88 (d, 2H), 2.57-2.62 (m, 8H), 2.13 (m, 2H), 1.48-1.63 (m, 8H), 1.08 (d, 6H).

Example 19

4-Isobutoxy-1H-indole-2-carboxylic acid (4-{[methyl-(tetrahydro-pyran-4-yl)-amino]-methyl}-cyclohexyl)-amide

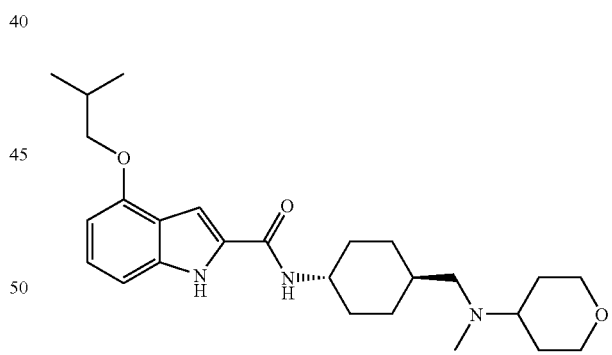

This compound is synthesized analogously to Example 1 from 4-isobutoxy-1H-indole-2-carboxylic acid 80 (preparation see Example 8) and trans-4-Amino-cyclohexylmethyl)-methyl-(tetrahydro-pyran-4-yl)-amine (WO2000068203)

MS (ESI): 442.3 [M+H]$^+$, 1H-NMR (DMSO-d$_6$): δ (ppm) 11.43 (s, 1H), 8.18 (d, 1H), 7.23 (s, 1H), 7.03 (t, 1H), 6.96 (d, 1H), 6.45 (d, 1H), 3.82-3.93 (m, 4H), 3.74 (m, 1H), 3.22-3.31 (m, 2H), 2.7 (s, 3H), 2.45 (m, 1H), 2.18 (m, 4H), 2.11 (m, 1H), 1.85 (m, 4H), 1.6 (m, 2H), 1.2-1.48 (m, 5H), 1.06 (d, 6H).

Example 20

4-Isobutoxy-1H-indole-2-carboxylic acid (4-{[methyl-(tetrahydro-pyran-4-yl)-amino]-methyl}-phenyl)-amide

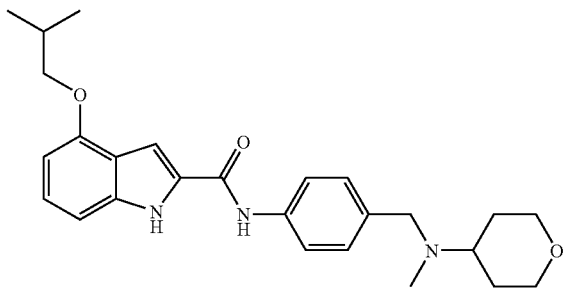

This compound is synthesized analogously to Example 1 from 4-Isobutoxy-1H-indole-2-carboxylic acid 80 (preparation see Example 8) and (4-Amino-benzyl)-methyl-(tetrahydro-pyran-4-yl)-amine (WO9932468).

MS (ESI): 436.2 [M+H]$^+$, 1H-NMR (DMSO-d$_6$): δ (ppm) 11.65 (s, 1H), 10.12 (s, 1H), 7.74 (d, 2H), 7.5 (s, 1H), 7.27 (d, 2H), 7.09 (t, 1H), 7.02 (d 1H), 6.5 (d, 1H), 3.84-3.94 (m, 4H), 3.52 (s, 2H), 3.22-3.32 (m, 2H), 2.6 (m, 1H), 2.08-2.2 (m, 4H), 1.72 (m, 2H), 1.53 (m, 2H), 1.07 (d, 6H).

Example 21

4-Isobutoxy-1H-indole-2-carboxylic acid (4-{(R)-1-[methyl-(tetrahydro-pyran-4-yl)-amino]-ethyl}-phenyl)-amide

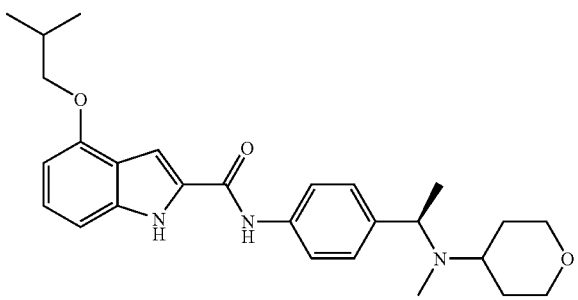

This compound is synthesized analogously to Example 1 from 4-Isobutoxy-1H-indole-2-carboxylic acid 80 (preparation see Example 8) and amine 72.

MS (ESI): 450.2 [M+H]$^+$, 1H-NMR (DMSO-d$_6$): δ (ppm) 11.66 (s, 1H), 10.12 (s, 1H), 7.73 (d, 2H), 7.5 (d, 1H), 7.3 (d, 2H), 7.09 (t, 1H), 7.02 (d, 1H), 6.5 (d, 1H), 3.76-3.91 (m, 5H), 3.1-3.33 (m, 2H), 2.68 (m, 1H), 2.04-2.2 (m, 4H), 1.36-1.68 (m, 4H), 1.28 (d, 3H), 1.08 (d, 6H).

Example 22

4-Cyclobutylmethoxy-1H-indole-2-carboxylic acid [1-(2-azepan-1-yl-ethyl)-piperidin-4-yl]-amide

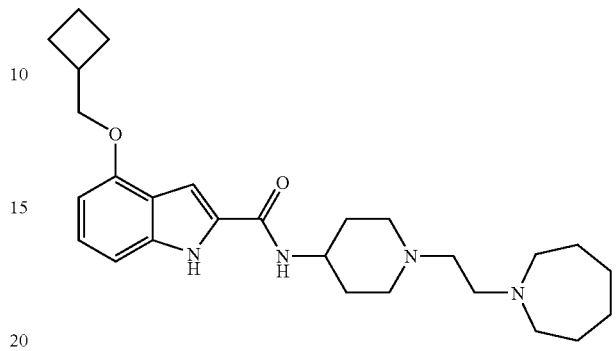

This compound is synthesized analogously to Example 1 from 4-Cyclobutylmethoxy-1H-indole-2-carboxylic acid 82 (preparation see below) and amine 5.

MS (ESI): 453.3 [M+H]$^+$, 1H-NMR (DMSO-d$_6$): δ (ppm) 11.43 (s, 1H), 8.21 (d, 1H), 7.19 (s, 1H), 7.03 (t, 1H), 6.96 (d, 1H), 6.47 (d, 1H), 4.05 (d, 2H), 3.74 (m, 1H), 2.86 (m, 2H), 2.78 (m, 1H), 2.55-2.7 (m, 6H), 2.4 (m, 2H), 1.83-2.18 (m, 8H), 1.76 (m, 2H) 1.47-1.63 (m, 10H).

Synthesis of 4-Cyclobutylmethoxy-1H-indole-2-carboxylic acid (82)

(1) Step A: 4-Cyclobutylmethoxy-1H-indole-2-carboxylic acid (83)

DEAD (2.1 ml, 13.65 mmol) is slowly added to a solution of 4-hydroxy-1H-indole-2-carboxylic acid ethyl ester 79 (2 g, 9.75 mmol), triphenylphosphine (3.58 g, 13.65 mmol) and cyclobutyl-methanol (1.25 ml, 12.26 mmol) in 20 ml of THF, so that the temperature always remained below 30° C. Stirring is continued for 2 hours and the solvent is then evaporated. The crude residue is purified by chromatography (cyclohexane:EtOAc/95:5).

Yield: 1.86 g (70%). MS (ESI): 274.2 [M+H]$^+$, 1H-NMR (CDCl$_3$): δ (ppm) 8.83 (s, 1H), 7.35 (s, 1H), 7.21 (t, 1H), 6.98 (d, 1H), 6.49 (d, 1H), 4.4 (q, 2H), 4.07 (d, 2H), 2.85 (m, 1H), 2.17 (m, 2H), 1.95 (m, 4H), 1.42 (t, 3H).

(2) Step B: 4-Cyclobutylmethoxy-1H-indole-2-carboxylic acid (82)

The 4-cyclobutylmethoxy-1H-indole-2-carboxylic acid ethyl ester 83 obtained above is mixed with a 2M-solution of KOH in EtOH (16.9 ml, 33.8 mmol) and stirred for 24 hours. The solvent is then evaporated and the residue is partitioned between water and DCM. The water layer is acidified with HCl and extracted twice with EtOAc. The combined organic layers are washed with brine, dried over anhydrous sodium sulfate, filtered and evaporated to give a white powder.

Yield: 1.65 g (99%). MS (ESI): 246.3 [M+H]$^+$, 1H-NMR (CDCl$_3$): δ (ppm) 11.74 (br. s, 1H), 7.14 (t, 1H), 7.03 (s, 1H), 6.99 (d, 1H), 6.51 (d, 1H), 4.05 (d, 2H), 2.8 (m, 1H), 2.11 (m, 2H), 1.93 (m, 4H).

Example 23

4-Cyclobutylmethoxy-1H-indole-2-carboxylic acid {1-[2-(3-(R)-hydroxy-piperidin-1-yl)-ethyl]-piperidin-4-yl}-amide

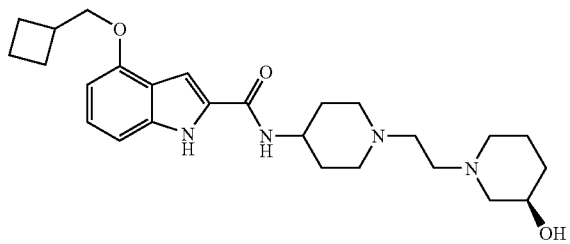

This compound is synthesized analogously to Example 1 from 4-Cyclobutylmethoxy-1H-indole-2-carboxylic acid 82 (preparation see Example 22) and amine 12.

MS (ESI): 455.4 [M+H]$^+$, 1H-NMR (DMSO-d$_6$): δ (ppm) 11.43 (s, 1H), 8.22 (d, 1H), 7.19 (s, 1H), 7.03 (t, 1H), 6.97 (d, 1H), 6.47 (d, 1H), 4.56 (br s, 1H), 4.05 (d, 2H), 3.75 (m, 1H), 3.43 (m, 1H), 2.88 (m, 3H), 2.78 (m, 1H), 2.68 (m, 1H), 2.42 (br. s, 4H), 1.83-2.2 (m, 8H), 1.77 (m, 4H), 1.56 (m, 4H), 1.38 (m, 2H).

Example 24

4-Cyclobutylmethoxy-1H-indole-2-carboxylic acid {1-[2-(4-hydroxy-piperidin-1-yl)-ethyl]-piperidin-4-yl}-amide

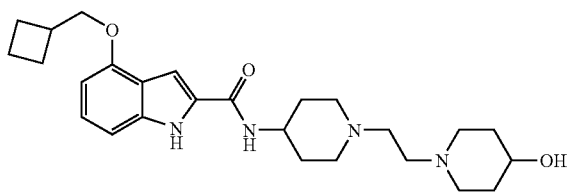

This compound is synthesized analogously to Example 1 from 4-Cyclobutylmethoxy-1H-indole-2-carboxylic acid 82 (preparation see Example 22) and amine 21.

MS (ESI): 455.4 [M+H]$^+$, 1H-NMR (DMSO-d$_6$): δ (ppm) 11.43 (s, 1H), 8.21 (d, 1H), 7.19 (s, 1H), 7.03 (t, 1H), 6.96 (d, 1H), 6.47 (d, 1H), 4.49 (s, 1H), 4.05 (d, 2H), 3.73 (m, 1H), 3.41 (m, 1H), 2.87 (m, 2H), 2.78 (m, 1H), 2.7 (m, 2H), 2.38 (m, 4H) 2.14 (m, 2H), 1.83-2.07 (m, 8H), 1.76 (m, 2H), 1.68 (m, 2H), 1.54 (m, 2H), 1.35 (m, 2H).

Example 25

4-Cyclobutylmethoxy-1H-indole-2-carboxylic acid {1-[2-((3S,4S)-4-hydroxy-3-methyl-piperidin-1-yl)-ethyl]-piperidin-4-yl}-amide

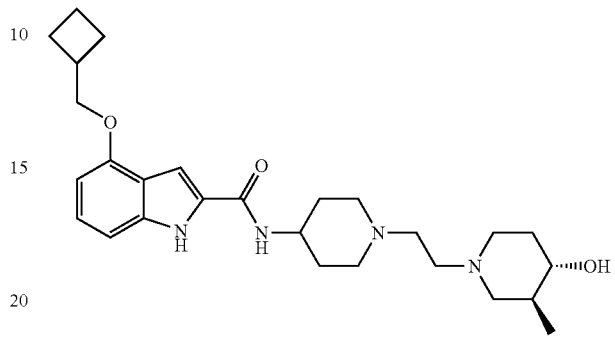

This compound is synthesized analogously to example 1 from 4-cyclobutylmethoxy-1H-indole-2-carboxylic acid, 82 (see example 22) and amine 14.

MS (ESI): 469.2 [M+H]$^+$, 1H-NMR (DMSO-d$_6$): δ (ppm) 11.44 (s, 1H), 8.21 (d, 1H), 7.19 (s, 1H), 7.03 (t, 1H), 6.96 (d, 1H), 6.46 (d, 1H), 4.48 (d, 1H), 4.04 (d, 2H), 3.73 (br m, 1H), 2.64-2.97 (m, 6H), 2.37 (m, 4H), 2.05-2.2 (m, 2H), 1.81-2.05 (m, 7H), 1.65-1.81 (m, 3H), 1.46-1.65 (m, 3H), 1.27-1.46 (m, 2H), 0.86 (d, 3H).

Example 26

4-Cyclobutylmethoxy-1H-indole-2-carboxylic acid {1-[2-(3-(R)-hydroxy-piperidin-1-yl)-ethyl]-piperidin-4-yl}-amide

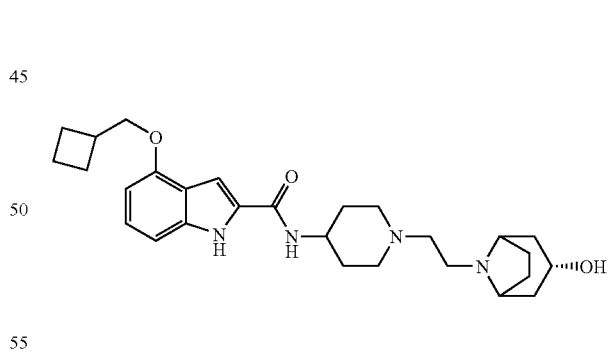

This compound is synthesized analogously to Example 1 from 4-Cyclobutylmethoxy-1H-indole-2-carboxylic acid 82 (preparation see Example 22) and amine 24.

MS (ESI): 481.3 [M+H]$^+$, 1H-NMR (DMSO-d$_6$): δ (ppm) 11.44 (s, 1H), 8.21 (d, 1H), 7.19 (s, 1H), 7.03 (t, 1H), 6.96 (d, 1H), 6.47 (d, 1H), 4.31 (brs, 1H), 4.04 (d, 2H), 3.8 (br. S, 1H), 3.74 (m, 1H), 2.89 (m, 2H), 2.78 (m, 1H), 2.42 (br. m, 6H), 1.7-2.2 (m, 16H), 1.56 (m, 4H).

Example 27

4-Cyclobutylmethoxy-1H-indole-2-carboxylic acid {1-[(S)-2-(4-hydroxy-piperidin-1-yl)-propyl]-piperidin-4-yl}-amide

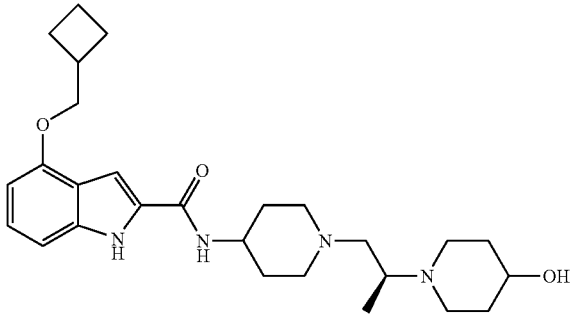

This compound is synthesized analogously to example 1 from 4-cyclobutylmethoxy-1H-indole-2-carboxylic acid, 82 (see example 22) and amine 50.

MS (ESI): 469.2 [M+H]$^+$, 1H-NMR (DMSO-d$_6$): δ (ppm) 11.45 (s, 1H), 8.21 (d, 1H), 7.18 (s, 1H), 7.03 (t, 1H), 6.96 (d, 1H), 6.46 (d, 1H), 4.46 (d, 1H), 4.05 (d, 2H), 3.74 (m, 1H), 3.36 (m, 1H), 2.6-2.95 (m, 6H), 2.04-2.4 (m, 7H), 1.83-2.0 (m, 4H), 1.64-1.81 (m, 4H), 1.45-1.63 (m, 2H), 1.23-1.42 (m, 2H), 0.92 (d, 3H).

Example 28

4-Cyclobutylmethoxy-1H-indole-2-carboxylic acid {1-[(S)-2-((3S,4S)-4-hydroxy-3-methyl-piperidin-1-yl)-propyl]-piperidin-4-yl}-amide

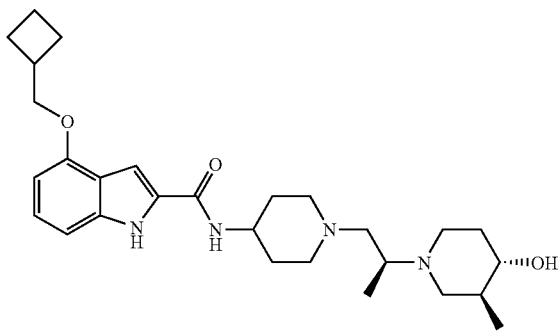

This compound is synthesized analogously to example 1 from 4-cyclobutylmethoxy-1H-indole-2-carboxylic acid, 82 (see example 22) and amine 56.

MS (ESI): 483.2 [M+H]$^+$, 1H-NMR (DMSO-d$_6$): δ (ppm) 11.46 (s, 1H), 8.22 (d, 1H), 7.19 (s, 1H), 7.03 (t, 1H), 6.96 (d, 1H), 6.46 (d, 1H), 4.44 (d, 1H), 4.04 (d, 2H), 3.74 (m, 1H), 2.6-2.95 (m, 7H), 2.33 (m, 1H), 2.24 (m, 1H), 2.02-2.19 (m, 4H), 1.82-2.01 (m, 6H), 1.66-1.81 (m, 3H), 1.45-1.64 (m, 2H), 1.2-1.43 (m, 2H), 0.91 (d, 3H), 0.87 (d, 3H).

Example 29

4-(3-Methyl-butyloxy)-1H-indole-2-carboxylic acid {1-[2-(4-hydroxy-piperidin-1-yl)-ethyl]-piperidin-4-yl}-amide dihydrochloride

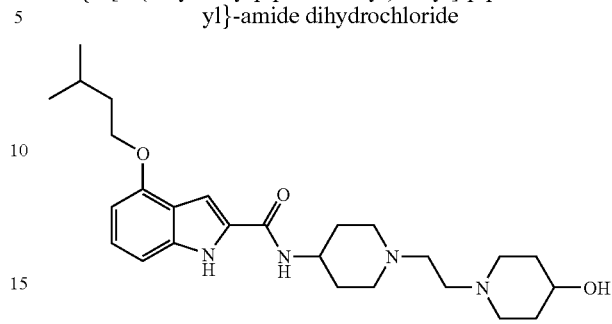

This compound is synthesized analogously to Example 1 from 4-(3-methyl-butyloxy)-1H-indole-2-carboxylic acid (84) (preparation see below) and amine 21.

Yield: 110 mg (43%). MS (ESI): 457 [M+H]$^+$, 1H-NMR (DMSO-d$_6$): δ (ppm) 11.4 (s, 1H), 10.5-10.8 (br, 2H), 8.58 (d, 1H), 7.22 (s, 1H), 7.05 (dd, 1H), 6.95 (d, 1H), 6.48 (d, 1H), 4.1 (t, 2H), 3.4-3.75 (m, 9H), 2.9-3.2 (m, 4H), 1.65-2.1 (m, 11H), 0.95 (d, 6H).

Synthesis of 4-(3-methyl-butyloxy)-1H-indole-2-carboxylic acid (84)

This compound is synthesized analogously to (85) from 3-methyl-butan-1-ol.

Yield: 0.54 g (100%). MS (ESI): 246 [M−H]$^−$.

Example 30

4-Cyclopentylmethoxy-1H-indole-2-carboxylic acid {1-[2-(4-hydroxy-piperidin-1-yl)-ethyl]-piperidin-4-yl}-amide

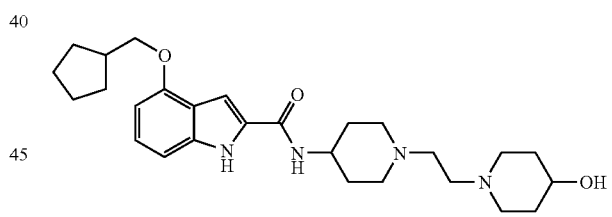

This compound is synthesized analogously to Example 1 from 4-Cyclopentylmethoxy-1H-indole-2-carboxylic acid 86 (preparation see below) and amine 21.

MS (ESI): 469.3 [M+H]$^+$, 1H-NMR (DMSO-d$_6$): δ (ppm) 11.42 (s, 1H), 8.19 (d, 1H), 7.18 (s, 1H), 7.01 (t, 1H), 6.95 (d, 1H), 6.45 (d, 1H), 4.48 (br. s, 1H), 3.93 (d, 2H), 3.72 (m, 1H), 3.4 (m, 1H), 3.15 (br. s, 1H), 2.86 (m, 2H), 2.7 (m, 2H), 2.37 (m, 4H) 1.99 (m, 4H), 1.25-1.88 (m, 16H).

Synthesis of 4-Cyclopentylmethoxy-1H-indole-2-carboxylic acid (86)

(1) Step A: 4-Cyclopentylmethoxy-1H-indole-2-carboxylic acid ethyl ester (87)

DEAD (5.3 ml, 34.1 mmol) is slowly added to a solution of 4-hydroxy-1H-indole-2-carboxylic acid ethyl ester 79 (2 g, 24.36 mmol), triphenylphosphine (8.95 g, 34.1 mmol) and cyclopentyl-methanol (3.58 ml, 33.13 mmol) in 30 ml of THF, so that the temperature always remained below 30° C. Stirring is continued for 2 hours and the solvent is then evaporated. The crude residue is purified by chromatography (cyclohexane:EtOAc/90:10).

Yield: 3.88 g (55%). MS (ESI): 288.3 [M+H]$^+$, 1H-NMR (CDCl$_3$): δ (ppm) 8.86 (br. s, 1H), 7.35 (s, 1H), 7.21 (t, 1H), 6.98 (d, 1H), 6.48 (d, 1H), 4.4 (q, 2H), 3.98 (d, 2H), 2.47 (m, 1H), 1.89 (m, 2H), 1.65 (m, 4H), 1.42 (t, 3H and overlapping m, 2H).

(2) Step B:
4-Cyclopentylmethoxy-1H-indole-2-carboxylic acid (86)

The 4-cyclopentylmethoxy-1H-indole-2-carboxylic acid ethyl ester 87 obtained above is mixed with a 2M-solution of KOH in EtOH (33.8 ml, 67.6 mmol) and stirred for 24 hours. The solvent is then evaporated and the residue is partitioned between water and ether. The water layer is acidified with HCl and extracted twice with EtOAc. The combined organic layers are washed with brine, dried over anhydrous sodium sulfate, filtered and evaporated to give a white powder.

Yield: 2.55 g (73%). MS (ESI): 260.1 [M+H]$^+$, 1H-NMR (DMSO-d$_6$): δ (ppm) 11.73 (br. s, 1H), 7.12 (t, 1H), 7.02 (s, 1H), 6.98 (d, 1H), 6.5 (d, 1H), 3.96 (d, 2H), 2.39 (m, 1H), 1.82 (m, 2H), 1.6 (m, 4H), 1.4 (m, 2H).

Example 31

4-(1,2-Dimethyl-propoxy)-1H-indole-2-carboxylic acid [1-(2-azepan-1-yl-ethyl)-piperidin-4-yl]-amide

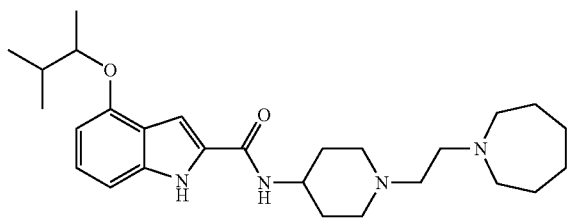

This compound is synthesized analogously to Example 1 from 4-(1,2-Dimethyl-propoxy)-1H-indole-2-carboxylic acid 88 (preparation see below) and amine 5.

MS (ESI): 455.2 [M+H]$^+$, 1H-NMR (DMSO-d$_6$): δ (ppm) 11.4 (s, 1H), 8.2 (d, 1H), 7.18 (d, 1H), 7.02 (dd, 1H), 6.93 (d, 1H), 6.47 (d, 1H), 4.37 (m, 1H), 3.74 (m, 1H), 2.88 (m, 2H), 2.52-2.62 (m, 6H), 2.37 (m, 2H), 1.89-2.06 (m, 3H), 1.75 (m, 2H), 1.46-1.62 (m, 10H), 1.24 (d, 3H), 1.0 (m, 6H).

Synthesis of 4-(1,2-Dimethyl-propoxy)-1H-indole-2-carboxylic acid (88)

(1) Step A: 4-(1,2-Dimethyl-propoxy)-1H-indole-2-carboxylic acid ethyl ester (89)

DEAD (5.3 ml, 34.1 mmol) is slowly added to a solution of 4-Hydroxy-1H-indole-2-carboxylic acid ethyl ester 79 (5 g, 24.36 mmol), triphenylphosphine (8.95 g, 34.1 mmol) and 3-Methyl-butan-2-ol (3.58 ml, 33.13 mmol) in 50 ml of THF, so that the temperature always remained below 30° C. Stirring is continued for 3 days and the solvent is then evaporated. The crude mixture is purified by chromatography on silicagel using first cyclohexane as eluent, then increasing amounts of EtOAc (from 5% to 50%).

Yield: 2.4 g (36%). MS (ESI): 276.3 [M+H]$^+$, 1H-NMR (CDCl$_3$): δ (ppm) 8.9 (br s, 1H), 7.35 (s, 1H), 7.2 (dd, 1H), 6.96 (d, 1H), 6.5 (d, 1H), 4.4 (q, 2H), 4.34 (t, 1H), 2.03 (m, 1H), 1.42 (t, 3H), 1.31 (d, 3H), 1.04 (m, 6H).

(2) Step B: 4-(1,2-Dimethyl-propoxy)-1H-indole-2-carboxylic acid (88)

4-(1,2-Dimethyl-propoxy)-1H-indole-2-carboxylic acid ethyl ester 89 (2.4 g, 8.72 mmol) is mixed with a 1M-solution of KOH in EtOH (43.6 ml, 87.2 mmol) and stirred for 48 hours. The solvent is then evaporated and the residue is partitioned between water and ether. The water layer is acidified with HCl and extracted twice with ether. The combined organic layers are washed with brine, dried over anhydrous sodium sulfate, filtered and evaporated to give a beige powder.

Yield: 2.14 g (99%). MS (ESI): 248.1 [M+H]$^+$, 1H-NMR (DMSO-d$_6$): δ (ppm) 8.92 (br s, 1H), 7.52 (s, 1H), 7.27 (m, 1H), 6.99 (d, 1H), 6.51 (d, 1H), 4.34 (m, 1H), 2.02 (m, 1H), 1.33 (d, 3H), 1.04 (m, 6H).

Example 32

4-(2,2-Dimethyl-propoxy)-1H-indole-2-carboxylic acid [1-(2-azepan-1-yl-ethyl)-piperidin-4-yl]-amide

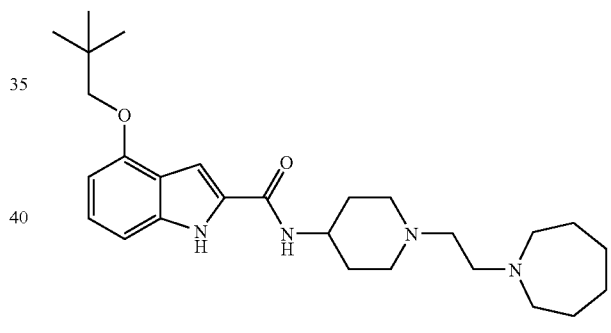

This compound is synthesized analogously to Example 1 from 4-(2,2-Dimethyl-propoxy)-1H-indole-2-carboxylic acid 85 (preparation see below) and amine 5.

MS (ESI): 455.3 [M+H]$^+$, 1H-NMR (DMSO-d$_6$): δ (ppm) 11.47 (s, 1H), 8.25 (d, 1H), 7.25 (d, 1H), 7.06 (t, 1H), 6.99 (d, 1H), 6.48 (d, 1H), 3.72-3.84 (m, 3H), 2.92 (m, 1H), 2.54-2.63 (m, 6H), 2.41 (m, 2H), 2.04 (m, 2H), 1.79 (m, 2H), 1.5-1.65 (m, 11H), 1.1 (s, 9H).

Synthesis of 4-(2,2-Dimethyl-propoxy)-1H-indole-2-carboxylic acid (85)

(1) Step A: 4-(2,2-Dimethyl-propoxy)-1H-indole-2-carboxylic acid methyl ester (90)

DEAD (0.414 ml, 2.66 mmol) is slowly added to a solution of 4-Hydroxy-1H-indole-2-carboxylic acid methyl ester 75 (363 mg, 1.9 mmol), triphenylphosphine (698 mg, 2.66 mmol) and 2,2-Dimethyl-propan-1-ol (228 mg, 2.58 mmol) in 8 ml of THF. Stirring is continued for 20 hours and the solvent is then evaporated. The crude mixture is purified by chromatography on silicagel using cyclohexane/EtOAc (9/1).

Yield: 271 mg (55%). MS (ESI): 261.9 [M+H]$^+$, 1H-NMR (CDCl$_3$): δ (ppm) 8.9 (br s, 1H), 7.39 (s, 1H), 7.23 (dd, 1H), 7.0 (d, 1H), 6.47 (d, 1H), 3.95 (s, 3H), 3.74 (s, 2H), 1.0 (s, 9H).

(2) Step B: 4-(2,2-Dimethyl-propoxy)-1H-indole-2-carboxylic acid (85)

4-(2,2-Dimethyl-propoxy)-1H-indole-2-carboxylic acid methyl ester 90 (270 mg, 1.03 mmol) is dissolved in 20 ml of THF. A 2M-solution of LiOH in water (5.2 ml, 11 mmol) is added and the mixture is stirred for 48 hours. The solvent is then evaporated and the residue is partitioned between water and ether. The water layer is acidified with HCl and extracted twice with EtOAc. The combined organic layers are washed with brine, dried over anhydrous sodium sulfate, filtered and evaporated to give a yellow powder.

Yield: 230 mg (90%). MS (ESI): 248.0 [M+H]$^+$, 1H-NMR (DMSO-d$_6$): δ (ppm) 11.75 (br s, 1H), 7.13 (dd, 1H), 7.08 (s, 1H), 7.0 (d, 1H), 6.49 (d, 1H), 4.74 (s, 2H), 1.07 (s, 9H).

Example 33

4-(4-Methyl-pentyloxy)-1H-indole-2-carboxylic acid {1-[2-(4-hydroxy-piperidin-1-yl)-ethyl]-piperidin-4-yl}-amide dihydrochloride

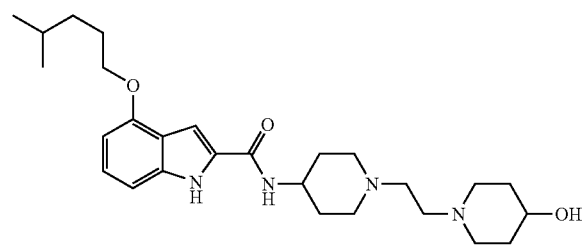

This compound is synthesized analogously to Example 1 from 4-(4-methyl-pentyloxy)-1H-indole-2-carboxylic acid (91) (preparation see below) and amine 21.

Yield: 145 mg (70%). MS (ESI): 471 [M+H]$^+$, 1H-NMR (DMSO-d$_6$): δ (ppm) 11.5 (s, 1H), 10.4-10.7 (br, 2H), 8.58 (d, 1H), 7.25 (s, 1H), 7.05 (dd, 1H), 6.95 (d, 1H), 6.45 (d, 1H), 3.95-4.2 (m, 4H), 2.95-3.8 (m, 12H), 1.7-2.1 (m, 10H), 1.6 (m, 2H), 1.35 (m, 2H), 0.9 (d, 6H).

Synthesis of 4-(4-methyl-pentyloxy)-1H-indole-2-carboxylic acid (91)

This compound is synthesized analogously to (85) from 4-methyl-pentan-1-ol.

Yield: 0.61 g (94%). MS (ESI): 260 [M−H]$^-$, 1H-NMR (DMSO-d$_6$): δ (ppm) 12.8 (s, 1H), 11.65 (s, 1H), 7.1 (dd, 1H), 7.0 (s, 1H), 6.98 (d, 1H), 6.48 (d, 1H), 4.05 (t, 2H), 1.77 (t, 2H), 1.63 (m, 1H), 1.35 (m, 2H), 0.9 (d, 6H).

Example 34

4-(3,3-Dimethyl-butoxy)-1H-indole-2-carboxylic acid {1-[2-(4-hydroxy-piperidin-1-yl)-ethyl]-piperidin-4-yl}-amide dihydrochloride

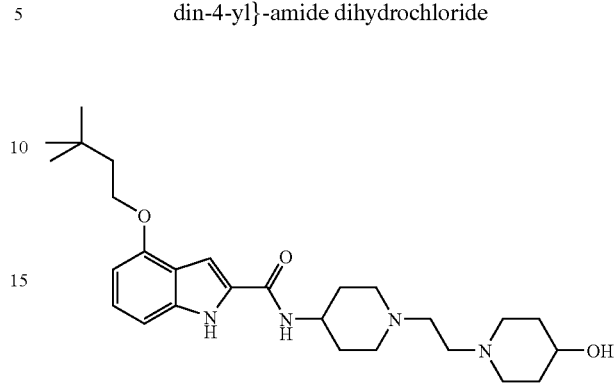

This compound is synthesized analogously to Example 1 from 4-(3,3-dimethyl-butoxy)-1H-indole-2-carboxylic acid (92) (preparation see below) and amine 21.

Yield: 60 mg (24%). MS (ESI): 471 [M+H]$^+$, 1H-NMR (DMSO-d$_6$): δ (ppm) 11.4 (s, 1H), 10.5 (br, 1H), 8.58 (d, 1H), 7.17 (s, 1H), 7.0-7.1 (m, 2H), 6.5 (d, 1H), 4.2 (m, 2H), 4.15 (m, 1H), 3.85 (m, 1H), 3.65 (m, 4H), 3.1-3.5 (m, 8H), 2.0-2.2 (m, 6H), 1.75-1.85 (m, 4H), 1.03 (s, 9H).

Synthesis of 4-(3,3-Dimethyl-butoxy)-1H-indole-2-carboxylic acid (92)

This compound is synthesized analogously to (85) from 3,3-dimethyl-butan-1-ol.

Yield: 1.1 g (100%). MS (ESI): 260 [M−H]$^-$, 1H-NMR (DMSO-d$_6$): δ (ppm) 12.8 (s, 1H), 11.65 (s, 1H), 7.12 (dd, 1H), 6.98 (s, 1H), 6.95 (d, 1H), 6.52 (d, 1H), 4.13 (t, 2H), 1.75 (t, 2H), 1.0 (s, 9H).

Example 35

4-(Furan-2-ylmethoxy)-1H-indole-2-carboxylic acid [1-(2-azepan-1-yl-ethyl)-piperidin-4-yl]amide

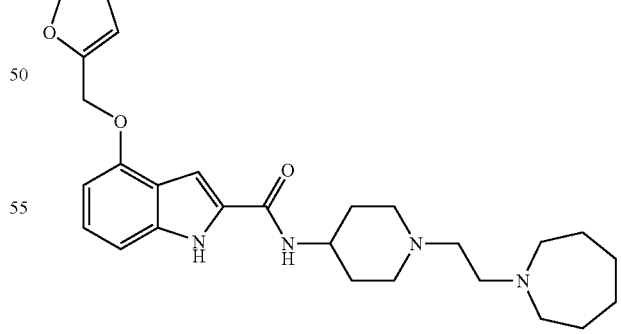

This compound is synthesized analogously to Example 1 from 4-(furan-2-ylmethoxy)-1H-indole-2-carboxylic acid 93 (preparation see below) and amine 5.

MS (ESI): 465.3 [M+H]$^+$, 1H-NMR (DMSO-d$_6$): δ (ppm) 11.48 (s, 1H), 8.13 (d, 1H), 7.71 (s, 1H), 7.23 (s, 1H), 7.06 (t, 1H), 7.0 (d, 1H), 6.63 (m, 2H), 6.48 (s, 1H), 5.13 (s, 2H), 3.72

(m, 1H), 2.86 (m, 2H), 2.5-2.6 (m, 6H), 2.36 (m, 2H), 2.0 (m, 2H), 1.74 (m, 2H) 1.45-1.6 (m, 10H).

Synthesis of 4-(furan-2-ylmethoxy)-1H-indole-2-carboxylic acid (93)

(1) Step A: 4-(furan-2-ylmethoxy)-1H-indole-2-carboxylic acid ethyl ester (94)

DEAD (2.1 ml, 13.65 mmol) is slowly added to a solution of 4-hydroxy-1H-indole-2-carboxylic acid ethyl ester 79 (2 g, 9.75 mmol), triphenylphosphine (3.58 g, 13.65 mmol) and furan-2-yl-methanol (1.18 ml, 12.26 mmol) in 10 ml of THF, so that the temperature always remained below 30° C. Stirring is continued for 2 hours and the solvent is then evaporated. The crude residue is purified by chromatography (cyclohexane:EtOAc/95:5).

Yield: 0.76 g (27%).

(2) Step B: 4-(furan-2-ylmethoxy)-1H-indole-2-carboxylic acid (93)

The 4-(furan-2-ylmethoxy)-1H-indole-2-carboxylic acid ethyl ester 94 obtained above is mixed with a 1M-solution of KOH in EtOH (13.3 ml, 13.3 mmol) and stirred for 24 hours. The solvent is then evaporated and the residue is partitioned between water and ether. The water layer is acidified with HCl and extracted twice with EtOAc. The combined organic layers are washed with brine, dried over anhydrous sodium sulfate, filtered and evaporated to give a white powder.

Yield: 0.329 mg (48%). 1H-NMR (DMSO-$d_6$): δ (ppm) 12.79 (br s, 1H), 11.73 (s, 1H), 7.69 (s, 1H), 7.14 (t, 1H), 7.02 (d, 1H), 6.98 (s, 1H), 6.68 (d, 1H), 6.61 (s, 1H), 6.47 (s, 1H), 5.16 (s, 2H).

Example 36

4-(Furan-3-ylmethoxy)-1H-indole-2-carboxylic acid [1-(2-azepan-1-yl-ethyl)-piperidin-4-yl]-amide

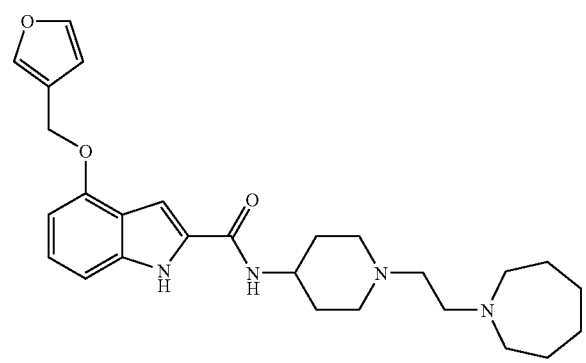

This compound is synthesized analogously to Example 1 from 4-(furan-3-ylmethoxy)-1H-indole-2-carboxylic acid 95 (preparation see below) and amine 5.

MS (ESI): 465.3 [M+H]$^+$, 1H-NMR (DMSO-$d_6$): δ (ppm) 11.46 (s, 1H), 8.14 (d, 1H), 7.82 (s, 1H), 7.68 (s, 1H), 7.22 (s, 1H), 7.06 (t, 1H), 6.99 (d, 1H), 6.62 (s, 1H), 6.6 (d, 1H), 5.03 (s, 2H), 3.72 (m, 1H), 2.87 (m, 2H), 2.52-2.62 (m, 6H), 2.37 (m, 2H), 2.0 (m, 2H), 1.75 (m, 2H) 1.45-1.62 (m, 10H).

Synthesis of 4-(furan-3-ylmethoxy)-1H-indole-2-carboxylic acid (95)

(1) Step A: 4-(furan-3-ylmethoxy)-1H-indole-2-carboxylic acid ethyl ester (96)

DEAD (2.1 ml, 13.65 mmol) is slowly added to a solution of 4-hydroxy-1H-indole-2-carboxylic acid ethyl ester 79 (2 g, 9.75 mmol), triphenylphosphine (3.58 g, 13.65 mmol) and furan-3-yl-methanol (1.18 ml, 12.26 mmol) in 10 ml of THF, so that the temperature always remained below 30° C. Stirring is continued for 2 hours and the solvent is then evaporated. The crude residue is triturated with ether and the white precipitate is filtered off. It contained mainly product. The mother liquor is purified by chromatography (cyclohexane:EtOAc/95:5) and combined with the first precipitate. Yield: 3 g (>100%).

(2) Step B: 4-(furan-3-ylmethoxy)-1H-indole-2-carboxylic acid (95)

The 4-(furan-3-ylmethoxy)-1H-indole-2-carboxylic acid ethyl ester 96 obtained above is mixed with a 1M-solution of KOH in EtOH (35 ml, 35 mmol) and stirred for 24 hours. The solvent is then evaporated and the residue is partitioned between water and ether. The water layer is acidified with HCl and extracted twice with EtOAc. The combined organic layers are washed with brine, dried over anhydrous sodium sulfate, filtered and evaporated to give a white powder.

Yield: 1.63 g (65%). MS (ESI): 258.0 [M+H]$^+$, 1H-NMR (DMSO-$d_6$): δ (ppm) 12.79 (brs, 1H), 11.71 (s, 1H), 7.81 (s, 1H), 7.67 (s, 1H), 7.13 (m, 1H), 7.01 (m, 2H), 6.62 (m, 2H), 5.07 (s, 2H).

Example 37

4-(Furan-3-ylmethoxy)-1H-indole-2-carboxylic acid {1-[2-(4-hydroxy-piperidin-1-yl)-ethyl]-piperidin-4-yl}-amide

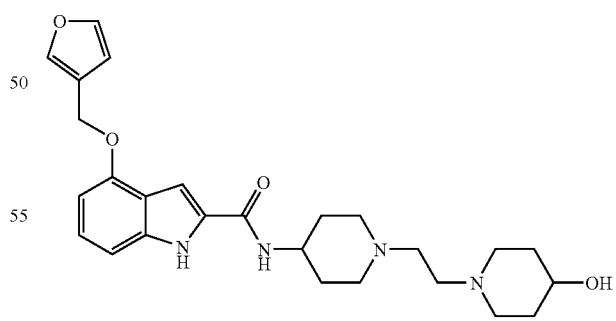

This compound is synthesized analogously to example 1 from 4-(furan-3-ylmethoxy)-1H-indole-2-carboxylic acid 95 (see example 36) and amine 21.

MS (ESI): 467 [M+H]$^+$, 1H-NMR (DMSO-$d_6$): δ (ppm) 11.48 (s, 1H), 8.13 (d, 1H), 7.81 (s, 1H), 7.68 (t, 1H), 7.22 (d, 1H), 7.06 (t, 1H), 6.98 (d, 1H), 6.62 (s, 1H), 6.6 (d, 1H), 5.03

(s, 2H), 4.48 (d, 1H), 3.73 (m, 1H), 3.4 (m, 1H), 2.86 (m, 2H), 2.7 (m, 2H), 2.36 (br. s, 4H) 2.0 (m, 4H), 1.72 (m, 4H), 1.52 (m, 2H), 1.35 (m, 2H).

Example 38

4-(Furan-3-ylmethoxy)-1H-indole-2-carboxylic acid {1-[2-((3S,4S)-4-hydroxy-3-methyl-piperidin-1-yl)-ethyl]-piperidin-4-yl}-amide

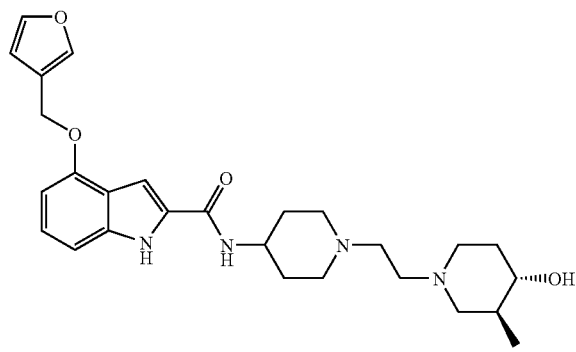

This compound is synthesized analogously to example 1 from 4-(furan-3-ylmethoxy)-1H-indole-2-carboxylic acid 95 (preparation see example 36) and amine 14.

MS (ESI): 481.2 [M+H]$^+$, 1H-NMR (CD$_3$OD): δ (ppm) 7.63 (s, 1H), 7.51 (s, 1H), 7.23 (s, 1H), 7.13 (t, 1H), 7.04 (d, 1H), 6.6 (d, 1H), 6.57 (s, 1H), 5.08 (s, 2H), 3.9 (m, 1H), 2.83-3.12 (m, 5H), 2.55 (m, 4H), 2.21 (m, 2H), 2.11 (m, 1H), 1.84-2.0 (m, 3H), 1.51-1.83 (m, 5H), 0.99 (d, 3H).

Example 39

4-(Furan-3-ylmethoxy)-1H-indole-2-carboxylic acid {1-[(S)-2-(4-hydroxy-piperidin-1-yl)-propyl]-piperidin-4-yl}-amide

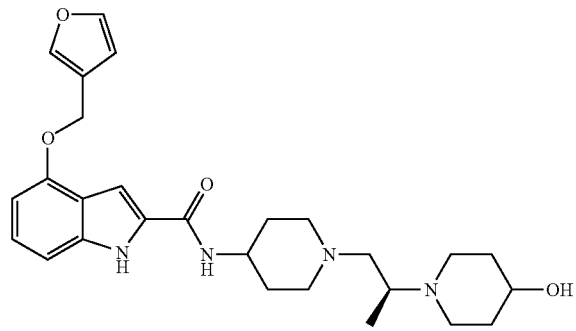

This compound is synthesized analogously to example 1 from 4-(furan-3-ylmethoxy)-1H-indole-2-carboxylic acid, 95 (see example 36) and amine 50.

MS (ESI): 481.2 [M+H]$^+$, 1H-NMR (DMSO-d$_6$): δ (ppm) 11.47 (s, 1H), 8.14 (d, 1H), 7.82 (s, 1H), 7.68 (s, 1H), 7.22 (s, 1H), 7.05 (t, 1H), 6.99 (d, 1H), 6.62 (s, 1H), 6.60 (d, 1H), 5.03 (d, 2H), 4.45 (d, 1H), 3.73 (m, 1H), 3.37 (m, 1H), 2.9 (m, 1H), 2.8 (m, 1H), 2.6-2.75 (m, 3H), 2.05-2.37 (m, 5H), 1.9 (m, 1H), 1.65-1.8 (m, 4H), 1.42-1.62 (m, 2H), 1.2-1.4 (m, 2H), 0.92 (d, 3H).

Example 40

4-(Furan-3-ylmethoxy)-1H-indole-2-carboxylic acid {1-[(S)-2-((3S,4S)-4-hydroxy-3-methyl-piperidin-1-yl)-propyl]-piperidin-4-yl}-amide

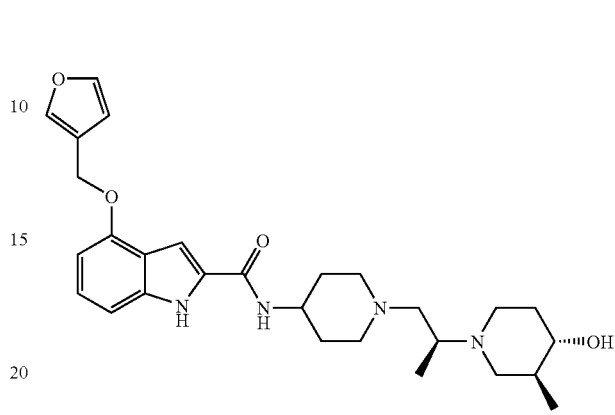

This compound is synthesized analogously to example 1 from 4-(furan-3-ylmethoxy)-1H-indole-2-carboxylic acid, 95 (see example 36) and amine 56.

MS (ESI): 495.2 [M+H]$^+$, 1H-NMR (DMSO-d$_6$): δ (ppm) 11.46 (s, 1H), 8.14 (d, 1H), 7.82 (s, 1H), 7.68 (s, 1H), 7.23 (s, 1H), 7.05 (t, 1H), 6.99 (d, 1H), 6.62 (s, 1H), 6.6 (d, 1H), 5.03 (s, 2H), 4.43 (d, 1H), 3.72 (m, 1H), 2.58-2.94 (m, 5H), 2.32 (m, 1H), 2.24 (m, 1H), 2.03-2.19 (m, 2H), 1.84-1.96 (m, 2H), 1.66-1.79 (m, 3H), 1.42-1.62 (m, 2H), 1.2-1.41 (m, 3H), 0.91 (d, 3H), 0.86 (d, 3H).

Example 41

4-Benzyloxy-1H-indole-2-carboxylic acid [1-(2-azepan-1-yl-ethyl)-piperidin-4-yl]-amide

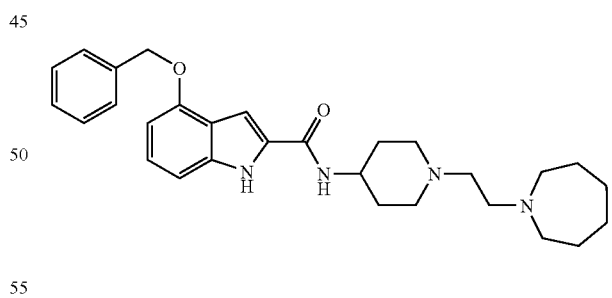

This compound is synthesized analogously to Example 1 from 4-Benzyloxy-1H-indole-2-carboxylic acid and amine 5.

MS (ESI): 475.3 [M+H]$^+$, 1H-NMR (DMSO-d$_6$): δ (ppm) 11.5 (s, 1H), 8.16 (d, 1H), 7.3-7.54 (m, 5H), 7.26 (d, 1H), 7.06 (t, 1H), 7.0 (d, 1H), 6.6 (d, 1H), 5.18 (s, 2H), 3.74 (m, 1H), 2.86 (m, 2H), 2.47-2.62 (m, 6H), 2.37 (m, 2H), 2.0 (m, 2H), 1.75 (m, 2H), 1.45-1.64 (m, 10H).

Example 42

4-(5-chloro-benzofuran-3-ylmethoxy)-1H-indole-2-carboxylic acid {1-[(1S,9aR)-1-(octahydro-quinolizin-1-yl)methyl]-piperidin-4-yl}-amide dihydrochloride

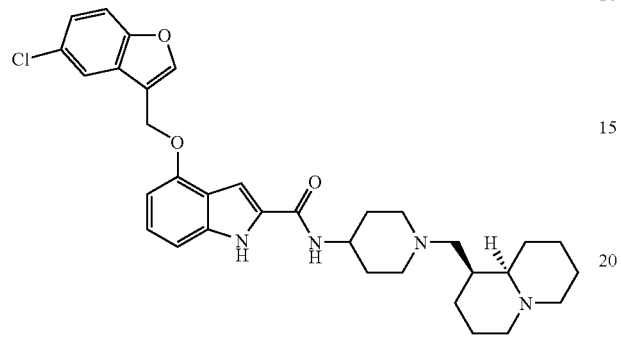

This compound is synthesized from 4-(5-chloro-benzofuran-3-ylmethoxy)-1H-indole-2-carboxylic acid (97) (preparation see below) and amine 61 analogously to the method described in example 1.

Yield: 200 mg (59%). MS (ESI): 575 [M+H]$^+$, 1H-NMR (DMSO-d$_6$): δ (ppm) 11.5 (s, 1H), 10.1-10.7 (m, 2H), 8.5 (t, 1H), 8.24 (s, 1H), 7.75 (d, 1H), 7.68 (d, 1H), 7.37 (dd, 1H), 7.25 (m, 1H), 7.1 (m, 1H), 7.05 (d, 1H), 6.7 (d, 1H), 5.35 (s, 2H), 4.0 (m, 1H), 2.8-3.6 (m, 14H), 1.3-2.1 (m, 12H).

Reaction Scheme 13:

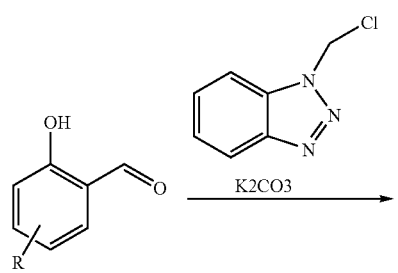

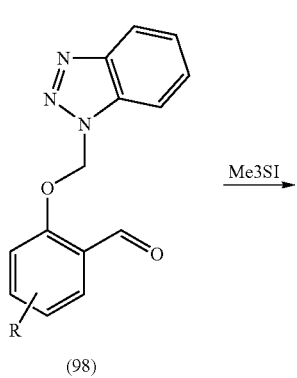

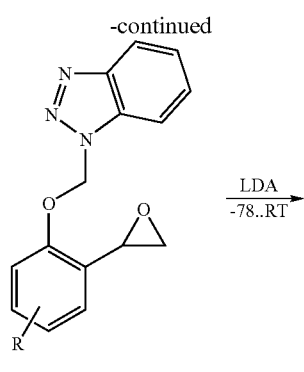

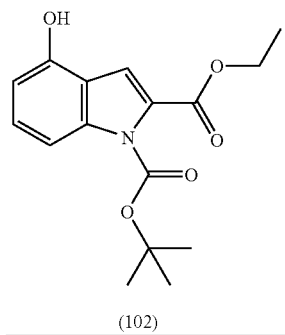

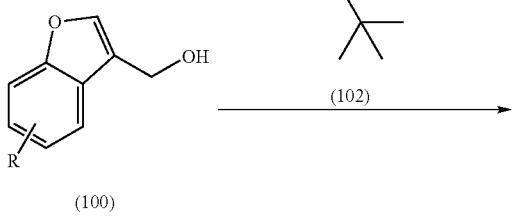

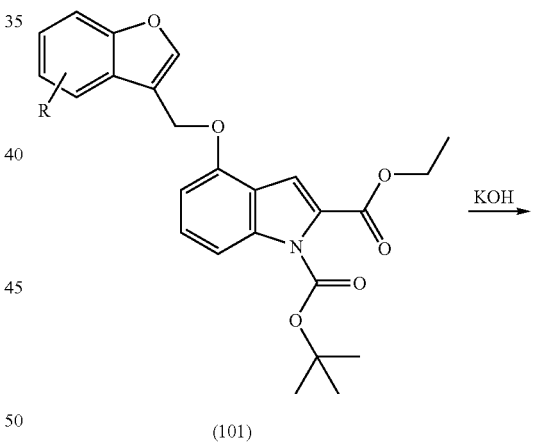

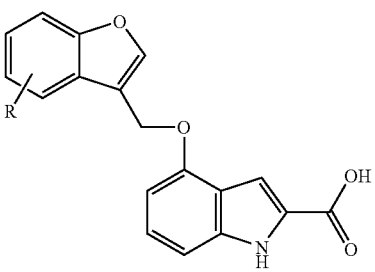

Synthesis of 4-Hydroxy-indole-1,2-dicarboxylic acid 1-tert-butyl ester 2-ethyl ester (102)

(1) Step A: 4-Benzyloxy-indole-1,2-dicarboxylic acid 1-tert-butyl ester 2-ethyl ester (103)

4-Benzyloxy-1H-indole-2-carboxylic acid ethyl ester (50 g, 169.3 mmol) is dissolved in 500 ml of ethyl acetate and DMAP (141 mg, 3.4 mmol) is added. Then the mixture is cooled to 0° C. and BOC$_2$O (36.9 g, 169.3 mmol), dissolved in 20 ml of ethyl acetate, is added dropwise. After completion of addition the reaction mixture is allowed to stir over night at room temperature. The mixture is washed with 1M tartaric acid and brine. The organic layers are dried over sodium sulfate and evaporated Yield: 72 g of a colorless oil, which is used in the next step without further purification. MS (ESI): 396 [M+H]$^+$, 1H-NMR (DMSO-d$_6$): δ (ppm) 7.51 (m, 1H), 7.47 (m, 2H), 7.40 (m, 1H), 7.38 (m, 2H), 7.31 (m, 1H), 7.21 (s, 1H), 6.92 (d, 1H), 5.26 (s, 2H), 4.28 (q, 2H), 1.56 (s, 9H), 1.31 (t, 3H).

(2) Step B: 4-Hydroxy-indole-1,2-dicarboxylic acid 1-tert-butyl ester 2-ethyl ester (102)

103 (46.2 g, 116.8 mmol) is dissolved in ethanol (300 ml) and after addition of ammonium formiate (8.3 g, 128.5 mmol) and 10% Pd—C (5 g) the mixture is stirred at room temperature for 1 h. Then the mixture is filtered off. Evaporation under reduced pressure gave 6.89 g of a white solid, which is further purified by recrystallisation from ether/hexanes.

Yield: 27.75 g (78%). MS (ESI): 304 [M–H]$^-$, 1H-NMR (DMSO-d$_6$): δ (ppm) 10.1 (s, 1H), 7.38 (d, 1H), 7.25 (s, 1H), 7.23 (dd, 1H), 6.65 (d, 1H), 4.3 (q, 2H), 1.55 (s, 9H), 1.3 (t, 3H).

Synthesis of 4-(5-chloro-benzofuran-3-ylmethoxy)-1H-indole-2-carboxylic acid (97)

(1) Step A: 2-(Benzotriazol-1-ylmethoxy)-5-chloro-benzaldehyde (98)

5-Chloro-2-hydroxy-benzaldehyde (8.45 g, 54 mmol) is dissolved in DMF (100 ml) and after addition of 1-(chlormethyl)-1H-benzotriazole (9.96 g, 59.4 mmol) and K$_2$CO$_3$ (9.7 g, 70.2 mmol) the mixture is stirred at 45° C. for 1 h (TLC control). Then the mixture is evaporated under high vacuum. The residue is diluted with ethyl acetate, washed with brine and dried over Na$_2$SO$_4$. Evaporation gave 3.9 g of a colorless solid. The product is used in the next step without further purification.

Yield: 17 g (100%) of a white solid. MS (ESI): 288 [M+H]$^+$, 1H-NMR (DMSO-d$_6$): δ (ppm) 10.01 (s, 1H), 8.08 (d, 1H), 7.97 (d, 1H), 7.78 (dd, 1H), 7.68 (d, 1H), 7.62 (dd, 1H), 7.55 (d, 1H), 7.43 (dd, 1H), 6.95 (s, 2H).

(2) Step B: 1-(4-Chloro-2-oxiranyl-phenoxymethyl)-1H-benzotriazole (99)

98 (15.5 g, 54 mmol) is dissolved in 150 ml of DCM and 150 ml of 40% aqueous sodium hydroxide solution. After addition of trimethylsulfonium iodide (14.3 g, 70.2 mmol) and tetrabutylammoniumiodide (1.4 g, 3.8 mmol), the mixture is refluxed for 18 h. The reaction mixture is diluted with DCM, washed with water and the organic layers are dried over Na$_2$SO$_4$. Evaporation gave 18.7 g of a yellow oil, which is further purified by flash-chromatography (silicagel, ethyl acetate/hexanes 3:7)

Yield: 11.7 g (72%) of a colorless oil. MS (ESI): 302 [M+H]$^+$, 1H-NMR (DMSO-d$_6$): δ (ppm) 8.08 (d, 1H), 7.92 (d, 1H), 7.62 (dd, 1H), 7.5 (dd, 1H), 7.45 (dd, 1H), 7.4 (dd, 1H), 6.92 (d, 1H), 6.83 (dd, 1H), 3.8 (m, 1H), 2.8 (dd, 2H), 2.48 (dd, 1H).

(3) Step C: (5-Chloro-benzofuran-3-yl)-methanol (100)

99 (25.7 g, 85.1 mmol) is dissolved in 300 ml of tetrahydrofurane and cooled to –78° C. A 2M solution of LDA in THF (93.7 ml, 187.4 mmol) is added dropwise within 45 min. The reaction mixture is allow to warmup to room temperature within 17 h. Then the reaction mixture is quenched with saturated aqueous ammonium chloride solution and evaporated under reduced pressure. The residue is diluted with ethyl acetate, washed with water and brine and dried over sodium sulfate. Evaporation gave 17.2 g of an brown resin which is further purified by flash-chromatography (silicagel, ethyl acetate/hexanes 2:8).

Yield: 10.4 g mg of a white solid (67%). MS (ESI): 181 [M–H]$^-$, 1H-NMR (DMSO-d$_6$): δ (ppm) 7.91 (d, 1H), 7.72 (d, 1H), 7.56 (d, 1H), 7.32 (dd, 1H), 5.18 (t, 1H), 4.58 (d, 2H).

(4) Step D: 4-(5-Chloro-benzofuran-3-ylmethoxy)-indole-1,2-dicarboxylic acid 1-tert-butyl ester 2-ethyl ester (101)

100 (4 g, 21.9 mmol), 102 (6.7 g, 21.9 mmol), triphenylphosphine (17.3 g, 65.8 mmol) and 40% diethyl azadicarboxylate solution (31.8 ml, 65.8 mmol) are dissolved in THF and cooled to 0° C. Then a solution of N-ethyldiisopropylamine (11.2 ml, 65.8 mmol) in THF is added dropwise. After the addition is completed, the mixture is stirred at room temperature for 2 h. Then the mixture is evaporated under reduced pressure. The residue is diluted with ethyl acetate, washed with saturated NaHCO3-solution and dried over Na2SO4. The crude product is purified by Flash-chromatography (ethyl acetate/hexanes (3:7), silicagel).

Yield: 7.7 g (75%) of a slightly colored oil. MS (ESI): 469 [M]$^+$, 1H-NMR (DMSO-d$_6$): δ (ppm) 8.27 (s, 1H), 7.79 (d, 1H), 7.63 (d, 1H), 7.53 (d, 1H), 7.40 (d, 1H), 7.36 (dd, 1H), 7.21 (s, 1H), 7.04 (d, 1H), 5.42 (s, 2H), 4.29 (q, 2H), 1.55 (s, 9H), 1.29 (t, 3H).

(5) Step E: 4-(5-Chloro-benzofuran-3-ylmethoxy)-1H-indole-2-carboxylic acid (97)

101 (7.7 g, 16.3 mmol) is dissolved in 15 ml of a 1:1:1 mixture of THF/water/ethanol and after addition of KOH pellets (5.4 g, 81.9 mmol) the mixture is stirred for 2 h at 85° C. Then the organic phase is evaporated under reduced pressure. The residue is dissolved in ethyl acetate, acidified with 2M HCl and filtered off. The crude product is purified by crystallisation from ethyl acetate.

Yield: 4.4 g (79%) of white crystals. MS (ESI): 340 [M–H]$^-$, 1H-NMR (DMSO-d$_6$): δ (ppm) 12.8 (s, 1H), 11.7 (s, 1H), 8.25 (s, 1H), 7.79 (d, 1H), 7.62 (dd, 1H), 7.35 (dd, 1H), 7.15 (dd, 1H), 7.0-7.05 (m, 2H), 6.71 (d, 1H), 5.39 (s, 2H).

Example 43

4-(5-Chloro-benzofuran-3-ylmethoxy)-1H-indole-2-carboxylic acid [1-(2-azepan-1-yl-ethyl)-piperidin-4-yl]-amide

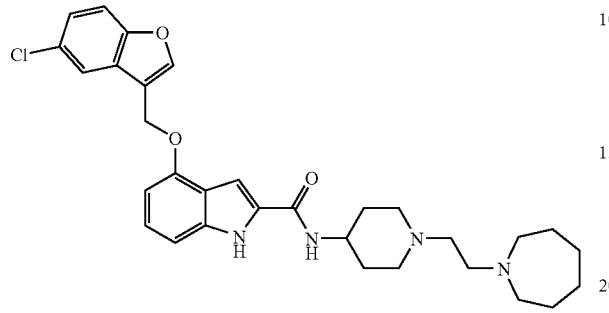

This compound is synthesized from 4-(5-chloro-benzofuran-3-ylmethoxy)-1H-indole-2-carboxylic acid (97, see example 42) and amine 5 analogously to the method described in example 1.

Yield: 52 mg (16%). MS (ESI): 549 [M+H]$^+$, 1H-NMR (DMSO-d$_6$): δ (ppm) 10.98 (br s, 1H), 8.12 (s, 1H), 7.68 (d, 1H), 7.53 (d, 1H), 7.0-7.2 (m, 5H), 6.65 (d, 1H), 5.43 (s, 2H), 3.75 (m, 1H), 2.35-2.65 (m, 12H), 2.1 (m, 2H), 1.8 (m, 2H), 1.5-1.6 (m, 8H).

Example 44

4-(5-Chloro-benzofuran-3-ylmethoxy)-1H-indole-2-carboxylic acid {1-[2-(4-hydroxy-piperidin-1-yl)-ethyl]-piperidin-4-yl}-amide

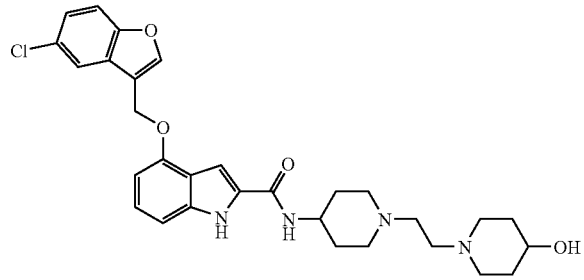

This compound is synthesized from 4-(5-chloro-benzofuran-3-ylmethoxy)-1H-indole-2-carboxylic acid (97, see example 42) and amine 21 analogously to the method described in example 1.

Yield: 50 mg (24%). MS (ESI): 551 [M+H]$^+$, 1H-NMR (DMSO-d$_6$): δ (ppm) 11.45 (s, 1H), 8.22 (s, 1H), 8.12 (d, 1H), 7.78 (s, 1H), 7.67 (d, 1H), 7.37 (d, 1H), 7.18 (s, 1H), 7.08 (dd, 1H), 7.02 (d, 1H), 6.67 (m, 1H), 5.33 (s, 2H), 4.49 (b, 1H), 3.7 (m, 1H), 3.4 (m, 1H), 2.85 (m, 2H), 2.7 (m, 2H), 2.5 (m, 2H), 2.35 (m, 2H), 1.95 (m, 4H), 1.25-1.8 (m, 8H).

Example 45

4-(5-Chloro-benzofuran-3-ylmethoxy)-1H-indole-2-carboxylic acid {1-[2-((3S,4S)-4-hydroxy-3-methyl-piperidin-1-yl)-ethyl]-piperidin-4-yl}-amide

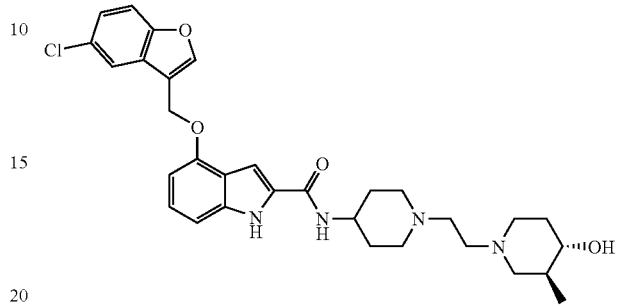

This compound is synthesized from 4-(5-chloro-benzofuran-3-ylmethoxy)-1H-indole-2-carboxylic acid (97, see example 42) and amine 14 analogously to the method described in example 1.

Yield: 85 mg (45%). MS (ESI): 565 [M+H]$^+$, 1H-NMR (120° C., DMSO-d$_6$): δ (ppm) 11.29 (br s, 1H), 8.2 (d, 1H), 8.1 (s, 1H), 7.74 (s, 1H), 7.57 (d, 1H), 7.34 (d, 1H), 7.22 (s, 1H), 7.09 (m, 1H), 6.72 (d, 1H), 5.39 (s, 2H), 2.6-4.1 (m, 15H), 1.75-2.2 (m, 8H), 1.00 (d, 3H).

Example 46

4-(5-Chloro-benzofuran-3-ylmethoxy)-1H-indole-2-carboxylic acid {1-[(S)-2-(4-hydroxy-piperidin-1-yl)-propyl]-piperidin-4-yl}-amide dihydrochloride

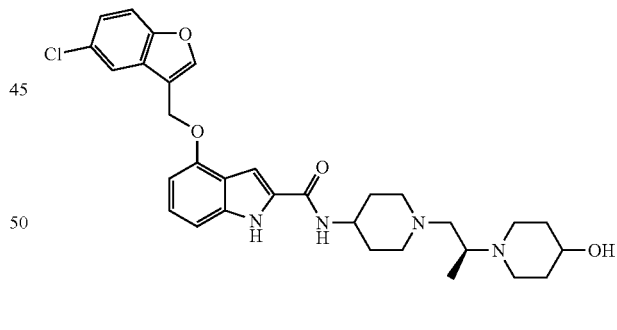

This compound is synthesized from 4-(5-chloro-benzofuran-3-ylmethoxy)-1H-indole-2-carboxylic acid (97, see example 42) and amine 50 analogously to the method described in example 1.

Yield: 125 mg (71%). MS (ESI): 565 [M+H]$^+$, 1H-NMR (DMSO-d$_6$): δ (ppm) 11.5 (s, 1H), 10.3-10.7 (br, 2H), 8.52 (d, 1H), 8.24 (s, 1H), 7.75 (d, 1H), 7.68 (d, 1H), 7.35 (dd, 1H), 7.23 (s, 1H), 7.1 (dd, 1H), 7.03 (d, 1H), 6.7 (d, 1H), 5.35 (s, 2H), 5.1 (br, 1H), 4.05 (m, 1H), 2.7-3.7 (m, 12H), 1.7-2.1 (m, 8H), 1.35/1.3 (d, 3H) (rotamers).

Example 47

4-(5-Chloro-benzofuran-3-ylmethoxy)-1H-indole-2-carboxylic acid {1-[(S)-2-((3S,4S)-4-hydroxy-3-methyl-piperidin-1-yl)-propyl]-piperidin-4-yl}-amide dihydrochloride

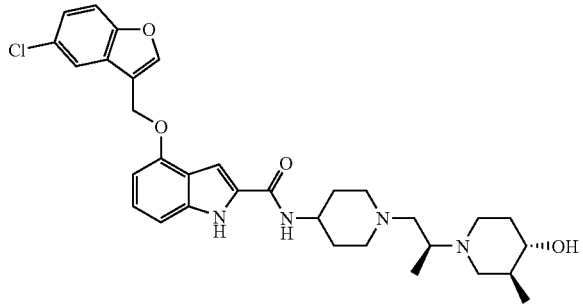

This compound is synthesized from 4-(5-chloro-benzofuran-3-ylmethoxy)-1H-indole-2-carboxylic acid (97, see example 42) and amine 56 analogously to the method described in example 1.

Yield: 123 mg (64%). MS (ESI): 579 [M+H]$^+$, 1H-NMR (DMSO-d$_6$): δ (ppm) 11.5 (s, 1H), 10.4-10.6 (br, 2H), 8.52 (d, 1H), 8.26 (s, 1H), 7.77 (d, 1H), 7.68 (d, 1H), 7.38 (dd, 1H), 7.23 (s, 1H), 7.12 (dd, 1H), 7.03 (d, 1H), 6.7 (d, 1H), 5.35 (s, 2H), 5.1 (br, 1H), 4.05 (m, 1H), 2.8-3.9 (m, 13H), 1.9-2.1 (m, 6H), 1.31 (d, 3H), 0.94 (d, 3H).

Example 48

4-(4-Fluoro-benzofuran-3-ylmethoxy)-1H-indole-2-carboxylic acid {1-[(1S,9aR)-1-(octahydro-quinolizin-1-yl)methyl]-piperidin-4-yl}-amide dihydrochloride

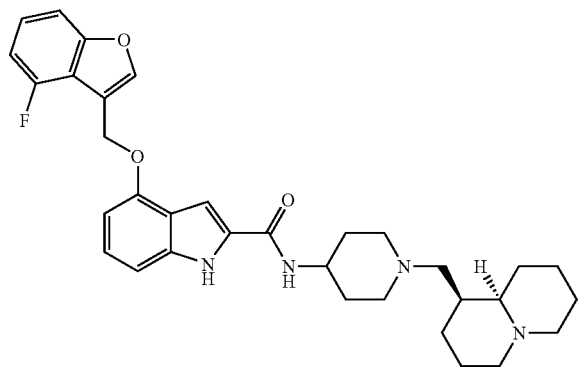

This compound is synthesized from 4-(4-fluoro-benzofuran-3-ylmethoxy)-1H-indole-2-carboxylic acid (104) (preparation see below) and amine 61 analogously to the method described in example 1.

Yield: 49 mg (22.5%). MS (ESI): 559.3 [M+H]$^+$, 1H-NMR (DMSO-d$_6$): δ (ppm) 11.5 (s, 1H), 10.5 (br d, 1H), 10.2 (br d, 1H), 8.45 (m, 1H), 8.25 (s, 1H), 7.5 (d, 1H), 7.38 (m, 1H), 7.25 (m, 1H), 7.1 (m, 2H), 7.03 (d, 1H), 6.7 (d, 1H), 5.3 (s, 2H), 4.0 (m, 1H), 2.8-3.6 (m, 14H), 1.3-2.1 (m, 12H).

Synthesis of 4-(4-fluoro-benzofuran-3-ylmethoxy)-1H-indole-2-carboxylic acid (104)

This compound is synthesized from 2-fluoro-6-hydroxy-benzaldehyde analogously to the method described for 97 (see example 42).

Yield: 220 mg (49%) of white crystals. MS (ESI): 324.3 [M−H]$^−$.

Example 49

4-(4-Fluoro-benzofuran-3-ylmethoxy)-1H-indole-2-carboxylic acid {1-[2-(4-hydroxy-piperidin-1-yl)-ethyl]-piperidin-4-yl}-amide dihydrochloride

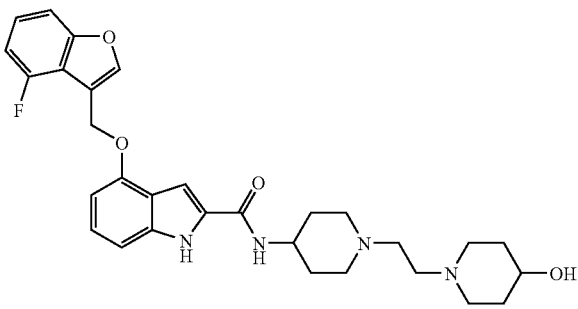

This compound is synthesized from 4-(4-fluoro-benzofuran-3-ylmethoxy)-1H-indole-2-carboxylic acid (104, see example 48) and amine 21 analogously to the method described in example 1.

Yield: 100 mg (61%). MS (ESI): 535 [M+H]$^+$, 1H-NMR (DMSO-d$_6$): δ (ppm) 11.45 (s, 1H), 10.5 (br, 1H), 10.35 (br, 1H), 8.48 (d, 1H), 8.23 (m, 2H), 7.5 (d, 1H), 7.35 (m, 1H), 7.2 (s, 1H), 7.1 (m, 1H), 7.03 (d, 1H), 6.7 (d, 1H), 5.3 (s, 2H), 5.05 (br, 1H), 4.05 (m, 1H), 2.9-3.75 (m, 13H), 1.65-2.1 (m, 8H).

Example 50

4-(Benzofuran-3-ylmethoxy)-1H-indole-2-carboxylic acid {1-[(1S,9aR)-1-(octahydro-quinolizin-1-yl)methyl]-piperidin-4-yl}-amide dihydrochloride

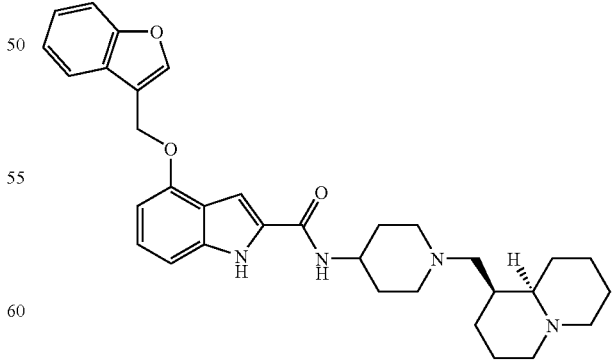

This compound is synthesized from 4-(benzofuran-3-ylmethoxy)-1H-indole-2-carboxylic acid (105) (preparation see below) and amine 61 analogously to the method described in example 1.

Yield: 68 mg (34%). MS (ESI): 541 [M+H]+, 1H-NMR (DMSO-d6): δ (ppm) 11.56 (s, 1H), 10.5 (br d, 1H), 10.2 (br d, 1H), 8.5 (t, 1H), 8.18 (s, 1H), 7.72 (d, 1H), 7.6 (d, 1H), 7.25-7.35 (m, 3H), 7.12 (d, 1H), 7.03 (d, 1H), 6.75 (d, 1H), 5.57 (s, 2H), 4.01 (m, 1H), 2.8-3.6 (m, 14H), 1.3-2.1 (m, 12H).

Synthesis of 4-(benzofuran-3-ylmethoxy)-1H-indole-2-carboxylic acid (105)

This compound is synthesized from 2-hydroxy-benzaldehyde analogously to the method described for 97 (see example 42).

MS (ESI): 306 [M–H]−, 1H-NMR (DMSO-d6): δ (ppm) 12.8 (br s, 1H), 11.7 (s, 1H), 8.15 (s, 1H), 7.73 (d, 1H), 7.58 (d, 1H), 7.33 (dd, 1H), 7.29 (dd, 1H), 7.15 (dd, 1H), 7.05 (s, 1H), 7.02 (d, 1H), 6.73 (d, 1H), 5.38 (s, 2H).

Example 51

4-(Benzofuran-3-ylmethoxy)-1H-indole-2-carboxylic acid {1-[2-(4-hydroxy-piperidin-1-yl)-ethyl]-piperidin-4-yl}-amide

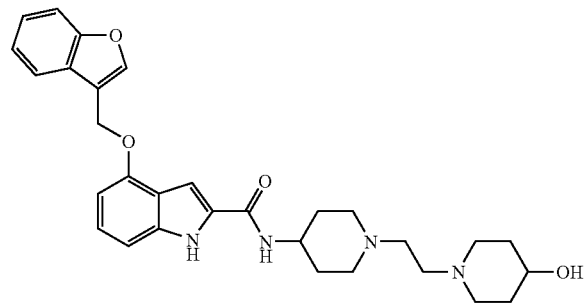

This compound is synthesized analogously to example 1 from 4-(benzofuran-3-ylmethoxy)-1H-indole-2-carboxylic acid, 105 (see example 50) and amine 21.

MS (ESI): 517.2 [M+H]+, 1H-NMR (DMSO-d6): δ (ppm) 11.48 (s, 1H), 8.17 (s, 1H), 8.1 (d, 1H), 7.72 (d, 1H), 7.61 (d, 1H), 7.35 (t, 1H), 7.28 (d, 1H), 7.18 (s, 1H), 7.09 (t, 1H), 7.01 (d, 1H), 6.71 (d, 1H), 5.35 (s, 2H), 4.48 (d, 1H), 3.71 (m, 1H), 3.39 (m, 1H), 2.84 (m, 2H), 2.69 (m, 2H), 2.35 (m, 4H) 1.98 (m, 4H), 1.69 (m, 4H), 1.48 (m, 2H), 1.34 (m, 2H).

Example 52

4-(Benzofuran-3-ylmethoxy)-1H-indole-2-carboxylic acid {1-[2-((3S,4S)-4-hydroxy-3-methyl-piperidin-1-yl)-ethyl]-piperidin-4-yl}-amide

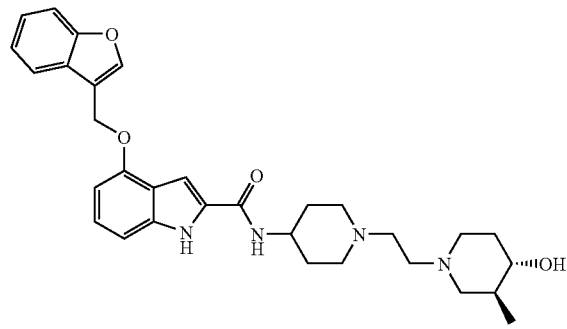

This compound is synthesized analogously to example 1 from 4-(benzofuran-3-ylmethoxy)-1H-indole-2-carboxylic acid (105, see example 50) and amine 14.

MS (ESI): 531.2 [M+H]+, 1H-NMR (DMSO-d6): δ (ppm) 11.48 (s, 1H), 8.17 (s, 1H), 8.11 (d, 1H), 7.72 (d, 1H), 7.61 (d, 1H), 7.35 (t, 1H), 7.29 (t, 1H), 7.19 (s, 1H), 7.09 (t, 1H), 7.01 (d, 1H), 6.71 (d, 1H), 5.35 (d, 2H), 4.47 (d, 1H), 3.7 (m, 1H), 3.3 (m, 1H), 2.65-2.91 (m, 5H), 2.34 (m, 4H), 1.83-2.04 (m, 3H), 1.65-1.77 (m, 3H), 1.27-1.63 (m, 5H), 0.85 (d, 3H).

Example 53

4-(Benzofuran-3-ylmethoxy)-1H-indole-2-carboxylic acid {1-[(S)-2-(4-hydroxy-piperidin-1-yl)-propyl]-piperidin-4-yl}-amide

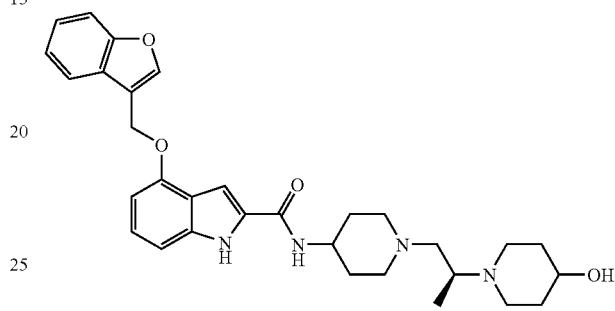

This compound is synthesized analogously to example 1 from 4-(benzofuran-3-ylmethoxy)-1H-indole-2-carboxylic acid, 105 (see example 50) and amine 50.

MS (ESI): 531.3 [M+H]+, 1H-NMR (DMSO-d6): δ (ppm) 11.48 (s, 1H), 8.17 (s, 1H), 8.11 (d, 1H), 7.72 (d, 1H), 7.61 (d, 1H), 7.35 (t, 1H), 7.29 (t, 1H), 7.19 (d, 1H), 7.09 (t, 1H), 7.01 (d, 1H), 6.71 (d, 1H), 5.35 (s, 2H), 4.44 (d, 1H), 3.7 (br m, 1H), 3.35 (m, 1H), 2.97 (m, 1H), 2.6-2.9 (m, 4H), 2.0-2.35 (m, 4H), 1.89 (m, 1H), 1.63-1.77 (m, 3H), 1.4-1.6 (m, 3H), 1.2-1.38 (m, 3H), 0.90 (d, 3H).

Example 54

4-(Benzofuran-3-ylmethoxy)-1H-indole-2-carboxylic acid {1-[(S)-2-((3S,4S)-4-hydroxy-3-methyl-piperidin-1-yl)-propyl]-piperidin-4-yl}-amide

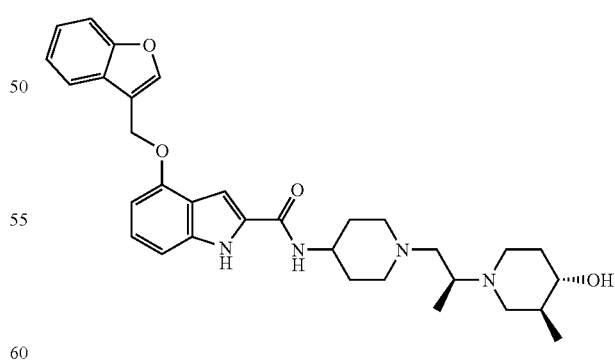

This compound is synthesized analogously to example 1 from 4-(benzofuran-3-ylmethoxy)-1H-indole-2-carboxylic acid, 105 (see example 50) and amine 56.

MS (ESI): 545.2 [M+H]+, 1H-NMR (DMSO-d6): δ (ppm) 11.48 (s, 1H), 8.17 (s, 1H), 8.11 (d, 1H), 7.72 (d, 1H), 7.61 (d, 1H), 7.35 (t, 1H), 7.29 (t, 1H), 7.19 (s, 1H), 7.09 (t, 1H), 7.01

(d, 1H), 6.71 (d, 1H), 5.35 (s, 2H), 4.43 (d, 1H), 3.71 (m, 1H), 2.59-2.92 (m, 6H), 2.31 (m, 1H), 2.22 (m, 1H), 2.01-2.17 (m, 2H), 1.88 (m, 2H), 1.66-1.76 (m, 3H), 1.2-1.58 (m, 4H), 0.89 (d, 3H), 0.86 (d, 3H).

Example 55

4-(6-Fluoro-benzofuran-3-ylmethoxy)-1H-indole-2-carboxylic acid {1-[(1S,9aR)-1-(octahydro-quinolizin-1-yl)methyl]-piperidin-4-yl}-amide dihydrochloride

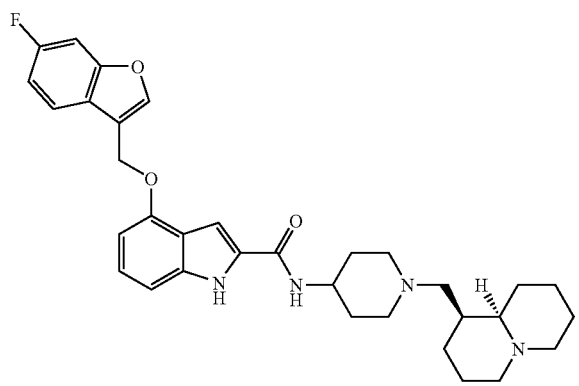

This compound is synthesized from 4-(6-fluoro-benzofuran-3-ylmethoxy)-1H-indole-2-carboxylic acid (106) (preparation see below) and amine 61 analogously to the method described in example 1.

Yield: 80 mg (41.2%). MS (ESI): 559 [M+H]$^+$, 1H-NMR (DMSO-d$_6$): δ (ppm) 11.55 (s, 1H), 10.63 (br d, 1H), 10.35 (br d, 1H), 8.5 (m, 1H), 8.2 (s, 1H), 7.72 (dd, 1H), 7.58 (dd, 1H), 7.25 (m, 1H), 7.2 (m, 1H), 7.1 (d, 1H), 7.03 (d, 1H), 6.7 (d, 1H), 5.35 (s, 2H), 4.0 (m, 1H), 2.6-3.6 (m, 14H), 1.3-2.1 (m, 12H).

Reaction Scheme 14:

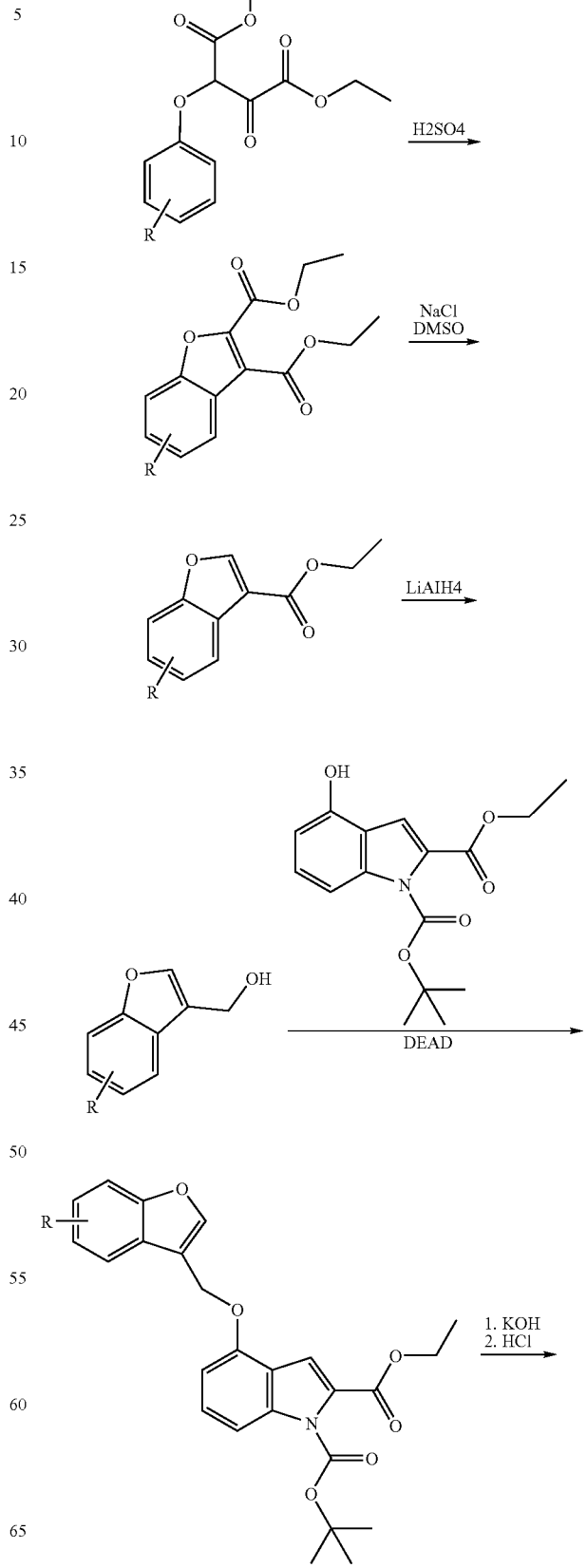

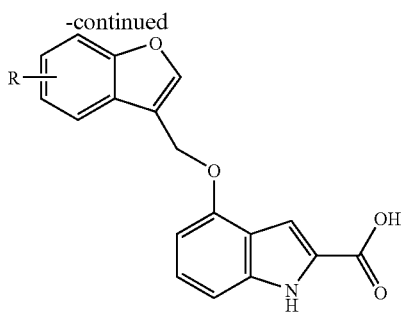

Synthesis of 4-(6-fluoro-benzofuran-3-ylmethoxy)-1H-indole-2-carboxylic acid (106)

(1) Step A: (3-Fluoro-phenoxy)-acetic acid ethyl ester (107)

3-Fluoro-phenol (100 g, 892 mmol) is dissolved in acetone (250 ml) and after addition of chloro-acetic acid ethyl ester (114 ml, 1.07 mol) and K2CO3 (249 g, 1.78 mol) the mixture is refluxed for 24 h. After cooling down to 0° C., the mixture is filtrated and the filtrate is evaporated under reduced pressure. Yield: 198 g (100%) of a red oil.

(2) Step B: 2-(3-Fluoro-phenoxy)-3-oxo-succinic acid diethyl ester (108)

60% NaH in mineral oil (19.5 g, 488.4 mmol) is covered with 600 ml of dry diethyl ether. Ethanol (28.1 ml, 444 mmol) is added dropwise within 25 min. Then oxalic acid diethyl ester (66 ml, 488 mmol) is added dropwise within 20 min. After 10 min stirring at room temperature, the mixture is heated to reflux. A solution of 107 (88 g, 444 mmol) in 80 ml of dry diethyl ether is added dropwise within 30 min and the mixture is allowed to reflux for 1 hour. After cooling down to room temperature, the reaction mixture is poured on 2M HCl (400 ml)/ice (400 g) and extracted with diethyl ether. The organic layers are dried over sodium sulfate, filtrated and evaporated. The crude product is purified by filtration over silica gel (ethyl acetate/hexane 1:1). Evaporation gave 140 g of an red oil. The mineral oil could be removed using a separatory funnel. Yield: 132 g (100%).

(3) Step C: 6-Fluoro-benzofuran-2,3-dicarboxylic acid diethyl ester (109)

108 (66 g, 221.3 mmol) is dissolved in 245 ml of cooled (−15° C.) conc. sulfuric acid and stirred for 3 h whereas the reaction mixture slowly warmed up to room temperature. Then the mixture is poured onto 1 kg of ice and extracted with diethyl ether. The organic layers are washed with brine, dried over sodium sulfate, filtrated and evaporated. The crude product is used in the next step without further purification.
Yield: 19.7 g (32%) of a yellow oil. MS (ESI): 281 [M+H]$^+$, 1H-NMR (DMSO-d$_6$): δ (ppm) 7.88 (dd, 1H), 7.82 (dd, 1H), 7.35 (ddd, 1H), 4.38 (m, 4H), 1.33 (t, 3H), 1.32 (t, 6H). The cyclisation gave exclusively the 6-substituted benzofurane.

(4) Step D: 6-Fluoro-benzofuran-3-carboxylic acid ethyl ester (110)

109 (40 g, 142.7 mmol) is dissolved in 300 ml of a DMSO and after addition of sodium chloride (16.7 g, 285.4 mmol) and water (5.1 ml) the mixture is stirred for 4 h at 160° C. (temperature of reaction mixture). Then the mixture is allowed to cool down and evaporated at high vacuum. The residue is dissolved in ethyl acetate, washed with water and brine and dried over sodium sulfate. Evaporation gave 14.8 g of an red oil, which is further purified by filtration over silica gel (ethyl acetate/hexanes 2:8).
Yield: 7.8 g (26%) of a yellow solid. MS (ESI): 208 [M]$^+$, 1H-NMR (DMSO-d$_6$): δ (ppm) 8.77 (s, 1H), 7.92 (dd, 1H), 7.68 (dd, 1H), 7.29 (ddd, 1H), 4.35 (q, 2H), 1.32 (t, 3H).

(5) Step E: (6-Fluoro-benzofuran-3-yl)-methanol (111)

1M LiAlH4-solution in THF (75.9 ml, 75.9 mmol) is diluted with 100 ml of THF and cooled to 0° C. 110 (7.9 g, 37.9 mmol) is dissolved in 100 ml of THF and added dropwise within 30 min. After completed addition the mixture is allowed to stir at rt for 2 h. Then the reaction mixture is cooled to −15° C. and 10 ml of a 1M NaOH solution is added very slowly. The mixture is filtrated over celite and evaporation under reduced pressure gave 5.3 g of a yellow oil.

(6) Step F: 4-(6-Fluoro-benzofuran-3-ylmethoxy)-indole-1,2-dicarboxylic acid 1-tert-butyl ester 2-ethyl ester (112)

111 (2 g, 12 mmol), 102 (3.7 g, 12 mmol), triphenylphosphine (9.4 g, 36.1 mmol) and DIPEA (6.2 ml, 36.1 mmol) are dissolved in 50 ml of THF and cooled to 0° C. Then 40% ethyl azodicarboxylate solution in THF (15.7 ml, 36.1 mmol) is added dropwise. After completed addition the mixture is stirred for 16 h (TLC control) at rt. Then the mixture is evaporated under reduced pressure. The residue is diluted with ethyl acetate, washed sat. NaHCO3- and NaCl-solution, and dried over Na2SO4. The crude product is purified by Flash-chromatography (ethyl acetate/hexanes (1:9), silica-gel).
Yield: 1.2 g (22%) of a red oil. MS (ESI): 454 [M+H]$^+$, 1H-NMR (DMSO-d$_6$): δ (ppm) 8.22 (s, 1H), 7.73 (dd, 1H), 7.58 (dd, 1H), 7.53 (d, 1H), 7.38-7.40 (m, 2H), 7.15-7.7.25 (m, 1H), 7.05 (d, 1H), 5.43 (s, 2H), 4.05 (q, 2H), 1.55 (s, 9H), 1.29 (t, 3H).

(7) Step G: 4-(6-Fluoro-benzofuran-3-ylmethoxy)-1H-indole-2-carboxylic acid (106)

112 (1.2 g, 2.6 mmol) is dissolved in 30 ml of a 1:1:1 mixture of THF, ethanol and water. And after addition of KOH pellets (742 mg, 13.2 mmol) the mixture is stirred for 2 h (TLC control) at 85° C. Then the organic solvent are removed under reduced pressure. The residue is cooled to 0° C. and treated with 2M HCl. The crude product is filtered off and dried under high vacuum. The crude product (800 mg) is recrystallized from ethyl acetate.
Yield: 520 mg (60%) of colorless crystals. MS (ESI): 324 [M−H]$^−$, 1H-NMR (DMSO-d$_6$): δ (ppm) 12.8 (brs, 1H), 11.7 (s, 1H), 8.18 (s, 1H), 7.73 (dd, 1H), 7.57 (dd, 1H), 7.18 (dd, 1H), 7.15 (d, 1H), 7.05 (s, 1H), 7.02 (d, 1H), 6.72 (d, 1H), 5.38 (s, 2H).

Example 56

4-(6-Fluoro-benzofuran-3-ylmethoxy)-1H-indole-2-carboxylic acid {1-[2-(4-hydroxy-piperidin-1-yl)-ethyl]-piperidin-4-yl}-amide dihydrochloride

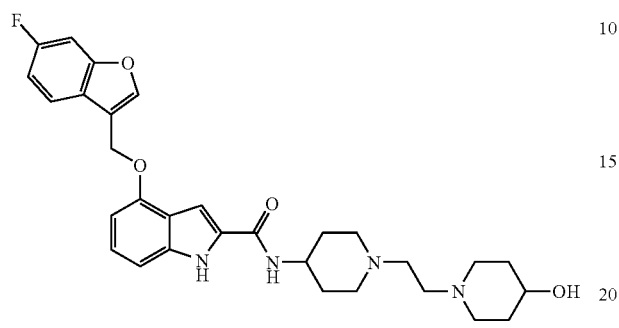

This compound is synthesized from 4-(6-fluoro-benzofuran-3-ylmethoxy)-1H-indole-2-carboxylic acid (106, see example 55) and amine 21 analogously to the method described in example 1.

Yield: 70 mg (38%). MS (ESI): 535 [M+H]$^+$, 1H-NMR (DMSO-d$_6$): δ (ppm) 11.5 (s, 1H), 10.55 (br, 1H), 10.45 (br, 1H), 8.5 (br d, 1H), 8.2 (s, 1H), 7.7 (dd, 1H), 7.6 (dd, 2H), 7.15-7.25 (m, 2H), 7.1 (dd, 1H), 7.03 (d, 1H), 5.35 (s, 2H), 5.0 (br, 1H), 4.05 (m, 1H), 2.9-3.7 (m, 13H), 1.7-2.1 (m, 8H).

Example 57

4-(6-Fluoro-benzofuran-3-ylmethoxy)-1H-indole-2-carboxylic acid {1-[2-((3S,4S)-4-hydroxy-3-methyl-piperidin-1-yl)-ethyl]-piperidin-4-yl}-amide dihydrochloride

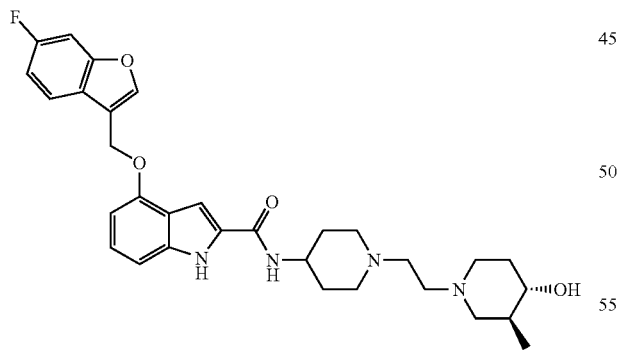

This compound is synthesized from 4-(6-fluoro-benzofuran-3-ylmethoxy)-1H-indole-2-carboxylic acid (106, see example 55) and amine 14 analogously to the method described in example 1.

Yield: 135 mg (71%). MS (ESI): 549 [M+H]$^+$, 1H-NMR (DMSO-d$_6$): δ (ppm) 11.5 (s, 1H), 10.65 (br, 2H), 8.52 (d, 1H), 8.2 (s, 1H), 7.72 (dd, 1H), 7.58 (dd, 1H), 7.24 (s, 1H), 7.2 (m, 1H), 7.1 (dd, 1H), 7.04 (d, 1H), 6.72 (d, 1H), 5.35 (s, 2H), 2.6-4.2 (m, 14H), 1.75-2.2 (m, 8H), 0.93 (d, 3H).

Example 58

4-(6-Fluoro-benzofuran-3-ylmethoxy)-1H-indole-2-carboxylic acid {1-[(S)-2-(4-hydroxy-piperidin-1-yl)-propyl]-piperidin-4-yl}-amide dihydrochloride

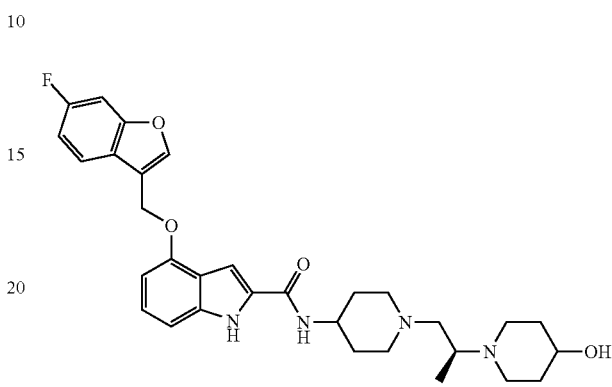

This compound is synthesized from 4-(6-fluoro-benzofuran-3-ylmethoxy)-1H-indole-2-carboxylic acid (106, see example 55) and amine 50 analogously to the method described in example 1.

Yield: 75 mg (39%). MS (ESI): 549 [M+H]$^+$, 1H-NMR (DMSO-d$_6$): δ (ppm) 11.55 (s, 1H), 10.3-10.7 (br, 2H), 8.53 (d, 1H), 8.2 (s, 1H), 7.72 (dd, 1H), 7.58 (dd, 1H), 7.24 (s, 1H), 7.2 (m, 1H), 7.1 (dd, 1H), 7.03 (d, 1H), 6.71 (d, 1H), 5.33 (s, 2H), 5.1 (br, 1H), 2.8-4.1 (m, 13H), 1.7-2.2 (m, 8H), 1.35/1.3 (d, 3H) (rotamers).

Example 59

4-(6-Fluoro-benzofuran-3-ylmethoxy)-1H-indole-2-carboxylic acid {1-[(S)-2-((3S,4S)-4-hydroxy-3-methyl-piperidin-1-yl)-propyl]-piperidin-4-yl}-amide

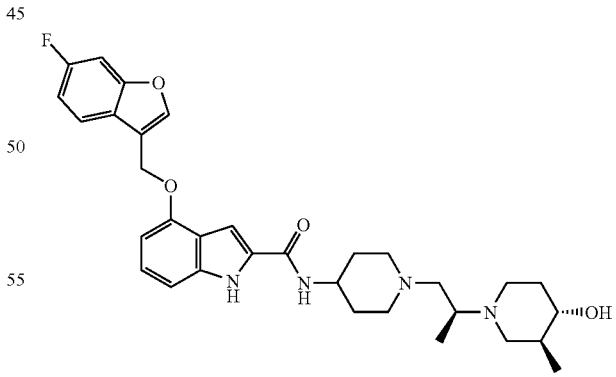

This compound is synthesized analogously to example 1 from 4-(6-fluoro-benzofuran-3-ylmethoxy)-1H-indole-2-carboxylic acid, 106 (see example 55) and amine 56.

MS (ESI): 463.2 [M+H]$^+$, 1H-NMR (DMSO-d$_6$): δ (ppm) 11.48 (s, 1H), 8.19 (s, 1H), 8.11 (d, 1H), 7.71 (dd, 1H), 7.58 (dd, 1H), 7.19 (m, 2H), 7.09 (t, 1H), 7.01 (d, 1H), 6.7 (d, 1H), 5.34 (s, 2H), 4.43 (d, 1H), 3.71 (m, 1H), 2.58-2.92 (m, 6H), 2.31 (m, 1H), 2.22 (m, 1H), 2.02-2.18 (m, 2H), 1.89 (m, 2H), 1.64-1.78 (m, 3H), 1.42-1.59 (m, 2H), 1.2-1.4 (m, 2H), 0.9 (d, 3H), 0.86 (d, 3H).

Example 60

4-(5-Fluoro-benzofuran-3-ylmethoxy)-1H-indole-2-carboxylic acid {1-[(1S,9aR)-1-(octahydro-quinolizin-1-yl)methyl]-piperidin-4-yl}-amide

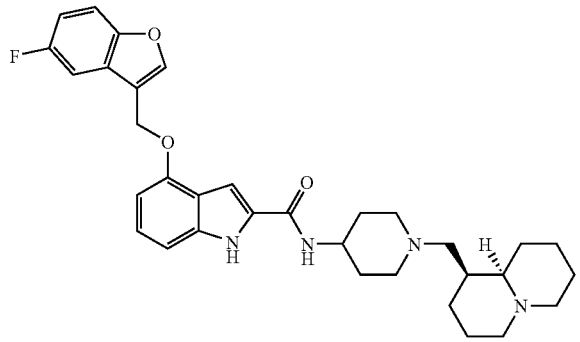

This compound is synthesized from 4-(5-fluoro-benzofuran-3-ylmethoxy)-1H-indole-2-carboxylic acid (113) (preparation see below) and amine 61 analogously to the method described in example 1.

Yield: 840 mg (72.5%). MS (ESI): 559 [M+H]$^+$, 1H-NMR (DMSO-d$_6$): δ (ppm) 11.45 (s, 1H), 8.23 (s, 1H), 8.1 (d, 1H), 7.64 (dd, 1H), 7.48 (dd, 1H), 7.17 (m, 2H), 7.08 (dd, 1H), 7.0 (d, 1H), 6.68 (d, 1H), 5.35 (s, 2H), 3.75 (m, 1H), 2.65-2.85 (m, 4H), 2.47 (m, 1H), 2.25 (dd, 1H), 1.2-2.05 (m, 20H).

Synthesis of 4-(5-fluoro-benzofuran-3-ylmethoxy)-1H-indole-2-carboxylic acid (113)

This compound is synthesized from 4-fluoro-phenol analogously to the method described for 106 (see example 55).

MS (ESI): 324.2 [M−H]$^-$, 1H-NMR (DMSO-d$_6$): δ (ppm) 12.81 (br s, 1H), 11.7 (s, 1H), 8.24 (s, 1H), 7.64 (dd, 1H), 7.51 (dd, 1H), 7.15 (m, 2H), 7.05 (m, 2H), 6.7 (d, 1H), 5.37 (s, 2H).

Example 61

4-(5-Fluoro-benzofuran-3-ylmethoxy)-1H-indole-2-carboxylic acid {1-[2-(4-hydroxy-piperidin-1-yl)-ethyl]-piperidin-4-yl}-amide dihydrochloride

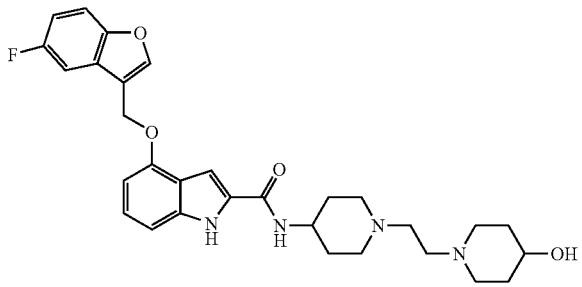

This compound is synthesized from 4-(5-fluoro-benzofuran-3-ylmethoxy)-1H-indole-2-carboxylic acid (113, see example 60) and amine 21 analogously to the method described in example 1.

Yield: 160 mg (57%). MS (ESI): 535 [M+H]$^+$, 1H-NMR (DMSO-d$_6$): δ (ppm) 11.5 (s, 1H), 10.65 (br, 1H), 10.55 (br, 1H), 8.51 (br d, 1H), 8.25 (s, 1H), 7.65 (m, 1H), 7.45 (dd, 2H), 7.2 (s, 1H), 7.05-7.15 (m, 3H), 6.7 (d, 1H), 5.35 (s, 2H), 4.12 (m, 1H), 3.84 (m, 1H), 2.9-3.7 (m, 13H), 1.75-2.2 (m, 8H).

Example 62

4-(5-Fluoro-benzofuran-3-ylmethoxy)-1H-indole-2-carboxylic acid {1-[2-((3R,4R,5S)-4-hydroxy-3,5-dimethyl-piperidin-1-yl)-ethyl]-piperidin-4-yl}-amide dihydrochloride

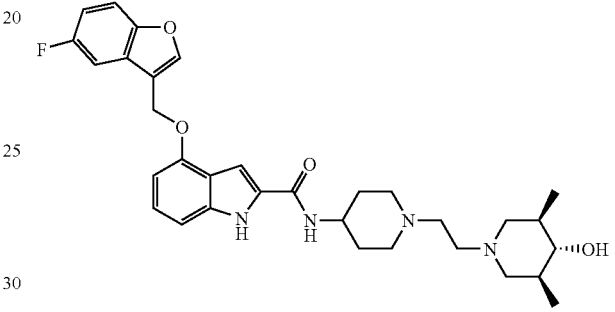

This compound is synthesized from 4-(5-fluoro-benzofuran-3-ylmethoxy)-1H-indole-2-carboxylic acid (113, see example 60) and amine 41 analogously to the method described in example 1.

Yield: 110 mg (56%). MS (ESI): 563 [M+H]$^+$, 1H-NMR (DMSO-d$_6$): δ (ppm) 11.5 (s, 1H), 10.5-10.7 (br, 2H), 8.5 (d, 1H), 8.22 (s, 1H), 7.63 (dd, 1H), 7.49 (dd, 1H), 7.2 (m, 2H), 7.1 (d, 1H), 7.02 (d, 1H), 6.7 (d, 1H), 5.32 (s, 2H), 5.05 (br, 1H), 4.05 (m, 1H), 2.6-3.8 (m, 13H), 1.8-2.1 (m, 6H), 0.93 (d, 6H).

Example 63

4-(5-Fluoro-benzofuran-3-ylmethoxy)-1H-indole-2-carboxylic acid {1-[(S)-2-(4-hydroxy-piperidin-1-yl)-propyl]-piperidin-4-yl}-amide dihydrochloride

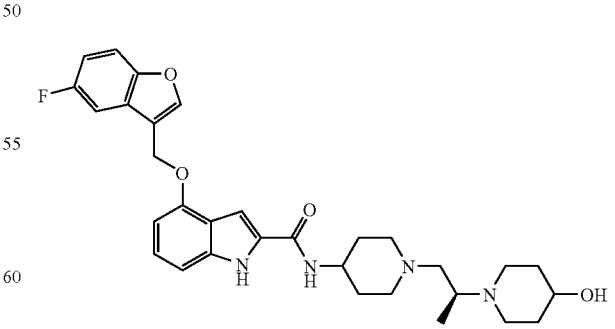

This compound is synthesized from 4-(5-fluoro-benzofuran-3-ylmethoxy)-1H-indole-2-carboxylic acid (113, see example 60) and amine 50 analogously to the method described in example 1.

Yield: 85 mg (45%). MS (ESI): 549 [M+H]+, 1H-NMR (DMSO-d6): δ (ppm) 11.55 (s, 1H), 10.2-10.6 (br, 2H), 8.5 (d, 1H), 8.24 (s, 1H), 7.65 (dd, 1H), 7.5 (m, 1H), 7.15-7.3 (m, 2H), 7.1 (dd, 1H), 7.03 (d, 1H), 6.71 (d, 1H), 5.33 (s, 2H), 5.04 (br, 1H), 2.8-4.1 (m, 13H), 1.7-2.2 (m, 8H), 1.35/1.3 (d, 3H) (rotamers).

Example 64

4-(5-Fluoro-benzofuran-3-ylmethoxy)-1H-indole-2-carboxylic acid {1-[(S)-2-((3S,4S)-4-hydroxy-3-methyl-piperidin-1-yl)-propyl]-piperidin-4-yl}-amide

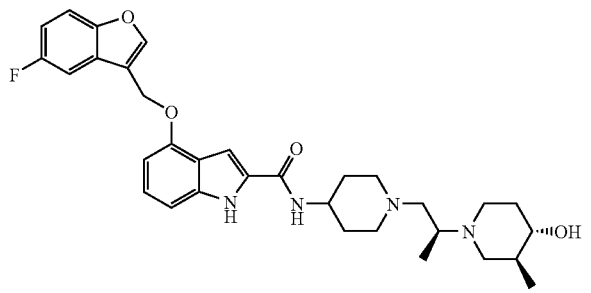

This compound is synthesized analogously to example 1 from 4-(5-fluoro-benzofuran-3-ylmethoxy)-1H-indole-2-carboxylic acid, 113 (see example 60) and amine 56.

MS (ESI): 563.1 [M+H]+, 1H-NMR (CD3OD): δ (ppm) 7.95 (s, 1H), 7.48 (dd, 1H), 7.43 (dd, 1H), 7.21 (s, 1H), 7.15 (t, 1H), 7.02-7.12 (m, 2H), 6.69 (d, 1H), 5.34 (s, 2H), 3.86 (m, 1H), 2.72-3.12 (m, 6H), 2.51 (m, 1H), 2.17-2.41 (m, 3H), 1.97-2.15 (m, 2H), 1.81-1.96 (m, 3H), 1.45-1.76 (m, 4H), 1.05 (d, 3H), 0.98 (d, 3H).

Example 65

4-(7-Fluoro-benzofuran-3-ylmethoxy)-1H-indole-2-carboxylic acid {1-[(1S,9aR)-1-(octahydro-quinolizin-1-yl)methyl]-piperidin-4-yl}-amide dihydrochloride

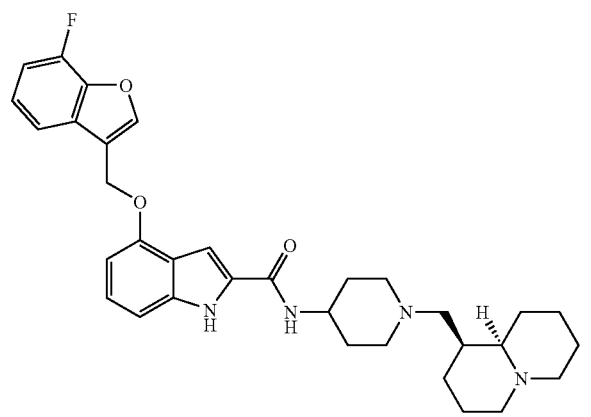

This compound is synthesized from 4-(7-fluoro-benzofuran-3-ylmethoxy)-1H-indole-2-carboxylic acid (114) (preparation see below) and amine 61 analogously to the method described in example 1.

Yield: 194 mg (40%). MS (ESI): 559 [M+H]+, 1H-NMR (DMSO-d6): δ (ppm) 11.5 (s, 1H), 10.2-10.7 (br, 2H), 8.45 (dd, 1H), 8.28 (s, 1H), 7.58 (dd, 1H), 7.2-7.3 (m, 3H), 7.1 (m, 1H), 7.05 (d, 1H), 6.72 (d, 1H), 5.38 (s, 2H), 4.0 (m, 1H), 2.65-2.85 (m, 6H), 1.2-2.05 (m, 20H).

Synthesis of 4-(7-fluoro-benzofuran-3-ylmethoxy)-1H-indole-2-carboxylic acid (114)

This compound is synthesized from 2-fluoro-phenol analogously to the method described for 106 (see example 55).

MS (ESI): 324.2 [M−H]−, 1H-NMR (DMSO-d6): δ (ppm) 12.85 (br s, 1H), 11.75 (s, 1H), 8.25 (s, 1H), 7.58 (dd, 1H), 7.2-7.3 (m, 2H), 7.15 (dd, 1H), 7.05 (s, 1H), 7.02 (d, 1H), 6.72 (d, 1H), 5.4 (s, 2H).

Example 66

4-(4,6-Difluoro-benzofuran-3-ylmethoxy)-1H-indole-2-carboxylic acid {1-[(1S,9aR)-1-(octahydro-quinolizin-1-yl)methyl]-piperidin-4-yl}-amide dihydrochloride

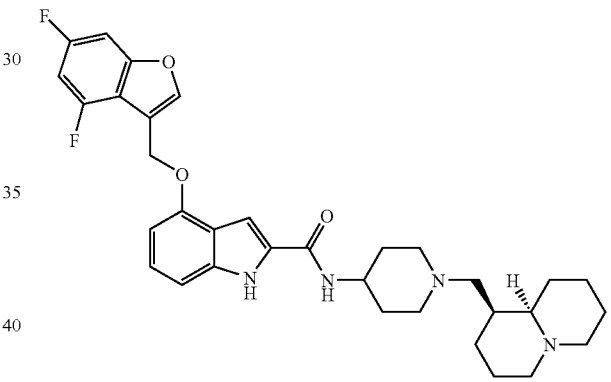

This compound is synthesized from 4-(4,6-difluoro-benzofuran-3-ylmethoxy)-1H-indole-2-carboxylic acid (115) (preparation see below) and amine 61 analogously to the method described in example 1.

Yield: 155 mg (82%). MS (ESI): 577 [M+H]+, 1H-NMR (DMSO-d6): δ (ppm) 11.5 (s, 1H), 10.5 (br d, 1H), 10.2 (br d, 1H), 8.45 (br d, 1H), 8.25 (s, 1H), 7.55 (d, 1H), 7.2-7.25 (m, 2H), 7.1 (m, 1H), 7.05 (d, 1H), 6.7 (d, 1H), 5.3 (s, 2H), 4.0 (m, 1H), 2.8-3.6 (m, 14H), 1.3-2.1 (m, 12H).

Synthesis of 4-(4,6-Difluoro-benzofuran-3-ylmethoxy)-1H-indole-2-carboxylic acid (115)

This compound is synthesized from 3,5-difluoro-phenol analogously to the method described for 106 (see example 55).

MS (ESI): 342 [M−H]−, 1H-NMR (DMSO-d6): δ (ppm) 12.8 (br s, 1H), 11.6 (s, 1H), 8.24 (s, 1H), 7.51 (dd, 1H), 7.2 (ddd, 1H), 7.15 (dd, 1H), 7.04 (d, 1H), 7.02 (s, 1H), 6.7 (d, 1H), 5.32 (s, 2H).

Example 67

4-(4,6-Difluoro-benzofuran-3-ylmethoxy)-1H-indole-2-carboxylic acid {1-[2-(4-hydroxy-piperidin-1-yl)-ethyl]-piperidin-4-yl}-amide dihydrochloride

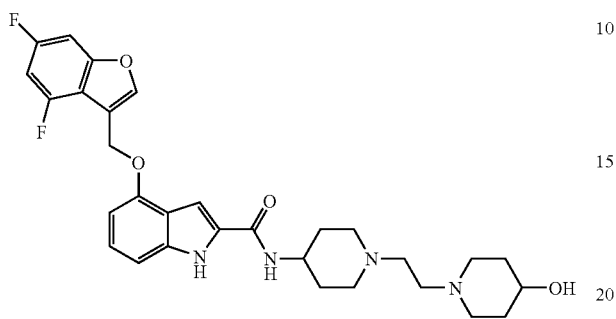

This compound is synthesized from 4-(4,6-difluoro-benzofuran-3-ylmethoxy)-1H-indole-2-carboxylic acid (115, see example 66)) and amine 21 analogously to the method described in example 1.

Yield: 90 mg (49%). MS (ESI): 553 [M+H]$^+$, 1H-NMR (DMSO-d$_6$): δ (ppm) 11.5 (s, 1H), 10.5 (br, 1H), 10.35 (br, 1H), 8.48 (br d, 1H), 8.25 (s, 1H), 7.54 (d, 1H), 7.2 (m, 2H), 7.12 (dd, 1H), 7.03 (d, 1H), 6.7 (d, 1H), 5.3 (s, 2H), 5.05 (br, 1H), 4.07 (m, 1H), 2.9-3.75 (m, 13H), 1.65-2.1 (m, 8H).

Example 68

4-(4,6-Difluoro-benzofuran-3-ylmethoxy)-1H-indole-2-carboxylic acid {1-[2-((3S,4S)-4-hydroxy-3-methyl-piperidin-1-yl)-ethyl]-piperidin-4-yl}-amide dihydrochloride

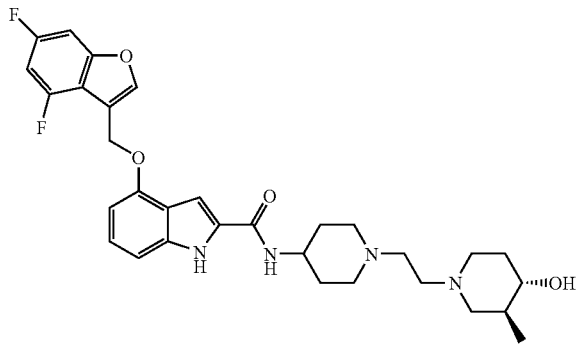

This compound is synthesized from 4-(4,6-difluoro-benzofuran-3-ylmethoxy)-1H-indole-2-carboxylic acid (115, see example 66) and amine 14 analogously to the method described in example 1.

Yield: 125 mg (67%). MS (ESI): 567 [M+H]$^+$, 1H-NMR (DMSO-d$_6$): δ (ppm) 11.5 (s, 1H), 10.65 (br, 2H), 8.5 (d, 1H), 8.25 (s, 1H), 7.53 (dd, 1H), 7.2-7.3 (m, 2H), 7.1 (dd, 1H), 7.02 (d, 1H), 6.7 (d, 1H), 5.3 (s, 2H), 2.6-4.1 (m, 14H), 1.75-2.2 (m, 8H), 0.93 (d, 3H).

Example 69

4-(4,6-Difluoro-benzofuran-3-ylmethoxy)-1H-indole-2-carboxylic acid {1-[(S)-2-(4-hydroxy-piperidin-1-yl)-propyl]-piperidin-4-yl}-amide dihydrochloride

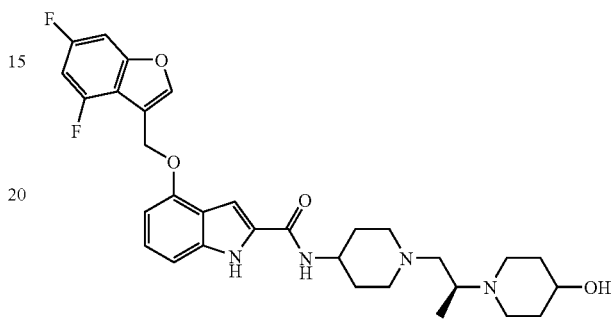

This compound is synthesized from 4-(4,6-difluoro-benzofuran-3-ylmethoxy)-1H-indole-2-carboxylic acid (115, see example 66) and amine 50 analogously to the method described in example 1.

Yield: 105 mg (56%). MS (ESI): 567 [M+H]$^+$, 1H-NMR (120° C., DMSO-d$_6$): δ (ppm) 11.5 (s, 1H), 10.3-10.7 (br, 2H), 8.52 (d, 1H), 8.26 (s, 1H), 7.53 (d, 1H), 7.2 (m, 2H), 7.1 (dd, 1H), 7.02 (d, 1H), 6.7 (d, 1H), 5.3 (s, 2H), 5.05 (br, 1H), 4.05 (m, 1H), 2.9-3.9 (m, 12H), 1.7-2.2 (m, 8H), 1.34 (d, 3H).

Example 70

4-(4,6-Difluoro-benzofuran-3-ylmethoxy)-1H-indole-2-carboxylic acid {1-[(S)-2-((3S,4S)-4-hydroxy-3-methyl-piperidin-1-yl)-propyl]-piperidin-4-yl}-amide dihydrochloride

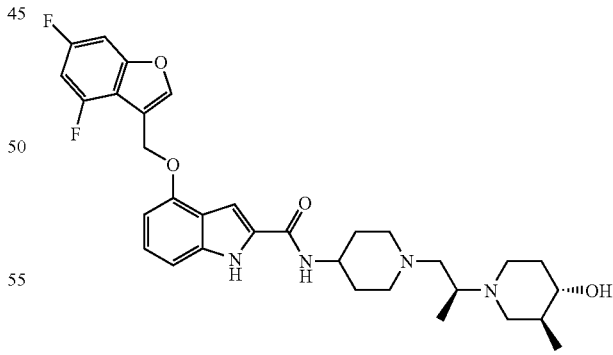

This compound is synthesized from 4-(4,6-difluoro-benzofuran-3-ylmethoxy)-1H-indole-2-carboxylic acid (115, see example 66) and amine 56 analogously to the method described in example 1.

Yield: 130 mg (68%). MS (ESI): 581 [M+H]$^+$, 1H-NMR (DMSO-d$_6$): δ (ppm) 11.5 (s, 1H), 10.4-10.6 (br, 2H), 8.5 (d, 1H), 8.27 (s, 1H), 7.55 (d, 1H), 7.2 (m, 2H), 7.1 (dd, 1H), 7.03 (d, 1H), 6.7 (d, 1H), 5.3 (s, 2H), 5.1 (br, 1H), 4.05 (m, 1H), 2.8-3.9 (m, 13H), 1.9-2.1 (m, 6H), 1.3 (d, 3H), 0.93 (d, 3H).

Example 71

4-(7-Chloro-benzofuran-3-ylmethoxy)-1H-indole-2-carboxylic acid {1-[(1S,9aR)-1-(octahydro-quinolizin-1-yl)methyl]-piperidin-4-yl}-amide dihydrochloride

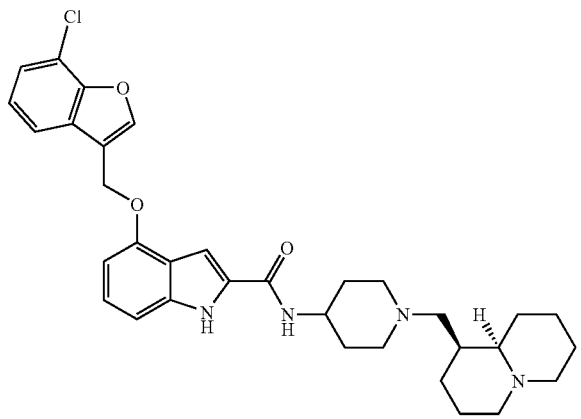

This compound is synthesized from 4-(7-chloro-benzofuran-3-ylmethoxy)-1H-indole-2-carboxylic acid (116) (preparation see below) and amine 61 analogously to the method described in example 1.

Yield: 55 mg (29%). MS (ESI): 575 [M+H]$^+$, 1H-NMR (DMSO-d$_6$): δ (ppm) 11.5 (s, 1H), 10.1-10.6 (br, 2H), 8.5 (dd, 1H), 8.3 (s, 1H), 7.7 (d, 1H), 7.48 (d, 1H), 7.32 (dd, 1H), 7.25 (m, 1H), 7.1 (m, 1H), 7.05 (d, 1H), 6.7 (d, 1H), 5.38 (s, 2H), 4.0 (m, 1H), 2.65-2.85 (m, 6H), 1.2-2.05 (m, 20H).

Synthesis of 4-(7-chloro-benzofuran-3-ylmethoxy)-1H-indole-2-carboxylic acid (116)

This compound is synthesized from 2-chloro-phenol analogously to the method described for 106 (see example 55).

MS (ESI): 340 [M−H]$^-$, 1H-NMR (DMSO-d$_6$): δ (ppm) 10.86 (s, 1H), 8.25 (s, 1H), 7.71 (d, 1H), 7.42 (d, 1H), 7.30 (dd, 1H), 6.93 (m, 2H), 6.58 (d, 1H), 6.34 (s, 1H), 5.36 (s, 2H) (potassium salt).

Example 72

4-(6-Chloro-benzofuran-3-ylmethoxy)-1H-indole-2-carboxylic acid {1-[(1S,9aR)-1-(octahydro-quinolizin-1-yl)methyl]-piperidin-4-yl}-amide dihydrochloride

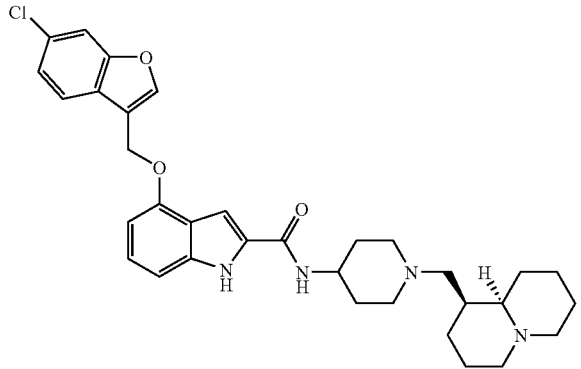

This compound is synthesized from 4-(6-chloro-benzofuran-3-ylmethoxy)-1H-indole-2-carboxylic acid (117) (preparation see below) and amine 61 analogously to the method described in example 1.

Yield: 85 mg (49.8%). MS (ESI): 575 [M+H]$^+$, 1H-NMR (DMSO-d$_6$): δ (ppm) 11.5 (s, 1H), 10.6 (br d, 1H), 10.3 (br d, 1H), 8.49 (br dd, 1H), 8.22 (s, 1H), 7.8 (d, 1H), 7.72 (d, 1H), 7.38 (dd, 1H), 7.25 (m, 1H), 7.1 (m, 1H), 7.03 (d, 1H), 6.7 (d, 1H), 5.35 (s, 2H), 4.0 (m, 1H), 2.8-3.8 (m, 14H), 1.3-2.1 (m, 12H).

Synthesis of 4-(6-chloro-benzofuran-3-ylmethoxy)-1H-indole-2-carboxylic acid (117)

This compound is synthesized from 3-chloro-phenol analogously to the method described for 106 (see example 55). The cyclisation with concentrated sulphuric acid (Step C) gave a 1:1 mixture of the 4- and 6-substituted benzofuranes, which could be separated in step D. MS (ESI): 340 [M−H].

Example 73

4-(6-Chloro-benzofuran-3-ylmethoxy)-1H-indole-2-carboxylic acid {1-[2-(4-hydroxy-piperidin-1-yl)-ethyl]-piperidin-4-yl}-amide

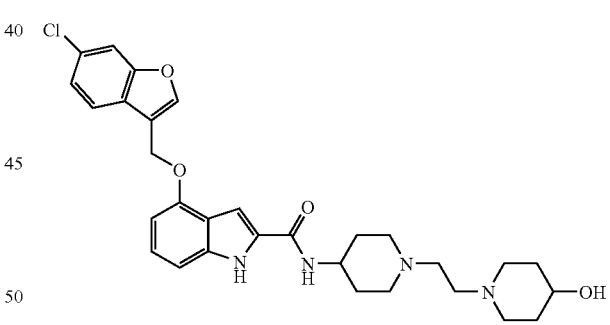

This compound is synthesized from 4-(6-chloro-benzofuran-3-ylmethoxy)-1H-indole-2-carboxylic acid (117, see example 72) and amine 21 analogously to the method described in example 1.

Yield: 63 mg (34%). MS (ESI): 551 [M+H]$^+$, 1H-NMR (DMSO-d$_6$): δ (ppm) 11.5 (s, 1H), 8.22 (s, 1H), 8.15 (br d, 1H), 7.81 (s, 1H), 7.75 (d, 1H), 7.35 (dd, 1H), 7.18 (s, 1H), 7.1 (dd, 1H), 7.02 (d, 1H), 6.7 (d, 1H), 5.35 (s, 2H), 4.75 (b, 1H), 2.1-3.9 (m, 14H), 1.4-1.8 (m, 8H).

Example 74

4-(6-Chloro-benzofuran-3-ylmethoxy)-1H-indole-2-carboxylic acid {1-[2-((3S,4S)-4-hydroxy-3-methyl-piperidin-1-yl)-ethyl]-piperidin-4-yl}-amide

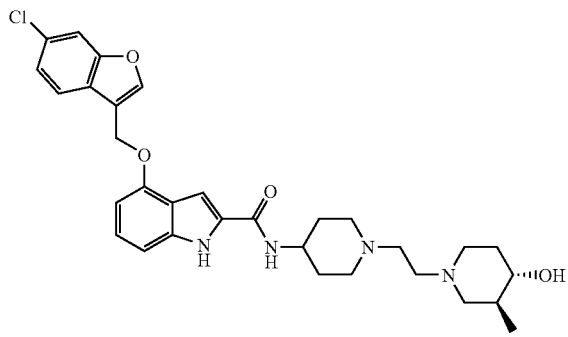

This compound is synthesized from 4-(6-chloro-benzofuran-3-ylmethoxy)-1H-indole-2-carboxylic acid (117, see example 72) and amine 14 analogously to the method described in example 1.

Yield: 55 mg (32%). MS (ESI): 565 [M+H]$^+$, 1H-NMR (DMSO-d$_6$): δ (ppm) 11.55 (s, 1H), 10.5 (br, 2H), 8.48 (d, 1H), 8.22 (s, 1H), 7.80 (s, 1H), 7.70 (d, 1H), 7.37 (d, 1H), 7.22 (s, 1H), 7.1 (dd, 1H), 7.02 (d, 1H), 6.71 (d, 1H), 5.34 (s, 2H), 2.6-4.2 (m, 14H), 1.75-2.2 (m, 8H), 0.93 (d, 3H).

Example 75

4-(6-Chloro-benzofuran-3-ylmethoxy)-1H-indole-2-carboxylic acid {1-[(S)-2-(4-hydroxy-piperidin-1-yl)-propyl]-piperidin-4-yl}-amide dihydrochloride

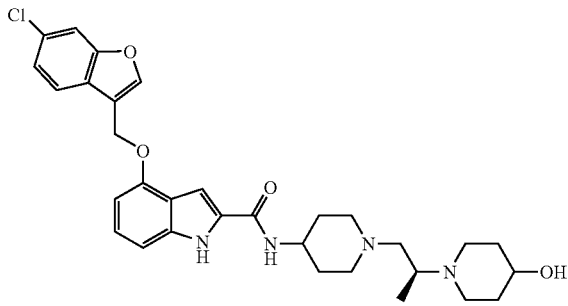

This compound is synthesized from 4-(6-chloro-benzofuran-3-ylmethoxy)-1H-indole-2-carboxylic acid (117, see example 72) and amine 50 analogously to the method described in example 1.

Yield: 85 mg (46%). MS (ESI): 565 [M+H]$^+$, 1H-NMR (DMSO-d$_6$): δ (ppm) 11.5 (s, 1H), 10.2-10.6 (br, 2H), 8.5 (d, 1H), 8.21 (s, 1H), 7.8 (d, 1H), 7.7 (d, 1H), 7.35 (dd, 1H), 7.24 (s, 1H), 7.1 (dd, 1H), 7.03 (d, 1H), 6.7 (d, 1H), 5.35 (s, 2H), 5.0 (br, 1H), 2.85-4.2 (m, 13H), 1.7-2.2 (m, 8H), 1.35/1.3 (d, 3H) (rotamers).

Example 76

4-(4-Chloro-benzofuran-3-ylmethoxy)-1H-indole-2-carboxylic acid {1-[(1S,9aR)-1-(octahydro-quinolizin-1-yl)methyl]-piperidin-4-yl}-amide dihydrochloride

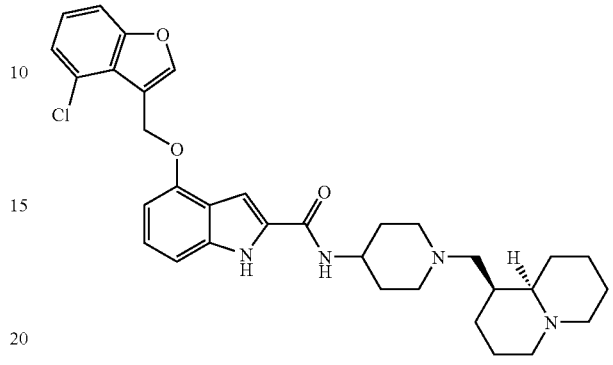

This compound is synthesized from 4-(4-chloro-benzofuran-3-ylmethoxy)-1H-indole-2-carboxylic acid (118) (preparation see below) and amine 61 analogously to the method described in example 1.

Yield: 230 mg (58.8%). MS (ESI): 575 [M+H]$^+$, 1H-NMR (DMSO-d$_6$): δ (ppm) 11.5 (s, 1H), 10.6 (br d, 1H), 10.3 (br d, 1H), 8.45 (br dd, 1H), 8.3 (s, 1H), 7.65 (dd, 1H), 7.3-7.4 (m, 2H), 7.25 (m, 1H), 7.1 (m, 1H), 7.03 (d, 1H), 6.7 (d, 1H), 5.35 (s, 2H), 4.0 (m, 1H), 2.8-3.8 (m, 14H), 1.3-2.1 (m, 12H).

Synthesis of 4-(4-chloro-benzofuran-3-ylmethoxy)-1H-indole-2-carboxylic acid (118)

This compound is synthesized from 3-chloro-phenol analogously to the method described for 106 (see example 55). The cyclisation with concentrated sulphuric acid (Step C) gave a 1:1 mixture of the 4- and 6-substituted benzofuranes, which could be separated in step D.

MS (ESI): 340 [M–H]$^-$, 1H-NMR (DMSO-d$_6$): δ (ppm) 12.75 (br s, 1H), 11.7 (s, 1H), 8.31 (s, 1H), 7.6 (dd, 1H), 7.35 (m, 2H), 7.15 (dd, 1H), 7.02 (m, 2H), 6.75 (d, 1H), 5.42 (s, 2H).

Example 77

4-(4-Chloro-benzofuran-3-ylmethoxy)-1H-indole-2-carboxylic acid {1-[2-(4-hydroxy-piperidin-1-yl)-ethyl]-piperidin-4-yl}-amide dihydrochloride

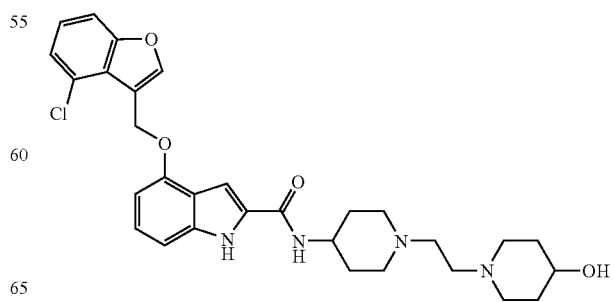

This compound is synthesized from 4-(4-chloro-benzofuran-3-ylmethoxy)-1H-indole-2-carboxylic acid (118, see example 76) and amine 21 analogously to the method described in example 1.

Yield: 160 mg (99%). MS (ESI): 551 [M+H]⁺, 1H-NMR (DMSO-d₆): δ (ppm) 11.52 (s, 1H), 10.35 (br, 1H), 10.2 (br, 1H), 8.5 (br, 1H), 8.31 (s, 1H), 7.63 (d, 1H), 7.36 (m, 2H), 7.22 (s, 1H), 7.11 (dd, 1H), 7.03 (d, 1H), 6.71 (d, 1H), 5.37 (s, 2H), 5.02 (br, 1H), 4.05 (m, 1H), 2.9-3.75 (m, 13H), 1.65-2.1 (m, 8H).

Example 78

4-(4-Chloro-benzofuran-3-ylmethoxy)-1H-indole-2-carboxylic acid {1-[2-((3R,4R,5S)-4-hydroxy-3,5-dimethyl-piperidin-1-yl)-ethyl]-piperidin-4-yl}-amide dihydrochloride

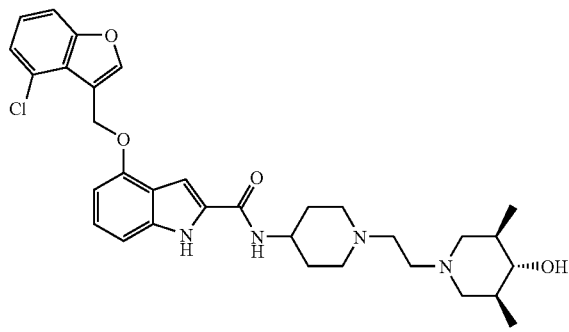

This compound is synthesized from 4-(4-chloro-benzofuran-3-ylmethoxy)-1H-indole-2-carboxylic acid (118, see example 76) and amine 41 analogously to the method described in example 1.

Yield: 45 mg (39%). MS (ESI): 577 [M-H]⁻, 1H-NMR (DMSO-d₆): δ (ppm) 11.5 (s, 1H), 10.45-10.7 (br, 2H), 8.47 (d, 1H), 8.32 (s, 1H), 7.65 (d, 1H), 7.35 (m, 2H), 7.21 (s, 1H), 7.1 (dd, 1H), 7.02 (d, 1H), 6.71 (d, 1H), 5.35 (s, 2H), 5.0 (br, 1H), 4.05 (m, 1H), 2.6-3.8 (m, 13H), 1.8-2.1 (m, 6H), 0.93 (d, 6H).

Example 79

4-(4-Chloro-benzofuran-3-ylmethoxy)-1H-indole-2-carboxylic acid {1-[(S)-2-(4-hydroxy-piperidin-1-yl)-propyl]-piperidin-4-yl}-amide

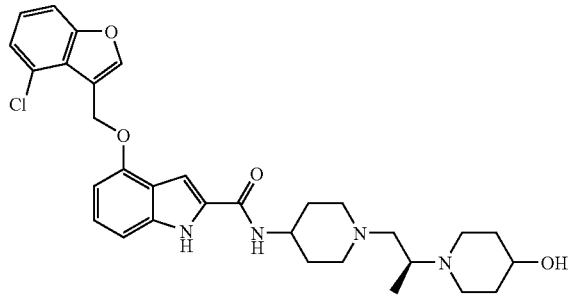

This compound is synthesized from 4-(4-chloro-benzofuran-3-ylmethoxy)-1H-indole-2-carboxylic acid (118, see example 76) and amine 50 analogously to the method described in example 1.

Yield: 20 mg (13%). MS (ESI): 565 [M+H]⁺, 1H-NMR (DMSO-d₆): δ (ppm) 11.5 (s, 1H), 8.3 (s, 1H), 8.1 (d, 1H), 7.62 (d, 1H), 7.35 (m, 2H), 7.2 (s, 1H), 7.1 (dd, 1H), 7.0 (d, 1H), 6.7 (d, 1H), 5.4 (s, 2H), 4.5 (br, 1H), 4.05 (m, 1H), 3.7 (m, 1H), 2.6-2.9 (m, 4H), 1.1-2.4 (m, 15H), 0.9 (d, 3H).

Example 80

4-(7-Methoxy-benzofuran-3-ylmethoxy)-1H-indole-2-carboxylic acid {1-[(1S,9aR)-1-(octahydro-quinolizin-1-yl)methyl]-piperidin-4-yl}-amide dihydrochloride

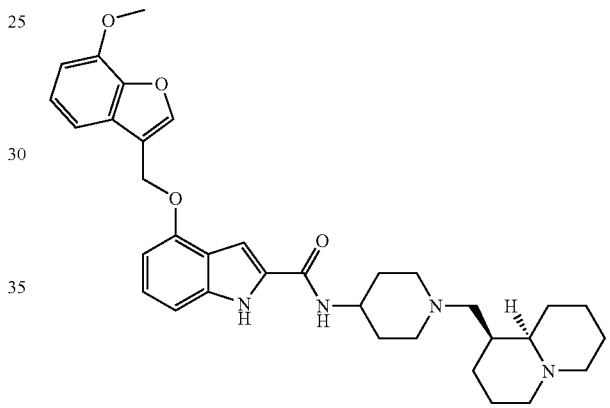

This compound is synthesized from 4-(7-methoxy-benzofuran-3-ylmethoxy)-1H-indole-2-carboxylic acid (119) (preparation see below) and amine 61 analogously to the method described in example 1.

Yield: 130 mg (68.1%). MS (ESI): 571 [M+H]⁺, 1H-NMR (DMSO-d₆): δ (ppm) 11.55 (s, 1H), 10.5 (br d, 1H), 10.2 (br d, 1H), 8.47 (dd, 1H), 8.13 (s, 1H), 7.25 (m, 2H), 7.2 (dd, 1H), 7.09 (d, 1H), 7.02 (d, 1H), 6.95 (d, 1H), 6.72 (d, 1H), 5.32 (s, 2H), 4.0 (m, 1H), 3.83 (s, 3H), 2.8-3.8 (m, 14H), 1.3-2.1 (m, 12H).

Synthesis of 4-(7-methoxy-benzofuran-3-ylmethoxy)-1H-indole-2-carboxylic acid (119)

This compound is synthesized from 2-methoxy-phenol analogously to the method described for 106 (see example 55).

MS (ESI): 336 [M-H]⁻, 1H-NMR (DMSO-d₆): δ (ppm) 12.8 (br s, 1H), 11.54 (br s, 1H), 8.11 (s, 1H), 7.28 (d, 1H), 7.18 (dd, 1H), 7.09 (m, 1H), 7.0 (d, 1H), 6.95 (d, 1H), 6.92 m, 1H), 6.70 (d, 1H), 5.35 (s, 2H), 3.92 (s, 3H).

Example 81

4-(7-Methoxy-benzofuran-3-ylmethoxy)-1H-indole-2-carboxylic acid [1-(2-piperidin-1-yl-ethyl)-piperidin-4-yl]-amide

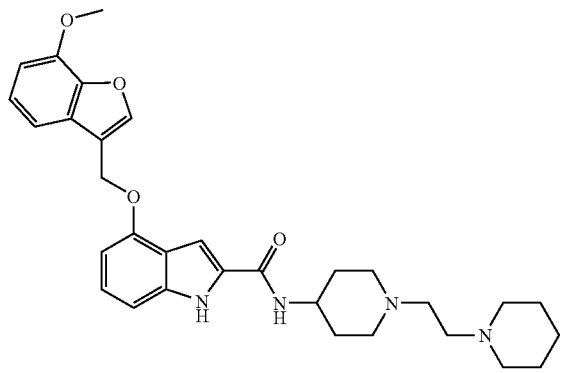

This compound is synthesized from 4-(7-methoxy-benzofuran-3-ylmethoxy)-1H-indole-2-carboxylic acid (119, see example 80) and amine 1 analogously to the method described in example 1.

Yield: 162 mg (48%). MS (ESI): 531 [M+H]$^+$, 1H-NMR (DMSO-d$_6$): δ (ppm) 11.53 (s, 1H), 10.55 (br, 1H), 10.31 (br, 1H), 8.49 (d, 1H), 8.12 (s, 1H), 7.25 (dd, 1H), 7.22 (brs, 1H), 7.19 (dd, 1H), 7.1 (dd, 1H), 7.02 (d, 1H), 7.95 (d, 1H), 6.7 (d, 1H), 5.31 (s, 2H), 4.05 (m, 1H), 3.93 (s, 3H), 3.5-3.8 (m, 8H), 3.1 (m, 2H), 2.9 (m, 2H), 1.7-2.1 (m, 8H), 1.4 (m, 2H).

Example 82

4-(7-Methoxy-benzofuran-3-ylmethoxy)-1H-indole-2-carboxylic acid {1-[2-(4-hydroxy-piperidin-1-yl)-ethyl]-piperidin-4-yl}-amide dihydrochloride

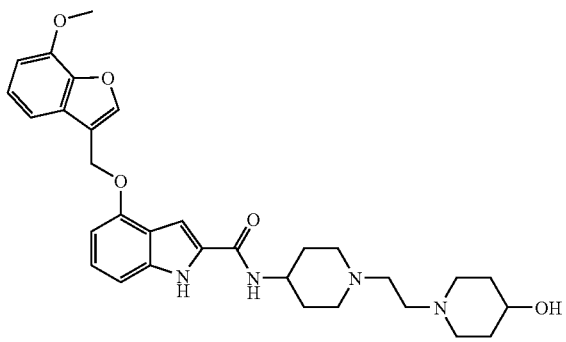

This compound is synthesized from 4-(7-methoxy-benzofuran-3-ylmethoxy)-1H-indole-2-carboxylic acid (119, see example 80) and amine 21 analogously to the method described in example 1.

Yield: 135 mg (73%). MS (ESI): 547 [M+H]$^+$, 1H-NMR (DMSO-d$_6$): δ (ppm) 11.45 (s, 1H), 10.5 (br, 1H), 10.4 (br, 1H), 8.5 (br, 1H), 8.14 (s, 1H), 7.2-7.3 (m, 3H), 7.1 (dd, 1H), 7.0 (d, 1H), 6.95 (d, 1H), 6.7 (d, 1H), 5.32 (s, 2H), 5.05 (br, 1H), 4.05 (m, 1H), 3.93 (s, 3H), 2.7-3.7 (m, 13H), 1.6-2.1 (m, 8H).

Example 83

4-(7-Methoxy-benzofuran-3-ylmethoxy)-1H-indole-2-carboxylic acid {1-[2-((3S,4S)-4-hydroxy-3-methyl-piperidin-1-yl)-ethyl]-piperidin-4-yl}-amide dihydrochloride

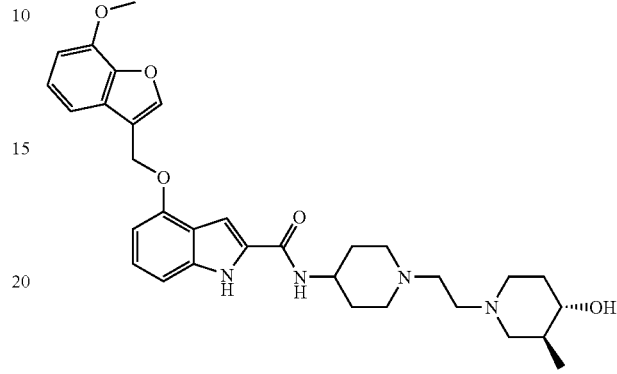

This compound is synthesized from 4-(7-methoxy-benzofuran-3-ylmethoxy)-1H-indole-2-carboxylic acid (119, see example 80) and amine 14 analogously to the method described in example 1.

Yield: 100 mg (53%). MS (ESI): 561 [M+H]$^+$, 1H-NMR (DMSO-d$_6$): δ (ppm) 11.5 (s, 1H), 10.6 (br, 2H), 8.5 (d, 1H), 8.13 (s, 1H), 7.18-7.3 (m, 3H), 7.1 (dd, 1H), 7.03 (d, 1H), 6.96 (d, 1H), 6.71 (d, 1H), 5.33 (s, 2H), 3.95 (s, 3H), 2.6-4.2 (m, 14H), 1.75-2.2 (m, 8H), 0.93 (d, 3H).

Example 84

4-(7-Methoxy-benzofuran-3-ylmethoxy)-1H-indole-2-carboxylic acid {1-[(S)-2-(4-hydroxy-piperidin-1-yl)-propyl]-piperidin-4-yl}-amide dihydrochloride

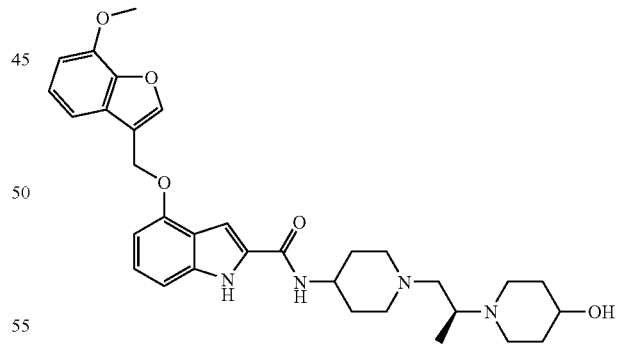

This compound is synthesized from 4-(7-methoxy-benzofuran-3-ylmethoxy)-1H-indole-2-carboxylic acid (119, see example 80) and amine 50 analogously to the method described in example 1.

Yield: 166 mg (94%). MS (ESI): 561 [M+H]$^+$, 1H-NMR (DMSO-d$_6$): δ (ppm) 11.5 (s, 1H), 10.2-10.6 (br, 2H), 8.5 (d, 1H), 8.14 (s, 1H), 7.28 (d, 1H), 7.23 (s, 1H), 7.2 (dd, 1H), 7.1 (dd, 1H), 7.03 (d, 1H), 6.95 (d, 1H), 6.7 (d, 1H), 5.33 (s, 2H), 5.05 (br, 1H), 3.93 (s, 3H), 2.9-4.1 (m, 13H), 1.7-2.2 (m, 8H), 1.35/1.3 (d, 3H) (rotamers).

Example 85

4-(7-Methoxy-benzofuran-3-ylmethoxy)-1H-indole-2-carboxylic acid {1-[(S)-2-((3S,4S)-4-hydroxy-3-methyl-piperidin-1-yl)-propyl]-piperidin-4-yl}-amide

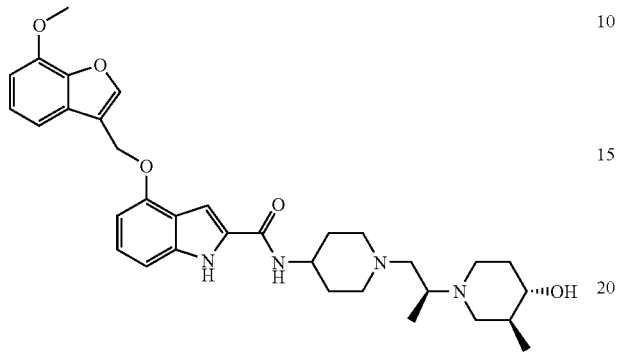

This compound is synthesized analogously to example 1 from 4-(7-methoxy-benzofuran-3-ylmethoxy)-1H-indole-2-carboxylic acid, 119 (see example 80) and amine 56.

MS (ESI): 575.1 [M+H]$^+$, 1H-NMR (DMSO-d$_6$): δ (ppm) 11.49 (s, 1H), 8.15 (s, 1H), 8.13 (d, 1H), 7.26 (d, 1H), 7.22 (t, 1H), 7.2 (s, 1H), 7.1 (t, 1H), 7.02 (d, 1H), 6.97 (d, 1H), 6.71 (d, 1H), 5.34 (s, 2H), 4.43 (d, 1H), 3.95 (s, 3H), 3.72 (m, 1H), 2.6-2.93 (m, 6H), 2.31 (m, 1H), 2.23 (m, 1H), 2.03-2.17 (m, 2H), 1.89 (m, 2H), 1.66-1.77 (m, 3H), 1.42-1.58 (m, 2H), 1.2-1.4 (m, 2H), 0.89 (d, 3H), 0.85 (d, 3H).

Example 86

4-(6-Methoxy-benzofuran-3-ylmethoxy)-1H-indole-2-carboxylic acid {1-[(1S,9aR)-1-(octahydro-quinolizin-1-yl)methyl]-piperidin-4-yl}-amide

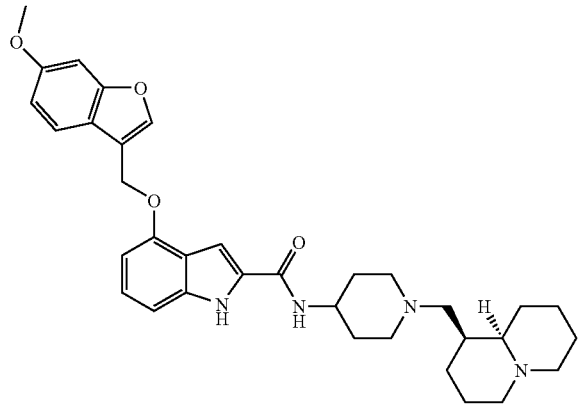

This compound is synthesized from 4-(6-methoxy-benzofuran-3-ylmethoxy)-1H-indole-2-carboxylic acid (120) (preparation see below) and amine 61 analogously to the method described in example 1.

Yield: 108 mg (63.8%). MS (ESI): 571 [M+H]$^+$, 1H-NMR (DMSO-d$_6$): δ (ppm) 11.45 (s, 1H), 8.1 (d, 1H), 8.03 (s, 1H), 7.55 (d, 1H), 7.2 (m, 2H), 7.08 (dd, 1H), 7.0 (d, 1H), 6.93 (dd, 1H), 6.7 (d, 1H), 5.3 (s, 2H), 3.78 (s, 3H), 3.73 (m, 1H), 2.65-2.85 (m, 4H), 2.47 (m, 1H), 2.25 (dd, 1H), 1.2-2.05 (m, 20H).

Synthesis of 4-(6-methoxy-benzofuran-3-yl-methoxy)-1H-indole-2-carboxylic acid (120)

This compound is synthesized from 3-methoxy-phenol analogously to the method described for 106 (see example 55). The cyclisation with concentrated sulphuric acid (Step C) gave exclusively the 6-substituted benzofurane.

MS (ESI): 336 [M–H]$^-$, 1H-NMR (DMSO-d$_6$): δ (ppm) 12.81 (brs, 1H), 11.71 (s, 1H), 8.02 (s, 1H), 7.56 (d, 1H), 7.18 (s, 1H), 7.13 (dd, 1H), 7.01 (s, 1H), 6.99 (m, 1H), 6.9 (dd, 1H), 6.71 (d, 1H), 5.33 (s, 2H), 3.78 (s, 3H).

Example 87

4-(6-Methoxy-benzofuran-3-ylmethoxy)-1H-indole-2-carboxylic acid [1-(2-azepan-1-yl-ethyl)-piperidin-4-yl]-amide

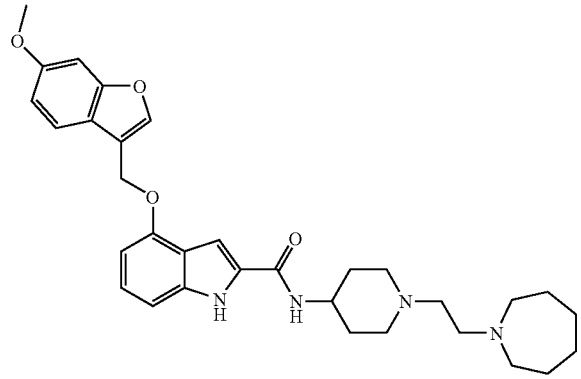

This compound is synthesized from 4-(6-methoxy-benzofuran-3-ylmethoxy)-1H-indole-2-carboxylic acid (120, see example 86) and amine 5 analogously to the method described in example 1.

Yield: 121 mg (50%). MS (ESI): 545 [M+H]$^+$, 1H-NMR (DMSO-d$_6$): δ (ppm) 11.5 (s, 1H), 8.12 (d, 1H), 8.05 (s, 1H), 7.55 (d, 1H), 7.2 (m, 2H), 7.08 (dd, 1H), 7.0 (d, 1H), 6.91 (dd, 1H), 6.7 (d, 1H), 5.3 (s, 2H), 3.8 (s, 3H), 3.7 (m, 1H), 2.85 (m, 2H), 2.5-2.6 (m, 8H), 2.35 (dd, 2H), 2.0 (m, 2H), 1.72 (m, 2H), 1.45-1.6 (m, 8H).

Example 88

4-(6-Methoxy-benzofuran-3-ylmethoxy)-1H-indole-2-carboxylic acid {1-[2-(4-hydroxy-piperidin-1-yl)-ethyl]-piperidin-4-yl}-amide

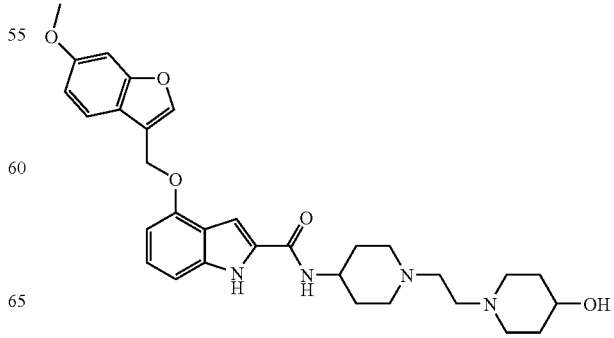

This compound is synthesized from 4-(6-methoxy-benzofuran-3-ylmethoxy)-1H-indole-2-carboxylic acid (120, see example 86) and amine 21 analogously to the method described in example 1.

Yield: 65 mg (27%). MS (ESI): 547 [M+H]$^+$, 1H-NMR (DMSO-d$_6$): δ (ppm) 11.45 (s, 1H), 8.1 (br d, 1H), 8.03 (s, 1H), 7.55 (d, 1H), 7.18 (m, 2H), 7.08 (dd, 1H), 7.0 (d, 1H), 6.9 (dd, 1H), 6.68 (d, 1H), 5.3 (s, 2H), 4.5 (br, 1H), 3.78 (s, 3H), 3.72 (m, 1H), 3.4 (m, 1H), 2.9 (m, 2H), 2.7 (m, 2H), 2.4 (m, 4H), 2.0 (m, 4H), 1.7 (m, 4H), 1.5 (m, 2H), 1.35 (m, 2H).

Example 89

4-(6-Methoxy-benzofuran-3-ylmethoxy)-1H-indole-2-carboxylic acid {1-[2-((3S,4S)-4-hydroxy-3-methyl-piperidin-1-yl)-ethyl]-piperidin-4-yl}-amide dihydrochloride

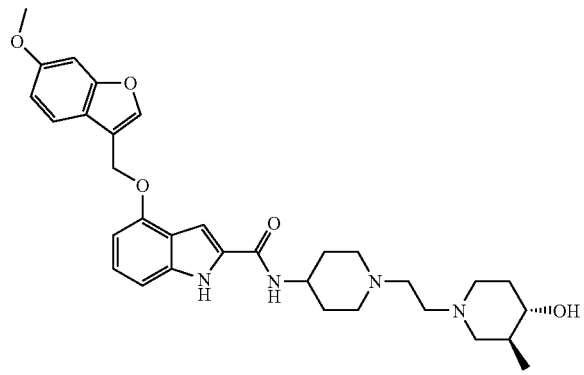

This compound is synthesized from 4-(6-methoxy-benzofuran-3-ylmethoxy)-1H-indole-2-carboxylic acid (120, see example 86) and amine 14 analogously to the method described in example 1.

Yield: 188 mg (89%). MS (ESI): 561 [M+H]$^+$, 1H-NMR (DMSO-d$_6$): δ (ppm) 11.55 (s, 1H), 10.6 (br, 2H), 8.5 (d, 1H), 8.04 (s, 1H), 7.55 (d, 1H), 7.1-7.3 (m, 3H), 7.0 (d, 1H), 6.9 (dd, 1H), 6.71 (d, 1H), 5.34 (s, 2H), 2.6-4.2 (m, 14H), 1.75-2.2 (m, 8H), 0.93 (d, 3H).

Example 90

4-(6-Methoxy-benzofuran-3-ylmethoxy)-1H-indole-2-carboxylic acid {1-[(S)-2-(4-hydroxy-piperidin-1-yl)-propyl]-piperidin-4-yl}-amide

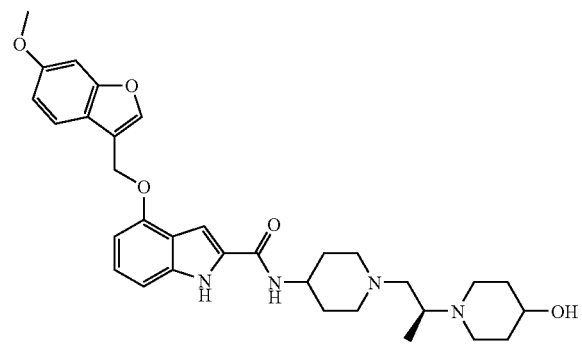

This compound is synthesized from 4-(6-methoxy-benzofuran-3-ylmethoxy)-1H-indole-2-carboxylic acid (120, see example 86) and amine 50 analogously to the method described in example 1.

Yield: 63 mg (38%). MS (ESI): 561 [M+H]$^+$, 1H-NMR (DMSO-d$_6$): δ (ppm) 11.5 (s, 1H), 8.18 (d, 1H), 8.04 (s, 1H), 7.55 (d, 1H), 7.2 (m, 2H), 7.08 (dd, 1H), 7.0 (d, 1H), 6.9 (dd, 1H), 6.7 (d, 1H), 5.3 (s, 2H), 4.75 (br, 1H), 2.6-4.1 (m, 7H), 0.9-2.4 (m, 20H).

Example 91

4-(6-Methoxy-benzofuran-3-ylmethoxy)-1H-indole-2-carboxylic acid {1-[(S)-2-((3S,4S)-4-hydroxy-3-methyl-piperidin-1-yl)-propyl]-piperidin-4-yl}-amide

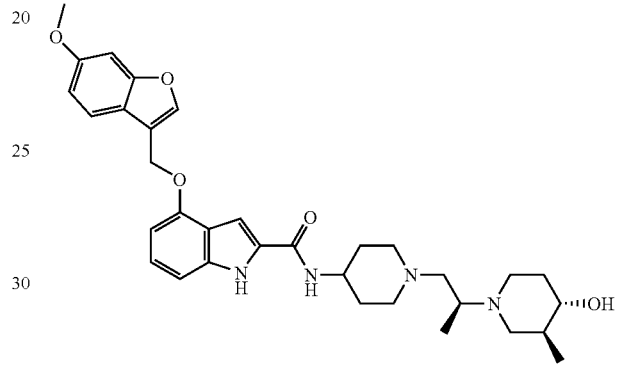

This compound is synthesized analogously to example 1 from 4-(6-methoxy-benzofuran-3-ylmethoxy)-1H-indole-2-carboxylic acid, 120 (see example 86) and amine 56.

MS (ESI): 575.1 [M+H]$^+$, 1H-NMR (DMSO-d$_6$): δ (ppm) 11.47 (s, 1H), 8.03 (s, 1H), 7.56 (d, 1H), 7.21 (d, 1H), 7.19 (s, 1H), 7.08 (t, 1H), 7.01 (d, 1H), 6.92 (d, 1H), 6.69 (d, 1H), 5.3 (s, 2H), 3.8 (s, 3H), 3.65-3.8 (m, 1H), 3.31 (m, 2H), 2.59-2.92 (m, 6H), 2.01-2.4 (m, 4H), 1.89 (m, 2H), 1.65-1.78 (m, 3H), 1.19-1.59 (m, 4H), 0.89 (d, 3H), 0.86 (d, 3H).

Example 92

4-(5-Methoxy-benzofuran-3-ylmethoxy)-1H-indole-2-carboxylic acid [1-(2-azepan-1-yl-ethyl)-piperidin-4-yl]-amide

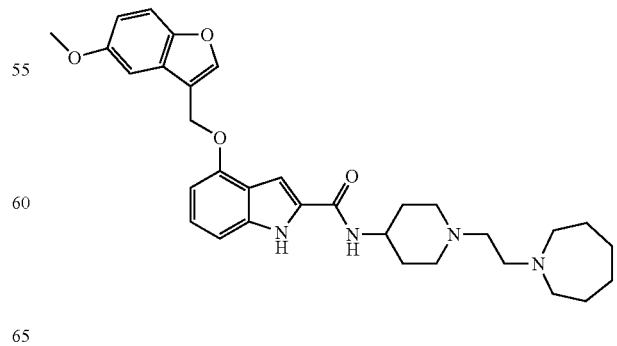

This compound is synthesized from 4-(5-methoxy-benzofuran-3-ylmethoxy)-1H-indole-2-carboxylic acid (121)

(preparation see below) and amine 5 analogously to the method described in example 1.

Yield: 77 mg (48%). MS (ESI): 545 [M+H]$^+$, 1H-NMR (DMSO-d$_6$): δ (ppm) 11.48 (s, 1H), 8.13 (m, 2H), 7.48 (d, 1H), 7.23 (s, 1H), 7.2 (d, 1H), 7.08 (dd, 1H), 7.02 (d, 1H), 6.92 (dd, 1H), 6.71 (d, 1H), 5.32 (s, 2H), 3.74 (s, 3H), 3.68 (m, 1H), 2.83 (m, 2H), 2.5-2.6 (m, 8H), 2.35 (dd, 2H), 1.98 (dd, 2H), 1.70 (m, 2H), 1.45-1.6 (m, 8H).

Synthesis of 4-(5-methoxy-benzofuran-3-yl-methoxy)-1H-indole-2-carboxylic acid (121)

This compound is synthesized from 4-methoxy-phenol analogously to the method described for 106 (see example 55).

460 mg (86%). MS (ESI): 336 [M−H]$^−$, 1H-NMR (DMSO-d$_6$): δ (ppm) 12.79 (br s, 1H), 11.73 (s, 1H), 8.1 (s, 1H), 7.46 (d, 1H), 7.22 (d, 1H), 7.15 (dd, 1H), 7.06 (d, 1H), 7.02 (d, 1H), 6.91 (dd, 1H), 6.73 (d, 1H), 5.37 (s, 2H), 3.75 (s, 3H).

Example 93

4-(5-Methoxy-benzofuran-3-ylmethoxy)-1H-indole-2-carboxylic acid {1-[2-(4-hydroxy-piperidin-1-yl)-ethyl]-piperidin-4-yl}-amide

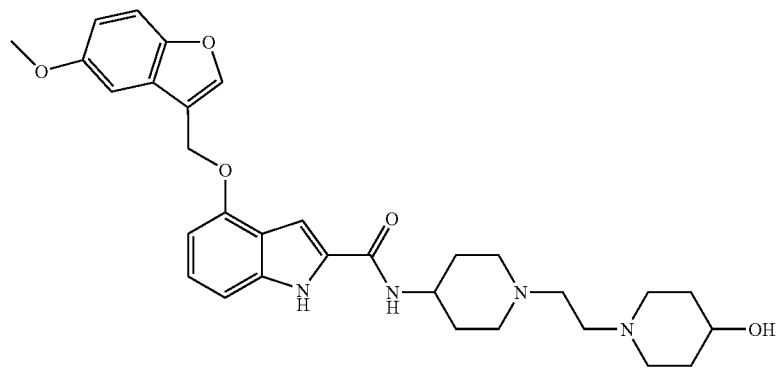

This compound is synthesized from 4-(5-methoxy-benzofuran-3-ylmethoxy)-1H-indole-2-carboxylic acid (121, see example 92) and amine 21 analogously to the method described in example 1.

Yield: 105 mg (65%). MS (ESI): 547 [M+H]$^+$, 1H-NMR (DMSO-d$_6$): δ (ppm) 11.5 (s, 1H), 8.15 (d, 1H), 8.11 (s, 1H), 7.49 (d, 1H), 7.24 (s, 1H), 7.20 (d, 1H), 7.09 (dd, 1H), 7.02 (d, 1H), 6.93 (dd, 1H), 6.71 (d, 1H), 5.33 (s, 2H), 4.51 (br, 1H), 3.75 (s, 3H), 3.7 (m, 1H), 3.41 (m, 1H), 2.85 (m, 2H), 2.7 (m, 2H), 2.39 (m, 4H), 2.0 (m, 4H), 1.71 (m, 4H), 1.52 (m, 2H), 1.35 (m, 2H).

Example 94

4-(4-Methoxy-benzofuran-3-ylmethoxy)-1H-indole-2-carboxylic acid {1-[(1S,9aR)-1-(octahydro-quinolizin-1-yl)methyl]-piperidin-4-yl}-amide

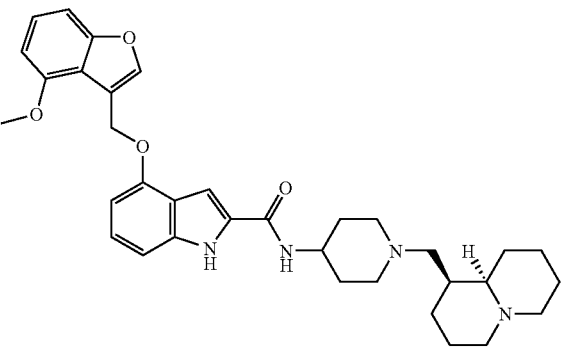

This compound is synthesized analogously to example 1 from 4-(4-methoxy-benzofuran-3-ylmethoxy)-1H-indole-2-carboxylic acid (122) (preparation see below) and 1-[(1S,9aR)-1-(octahydro-quinolizin-1-yl)methyl]-piperidin-4-ylamine, 61.

MS (ESI): 571.2 [M+H]$^+$, 1H-NMR (CD$_3$OD): δ (ppm) 7.75 (s, 1H), 7.27 (s, 1H), 7.25 (t, 1H), 7.18 (t, 1H), 7.10 (d, 1H), 7.07 (d, 1H), 6.75 (d, 1H), 6.67 (d, 1H), 5.43 (s, 2H), 4.15 (br s, 1H), 3.4-3.8 (br m, 7H), 3.83 (s, 3H), 2.9-3.25 (m, 4H), 2.53 (br m, 1H), 1.5-2.3 (m, 14H).

Synthesis of 4-(4-Methoxy-benzofuran-3-yl-methoxy)-1H-indole-2-carboxylic acid (122)

(1) 4-Methoxy-benzofuran-3-carbaldehyde, 123

To a solution of 4-methoxy-3-methyl-benzofuran (J. Chem. Res. Synopses (1996), 132) (4 g, 24.66 mmol) in 40 ml of dioxane is added selenium dioxide (3.39 g, 29.59 mmol) and the mixture is heated under reflux for 24 hours. It is then cooled and filtered. The solvent is evaporated and the crude red solid is used as such in the next step.

Yield: 4.86 g (>100%). MS (ESI): 177.0 [M+H]$^+$.

(2) (4-Methoxy-benzofuran-3-yl)-methanol, 124

The aldehyde 123 from above (4.34 g, 24.63 mmol) is dissolved in 10 ml of methanol and cooled in an ice-bath. Solid sodium borohydride (4.9 g, 123.2 mmol) is added in portions and the mixture is stirred for 2 hours. It is then poured onto ice-cold HCl, extracted three times with DCM, dried and evaporated. The crude material is purified by chromatography on silicagel using hexane and EtOAc (from 20% to 50%).

Yield: 1.82 g (41%). MS (ESI): 196.1 [M+NH$_4$]$^+$.

(3) 4-(4-Methoxy-benzofuran-3-ylmethoxy)-indole-1,2-dicarboxylic acid 1-tert-butyl ester 2-ethyl ester, 125

Indole ester 125 is prepared from alcohol 124 and 102 under Mitsunobu conditions (as described in example 50 for 105).

MS (ESI): 410.2 [(M−CMe$_3$)+H]$^+$.

(4) 4-(4-Methoxy-benzofuran-3-ylmethoxy)-1H-indole-2-carboxylic acid, 122

The title compound is prepared from ester 125 by cleavage with KOH/EtOH/THF (as described in example 50 for 105).

MS (ESI): 338.2 [M+H]$^+$, 1H-NMR (DMSO-d$_6$): δ (ppm) 11.76 (s, 1H), 8.07 (s, 1H), 7.29 (t, 1H), 7.21 (s, 1H), 7.19 (t, 1H), 7.1 (s, 1H), 7.04 (d, 1H), 6.83 (d, 1H), 6.69 (d, 1H), 5.39 (s, 2H), 3.84 (s, 3H).

Example 95

4-(4-Methoxy-benzofuran-3-ylmethoxy)-1H-indole-2-carboxylic acid {1-[2-(4-hydroxy-piperidin-1-yl)-ethyl]-piperidin-4-yl}-amide

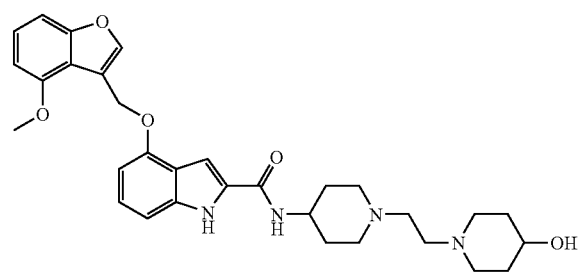

This compound is synthesized analogously to example 1 from 4-(4-methoxy-benzofuran-3-ylmethoxy)-1H-indole-2-carboxylic acid 122 (see example 94) and amine 21.

MS (ESI): 547.2 [M+H]$^+$, 1H-NMR (CD$_3$OD): δ (ppm) 7.63 (s, 1H), 7.13 (s, 1H), 7.12 (t, 1H), 7.04 (t, 1H), 6.98 (d, 1H), 6.94 (d, 1H), 6.62 (d, 1H), 6.53 (d, 1H), 5.3 (s, 2H), 3.76 (m, 1H), 3.71 (s, 3H), 3.54 (m, 1H), 2.85 (m, 2H), 2.73 (m, 2H), 2.42 (m, 4H), 2.07 (m, 4H), 1.81 (m, 2H), 1.74 (m, 2H), 1.53 (m, 2H), 1.45 (m, 2H).

Example 96

4-(4-Methoxy-benzofuran-3-ylmethoxy)-1H-indole-2-carboxylic acid {1-[2-((3S,4S)-4-hydroxy-3-methyl-piperidin-1-yl)-ethyl]-piperidin-4-yl}-amide

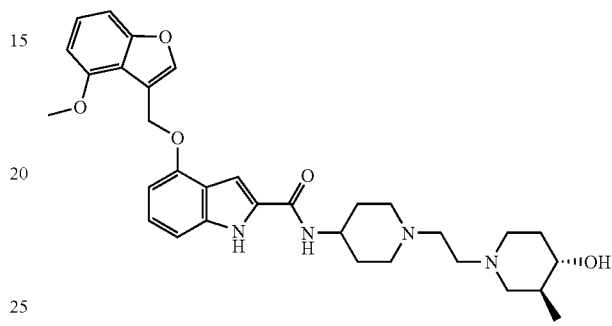

This compound is synthesized analogously to example 1 from 4-(4-methoxy-benzofuran-3-ylmethoxy)-1H-indole-2-carboxylic acid 122 (see example 94) and amine 14.

MS (ESI): 561.3 [M+H]$^+$, 1H-NMR (DMSO-d$_6$): δ (ppm) 11.47 (s, 1H), 8.09 (d, 1H), 8.01 (s, 1H), 7.27 (t, 1H), 7.23 (s, 1H), 7.2 (t, 1H), 7.09 (t, 1H), 7.01 (d, 1H), 6.81 (d, 1H), 6.65 (d, 1H), 5.34 (s, 2H), 4.47 (d, 1H), 3.79 (s, 3H), 3.7 (m, 1H), 2.64-2.93 (m, 4H), 2.35 (m, 4H), 1.82-2.05 (m, 3H), 1.63-1.8 (m, 3H), 1.26-1.63 (m, 6H), 0.85 (d, 3H).

Example 97

4-(4-Methoxy-benzofuran-3-ylmethoxy)-1H-indole-2-carboxylic acid {1-[(S)-2-(4-hydroxy-piperidin-1-yl)-propyl]-piperidin-4-yl}-amide

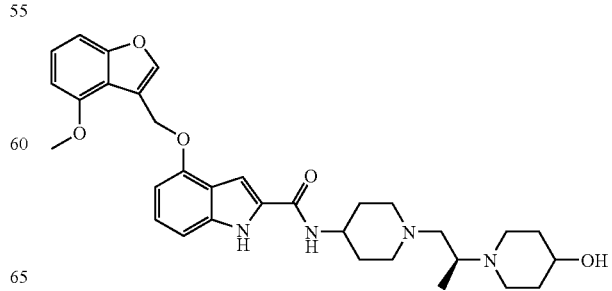

This compound is synthesized analogously to example 1 from 4-(4-methoxy-benzofuran-3-ylmethoxy)-1H-indole-2-carboxylic acid, 122 (see example 94) and amine 50.

MS (ESI): 561.2 [M+H]$^+$, 1H-NMR (CD$_3$OD): δ (ppm) 7.62 (s, 1H), 7.13 (s, 1H), 7.12 (t, 1H), 7.04 (t, 1H), 6.97 (d, 1H), 6.94 (d, 1H), 6.62 (d, 1H), 6.52 (d, 1H), 5.3 (s, 2H), 3.74 (m, 1H), 3.71 (s, 3H), 3.46 (br m, 1H), 2.93 (m, 1H), 2.77 (m, 1H), 2.65-2.75 (m, 3H), 2.4 (m, 1H), 2.28 (m, 2H), 2.12 (m, 2H), 1.97 (m, 1H) 1.75 (m, 4H), 1.35-1.65 (m, 5H), 0.93 (d, 3H).

Example 98

4-(4-Methoxy-benzofuran-3-ylmethoxy)-1H-indole-2-carboxylic acid {1-[(S)-2-((3S,4S)-4-hydroxy-3-methyl-piperidin-1-yl)-propyl]-piperidin-4-yl}-amide

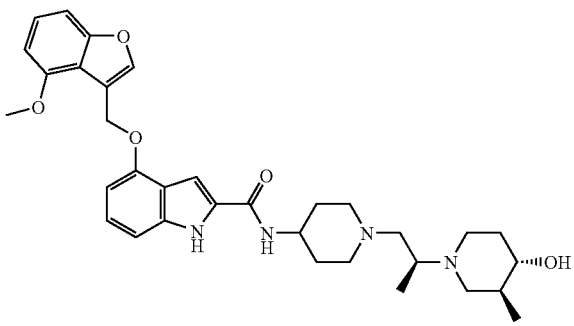

This compound is synthesized analogously to example 1 from 4-(4-methoxy-benzofuran-3-ylmethoxy)-1H-indole-2-carboxylic acid, 122 (see example 94) and amine 56.

MS (ESI): 575.1 [M+H]$^+$, 1H-NMR (DMSO-d$_6$): δ (ppm) 11.45 (s, 1H), 8.08 (m, 1H), 8.0 (s, 1H), 7.27 (t, 1H), 7.22 (s, 1H), 7.2 (t, 1H), 7.09 (t, 1H), 7.01 (d, 1H), 6.81 (d, 1H), 6.65 (d, 1H), 5.34 (s, 2H), 4.42 (m, 1H), 3.79 (s, 3H), 3.73 (m, 1H), 2.58-2.92 (m, 6H), 2.31 (m, 1H), 2.22 (m, 1H), 2.02-2.17 (m, 2H), 1.89 (m, 2H), 1.66-1.78 (m, 3H), 1.2-1.6 (m, 4H), 0.9 (d, 3H), 0.86 (d, 3H).

Example 99

4-(4,6-dimethoxy-benzofuran-3-ylmethoxy)-1H-indole-2-carboxylic acid {1-[(1S,9aR)-1-(octahydro-quinolizin-1-yl)methyl]-piperidin-4-yl}-amide dihydrochloride

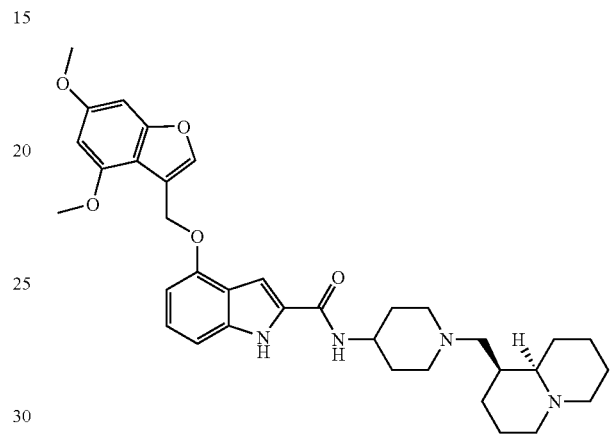

This compound is synthesized from 4-(4,6-dimethoxy-benzofuran-3-ylmethoxy)-1H-indole-2-carboxylic acid 126 (preparation see below) and amine 61 analogously to the method described in example 1.

Yield: 146 mg (76.3%). MS (ESI): 601 [M+H]$^+$, 1H-NMR (DMSO-d$_6$): δ (ppm) 11.5 (s, 1H), 10.1-10.7 (br, 2H), 8.1-8.5 (br, 1H), 7.89 (s, 1H), 7.3 (brs, 1H), 7.1 (dd, 1H), 7.0 (d, 1H), 6.8 (s, 1H), 6.62 (d, 1H), 6.42 (s, 1H), 5.28 (s, 2H), 4.0 (m, 1H), 3.8 (s, 3H), 3.75 (s, 3H), 2.8-3.8 (m, 14H), 1.3-2.1 (m, 12H).

Synthesis of 4-(4,6-dimethoxy-benzofuran-3-yl-methoxy)-1H-indole-2-carboxylic acid (126)

This compound is synthesized from 3,5-dimethoxyphenol analogously to the method described for 106 (see example 55).

MS (ESI): 366 [M–H]$^-$, 1H-NMR (DMSO-d$_6$): δ (ppm) 12.78 (br s, 1H), 11.7 (s, 1H), 7.89 (s, 1H), 7.14 (dd, 1H), 7.08 (d, 1H), 7.02 (d, 1H), 6.78 (d, 1H), 6.65 (d, 1H), 6.41 (d, 1H), 5.31 (s, 2H), 3.79 (s, 3H), 3.31 (s, 3H).

Example 100

4-(4,6-Dimethoxy-benzofuran-3-ylmethoxy)-1H-indole-2-carboxylic acid {1-[2-(4-hydroxy-piperidin-1-yl)-ethyl]-piperidin-4-yl}-amide

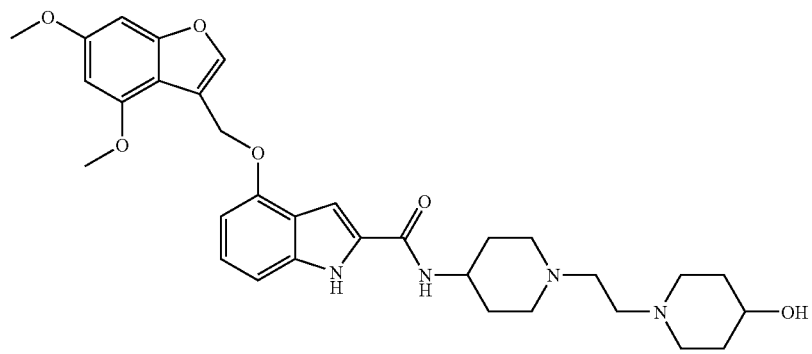

This compound is synthesized analogously to example 1 from 4-(4,6-dimethoxy-benzofuran-3-ylmethoxy)-1H-indole-2-carboxylic acid, 126 (see example 99) and amine 21.

MS (ESI): 577.2 [M+H]$^+$, 1H-NMR (DMSO-d$_6$): δ (ppm) 11.46 (s, 1H), 8.1 (d, 1H), 7.87 (s, 1H), 7.22 (s, 1H), 7.08 (t, 1H), 7.0 (d, 1H), 6.81 (s, 1H), 6.63 (d, 1H), 6.42 (s, 1H), 5.28 (s, 2H), 4.49 (m, 1H), 3.8 (s, 3H), 3.76 (s, 3H), 3.73 (m, 1H), 3.16 (m, 1H), 2.85 (m, 2H), 2.69 (m, 2H), 2.36 (m, 4H) 1.99 (m, 4H), 1.7 (m, 4H), 1.5 (m, 2H), 1.34 (m, 2H).

Example 101

4-(4,6-Dimethoxy-benzofuran-3-ylmethoxy)-1H-indole-2-carboxylic acid {1-[2-((3S,4S)-4-hydroxy-3-methyl-piperidin-1-yl)-ethyl]-piperidin-4-yl}-amide dihydrochloride

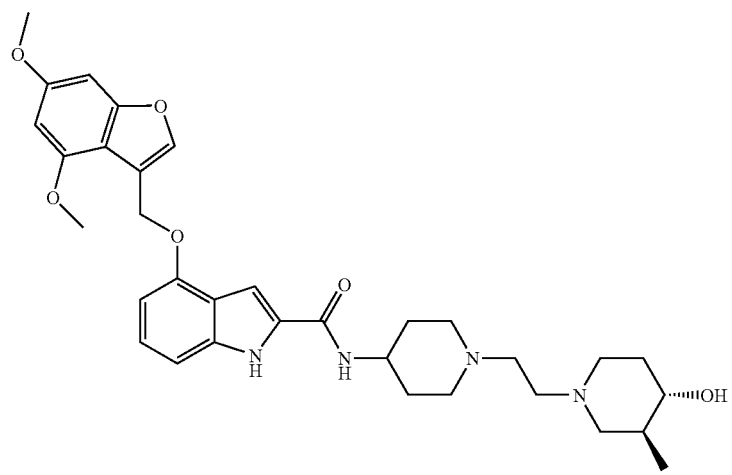

This compound is synthesized from 4-(4,6-dimethoxy-benzofuran-3-ylmethoxy)-1H-indole-2-carboxylic acid (126, see example 99) and amine 14 analogously to the method described in example 1.

Yield: 85 mg (47%). MS (ESI): 591 [M+H]$^+$, 1H-NMR (DMSO-d$_6$): δ (ppm) 11.5 (s, 1H), 10.6 (br, 2H), 8.5 (d, 1H), 7.87 (s, 1H), 7.25 (s, 1H), 7.1 (dd, 1H), 7.02 (d, 1H), 6.8 (d, 1H), 6.64 (d, 1H), 6.4 (d, 1H), 5.26 (s, 2H), 5.1 (br, 1H), 4.05 (m, 1H), 3.8 (s, 3H), 3.77 (s, 3H), 2.6-3.8 (m, 12H), 1.75-2.2 (m, 8H), 0.93 (d, 3H).

Example 102

4-(4,6-Dimethoxy-benzofuran-3-ylmethoxy)-1H-indole-2-carboxylic acid {1-[(S)-2-(4-hydroxy-piperidin-1-yl)-propyl]-piperidin-4-yl}-amide

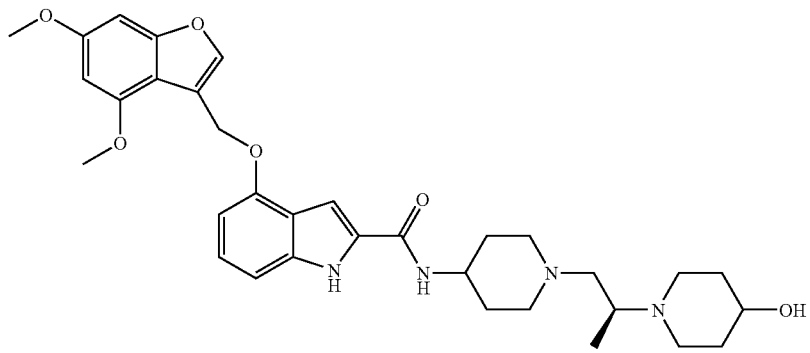

This compound is synthesized analogously to example 1 from 4-(4,6-dimethoxy-benzofuran-3-ylmethoxy)-1H-indole-2-carboxylic acid, 126 (see example 99) and amine 50.

MS (ESI): 591.3 [M+H]$^+$, 1H-NMR (CD$_3$OD): δ (ppm) 7.63 (s, 1H), 7.23 (s, 1H), 7.14 (t, 1H), 7.04 (d, 1H), 6.67 (s, 1H), 6.62 (d, 1H), 6.37 (s, 1H), 5.35 (d, 2H), 3.85 (m, 1H), 3.82 (s, 3H), 3.78 (s, 3H), 3.57 (m, 1H), 3.05 (m, 1H), 2.89 (m, 1H), 2.75-2.87 (m, 3H), 2.35-2.55 (m, 3H), 2.24 (m, 2H), 2.08 (m, 1H), 1.8-1.95 (m, 4H), 1.45-1.75 (m, 4H), 1.04 (d, 3H).

Example 103

4-(4,6-Dimethoxy-benzofuran-3-ylmethoxy)-1H-indole-2-carboxylic acid {1-[(S)-2-((3S,4S)-4-hydroxy-3-methyl-piperidin-1-yl)-propyl]-piperidin-4-yl}-amide

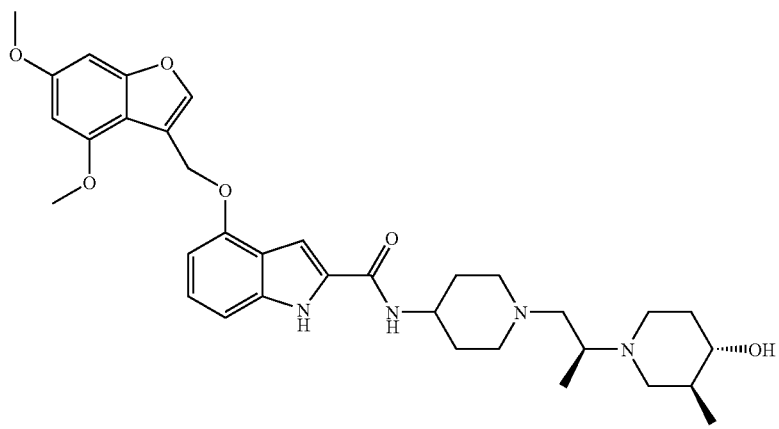

This compound is synthesized analogously to example 1 from 4-(4,6-dimethoxy-benzofuran-3-ylmethoxy)-1H-indole-2-carboxylic acid, 126 (see example 99) and amine 56.

MS (ESI): 605.1 [M+H]$^+$, 1H-NMR (CD$_3$OD): δ (ppm) 7.64 (s, 1H), 7.23 (s, 1H), 7.15 (t, 1H), 7.05 (d, 1H), 6.69 (s, 1H), 6.64 (d, 1H), 6.38 (s, 1H), 4.85 (s, 2H), 3.88 (m, 1H), 3.84 (s, 3H), 3.8 (s, 3H), 2.78-3.17 (m, 6H), 2.57 (m, 1H), 2.23-2.47 (m, 3H), 2.03-2.21 (m, 2H), 1.87-1.98 (m, 3H), 1.45-1.8 (m, 4H), 1.08 (d, 3H), 0.99 (d, 3H).

Example 104

4-(5,6-dimethyl-benzofuran-3-ylmethoxy)-1H-indole-2-carboxylic acid {1-[(1S,9aR)-1-(octahydro-quinolizin-1-yl)methyl]-piperidin-4-yl}-amide dihydrochloride

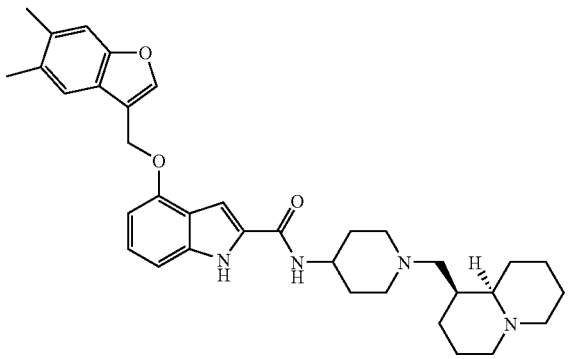

This compound is synthesized from 4-(5,6-dimethyl-benzofuran-3-ylmethoxy)-1H-indole-2-carboxylic acid 127 (preparation see below) and amine 61 analogously to the method described in example 1.

Yield: 146 mg (76.3%). MS (ESI): 569 [M+H]$^+$, 1H-NMR (DMSO-d$_6$): δ (ppm) 11.45 (s, 1H), 10.4-10.4 (br, 2H), 8.5 (br, 1H), 8.02 (s, 1H), 7.45 (s, 1H), 7.38 (s, 1H), 7.27 (br s, 1H), 7.1 (dd, 1H), 7.02 (d, 1H), 6.7 (d, 1H), 5.3 (s, 2H), 4.0 (m, 1H), 2.8-3.8 (m, 14H), 2.32 (s, 3H), 2.28 (s, 3H), 1.3-2.1 (m, 12H).

Synthesis of 4-(5,6-dimethyl-benzofuran-3-ylmethoxy)-1H-indole-2-carboxylic acid (127)

This compound is synthesized from 3,4-dimethylphenol analogously to the method described for 106 (see example 55).

MS (ESI): 334 [M−H]$^-$, 1H-NMR (DMSO-d$_6$): δ (ppm) 12.9 (brs, 1H), 11.55 (s, 1H), 8.02 (s, 1H), 7.47 (s, 1H), 7.38 (s, 1H), 7.15 (dd, 1H), 7.0 (m, 2H), 6.7 (d, 1H), 5.3 (s, 2H), 2.35 (s, 3H), 2.3 (s, 3H).

Example 105

4-(5,6-Dimethyl-benzofuran-3-ylmethoxy)-1H-indole-2-carboxylic acid {1-[2-(4-hydroxy-piperidin-1-yl)-ethyl]-piperidin-4-yl}-amide

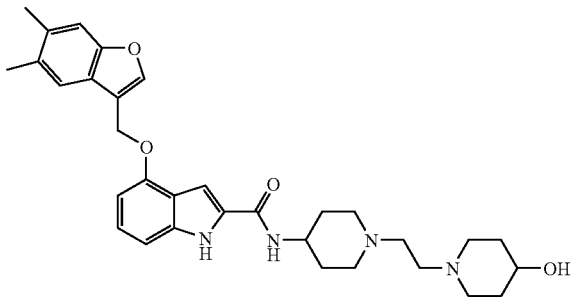

This compound is synthesized from 4-(5,6-dimethyl-benzofuran-3-ylmethoxy)-1H-indole-2-carboxylic acid (127, see example 104) and amine 21 analogously to the method described in example 1.

Yield: 96 mg (51%). MS (ESI): 545.5 [M+H]$^+$, 1H-NMR (DMSO-d$_6$): δ (ppm) 11.5 (s, 1H), 8.09 (d, 1H), 8.05 (s, 1H), 7.22 (s, 1H), 7.18 (s, 1H), 7.10 (dd, 1H), 7.0 (d, 1H), 6.88 (s, 1H), 6.7 (d, 1H), 5.28 (s, 2H), 4.45 (d, 1H), 3.7 (m, 1H), 3.38 (m, 1H), 2.84 (m, 2H), 2.7 (m, 2H), 2.5 (s, 3H), 2.38 (s, 3H), 2.35 (m, 4H), 1.95 (m, 4H), 1.7 (m, 4H), 1.45 (m, 2H), 1.3 (m, 2H).

Example 106

4-(5,6-Dimethyl-benzofuran-3-ylmethoxy)-1H-indole-2-carboxylic acid {1-[2-((3S,4S)-4-hydroxy-3-methyl-piperidin-1-yl)-ethyl]-piperidin-4-yl}-amide dihydrochloride

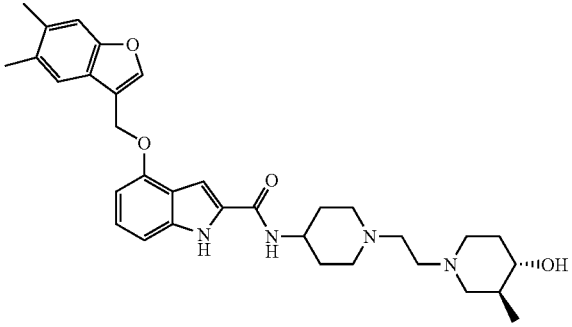

This compound is synthesized from 4-(5,6-dimethyl-benzofuran-3-ylmethoxy)-1H-indole-2-carboxylic acid (127, see example 104) and amine 14 analogously to the method described in example 1.

Yield: 105 mg (56%). MS (ESI): 559 [M+H]$^+$, 1H-NMR (DMSO-d$_6$): δ (ppm) 11.5 (s, 1H), 10.6 (br, 2H), 8.5 (d, 1H), 8.02 (s, 1H), 7.45 (s, 1H), 7.4 (s, 1H), 7.25 (d, 1H), 7.1 (dd, 1H), 7.02 (d, 1H), 6.7 (d, 1H), 5.29 (s, 2H), 4.05 (m, 1H), 2.6-3.8 (m, 13H), 2.33 (s, 3H), 2.3 (s, 3H), 1.75-2.2 (m, 8H), 0.93 (d, 3H).

Example 107

4-(5,6-Dimethyl-benzofuran-3-ylmethoxy)-1H-indole-2-carboxylic acid {1-[(S)-2-(4-hydroxy-piperidin-1-yl)-propyl]-piperidin-4-yl}-amide dihydrochloride

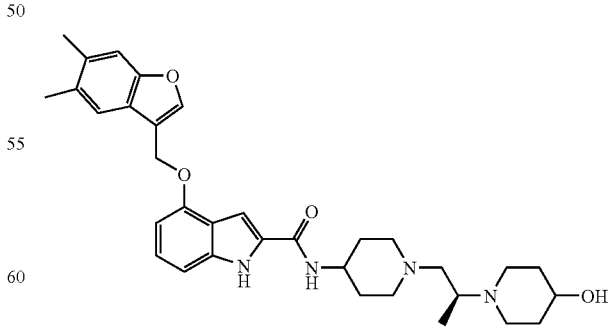

This compound is synthesized from 4-(5,6-dimethyl-benzofuran-3-ylmethoxy)-1H-indole-2-carboxylic acid (127, see example 104) and amine 50 analogously to the method described in example 1.

Yield: 112 mg (56.8%). MS (ESI): 559 [M+H]+, 1H-NMR (DMSO-d6): δ (ppm) 11.5 (s, 1H), 10.3-10.6 (br, 2H), 8.5 (d, 1H), 8.12 (s, 1H), 7.45 (s, 1H), 7.38 (s, 1H), 7.25 (s, 1H), 7.1 (dd, 1H), 7.03 (d, 1H), 6.7 (d, 1H), 5.3 (s, 2H), 5.05 (br, 1H), 2.9-4.1 (m, 13H), 2.35 (s, 3H), 2.28 (s, 3H), 1.7-2.2 (m, 8H), 1.35/1.3 (d, 3H) (rotamers).

Example 108

4-(5,6-Dimethyl-benzofuran-3-ylmethoxy)-1H-indole-2-carboxylic acid {1-[(S)-2-((3S,4S)-4-hydroxy-3-methyl-piperidin-1-yl)-propyl]-piperidin-4-yl}-amide dihydrochloride

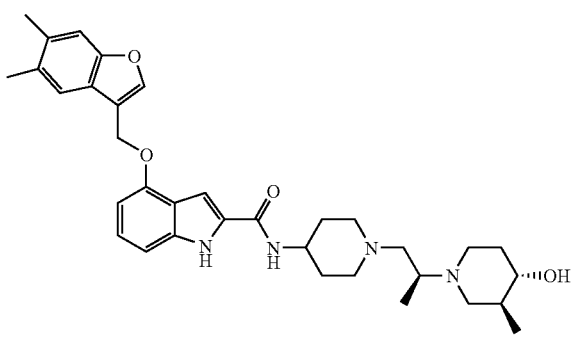

This compound is synthesized from 4-(5,6-dimethyl-benzofuran-3-ylmethoxy)-1H-indole-2-carboxylic acid (127, see example 104) and amine 56 analogously to the method described in example 1.

Yield: 130 mg (68%). MS (ESI): 573 [M+H]+, 1H-NMR (DMSO-d6): δ (ppm) 11.5 (s, 1H), 10.4-10.6 (br, 2H), 8.52 (d, 1H), 8.02 (s, 1H), 7.45 (s, 1H), 7.4 (s, 1H), 7.25 (s, 1H), 7.12 (dd, 1H), 7.03 (d, 1H), 6.7 (d, 1H), 5.3 (s, 2H), 5.1 (br, 1H), 4.05 (m, 1H), 2.8-3.9 (m, 13H), 2.32 (s, 3H), 2.29 (s, 3H), 1.9-2.1 (m, 6H), 1.32 (d, 3H), 0.93 (d, 3H).

Example 109

4-(4-Ethoxy-phenyl)-1H-indole-2-carboxylic acid {1-[(S)-2-(4-hydroxy-piperidin-1-yl)-propyl]-piperidin-4-yl}-amide

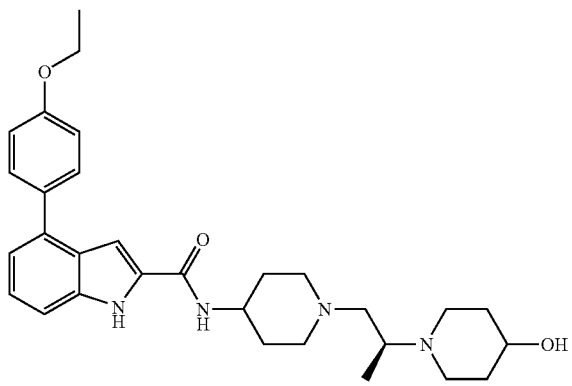

This compound is synthesized analogously to example 1 from 4-(4-ethoxy-phenyl)-1H-indole-2-carboxylic acid, (preparation analogously to 128, see example 141) and amine 50.

MS (ESI): 505.2 [M+H]+, 1H-NMR (DMSO-d6): δ (ppm) 11.6 (s, 1H), 8.25 (d, 1H), 7.56 (d, 2H), 7.36 (d, 1H), 7.31 (s, 1H), 7.2 (t, 1H), 7.05 (d, 2H), 7.02 (d, 1H), 4.48 (m, 1H), 4.09 (q, 2H), 3.76 (m, 1H), 3.37 (m, 1H), 2.58-2.96 (m, 5H), 1.85-2.43 (m, 6H), 1.42-1.83 (m, 6H), 1.37 (t, 3H), 1.33 (m, 2H), 0.93 (d, 3H).

Example 110

4-(4-Methoxy-phenyl)-1H-indole-2-carboxylic acid {1-[(S)-2-(4-hydroxy-piperidin-1-yl)-propyl]-piperidin-4-yl}-amide

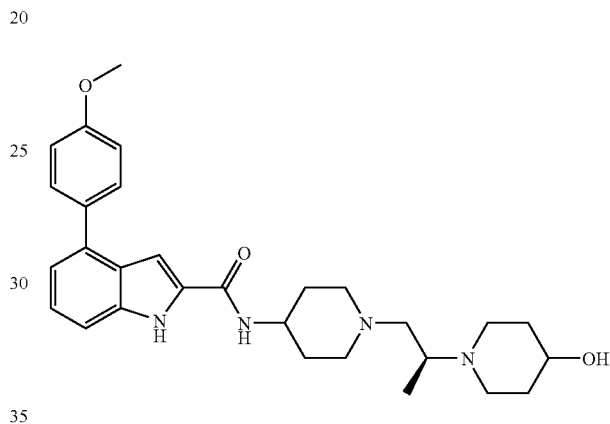

This compound is synthesized analogously to example 1 from 4-(4-methoxy-phenyl)-1H-indole-2-carboxylic acid, 128 (see example 141) and amine 50.

MS (ESI): 491 [M+H]+, 1H-NMR (DMSO-d6): δ (ppm) 11.59 (s, 1H), 8.23 (d, 1H), 7.56 (d, 2H), 7.34 (d, 1H), 7.31 (s, 1H), 7.2 (t, 1H), 7.06 (d, 2H), 7.01 (d, 1H), 4.44 (d, 1H), 3.81 (s, 3H), 3.75 (m, 1H), 2.96 (m, 1H), 2.6-2.95 (m, 5H), 2.04-2.4 (m, 5H), 1.92 (m, 1H), 1.2-1.85 (m, 8H), 0.91 (d, 3H).

The 4-aryloxy-indole-2-carboxamides are generally prepared by a coupling of the 4-hydroxy-indole-2-carboxamides with the corresponding 1-fluoro-2-nitro-benzenes (Reaction Scheme 15).

Reaction Scheme 15:

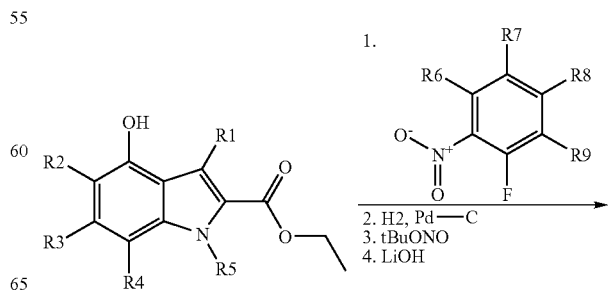

-continued

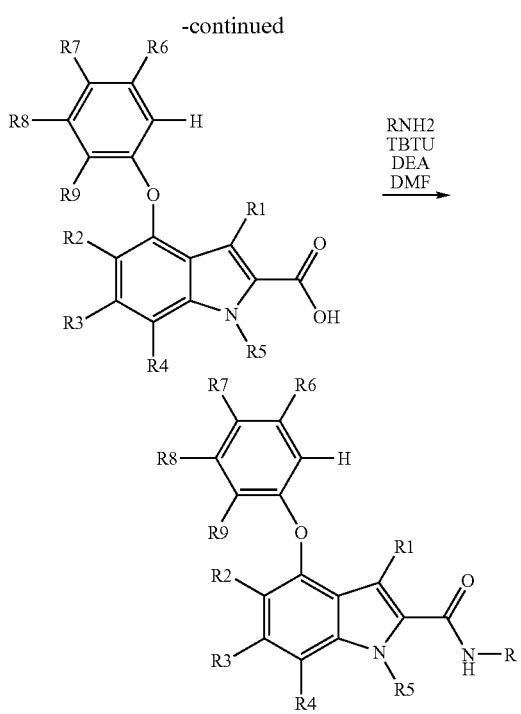

Example 111

4-Phenoxy-1H-indole-2-carboxylic acid [1-(2-azepan-1-yl-ethyl)-piperidin-4-yl]-amide

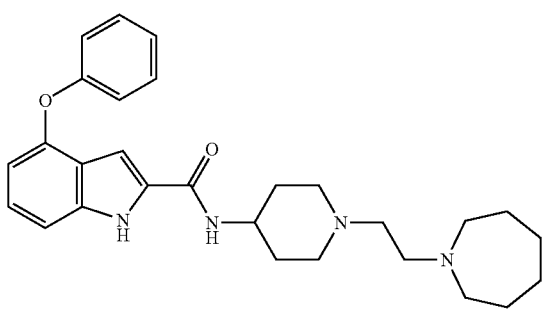

This compound is synthesized analogously to Example 1 from 4-phenoxy-1H-indole-2-carboxylic acid 129 (preparation see below) and amine 5.

Yield: 105 mg (41%) of a beige solid; MS (ESI): 459.4 [M−H]⁻, 1H-NMR (DMSO-d₆): δ (ppm) 11.7 (s, 1H), 8.22 (d, 1H), 7.34 (dd, 2H), 7.24 (d, 1H), 7.04-7.15 (m, 3H), 6.95 (d, 2H), 6.55 (d, 1H), 3.72 (m, 1H), 2.85 (m, 2H), 2.52-2.6 (m, 6H), 2.38 (m, 2H), 2.0 (t, 4H), 1.72 (m, 2H), 1.48 (m, 8H).

Synthesis of 4-Phenoxy-1H-indole-2-carboxylic acid (129)

(1) Step A: 4-(2-Nitro-phenoxy)-1H-indole-2-carboxylic acid ethyl ester (130)

4-Hydroxy-1H-indole-2-carboxylic acid ethyl ester (0.5 g, 2.436 mmol) and 2-fluoro-nitro-benzene (0.257 ml, 2.436 mmol) are dissolved in 10 ml of dimethylformamide. After addition of potassium carbonate (0.67 g, 4.87 mmol) the mixture is stirred over night at room temperature. Then the reaction mixture is evaporated under reduced pressure, dissolved with ethyl acetate and washed with water. The organic layers are dried over sodium sulfate and evaporated. The crude product is used in the next step without further purification.

Yield: 0.72 g (91%) of a beige solid. MS (ESI): 325.2 [M−H]⁻, 1H-NMR (DMSO-d₆): δ (ppm) 12.15 (s, 1H), 8.1 (d, 1H), 7.6 (dd, 1H), 7.32 (m, 2H), 7.25 (dd, 1H), 7.03 (d, 1H), 6.85 (m, 1H), 6.7 (d, 1H), 4.3 (q, 2H), 1.3 (t, 3H).

(2) Step B: 4-(2-Amino-phenoxy)-1H-indole-2-carboxylic acid ethyl (131)

130 (0.5 g, 1.532 mmol) is dissolved in 100 ml of ethanol and, after addition of Pd—C (100 mg), the mixture is hydrogenated at room temperature for 3 hours. The mixture is filtrated over celite to remove the catalyst and evaporated.

Yield: 390 mg (86%) of a grey solid. MS (ESI): 297 [M+H]⁺, 1H-NMR (DMSO-d₆): δ (ppm) 11.95 (s, 1H), 7.13 (m, 2H), 7.0 (s, 1H), 6.88 (m, 1H), 6.8 (dd, 1H), 6.75 (dd, 1H), 6.5 (m, 1H), 6.38 (m, 1H), 4.9 (br, 2H), 4.3 (q, 2H), 1.3 (t, 3H).

(3) Step C: 4-Phenoxy-1H-indole-2-carboxylic acid ethyl ester (132)

Tert-butyl nitrite (0.2 ml, 1.687 mmol) is dissolved in 5 ml of dimethylformamide and heated to 65° C. A solution of 131 (0.5 g, 1.687 mmol) in 5 ml of dimethylformamide is added dropwise and the mixture is stirred of additional 10 minutes. The brown solution is cooled to room temperature, diluted with diethyl ether and washed with 2N HCl and brine. The organic layers are dried over sodium sulphate and evaporated. The crude product (370 mg of a brown oil) is further purified by flash-chromatography (hexane/ethyl acetate 9:1).

Yield: 163 mg (34%) of a yellow solid; MS (ESI): 280.2 [M−H]⁻, 1H-NMR (DMSO-d₆): δ (ppm) 12.05 (s, 1H), 7.37 (d, 1H), 7.35 (d, 1H), 7.23 (m, 2H), 7.1 (dd, 1H), 7.0 (d, 2H), 6.82 (s, 1H), 6.6 (d, 1H), 4.3 (q, 2H), 1.3 (t, 3H).

(4) Step D: -Phenoxy-1H-indole-2-carboxylic acid (129)

132 (160 mg, 0.569 mmol) is dissolved in 5 ml of methanol and treated with a solution of LiOH (27.2 mg, 1.138 mmol) in 3 ml of water. The mixture is stirred at room temperature overnight. Since the reaction is not complete (TLC), additional LiOH (30 mg, 1.25 mmol) is added and the stirring is continued for additional 18 h. After evaporation, the crude product is acidified at 0° C. with 2M HCl and extracted with ethyl acetate. The organic layers are dried over sodium sulphate and evaporated.

Yield: 146 mg (100%) of a yellow solid; MS (ESI): 253 [M]+, 1H-NMR (DMSO-d₆): δ (ppm) 12.9 (s, 1H), 11.9 (s, 1H), 7.38 (d, 1H), 7.34 (d, 1H), 7.2 (m, 2H), 7.12 (m, 1H), 7.0 (d, 2H), 6.75 (s, 1H), 6.58 (d, 1H).

Example 112

4-m-Tolyloxy-1H-indole-2-carboxylic acid [1-(2-azepan-1-yl-ethyl)-piperidin-4-yl]-amide

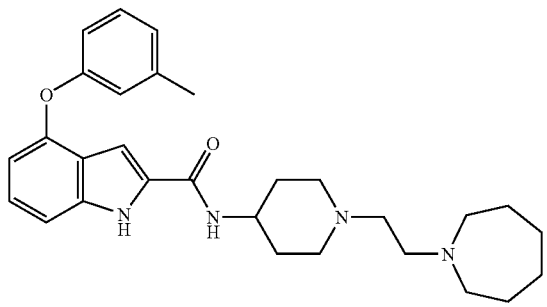

This compound is synthesized analogously to Example 1 from 4-m-tolyloxy-1H-indole-2-carboxylic acid 133 (preparation see below) and amine 5.

Yield: 12 mg (11.3%) of a white solid; MS (ESI): 473.3 [M−H]⁻, 1H-NMR (DMSO-d₆): δ (ppm) 11.65 (s, 1H), 8.2 (d, 1H), 7.2 (m, 2H), 7.1 (m, 2H), 6.88 (d, 1H), 6.78 (m, 1H), 6.7 (m, 1H), 6.54 (d, 1H), 3.72 (m, 1H), 2.85 (m, 2H), 2.48-2.58 (m, 8H), 2.35 (m, 2H), 2.25 (s, 3H), 1.98 (m, 2H), 1.75 (m, 2H), 1.48-1.55 (m, 8H).

Synthesis of 4-m-Tolyloxy-1H-indole-2-carboxylic acid (133)

(1) Step A: 4-(5-Methyl-2-nitro-phenoxy)-1H-indole-2-carboxylic acid ethyl ester (134)

4-Hydroxy-1H-indole-2-carboxylic acid ethyl ester (1 g, 4.87 mmol) and 2-Fluoro-4-methyl-1-nitro-benzene (756 mg, 4.87 mmol) are dissolved in 20 ml of dimethylformamide. After addition of potassium carbonate (1.3 g, 9.74 mmol) the mixture is stirred over night at room temperature. Then the reaction mixture is evaporated under reduced pressure, dissolved with ethyl acetate and washed with water. The organic layers are dried over sodium sulfate and evaporated. The crude product is used in the next step without further purification.

Yield: 1.59 g (96%) of a beige solid. MS (ESI): 341 [M+H]⁺, 1H-NMR (DMSO-d₆): δ (ppm) 12.15 (s, 1H), 7.98 (d, 1H), 7.3 (d, 1H), 7.25 (dd, 1H), 7.15 (d, 1H), 6.88 (d, 1H), 6.63 (d, 1H), 4.3 (q, 2H), 2.28 (s, 3H), 1.3 (t, 3H).

(2) Step B: 4-(2-Amino-5-methyl-phenoxy)-1H-indole-2-carboxylic acid ethyl ester (135)

134 (1.3 g, 3.82 mmol) is dissolved in 250 ml of ethyl acetate and, after addition of Pd—C (200 mg), the mixture is hydrogenated at room temperature for 3 hours. The mixture is filtrated over celite to remove the catalyst and evaporated.

Yield: 1.12 g (95%) of a grey solid. MS (ESI): 311 [M+H]⁺+, 1H-NMR (DMSO-d₆): δ (ppm) 11.95 (br, 1H), 7.13 (m, 2H), 7.03 (s, 1H), 6.72 (s, 2H), 6.58 (s, 1H), 6.37 (m, 1H), 4.68 (br, 2H), 4.3 (q, 2H), 2.08 (s, 3H), 1.3 (t, 3H).

(3) Step C: 4-m-Tolyloxy-1H-indole-2-carboxylic acid ethyl ester (136)

Tert-butyl nitrite (0.428 ml, 3.609 mmol) is dissolved in 5 ml of dimethylformamide and heated to 65° C. A solution of 135 (1.1 g, 3.609 mmol) in 5 ml of dimethylformamide is added dropwise and the mixture is stirred of additional 10 minutes. The brown solution is cooled to room temperature, diluted with diethyl ether and washed with 2N HCl and brine. The organic layers are dried over sodium sulphate and evaporated. The crude product (930 mg of a brown oil) is further purified by flash-chromatography (hexane/ethyl acetate 7:3).

Yield: 520 mg (49%) of a yellow solid; MS (ESI): 294.2 [M−H]⁻, 1H-NMR (DMSO-d₆): δ (ppm) 12.0 (s, 1H), 7.18-7.24 (m, 3H), 6.92 (m, 1H), 6.82 (m, 2H), 6.78 (dd, 1H), 6.58 (dd, 1H), 4.28 (q, 2H), 2.27 (s, 3H), 1.3 (t, 3H).

(4) Step D: 4-m-Tolyloxy-1H-indole-2-carboxylic acid (133)

136 (520 mg, 1.761 mmol) is dissolved in 10 ml of methanol and treated with a solution of LiOH (84.3 mg, 3.52 mmol) in 5 ml of water. The mixture is stirred at room temperature for 18 hours. After evaporation, the crude product is acidified at 0° C. with 2M HCl and extracted with ethyl acetate. The organic layers are dried over sodium sulphate and evaporated.

Yield: 460 mg (98%) of a beige solid; MS (ESI): 266.1 [M−H]⁻, 1H-NMR (DMSO-d₆): δ (ppm) 12.9 (s, 1H), 11.9 (s, 1H), 7.15-7.25 (m, 3H), 6.9 (m, 1H), 6.84 (m, 1H), 6.78 (m, 2H), 6.57 (m, 1H), 2.27 (s, 3H).

Example 113

4-m-Tolyloxy-1H-indole-2-carboxylic acid {1-[2-(3-(RS)-hydroxy-piperidin-1-yl)-ethyl]-piperidin-4-yl}-amide

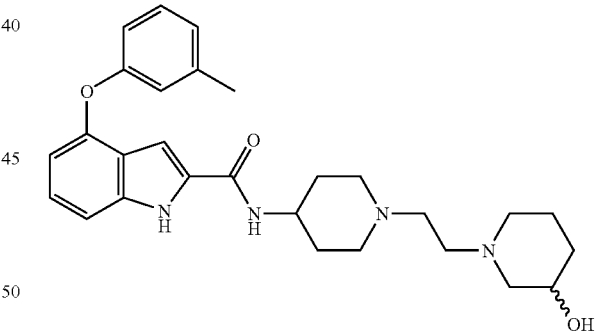

This compound is synthesized analogously to Example 1 from 4-m-Tolyloxy-1H-indole-2-carboxylic acid 133 (see example 112) and racemic amine 12.

Yield: 34 mg (21%) of a yellow solid; MS (ESI): 477.3 [M+H]⁺, 1H-NMR (80° C., DMSO-d₆): δ (ppm) 11.2 (s, 1H), 7.77 (d, 1H), 7.24 (dd, 1H), 7.2 (dd, 1H), 7.1 (ss, 1H), 7.04 (s, 1H), 6.88 (d, 1H), 6.8 (m, 1H), 6.75 (m, 1H), 6.54 (d, 1H), 3.75 (m, 1H), 3.5 (m, 1H), 2.7-2.9 (m, 4H), 2.6 (m, 1H), 2.44 (m, 4H), 2.3 (s, 3H), 2.13 (m, 2H), 2.05 (m, 1H), 1.95 (m, 1H), 1.7-1.85 (m, 3H), 1.55-1.65 (m, 3H), 1.4 (m, 1H), 1.15 (m, 1H).

Example 114

4-m-Tolyloxy-1H-indole-2-carboxylic acid {1-[2-(4-hydroxy-piperidin-1-yl)-ethyl]-piperidin-4-yl}-amide

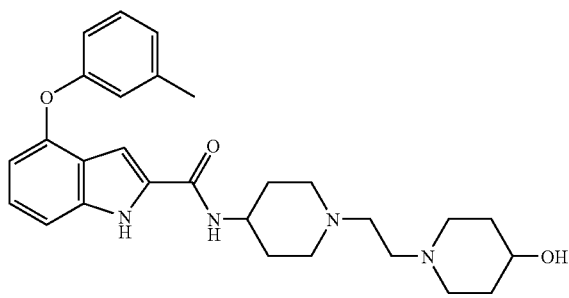

This compound is synthesized analogously to Example 1 from 4-m-tolyloxy-1H-indole-2-carboxylic acid 133 (see example 112) and amine 21.

Yield: 45 mg (28%) of a white solid; MS (ESI): 477 [M+H]$^+$, 1H-NMR (DMSO-d$_6$): δ (ppm) 11.7 (s, 1H), 8.2 (d, 1H), 7.2 (m, 2H), 7.1 (m, 2H), 6.88 (d, 1H), 6.78 (m, 1H), 6.7 (m, 1H), 6.54 (d, 1H), 4.47 (m, 1H), 3.72 (m, 1H), 3.38 (m, 1H), 2.85 (m, 2H), 2.7 (m, 2H), 2.38 (m, 4H), 2.28 (s, 3H), 1.98 (m, 4H), 1.63-1.75 (m, 4H), 1.5 (m, 2H), 1.35 (m, 2H).

Example 115

4-p-Tolyloxy-1H-indole-2-carboxylic acid [1-(2-azepan-1-yl-ethyl)-piperidin-4-yl]-amide

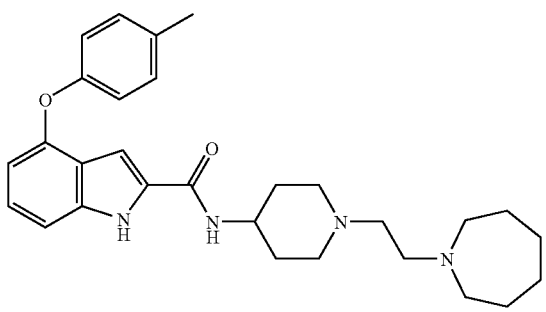

This compound is synthesized analogously to Example 1 from 4-p-tolyloxy-1H-indole-2-carboxylic acid 137 (preparation see below) and amine 5.

Yield: 12 mg (11.3%) of a white solid; MS (ESI): 473.3 [M−H]$^-$, 1H-NMR (DMSO-d$_6$): δ (ppm) 11.65 (s, 1H), 8.18 (d, 1H), 7.05-7.2 (m, 5H), 6.85 (d, 2H), 6.47 (m, 1H), 3.7 (m, 1H), 2.85 (m, 2H), 2.47-2.58 (m, 6H), 2.35 (m, 2H), 2.25 (s, 3H), 1.98 (m, 2H), 1.75 (m, 2H), 1.48-1.55 (m, 10H).

Synthesis of 4-p-Tolyloxy-1H-indole-2-carboxylic acid (137)

(1) Step A: 4-(3,5-Difluoro-2-nitro-phenoxy)-1H-indole-2-carboxylic acid ethyl ester (138)

4-Hydroxy-1H-indole-2-carboxylic acid ethyl ester (1 g, 4.87 mmol) and 1-Fluoro-4-methyl-2-nitro-benzene (0.6 ml, 4.87 mmol) are dissolved in 10 ml of dimethylformamide. After addition of potassium carbonate (1.3 g, 9.74 mmol) the mixture is stirred over night at room temperature. Then the reaction mixture is evaporated under reduced pressure, dissolved with ethyl acetate and washed with water. The organic layers are dried over sodium sulfate and evaporated. The crude product (1.51 g of a brown oil) is further purified by flash-chromatography (hexane/ethyl acetate 9:1).

Yield: 570 mg (34%) of a white solid. MS (ESI): 341 [M+H]$^+$, 1H-NMR (DMSO-d$_6$): δ (ppm) 12.1 (s, 1H), 7.88 (d, 1H), 7.45 (dd, 1H), 7.27 (d, 1H), 7.22 (dd, 1H), 6.98 (d, 1H), 6.87 (s, 1H), 6.6 (d, 1H), 4.3 (q, 2H), 2.35 (s, 3H), 1.3 (t, 3H).

(2) Step B: 4-(2-Amino-4-methyl-phenoxy)-1H-indole-2-carboxylic acid ethyl ester (139)

138 (570 mg, 1.675 mmol) is dissolved in 150 ml of ethanol and, after addition of Pd—C (200 mg), the mixture is hydrogenated at room temperature for 2 hours. The mixture is filtrated over celite to remove the catalyst and evaporated.

Yield: 3.08 g (100%) of a brown oil. MS (ESI): 311 [M+H]$^+$.

(3) Step C: 4-p-Tolyloxy-1H-indole-2-carboxylic acid ethyl ester (140)

Tert-butyl nitrite (0.176 ml, 1.48 mmol) is dissolved in 5 ml of dimethylformamide and heated to 65° C. A solution of 139 (460 mg, 1.48 mmol) in 5 ml of dimethylformamide is added dropwise and the mixture is stirred of additional 10 minutes. The brown solution is cooled to room temperature, diluted with diethyl ether and washed with 2N HCl and brine. The organic layers are dried over sodium sulphate and evaporated. The crude product (420 mg of a brown oil) is further purified by flash-chromatography (hexane/ethyl acetate 9:1).

Yield: 70 mg (16%) of a yellow solid; MS (ESI): 294.2 [M−H]$^-$, 1H-NMR (DMSO-d$_6$): δ (ppm) 12.0 (s, 1H), 7.15-7.24 (m, 4H), 7.4 (m, 2H), 6.85 (d, 1H), 6.52 (dd, 1H), 4.3 (q, 2H), 2.28 (s, 3H), 1.3 (t, 3H).

(4) Step D: 4-p-Tolyloxy-1H-indole-2-carboxylic acid (137)

140 (70 mg, 0.237 mmol) is dissolved in 5 ml of methanol and treated with a solution of LiOH (11.4 mg, 0.474 mmol) in 3 ml of water. The mixture is stirred at room temperature for 18 hours. After evaporation, the crude product is acidified at 0° C. with 2M HCl and extracted with ethyl acetate. The organic layers are dried over sodium sulphate and evaporated.

Yield: 60 mg (100%) of a beige solid; MS (ESI): 266.2 [M−H]$^-$, 1H-NMR (DMSO-d$_6$): δ (ppm) 12.9 (s, 1H), 11.8 (s, 1H), 7.13-7.2 (m, 4H), 6.9 (m, 2H), 6.77 (d, 1H), 6.52 (dd, 1H), 2.29 (s, 3H).

Example 116

4-p-Tolyloxy-1H-indole-2-carboxylic acid {1-[2-(3-(RS)-hydroxy-piperidin-1-yl)-ethyl]-piperidin-4-yl}-amide

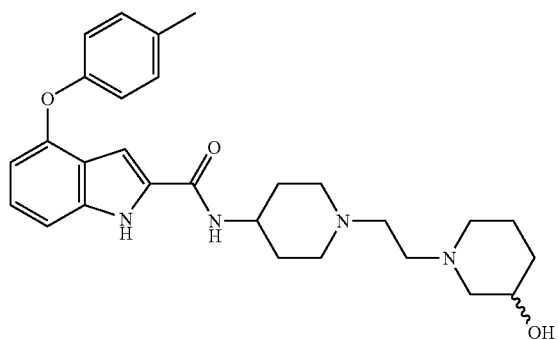

This compound is synthesized analogously to Example 1 from 4-p-tolyloxy-1H-indole-2-carboxylic acid 137 (see example 115) and racemic amine 12.

Yield: 87 mg (49%) of a beige solid; MS (ESI): 475.3 [M−H]⁻, 1H-NMR (DMSO-$d_6$): δ (ppm) 11.65 (s, 1H), 8.2 (d, 1H), 7.08-7.2 (m, 5H), 6.87 (d, 2H), 6.47 (d, 1H), 4.53 (d, 1H), 3.72 (m, 1H), 3.4 (m, 1H), 2.85 (m, 3H), 2.65 (m, 1H), 2.37 (m, 4H), 2.28 (s, 3H), 1.98 (t, 2H), 1.7-1.85 (m, 5H), 1.55 (m, 3H), 1.35 (m, 1H), 1.05 (m, 1H).

Example 117

4-p-Tolyloxy-1H-indole-2-carboxylic acid {1-[2-(4-hydroxy-piperidin-1-yl)-ethyl]-piperidin-4-yl}-amide

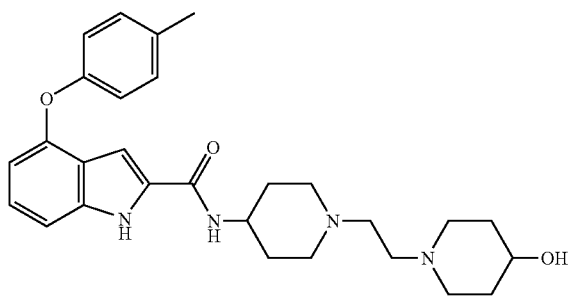

This compound is synthesized analogously to Example 1 from 4-p-tolyloxy-1H-indole-2-carboxylic acid 137 (see example 115) and amine 21.

Yield: 80 mg (45%) of a beige solid; MS (ESI): 475.3 [M−H]⁻, 1H-NMR (DMSO-$d_6$): δ (ppm) 11.65 (s, 1H), 8.2 (d, 1H), 7.07-7.2 (m, 5H), 6.85 (d, 2H), 6.47 (d, 1H), 4.48 (br, 1H), 3.72 (m, 1H), 3.4 (m, 1H), 2.85 (m, 2H), 2.7 (m, 2H), 2.35 (m, 4H), 2.27 (s, 3H), 1.95-2.05 (m, 4H), 1.65-1.75 (m, 4H), 1.5 (m, 2H), 1.35 (m, 2H).

Example 118

4-(3-Fluoro-phenoxy)-1H-indole-2-carboxylic acid [1-(2-azepan-1-yl-ethyl)-piperidin-4-yl]-amide

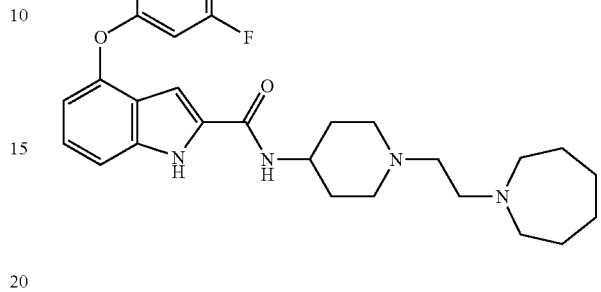

This compound is synthesized analogously to Example 1 from 4-(3-Fluoro-phenoxy)-1H-indole-2-carboxylic acid 141 (preparation see below) and amine 5.

Yield: 50 mg (28.3%) of a white solid; MS (ESI): 479.3 [M+H]⁺, 1H-NMR (DMSO-$d_6$): δ (ppm) 11.75 (s, 1H), 8.2 (d, 1H), 7.35 (dd, 1H), 7.28 (d, 1H), 7.18 (dd, 1H), 7.05 (s, 1H), 6.9 (dd, 1H), 6.73-6.8 (m, 2H), 6.68 (d, 1H), 3.72 (m, 1H), 2.85 (m, 2H), 2.5-2.58 (m, 6H), 2.35 (m, 2H), 1.98 (m, 2H), 1.72 (m, 2H), 1.48-1.55 (m, 10H).

Synthesis of 4-p-Tolyloxy-1H-indole-2-carboxylic acid (141)

(1) Step A: 4-(3,5-Difluoro-2-nitro-phenoxy)-1H-indole-2-carboxylic acid ethyl ester (142)

4-Hydroxy-1H-indole-2-carboxylic acid ethyl ester (1 g, 4.87 mmol) and 2,4-Difluoro-1-nitro-benzene (0.534 ml, 4.87 mmol) are dissolved in 20 ml of dimethylformamide. After addition of potassium carbonate (1.3 g, 9.74 mmol) the mixture is stirred over night at room temperature. Then the reaction mixture is evaporated under reduced pressure, dissolved with ethyl acetate and washed with water. The organic layers are dried over sodium sulfate and evaporated. The crude product is used in the next step without further purification.

Yield: 1.63 g (97%) of a grey resin; MS (ESI): 343.1 [M−H]⁻.

(2) Step B: 44-(2-Amino-5-fluoro-phenoxy)-1H-indole-2-carboxylic acid ethyl ester (143)

142 (1.6 g, 4.734 mmol) is dissolved in 250 ml of ethyl acetate and, after addition of Pd—C (200 mg), the mixture is hydrogenated at room temperature for 2 hours. The mixture is filtrated over celite to remove the catalyst and evaporated.

Yield: 1.41 g (95%) of a grey foam. MS (ESI): 315.2 [M+H]⁺.

(3) Step C: 4-(3-Fluoro-phenoxy)-1H-indole-2-carboxylic acid ethyl ester (144)

Tert-butyl nitrite (0.46 ml, 4.45 mmol) is dissolved in 5 ml of dimethylformamide and heated to 65° C. A solution of 143 (1.4 g, 4.45 mmol) in 5 ml of dimethylformamide is added dropwise and the mixture is stirred of additional 10 minutes. The brown solution is cooled to room temperature, diluted with diethyl ether and washed with 2N HCl and brine. The organic layers are dried over sodium sulphate and evaporated. The crude product (1.0 g of a brown oil) is further purified by flash-chromatography (hexane/ethyl acetate 7:3).

Yield: 440 mg (33%) of a yellow solid; MS (ESI): 298.2 [M−H]−, 1H-NMR (DMSO-d$_6$): δ (ppm) 12.1 (s, 1H), 7.35 (dd, 1H), 7.3 (d, 1H), 7.25 (dd, 1H), 6.92 (dd, 1H), 6.77-6.87 (m, 3H), 6.7 (d, 1H), 4.3 (q, 2H), 1.3 (t, 3H).

(4) Step D: 4-(3-Fluoro-phenoxy)-1H-indole-2-carboxylic acid (141)

144 (440 mg, 1.47 mmol) is dissolved in 10 ml of methanol and treated with a solution of LiOH (70 mg, 1.47 mmol) in 5 ml of water. The mixture is stirred at room temperature for 18 hours. After evaporation, the crude product is acidified at 0° C. with 2M HCl and extracted with ethyl acetate. The organic layers are dried over sodium sulphate and evaporated.

Yield: 420 mg (100%) of a yellow solid; MS (ESI): 270.1 [M−H]−, 1H-NMR (DMSO-d$_6$): δ (ppm) 12.95 (s, 1H), 11.9 (s, 1H), 7.35 (dd, 1H), 7.28 (d, 1H), 7.18 (dd, 1H), 6.9 (dd, 1H), 6.77-6.85 (m, 2H), 6.75 (s, 1H), 6.7 (d, 1H).

Example 119

4-(3-Fluoro-phenoxy)-1H-indole-2-carboxylic acid {1-[2-(4-hydroxy-piperidin-1-yl)-ethyl]-piperidin-4-yl}-amide

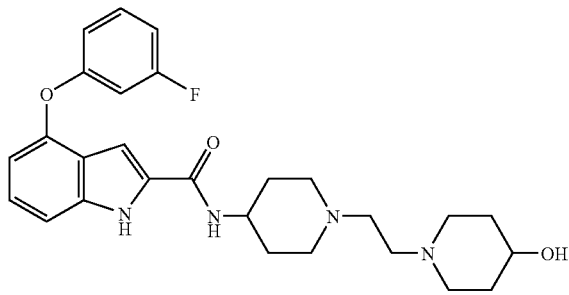

This compound is synthesized analogously to Example 1 from 4-(3-fluoro-phenoxy)-1H-indole-2-carboxylic acid 141 (see example 118) and amine 21.

Yield: 35 mg (20%) of a white solid; MS (ESI): 479 [M−H]−, 1H-NMR (DMSO-d$_6$): δ (ppm) 11.75 (s, 1H), 8.21 (d, 1H), 7.35 (dd, 1H), 7.29 (d, 1H), 7.18 (dd, 1H), 7.05 (s, 1H), 6.9 (dd, 1H), 6.73-6.8 (m, 2H), 6.68 (d, 1H), 4.49 (d, 1H), 3.72 (m, 1H), 3.4 (m, 1H), 2.85 (m, 2H), 2.7 (m, 2H), 2.37 (m, 4H), 1.95 (m, 4H), 1.63-1.77 (m, 4H), 1.5 (m, 2H), 1.35 (m, 2H).

Example 120

4-(4-Fluoro-phenoxy)-1H-indole-2-carboxylic acid [1-(2-azepan-1-yl-ethyl)-piperidin-4-yl]-amide

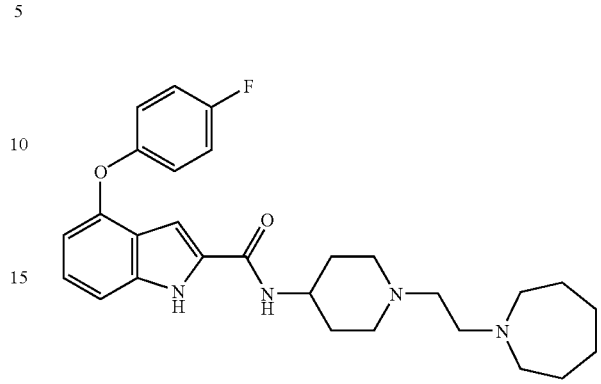

This compound is synthesized analogously to Example 1 from 4-(4-fluoro-phenoxy)-1H-indole-2-carboxylic acid 145 (preparation see below) and amine 5.

Yield: 86 mg (49%) of a white solid; MS (ESI): 477.3 [M−H]−, 1H-NMR (DMSO-d$_6$): δ (ppm) 11.75 (s, 1H), 8.2 (d, 1H), 7.14-7.24 (m, 5H), 7.0 (m, 2H), 6.5 (d, 1H), 3.72 (m, 1H), 2.85 (m, 2H), 2.5-2.6 (m, 6H), 2.36 (m, 2H), 1.98 (m, 2H), 1.72 (m, 2H), 1.48-1.57 (m, 10H).

Synthesis of 4-p-Tolyloxy-1H-indole-2-carboxylic acid (145)

(1) Step A: 4-(4-Fluoro-2-nitro-phenoxy)-1H-indole-2-carboxylic acid ethyl ester (146)

4-Hydroxy-1H-indole-2-carboxylic acid ethyl ester (0.92 g, 4.483 mmol) and 1,4-Difluoro-2-nitro-benzene (0.486 ml, 4.483 mmol) are dissolved in 10 ml of dimethylformamide. After addition of potassium carbonate (1.2 g, 8.96 mmol) the mixture is stirred over night at room temperature. Then the reaction mixture is evaporated under reduced pressure, dissolved with ethyl acetate and washed with water. The organic layers are dried over sodium sulfate and evaporated. The crude product is used in the next step without further purification.

Yield: 1.45 g (94%) of a grey resin; MS (ESI): 343.1 [M−H]−−, 1H-NMR (DMSO-d$_6$): δ (ppm) 12.15 (s, 1H), 8.08 (m, 1H), 7.55 (m, 1H), 7.3 (d, 1H), 7.24 (dd, 1H), 7.15 (dd, 1H), 6.9 (s, 1H), 6.62 (d, 1H), 4.3 (q, 2H), 1.32 (t, 3H).

(2) Step B: 4-(2-Amino-4-fluoro-phenoxy)-1H-indole-2-carboxylic acid ethyl ester (147)

146 (1.5 g, 4.21 mmol) is dissolved in 200 ml of ethyl acetate and, after addition of Pd—C (200 mg), the mixture is hydrogenated at room temperature for 2 hours. The mixture is filtrated over celite to remove the catalyst and evaporated.

Yield: 1.31 g (99%) of a beige solid. MS (ESI): 313.2 [M−H]−, 1H-NMR (DMSO-d$_6$): δ (ppm) 11.95 (s, 1H), 7.12 (m, 2H), 7.05 (m, 1H), 6.75 (dd, 1H), 6.58 (dd, 1H), 6.34 (m, 1H), 6.28 (dt, 1H), 5.25 (br, 2H), 4.3 (q, 2H), 1.32 (t, 3H).

(3) Step C: 4-(4-Fluoro-phenoxy)-1H-indole-2-carboxylic acid ethyl ester (148)

Tert-butyl nitrite (0.46 ml, 4.45 mmol) is dissolved in 5 ml of dimethylformamide and heated to 65° C. A solution of 147

(1.4 g, 4.45 mmol) in 5 ml of dimethylformamide is added dropwise and the mixture is stirred of additional 10 minutes. The brown solution is cooled to room temperature, diluted with diethyl ether and washed with 2N HCl and brine. The organic layers are dried over sodium sulphate and evaporated. The crude product (1.0 g of a brown oil) is further purified by flash-chromatography (hexane/ethyl acetate 7:3).

Yield: 440 mg (33%) of a yellow solid; MS (ESI): 298.2 [M−H]⁻, 1H-NMR (DMSO-$d_6$): δ (ppm) 12.05 (s, 1H), 7.2 (m, 4H), 7.05 (m, 2H), 6.85 (m, 1H), 6.54 (d, 1H), 4.3 (q, 2H), 1.3 (t, 3H).

(4) Step D: 4-(4-Fluoro-phenoxy)-1H-indole-2-carboxylic acid (145)

148 (510 mg, 1.7 mmol) is dissolved in 10 ml of methanol and treated with a solution of LiOH (82 mg, 3.4 mmol) in 5 ml of water. The mixture is stirred at room temperature for 18 hours. After evaporation, the crude product is acidified at 0° C. with 2M HCl and extracted with ethyl acetate. The organic layers are dried over sodium sulphate and evaporated.

Yield: 460 mg (100%) of a yellow solid; MS (ESI): 270.1 [M−H]⁻, 1H-NMR (DMSO-$d_6$): δ (ppm) 13.0 (s, 1H), 11.9 (s, 1H), 7.15-7.22 (m, 4H), 7.05 (m, 2H), 6.78 (m, 1H), 6.55 (d, 1H).

Example 121

4-(4-Fluoro-phenoxy)-1H-indole-2-carboxylic acid {1-[2-(4-hydroxy-piperidin-1-yl)-ethyl]-piperidin-4-yl}-amide

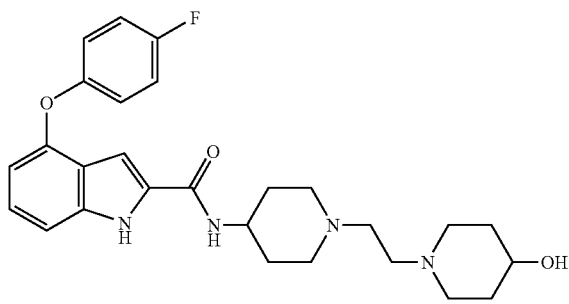

This compound is synthesized analogously to Example 1 from 4-(4-fluoro-phenoxy)-1H-indole-2-carboxylic acid 145 (see example 120) and amine 21.

Yield: 66 mg (37%) of a white solid; MS (ESI): 479 [M−H]⁻, 1H-NMR (DMSO-$d_6$): δ (ppm) 11.7 (s, 1H), 8.2 (d, 1H), 7.1-7.24 (m, 5H), 7.0 (m, 2H), 6.5 (d, 1H), 4.46 (br, 1H), 3.72 (m, 1H), 3.42 (m, 1H), 2.85 (m, 2H), 2.7 (m, 2H), 2.38 (m, 4H), 2.0 (m, 4H), 1.64-1.77 (m, 4H), 1.53 (m, 2H), 1.35 (m, 2H).

Example 122

4-(3,4-Difluoro-phenoxy)-1H-indole-2-carboxylic acid [1-(2-azepan-1-yl-ethyl)-piperidin-4-yl]-amide

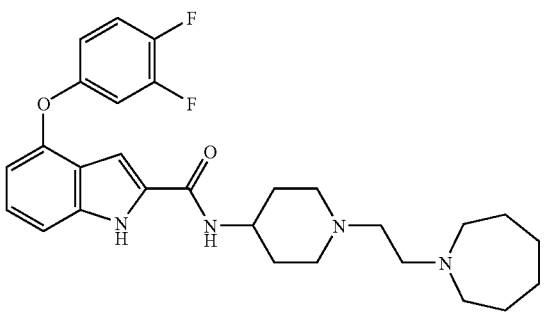

This compound is synthesized analogously to Example 1 from 4-(3,4-Difluoro-phenoxy)-1H-indole-2-carboxylic acid 149 (preparation see below) and amine 5.

Yield: 62 mg (36%) of a white solid; MS (ESI): 495.3 [M−H]⁻, 1H-NMR (DMSO-$d_6$): δ (ppm) 11.75 (s, 1H), 8.23 (d, 1H), 7.44 (m, 1H), 7.26 (d, 1H), 7.14 (m, 1H), 7.0 (m, 1H), 6.80 (m, 1H), 6.56 (d, 2H), 3.72 (m, 1H), 2.87 (m, 2H), 2.5-2.6 (m, 6H), 2.38 (m, 2H), 2.0 (m, 2H), 1.75 (m, 2H), 1.47-1.55 (m, 10H).

Synthesis of 4-(3,5-Difluoro-phenoxy)-1H-indole-2-carboxylic acid (149)

(1) Step A: 4-(3,5-Difluoro-2-nitro-phenoxy)-1H-indole-2-carboxylic acid ethyl ester (150)

4-Hydroxy-1H-indole-2-carboxylic acid ethyl ester (1 g, 4.87 mmol) and 1,2,4-Trifluoro-5-nitro-benzene (0.559 ml, 4.87 mmol) are dissolved in 10 ml of dimethylformamide. After addition of potassium carbonate (1.3 g, 9.74 mmol) the mixture is stirred over night at room temperature. Then the reaction mixture is evaporated under reduced pressure, dissolved with ethyl acetate and washed with water. The organic layers are dried over sodium sulfate and evaporated.

Yield: 1.79 g (100%) of a yellow foam. MS (ESI): 361.1 [M−H]⁻.

(2) Step B: 4-(2-Amino-4,5-difluoro-phenoxy)-1H-indole-2-carboxylic acid ethyl ester (151)

150 (1.8 g, 4.87 mmol) is dissolved in 150 ml of ethyl acetate and, after addition of Pd—C (500 mg), the mixture is hydrogenated at room temperature for 2 hours. The mixture is filtrated over celite to remove the catalyst and evaporated.

Yield: 1.61 g (99%) of a brown foam. MS (ESI): 333.2 [M+H]⁺.

(3) Step C: 4-(3,4-Difluoro-phenoxy)-1H-indole-2-carboxylic acid ethyl ester (152)

Tert-butyl nitrite (0.575 ml, 4.85 mmol) is dissolved in 5 ml of dimethylformamide and heated to 65° C. A solution of 151 (1.6 g, 4.85 mmol) in 5 ml of dimethylformamide is added dropwise and the mixture is stirred of additional 10 minutes. The brown solution is cooled to room temperature, diluted with diethyl ether and washed with 2N HCl and brine. The organic layers are dried over sodium sulphate and evaporated.

The crude product (1.78 g of a brown oil) is further purified by flash-chromatography (hexane/ethyl acetate 9:1).

Yield: 380 mg (25%) of a slightly yellow solid; MS (ESI): 316.2 [M−H]⁻, 1H-NMR (DMSO-d$_6$): δ (ppm) 12.1 (s, 1H), 7.45 (m, 1H), 7.27 (d, 1H), 7.2 (dd, 1H), 7.05 (m, 1H), 6.98 (m, 1H), 6.95 (m, 1H), 6.55 (d, 1H), 4.3 (q, 2H), 1.34 (t, 3H).

(4) Step D: 4-(3,4-Difluoro-phenoxy)-1H-indole-2-carboxylic acid (149)

152 (380 mg, 1.2 mmol) is dissolved in 10 ml of methanol and treated with a solution of LiOH (57 mg, 2.4 mmol) in 5 ml of water. The mixture is stirred at room temperature for 18 hours. After evaporation, the crude product is acidified at 0° C. with 2M HCl and extracted with ethyl acetate. The organic layers are dried over sodium sulphate and evaporated.

Yield: 310 mg (90%) of a yellow solid; MS (ESI): 288.1 [M−H]⁻, 1H-NMR (DMSO-d$_6$): δ (ppm) 13.0 (s, 1H), 12.0 (s, 1H), 7.45 (m, 1H), 7.25 (d, 1H), 7.18 (dd, 1H), 7.05 (m, 1H), 6.98 (m, 1H), 6.87 (s, 1H), 6.55 (d, 1H).

Example 123

4-(3,5-Difluoro-phenoxy)-1H-indole-2-carboxylic acid [1-(2-azepan-1-yl-ethyl)-piperidin-4-yl]-amide

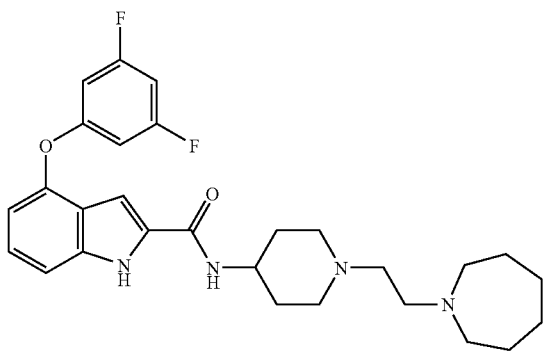

This compound is synthesized analogously to Example 1 from 4-(3,5-difluoro-phenoxy)-1H-indole-2-carboxylic acid 153 (preparation see below) and amine 5.

Yield: 180 mg (33.2%) of a yellow solid; MS (ESI): 495.3 [M−H]⁻, 1H-NMR (DMSO-d$_6$): δ (ppm) 11.8 (s, 1H), 8.21 (d, 1H), 7.33 (d, 1H), 7.2 (dd, 1H), 7.04 (d, 1H), 6.94 (m, 1H), 6.75 (d, 1H), 6.62 (m, 2H), 3.7 (m, 1H), 2.85 (m, 2H), 2.47-2.58 (m, 6H), 2.36 (m, 2H), 1.98 (m, 2H), 1.75 (m, 2H), 1.47-1.55 (m, 10H).

Synthesis of 4-(3,5-Difluoro-phenoxy)-1H-indole-2-carboxylic acid (153)

(1) Step A: 4-(3,5-Difluoro-2-nitro-phenoxy)-1H-indole-2-carboxylic acid ethyl ester (154)

4-Hydroxy-1H-indole-2-carboxylic acid ethyl ester (1 g, 4.87 mmol) and 1,3,5-Trifluoro-2-nitro-benzene (0.57 ml, 4.87 mmol) are dissolved in 10 ml of dimethylformamide. After addition of potassium carbonate (1.3 g, 9.74 mmol) the mixture is stirred over night at room temperature. Then the reaction mixture is evaporated under reduced pressure, dissolved with ethyl acetate and washed with water. The organic layers are dried over sodium sulfate and evaporated.

Yield: 1.8 g (100%) of a yellow foam. MS (ESI): 361.2 [M−H]⁻.

(2) Step B: 4-(2-Amino-3,5-difluoro-phenoxy)-1H-indole-2-carboxylic acid ethyl ester (155)

154 (1.8 g, 4.87 mmol) is dissolved in 150 ml of ethyl acetate and, after addition of Pd—C (500 mg), the mixture is hydrogenated at room temperature for 2 hours. The mixture is filtrated over celite to remove the catalyst and evaporated.

Yield: 1.53 g (94%) of a brown foam. MS (ESI): 333.2 [M+H]⁺.

(3) Step C: 4-(3,5-Difluoro-phenoxy)-1H-indole-2-carboxylic acid ethyl ester (156)

Tert-butyl nitrite (0.547 ml, 4.6 mmol) is dissolved in 5 ml of dimethylformamide and heated to 65° C. A solution of 155 (1.5 g, 4.6 mmol) in 5 ml of dimethylformamide is added dropwise and the mixture is stirred of additional 10 minutes. The brown solution is cooled to room temperature, diluted with diethyl ether and washed with 2N HCl and brine. The organic layers are dried over sodium sulphate and evaporated. The crude product (1.5 g of a brown oil) is further purified by flash-chromatography (hexane/ethyl acetate 9:1).

Yield: 260 mg (17.8%) of a yellow solid; MS (ESI): 316.2 [M−H]⁻, 1H-NMR (DMSO-d$_6$): δ (ppm) 12.2 (s, 1H), 7.35 (d, 1H), 7.28 (dd, 1H), 6.95 (m, 1H), 6.82 (d, 1H), 6.79 (d, 1H), 6.68 (dd, 1H), 4.3 (q, 2H), 1.3 (t, 3H).

(4) Step D: 4-(3,5-Difluoro-phenoxy)-1H-indole-2-carboxylic acid (153)

156 (260 mg, 0.82 mmol) is dissolved in 10 ml of methanol and treated with a solution of LiOH (40 mg, 1.6 mmol) in 5 ml of water. The mixture is stirred at room temperature for 18 hours. After evaporation, the crude product is acidified at 0° C. with 2M HCl and extracted with ethyl acetate. The organic layers are dried over sodium sulphate and evaporated.

Yield: 240 mg (100%) of a yellow solid;

Example 124

4-(3,5-Difluoro-phenoxy)-1H-indole-2-carboxylic acid {1-[2-(3-RS-hydroxy-piperidin-1-yl)-ethyl]-piperidin-4-yl}-amide

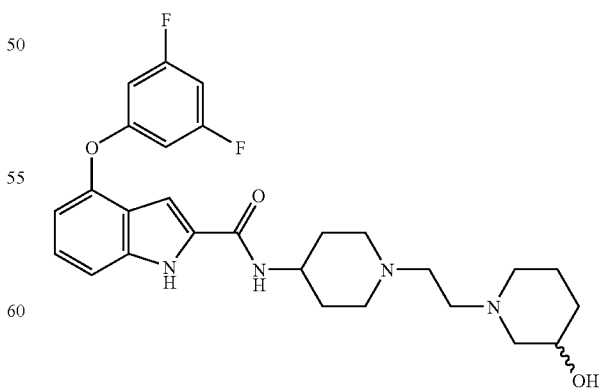

This compound is synthesized analogously to Example 1 from 4-(3,5-Difluoro-phenoxy)-1H-indole-2-carboxylic acid 153 (see example 123) and racemic amine 12.

Yield: 38 mg (32%) of a white solid; MS (ESI): 499 [M+H]+, 1H-NMR (DMSO-d6): δ (ppm) 11.8 (s, 1H), 8.25 (d, 1H), 7.33 (d, 1H), 7.2 (dd, 1H), 7.04 (s, 1H), 6.92 (dd, 1H), 6.76 (d, 1H), 6.63 (d, 1H), 4.02 (d, 1H), 3.72 (m, 1H), 3.4 (m, 1H), 2.8-2.9 (m, 3H), 2.67 (m, 2H), 2.38 (m, 4H), 1.99 (m, 2H), 1.68-1.88 (m, 5H), 1.47-1.6 (m, 3H), 1.371 (m, 1H), 1.05 (m, 1H).

Example 125

4-(3,5-Difluoro-phenoxy)-1H-indole-2-carboxylic acid {1-[2-(4-hydroxy-piperidin-1-yl)-ethyl]-piperidin-4-yl}-amide

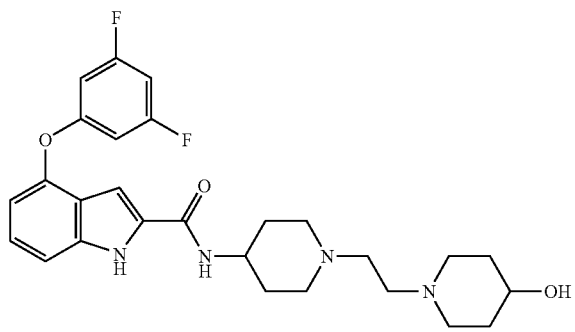

This compound is synthesized analogously to Example 1 from 4-(3,5-Difluoro-phenoxy)-1H-indole-2-carboxylic acid 153 (see example 123) and amine 21.

Yield: 23 mg (13%) of a white solid; MS (ESI): 497.2 [M−H]−, 1H-NMR (DMSO-d6): δ (ppm) 11.79 (s, 1H), 8.22 (br, 1H), 7.32 (d, 1H), 7.2 (dd, 1H), 7.04 (s, 1H), 6.9 (dd, 1H), 6.75 (d, 1H), 6.6 (d, 2H), 4.46 (s, 1H), 3.72 (m, 1H), 3.39 (m, 1H), 2.83 (m, 2H), 2.67 (m, 2H), 2.35 (m, 4H), 1.98 (m, 4H), 1.75 (m, 2H), 1.65 (m, 2H), 1.51 (m, 2H), 1.35 (m, 2H).

Alternatively, the 4-alkoxy-indole-2-carboxamides are prepared as shown in reaction scheme 16.

Reaction Scheme 1116:

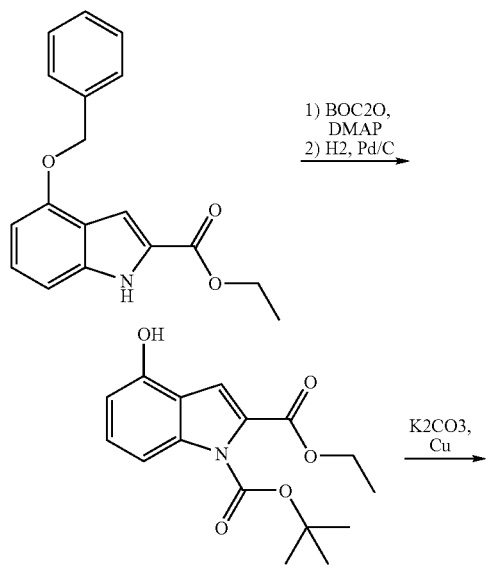

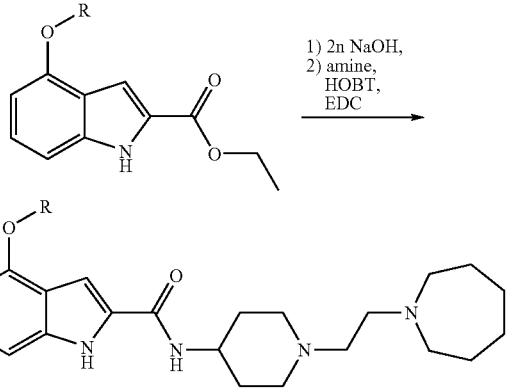

Example 126

4-(6-Chloro-pyridin-2-yloxy)-1H-carboxylic acid [1-(2-azepan-1-yl-ethyl)-piperidin-4-yl]-amide

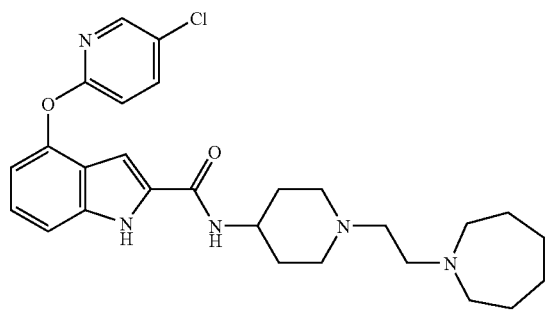

This compound is synthesized analogously to Example 1 from 4-(6-Chloro-pyridin-2-yloxy)-1H-indole-2-carboxylic acid 157 (preparation see below) and amine 5.

Yield: 85 mg (54%) of yellow crystals; MS (ESI): 494.3 [M−H]−, 1H-NMR (DMSO-d6): δ (ppm) 11.8 (s, 1H), 8.2 (d, 1H), 7.85 (dd, 1H), 7.3 (d, 1H), 7.2 (m, 2H), 6.95 (s, 1H), 6.9 (d, 1H), 6.8 (d, H), 3.7 (m, H), 2.85 (m, 2H), 2.5-2.6 (m, 6H), 2.35 (m, 2H), 2.0 (t, 2H), 1.75 (m, 2H), 1.5 (m, 10H).

Synthesis of 4-(6-Chloro-pyridin-2-yloxy)-1H-indole-2-carboxylic acid (157)

(1) Step A: 4-Benzyloxy-indole-1,2-dicarboxylic acid 1-tert-butyl ester 2-ethyl ester (158)

4-Benzyloxy-1H-indole-2-carboxylic acid ethyl ester (10 g, 34 mmol) and DMAP (80 mg) are dissolved in 80 ml of ethyl acetate. BOC2O (8.9 g, 41 mmol) dissolved in a small amount of ethyl acetate is added at room temperature. The mixture is stirred over night at room temperature. Then the reaction mixture is washed with 1 m aqueous tartaric acid, water and brine. The organic layers are dried over sodium sulfate and evaporated. The crude product is used in the next step without further purification.

Yield: 13.8 g (100%) of a yellow oil. 1H-NMR (CDCl3): δ (ppm) 7.7 (d, 1H), 7.3-7.5 (m, 7H), 6.75 (d, 1H), 5.2 (s, 2H), 4.4 (q, 2H), 1.7 (s, 9H), 1.4 (t, 3H).

(2) Step B: 4-Hydroxy-indole-1,2-dicarboxylic acid 1-tert-butyl ester 2-ethyl ester (159)

158 (8 g, 20 mmol) is dissolved in 80 ml of ethyl acetate and, after addition of 5% Pd—C (700 mg), the mixture is hydrogenated at room temperature for 7 hours. The mixture is filtered over celite to remove the catalyst and evaporated. The solid is suspended in ether/hexane and filtered.

Yield: 4.6 g (74%). 1H-NMR (CDCl3): δ (ppm) 7.7 (d, 1H), 7.3 (m, 2H), 6.7 (d, 1H), 5.5 (s, 1H), 4.4 (q, 2H), 1.7 (s, 9H), 1.4 (t, 3H).

(3) Step C: 4-(6-Chloro-pyridin-2-yloxy)-1H-indole-2-carboxylic acid ethyl ester (160)

159 (500 mg, 1.6 mmol), 2,6-Dichloro-pyridine (360 mg, 24 mmol) are dissolved in 15 ml of dimethylformamide. After addition of potassium carbonate (340 mg, 24 mmol) and a catalytic amount Cu-powder the mixture is heated to 160° C. for 3 hours. The reaction mixture is cooled to room temperature, diluted with ethyl acetate and washed with water. The organic layers are dried over sodium sulphate and evaporated. The crude product is solved in dichloromethane and after evaporation crystallized with cyclohexane.

Yield: 300 mg (58%) of a beige solid. MS (ESI): 317.2 [M+H]+, 1H-NMR (CDCl3): δ (ppm) 9.2 (br, 1H), 7.7 (dd, 1H), 7.3 (m, 2H), 7.1 (m, 2H), 6.95 (dd, 1H), 6.75 (d, 1H), 4.4 (q, 2H), 1.4 (t, 3H).

(4) Step D: 4-(6-Chloro-pyridin-2-yloxy)-1H-indole-2-carboxylic acid (157)

160 (100 mg, 0.315 mmol) is dissolved in 4 ml of methanol and treated with a solution of NaOH (1 ml, 2N). The mixture is stirred 1 hour at room temperature. The reaction mixture is acidified with HCl (1 ml, 2N) and evaporated. The crude mixture is used in the next step without further purification.

Alternatively, the 4-alkoxy-indole-2-carboxamides are prepared as shown in reaction scheme 17.

Reaction Scheme 17:

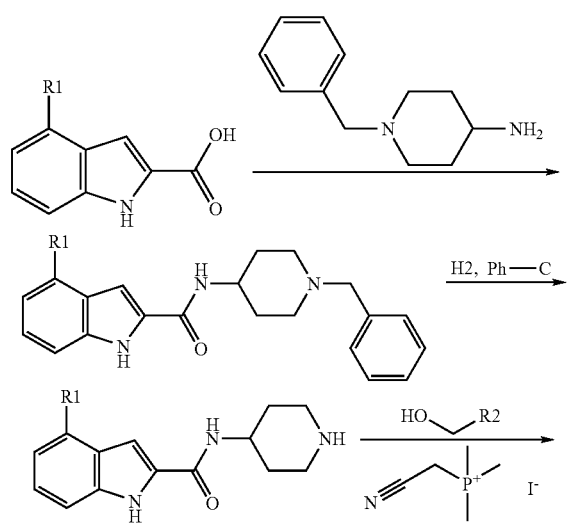

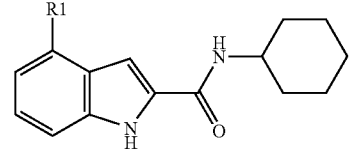

Example 127

4-Isobutoxy-1H-indole-2-carboxylic acid [1-(octahydro-quinolizin-1-ylmethyl)-piperidin-4-yl]-amide dihydrochloride

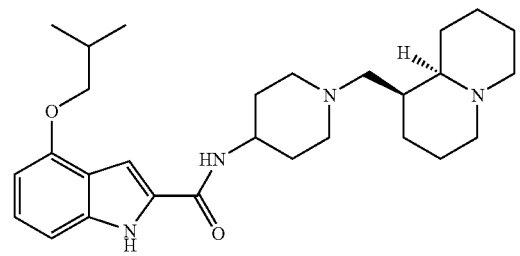

161 (preparation see below) (2.5 g, 7.1 mmol), octahydro-2H-chinolizin-1-ylmethanol (Lupinine) (1.2 g, 7.1 mmol) and ethyldiisopropylamine (12.2 ml, 71 mmol) are dissolved in 10 ml of propionitril. After addition of cyanomethyl-trimethyl-phosphonium iodide (4.1 g, 17 mmol) the mixture is refluxed for 3 h. After cooling down to room temperature, the mixture is diluted with ethyl acetate and washed with potassium carbonate solution. The crude product 3.9 g of a brown oil) is crystallized from methanol.

Yield: 2 g (52%) of a white solid. MS (ESI): 467 [M+H]+, 1H-NMR (DMSO-$d_6$): δ (ppm) 11.42 (s, NH), 8.16 (d, NH), 7.22 (d, 1H), 7.02 (dd, 1H), 6.96 (d, 1H), 6.45 (d, 1H), 3.83 (d, 2H), 3.75 (m, 1H), 3.49 (s, 2H), 2.81 (m, 2H), 2.70 (m, 2H), 2.29 (m, 1H), 2.15-2.00 (m, 2H), 1.95-1.73 (m, 7H), 1.72-1.27 (m, 9H), 1.26-1.10 (m, 2H), 1.05 (d, 6H).

Synthesis of 4-Isobutoxy-1H-indole-2-carboxylic acid (1-benzyl-piperidin-4-yl)-amide (161)

(1) Step A: 4-Isobutoxy-1H-indole-2-carboxylic acid (1-benzyl-piperidin-4-yl)-amide (161)

4-Isobutoxy-1H-indole-2-carboxylic acid 80 (4.7 g, 20.1 mmol, preparation see Example 8) and 1-benzyl-piperidin-4-ylamine (4.2 ml, 20.1 mmol) are dissolved in 70 ml of DMF and after addition of TBTU (7.3 g, 22.1 mmol) and ethyldiisopropylamine (13.8 ml, 80.4 mmol) the mixture is stirred at room temperature for 2 h. Then the solvent is evaporated at high vacuum. The residue is dissolved in ethyl acetate, washed with saturated aqueous sodium hydrogen carbonate and brine. The organic layers are dried over sodium sulfate and evaporated under reduced pressure.

Yield: 8.96 g of a beige solid. MS (ESI): 406.5 [M+H]+

(2) Step B: 4-Isobutoxy-1H-indole-2-carboxylic acid piperidin-4-ylamide hydrochloride (161)

161 (8.1 g, 20 mmol) is dissolved in 200 ml of ethanol and, after addition of Pd—C (200 mg) and 10 ml of 4M HCl the mixture is hydrogenated at room temperature for 3 hours. The mixture is filtrated over celite to remove the catalyst and evaporated.

Yield: 7.13 g (100%) of a white solid. MS (ESI): 316 [M+H]$^+$, 1H-NMR (DMSO-d$_6$): δ (ppm) 11.5 (s, 1H), 8.42 (d, 1H), 7.25 (s, 2H), 7.04 (dd, 1H), 6.95 (d, 1H), 6.45 (d, 1H), 4.0 (m, 1H), 3.83 (d, 2H), 3.22 (m, 2H), 2.88 (m, 2H), 2.1 (m, 1H), 1.9 (m, 2H), 1.7 (m, 2H), 1.05 (d, 6H).

Example 128

4-Isobutoxy-1H-indole-2-carboxylic acid [1-(1-methyl-piperidin-3-ylmethyl)-piperidin-4-yl]-amide

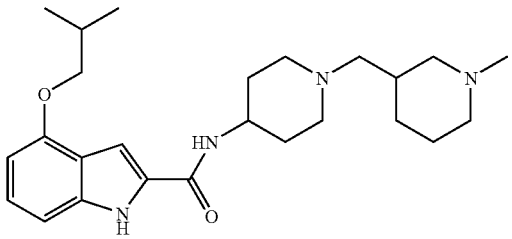

This compound is synthesized from the compound 161 (see example 127) and (1-Methyl-piperidin-3-yl)-methanol analogously to the method described in Example 127.

Yield: 60 mg (50%). MS (ESI): 427 [M+H]$^+$, 1H-NMR (DMSO-d$_6$): δ (ppm) 11.45 (s, NH), 8.18 (d, NH), 7.21 (s, 1H), 7.02 (dd, 1H), 6.95 (d, 1H), 6.45 (d, 1H), 3.85 (d, 2H), 3.75 (m, 1H), 2.88 (m, 1H), 2.78 (m, 2H), 2.62 (m, 1H), 2.12 (s, 3H), 2.13-2.05 (m, 3H), 2.00-1.84 (m, 2H), 1.84-1.40 (m, 10H), 1.05 (d, 6H), 0.82 (m, 1H).

Example 129

4-Cyclobutylmethoxy-1H-indole-2-carboxylic acid {1-[(1S,9aR)-1-(octahydro-quinolizin-1-yl)methyl]-piperidin-4-yl}-amide

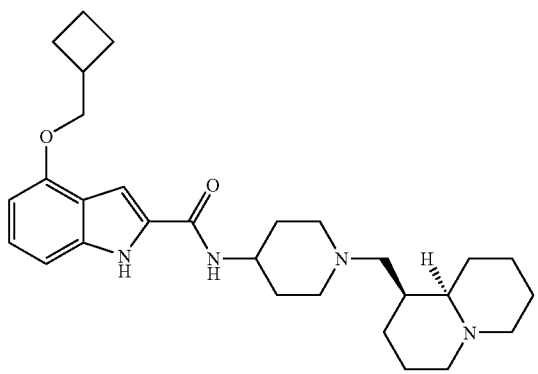

This compound is synthesized from 4-cyclobutylmethoxy-1H-indole-2-carboxylic acid piperidin-4-ylamide, 162 (preparation see below) and (1R,9aR)-1-(octahydro-quinolizin-1-yl)-methanol analogously to the method described in example 127.

MS (ESI): 479.1 [M+H]$^+$, 1H-NMR (DMSO-d$_6$): δ (ppm) 11.44 (s, 1H), 8.2 (d, 1H), 7.2 (d, 1H), 7.03 (t, 1H), 6.96 (d, 1H), 6.47 (d, 1H), 4.04 (d, 2H), 3.76 (m, 1H), 2.6-2.9 (m, 5H), 2.22-2.54 (m, 2H), 1.08-2.17 (m, 26H).

Synthesis of 4-Cyclobutylmethoxy-1H-indole-2-carboxylic acid piperidin-4-ylamide, 162

(1) Step A: 4-[(4-Cyclobutylmethoxy-1H-indole-2-carbonyl)-amino]-piperidine-1-carboxylic acid tert-butyl ester, 163

To a solution of 4-cyclobutylmethoxy-1H-indole-2-carboxylic acid (82) from example 34 (2.2 g, 8.97 mmol) in 20 ml of DCM is added 4-amino-piperidine-1-carboxylic acid tert-butyl ester (1.98 g, 9.87 mmol), HOBT (1.37 g, 8.97 mmol), triethylamine (2.5 ml, 17.94 mmol) and EDC (1.72 g, 8.97 mmol). The mixture is stirred at room temperature over night. It is then washed with 2N—NaOH and brine, dried over anhydrous sodium sulphate and evaporated to give a yellow powder. The crude material is purified by chromatography on silicagel using hexane and EtOAc (from 0% to 20%).

Yield: 3.02 g (79%). MS (ESI): 426.3 [M−H]$^-$, 1H-NMR (CDCl$_3$): δ (ppm) 9.33 (s, 1H), 7.17 (t, 1H), 7.03 (d, 1H), 6.97 (s, 1H), 6.5 (d, 1H), 6.12 (d, 1H), 4.13 (m, 4H), 4.07 (d, 2H), 2.78-2.97 (m, 4H), 1.88-2.25 (m, 8H), 1.46 (s, 9H).

(2) Step B: 4-Cyclobutylmethoxy-1H-indole-2-carboxylic acid piperidin-4-ylamide, 162

The tert-butyl ester (163) from above (3.02 g, 7.05 mmol) is dissolved in 20 ml of dioxane. A 4M-solution of HCl in dioxane (14.1 ml, 56.4 mmol) is added and the mixture is stirred for 24 hours. Evaporation gave the hydrochloride as a white powder.

Yield: 2.93 g (>100%, not completely dry).

MS (ESI): 328.2 [M+H]$^+$, 1H-NMR (DMSO-d$_6$): δ (ppm) 11.59 (s, 1H), 8.75 (br m, 2H), 8.51 (d, 1H), 7.25 (s, 1H), 7.07 (t, 1H), 6.99 (d, 1H), 6.5 (d, 1H), 4.1 (m, 1H), 4.05 (d, 2H), 3.25-3.45 (m, 2H), 3.02 (m, 2H), 2.78 (m, 1H), 2.14 (m, 2H), 1.85-2.04 (m, 5H), 1.76 (m, 2H).

Example 130

4-Cyclobutylmethoxy-1H-indole-2-carboxylic acid {1-[(S)-2-((3R,4R)-4-hydroxy-3-methyl-piperidin-1-yl)-propyl]-piperidin-4-yl}-amide

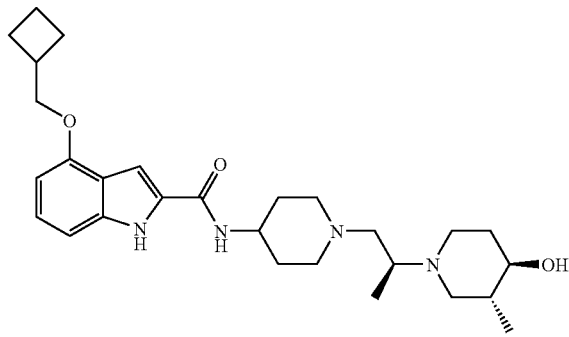

This compound is synthesized from 4-cyclobutylmethoxy-1H-indole-2-carboxylic acid piperidin-4-ylamide, 162 (see example 129) and 2,2-dimethyl-propionic acid (3R,4R)-1-((R)-2-hydroxy-propyl)-3-methyl-piperidin-4-yl ester, 164 (preparation see below) analogously to the method described in example 127, followed by pivaloyl cleavage as described for amine 55.

MS (ESI): 483.2 [M+H]$^+$, 1H-NMR (DMSO-d$_6$): δ (ppm) 11.43 (s, 1H), 8.2 (br s, 1H), 7.19 (s, 1H), 7.03 (t, 1H), 6.96 (d, 1H), 6.47 (d, 1H), 4.44 (m, 1H), 4.04 (d, 2H), 3.73 (m, 1H), 2.58-2.96 (m, 7H), 2.04-2.41 (m, 6H), 1.83-2.02 (m, 6H), 1.66-1.82 (m, 3H), 1.45-1.65 (m, 2H), 1.2-1.44 (m, 2H), 0.91 (d, 3H), 0.86 (d, 3H).

(1) 2,2-Dimethyl-propionic acid (3R,4R)-1-((R)-2-hydroxy-propyl)-3-methyl-piperidin-4-yl ester (164)

A solution of piperidine 20 (3 g, 15.05 mmol) and (R)-2-methyl-oxirane (15.05 ml, 150.5 mmol) in 10 ml of ethanol is stirred for 24 hours in a closed flask. The solvent is evaporated and the residue distilled in a Kugelrohr apparatus (0.08 mbar, 80-90 C).

Yield: 3.82 g (99%). MS (ESI): 258.2 [M+H]$^+$, 1H-NMR (DMSO-d$_6$): δ (ppm) 4.34 (br s, 1H), 4.24 (td, 1H), 3.70 (sextett, 1H), 2.79 (m, 2H), 2.03-2.28 (m, 3H), 1.65-1.9 (m, 3H), 1.45 (qd, 1H), 1.14 (s, 9H), 1.02 (d, 3H), 0.81 (d, 3H), [α]$_D$=−66.1 (c=1.5 in MeOH)

Example 131

4-Cyclobutylmethoxy-1H-indole-2-carboxylic acid {1-[(S)-2-((3S,4R,5S)-3,4-dihydroxy-5-methyl-piperidin-1-yl)-propyl]-piperidin-4-yl}-amide

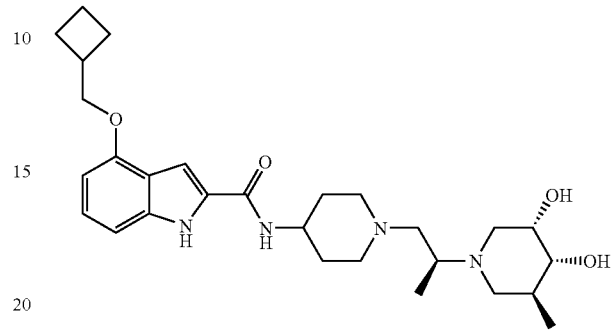

This compound is synthesized from 4-cyclobutylmethoxy-1H-indole-2-carboxylic acid piperidin-4-ylamide, 162 (see example 129) and amine 35 analogously to the method described in 54, followed by cleavage of the protecting group.

MS (ESI): 499.4 [M+H]$^+$, 1H-NMR (DMSO-d$_6$): δ (ppm) 11.47 (s, 1H), 8.28 (br s, 1H), 7.23 (s, 1H), 7.04 (t, 1H), 6.99 (d, 1H), 6.49 (d, 1H), 4.07 (m, 1H), 4.06 (d, 2H), 4.02 (m, 1H), 3.76 (m, 1H), 3.55 (m, 1H), 2.58-2.96 (m, 6H), 2.25-2.4 (m, 3H), 1.83-2.15 (m, 11H), 1.66-1.82 (m, 2H), 1.45-1.65 (m, 2H), 0.91 (d, 3H), 0.86 (d, 3H).

Example 132

4-Cyclobutylmethoxy-1H-indole-2-carboxylic acid {1-[(R)-3-hydroxy-2-((3S,4S)-4-hydroxy-3-methyl-piperidin-1-yl)-propyl]-piperidin-4-yl}-amide

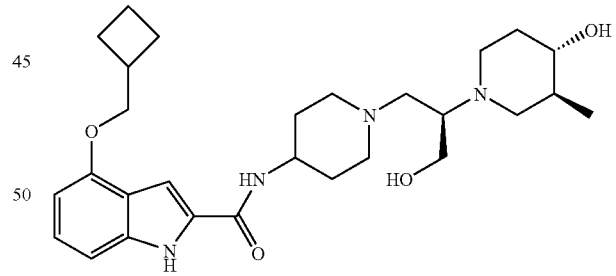

This compound is synthesized from 4-cyclobutylmethoxy-1H-indole-2-carboxylic acid piperidin-4-ylamide, 162 (see example 129) and 2,2-dimethyl-propionic acid (3S,4S)-1-((S)-2-hydroxy-3-trityloxy-propyl)-3-methyl-piperidin-4-yl ester (60) analogously to the method described in 56, followed by subsequent removal of the protection groups with sodium methylate and 80% acetic acid.

MS (ESI): 499.5 [M+H]$^+$, 1H-NMR (DMSO-d$_6$): δ (ppm) 11.44 (s, 1H), 8.22 (d, 1H), 7.2 (d, 1H), 7.03 (t, 1H), 6.96 (d, 1H), 6.47 (d, 1H), 4.45 (d, 1H), 4.28-4.45 (m, 1H), 4.04 (d, 2H), 3.7-3.8 (m, 1H), 3.42 (d, 2H), 2.6-2.98 (m, 7H), 2.25-2.42 (m, 2H) 1.15-2.18 (m, 16H), 0.86 (d, 3H).

Example 133

4-(Furan-3-ylmethoxy)-1H-indole-2-carboxylic acid {1-[(1S,9aR)-1-(octahydro-quinolizin-1-yl)methyl]-piperidin-4-yl}-amide

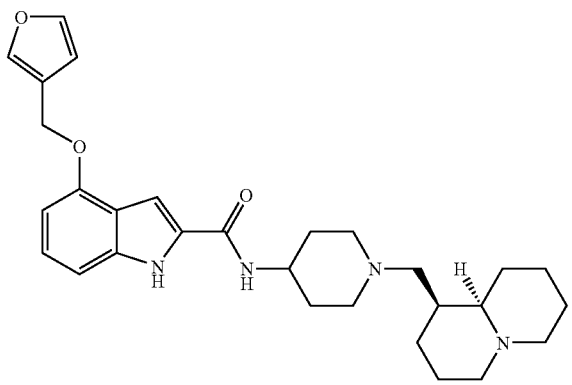

This compound is synthesized from 4-(furan-3-yl-methoxy)-1H-indole-2-carboxylic acid piperidin-4-ylamide, 165 (preparation see below) and (1R,9aR)-1-(octahydro-quinolizin-1-yl)-methanol analogously to the method described in example 127.

MS (ESI): 491.1 [M+H]$^+$, 1H-NMR (DMSO-d$_6$): δ (ppm) 11.45 (s, 1H), 8.13 (d, 1H), 7.82 (s, 1H), 7.68 (t, 1H), 7.22 (d, 1H), 7.05 (t, 1H), 6.98 (d, 1H), 6.62 (s, 1H), 6.59 (d, 1H), 5.03 (s, 2H), 3.74 (m, 1H), 2.8 (m, 2H), 2.69 (m, 2H), 2.43-2.53 (m, 1H), 2.27 (m, 1H), 2.02 (m, 1H), 1.07-1.95 (m, 19H).

Synthesis of 4-(Furan-3-ylmethoxy)-1H-indole-2-carboxylic acid piperidin-4-ylamide (165)

(1) Step A: 4-{[4-(Furan-3-ylmethoxy)-1H-indole-2-carbonyl]-amino}-piperidine-1-carboxylic acid tert-butyl ester (166)

To a solution of 4-(furan-3ylmethoxy)-1H-indole-2-carboxylic acid (95) from Example 33 (5 g, 19.44 mmol) in 10 ml of DCM is added 4-amino-piperidine-1-carboxylic acid tert-butyl ester (3.89 g, 19.44 mmol), HOBT (2.98 g, 19.44 mmol), triethylamine (5.4 ml, 38.88 mmol) and EDC (3.73 g, 19.44 mmol). The mixture is stirred at room temperature over night. It is then washed with 2N—NaOH and brine, dried over anhydrous sodium sulphate and evaporated to give a yellow powder. The crude material is purified by chromatography on silicagel using DCM and EtOAc (from 0% to 10%).

Yield: 7.51 g (88%). MS (ESI): 438.3 [M−H]$^-$, 1H-NMR (CDCl$_3$): δ (ppm) 9.42 (s, 1H), 7.57 (s, 1H), 7.46 (s, 1H), 7.21 (t, 1H), 7.05 (d, 1H), 6.96 (s, 1H), 6.6 (d, 1H), 6.55 (s, 1H), 6.08 (d, 1H), 5.07 (d, 2H), 4.04-4.2 (overlapping m, 3H), 2.91 (m, 2H), 2.01 (m, 2H), 1.48 (s, 9H) 1.42 (m, 2H).

(2) Step B: 4-(Furan-3-ylmethoxy)-1H-indole-2-carboxylic acid piperidin-4-ylamide (165)

The tert-butyl ester (166) from above (695 mg, 1.58 mmol) is dissolved in 5 ml of dioxane. A 4M-solution of HCl in dioxane (3.2 ml, 12.8 mmol) is added and the mixture is stirred for 24 hours. Evaporation gave the hydrochloride as a white powder.

Yield: 595 mg (100%). MS (ESI): 340.2 [M+H]$^+$, 1H-NMR (DMSO-d$_6$): δ (ppm) 11.65 (s, 1H), 9.0 (br m, 2H), 8.5 (d, 1H), 7.85 (s, 1H), 7.71 (s, 1H), 7.3 (s, 1H), 7.09 (t, 1H), 7.02 (d, 1H), 6.62 (d, 1H), 6.64 (s, 1H), 5.05 (d, 2H), 4.07 (m, 1H), 3.31 (m, 2H), 3.0 (m, 2H), 1.96 (m, 2H), 1.78 (m, 2H).

Example 134

4-(Furan-3-ylmethoxy)-1H-indole-2-carboxylic acid {1-[(S)-2-((3R,4R)-4-hydroxy-3-methyl-piperidin-1-yl)-propyl]-piperidin-4-yl}-amide

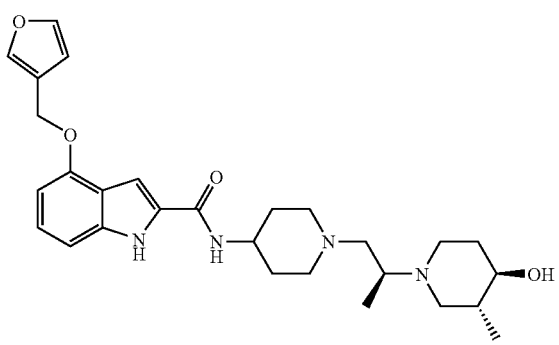

This compound is synthesized from 4-(furan-3-yl-methoxy)-1H-indole-2-carboxylic acid piperidin-4-ylamide, 165 (see example 133) and 2,2-dimethyl-propionic acid (3R,4R)-1-((R)-2-hydroxy-propyl)-3-methyl-piperidin-4-yl ester, 164 (preparation see example 130) analogously to the method described in example 127, followed by pivaloyl cleavage as described for amine 55.

MS (ESI): 495.2 [M+H]$^+$, 1H-NMR (DMSO-d$_6$): δ (ppm) 11.46 (s, 1H), 8.14 (d, 1H), 7.82 (s, 1H), 7.68 (br s, 1H), 7.23 (s, 1H), 7.05 (t, 1H), 6.99 (d, 1H), 6.62 (s, 1H), 6.6 (d, 1H), 5.03 (s, 2H), 4.43 (d, 1H), 3.72 (m, 1H), 2.56-2.95 (m, 5H), 2.32 (m, 1H), 2.24 (m, 1H), 2.04-2.19 (m, 2H), 1.9 (m, 2H), 1.67-1.79 (m, 3H), 1.43-1.61 (m, 2H), 1.21-1.41 (m, 3H), 0.91 (d, 3H), 0.86 (d, 3H).

Example 135

4-(2-Methyl-thiazol-4-ylmethoxy)-1H-indole-2-carboxylic acid [1-(octahydro-quinolizin-1-ylmethyl)-piperidin-4-yl]-amide

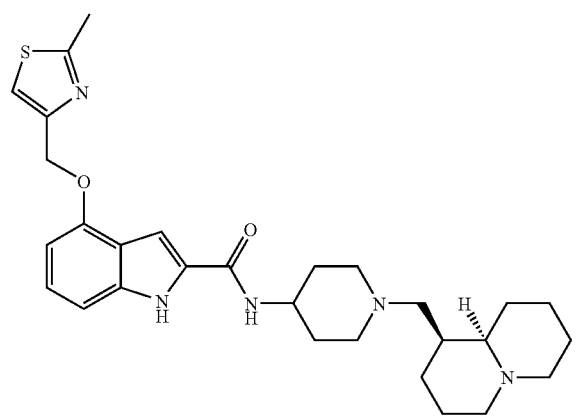

This compound is synthesized from 4-(2-methyl-thiazol-4-ylmethoxy)-1H-indole-2-carboxylic acid piperidin-4-ylamide, (167, preparation see below) and (1R,9aR)-1-(octahydro-quinolizin-1-yl)-methanol analogously to the method described in example 127.

MS (ESI): 522 [M+H]$^+$, 1H-NMR (DMSO-d$_6$): δ (ppm) 11.5 (s, 1H), 8.15 (d, 1H), 7.57 (s, 1H), 7.25 (s, 1H), 7.05 (dd, 1H), 6.98 (d, 1H), 6.62 (s, 1H), 5.18 (s, 2H), 3.74 (m, 1H), 2.8 (m, 2H), 2.69 (m, 2H), 2.68 (s, 3H), 2.43-2.53 (m, 1H), 2.27 (m, 1H), 2.02 (m, 1H), 1.07-1.95 (m, 19H).

Synthesis of 4-(methyl-thiazol-4-ylmethoxy)-1H-indole-2-carboxylic acid piperidin-4-ylamide (167)

(1) Step A: (2-Methyl-thiazol-4-yl)-methanol (168)

2-Methyl-thiazole-4-carboxylic acid ethyl ester (966 mg, 5.64 mmol) is dissolved in 5 ml of diethylether and cooled to −78° C. A 1M solution of lithium aluminium hydride in THF (16.9 ml, 16.9 mmol) is added dropwise and the mixture is stirred for 3.5 h at −78° C. The mixture is quenched at this temperature with a saturated solution of sodium sulphate and is allowed to warm up to room temperature, followed by extraction with ether and evaporation.

Yield: 670 mg (92%). MS (ESI): 130.0 [M−H]$^-$, 1H-NMR (CDCl$_3$): δ (ppm) 7.20 (s, 1H), 5.27 (dd, 1H), 4.50 (d, 2H), 2.62 (s, 3H).

(2) Step B: 4-(2-Methyl-thiazol-4-ylmethoxy)-indole-1,2-dicarboxylic acid 1-tert-butyl ester 2-ethyl ester (169)

(2-Methyl-thiazol-4-yl)-methanol (168, 670 mg, 5.2 mmol) is dissolved in 12 ml of dry THF under argon, followed by addition of 4-Hydroxy-indole-1,2-dicarboxylic acid 1-tert-butyl ester 2-ethyl ester (102, see example 42, 1.58 g, 5.2 mmol), triphenylphosphine (1.63 g, 6.2 mmol), and the solution is cooled to 0° C. A 40% solution of ethyl azadicarboxylate in toluene (2.7 ml, 6.2 mmol) is added dropwise and the mixture is stirred for 2.5 h at 0° C. The solvents are removed under reduced pressure and the residue is dissolved in ethyl acetate and washed with sodiumhydrogencarbonate solution and brine. The organic layers are dried over sodium sulphate, filtrated and evaporated. The crude product is purified by flash chromatography (silica gel, ethyl acetate/hexanes 3:7)

Yield: 1.75 g (81%). MS (ESI): 417.2 [M+H]$^+$, 1H-NMR (DMSO-d$_6$): δ (ppm) 7.67 (s, 1H), 7.55 (d, 1H), 7.41 (dd, 1H), 7.27 (s, 1H), 6.99 (d, 1H), 5.27 (s, 2H), 4.31 (q, 2H), 2.68 (s, 3H), 1.57 (s, 9H), 1.32 (t, 3H).

(3) Step C: 4-(2-Methyl-thiazol-4-ylmethoxy)-1H-indole-2-carboxylic acid (170)

4-(2-Methyl-thiazol-4-ylmethoxy)-indole-1,2-dicarboxylic acid 1-tert-butyl ester 2-ethyl ester (169) (1.75 g, 4.2 mmol) is dissolved in 20 ml of ethanol. After addition of a 0.5M aqueous sodium hydroxide solution (33.6 ml, 16.8 mmol) the solution is heated to 60° C. and stirred at this temperature for 18 h. Then the reaction mixture is evaporated and the residue is dissolved in ethyl acetate. AT 0° C. conc HCl is added until a pH of 1 is reached. The organic phase is washed with water and brine. The organic layers are dried over sodium sulphate, filtrated. The product crystallized upon evaporation and could be filtrated off.

Yield: 1.21 g (100%). MS (ESI): 289.0 [M+H]$^+$, 1H-NMR (DMSO-d$_6$): δ (ppm) 11.76 (br s, 1H), 7.62 (s, 1H), 7.14 (dd, 1H), 7.07 (s, 1H), 7.02 (d, 1H), 6.66 (d, 1H), 5.22 (s, 2H), 2.68 (s, 3H).

(4) Step D: 4-{[4-(2-Methyl-thiazol-4-ylmethoxy)-1H-indole-2-carbonyl]-amino}-piperidine-1-carboxylic acid tert-butyl ester (171)

4-(2-Methyl-thiazol-4-ylmethoxy)-1H-indole-2-carboxylic acid (170) (1.21 g, 4.2 mmol) is dissolved in 10 ml of DMF and the solution is cooled to 0° C. After addition of Huenigs base (2.16 ml, 12.6 mmol), piperidin-4-yl-carbamic acid tert-butyl ester (3) (841 mg, 4.2 mmol) and PyBOP (2.4 g, 4.6 mmol) the mixture is stirred at room temperature for 18 h. Ethyl acetate is added followed by concentrated sodium hydroxide, until a pH of 11 is reached. The organic layer is washed with brine, dried over sodium sulphate and evaporated under reduced pressure. The crude product is purified by flash-chromatography (silica gel, ethyl acetate/cyclohexane 1:1).

Yield: 1.58 g (80%). MS (ESI): 471.2 [M+H]$^+$, 1H-NMR (DMSO-d$_6$): δ (ppm) 11.58 (br s, 1H), 8.25 (d, 1H), 7.61 (s, 1H), 7.27 (s, 1H), 7.09 (dd, 1H), 7.02 (d, 1H), 6.63 (d, 1H), 5.18 (s, 2H), 3.93 (m, 3H), 2.85 (m, 2H), 2.69 (s, 3H), 1.78 (m, 2H), 1.4 (s, 9H), 1.38 (m, 2H).

(5) Step E: 4-(2-Methyl-thiazol-4-ylmethoxy)-1H-indole-2-carboxylic acid piperidin-4-ylamide (167)

171 from above (1.58 g, 3.36 mmol) is dissolved in a 4M solution of HCl in dioxane (32 ml, 128 mmol) and stirred for 45 min at room temperature. Then the reaction mixture is evaporated, dissolved in ethyl acetate and conc sodium hydroxide is added until a pH of 11 is reached. The organic layer is washed with brine, dried over sodium sulphate and evaporated under reduced pressure.

Yield: 1.28 g (100%). %). MS (ESI): 371.2 [M+H]$^+$, 1H-NMR (DMSO-d$_6$): δ (ppm) 11.56 (br, 1H), 8.28 (d, 1H), 7.61 (s, 1H), 7.3 (s, 1H), 7.09 (dd, 1H), 7.02 (d, 1H), 6.62 (d, 1H), 5.19 (s, 2H), 3.90 (m, 1H), 3.07 (m, 2H), 2.70 (s, 3H), 2.62-2.75 (m, 2H), 1.72-1.85 (m, 3H), 1.4-1.55 (m, 2H).

Example 136

4-(Benzofuran-3-ylmethoxy)-1H-indole-2-carboxylic acid {1-[2-(3,4-dihydroxy-5-methyl-piperidin-1-yl)-propyl]-piperidin-4-yl}-amide

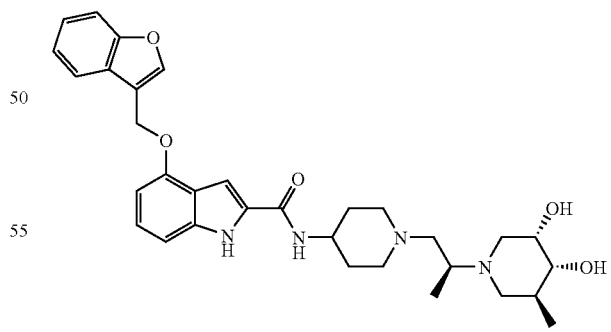

This compound is synthesized from 4-(benzofuran-3-ylmethoxy)-1H-indole-2-carboxylic acid piperidin-4-ylamide, 172 (preparation see below) and amine 35 analogously to the method described in 54, followed by cleavage of the protecting group.

MS (ESI): 561 [M+H]$^+$, 1H-NMR (DMSO-d$_6$): δ (ppm) 11.48 (s, 1H), 8.16 (s, 1H), 8.15 (d, 1H), 7.72 (d, 1H), 7.61 (d, 1H), 7.35 (dd, 1H), 7.29 (dd, 1H), 7.19 (s, 1H), 7.09 (dd, 1H), 7.01 (d, 1H), 6.71 (d, 1H), 5.35 (s, 2H), 4.04 (d, 1H), 3.98 (m, 1H), 3.72 (m, 1H), 3.53 (m, 1H), 2.50-2.90 (m, 7H), 2.24-2.38 (m, 2H), 1.88-2.08 (m, 3H), 1.66-1.78 (m, 3H), 1.45-1.58 (m, 2H), 0.86 (d, 3H), 0.83 (d, 3H).

Synthesis of 4-(Benzofuran-3-ylmethoxy)-1H-indole-2-carboxylic acid piperidin-4-ylamide (172)

(1) Step A: 4-{[4-(Benzofuran-3-ylmethoxy)-1H-indole-2-carbonyl]-amino}-piperidine-1-carboxylic acid tert-butyl ester (173)

To a ice-cold solution of 4-(benzofuran-3ylmethoxy)-1H-indole-2-carboxylic acid (105, see example 50) (200 mg, 0.651 mmol) in 2 ml of dimethylformamide is added Huenigs base (334 ul, 1.95 mmol). After stirring at 0° C. for 10 min, 4-amino-piperidine-1-carboxylic acid tert-butyl ester (130 mg, 0.651 mmol) and PyBOP (356 mg, 0.684 mmol) are added subsequently. The mixture is stirred at room temperature over night. It is then diluted with ethyl acetate, washed with 1N—NaOH and brine, dried over anhydrous sodium sulphate and evaporated to give 980 mg of a lightbrown oil. The crude material is purified by chromatography on silicagel using cyclohexane and ethylacetate (1:1).

Yield: 318 mg (100%). MS (ESI): 488.2 [M–H]$^-$, 1H-NMR (CDCl$_3$): δ (ppm) 9.15 (s, 1H), 7.77 (s, 1H), 7.72 (d, 1H), 7.55 (d, 1H), 7.38 (dd, 1H), 7.3 (dd, 1H), 7.23 (d, 1H), 7.08 (d, 1H), 6.91 (s, 1H), 6.7 (d, 1H), 5.96 (d, 1H), 5.34 (s, 2H), 4.04-4.2 (overlapping m, 3H), 2.91 (m, 2H), 2.01 (m, 2H), 1.48 (s, 9H), 1.40 (m, 2H).

(2) Step B: 4-(Benzofuran-3-ylmethoxy)-1H-indole-2-carboxylic acid piperidin-4-ylamide (172)

The tert-butyl ester (173) from above (318 mg, 0.65 mmol) is dissolved in a 4M-solution of HCl in dioxane (6 ml, 1.2 mmol) and stirred for 1 hour at room temperature. Evaporation gave the hydrochloride as a white powder, which is dissolved in water, treated with conc NaOH solution at 0° C. to an pH of 11 and extracted with ethyl acetate. The organic layers are washed with brine, dried over sodium sulphate and evaporated.

Yield: 248 mg (98%) of a light yellow solid. MS (ESI): 390.2 [M+H]$^+$.

Example 137

4-(5-Fluoro-benzofuran-3-ylmethoxy)-1H-indole-2-carboxylic acid {1-[2-(3,4-dihydroxy-piperidin-1-yl)-propyl]-piperidin-4-yl}-amide

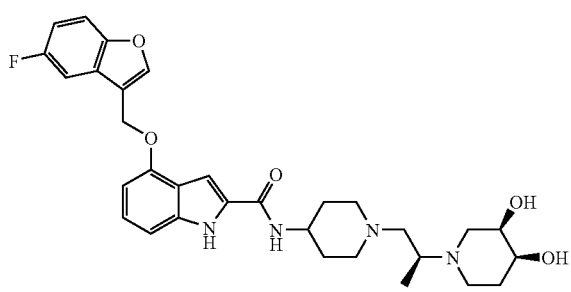

This compound is synthesized from 4-(5-fluoro-benzofuran-3-ylmethoxy)-1H-indole-2-carboxylic acid piperidin-4-ylamide (174, preparation see below) and amine 34 analogously to the method described for 54, followed by cleavage of the protecting group.

MS (ESI): 565 [M+H]$^+$, 1H-NMR (DMSO-d$_6$): δ (ppm) 11.52 (s, 1H), 8.28 (s, 1H), 7.68 (dd, 1H), 7.52 (d, 1H), 7.23 (s, 1H), 7.21 (dd, 1H), 7.11 (dd, 1H), 7.03 (d, 1H), 6.72 (d, 1H), 5.35 (s, 2H), 4.19 (m, 1H), 4.13 (d, 1H), 3.73 (m, 1H), 3.52 (br s, 1H), 3.44 (br s, 1H), 2.9 (m, 3H), 2.52 (m, 2H), 2.33 (m, 3H), 2.11 (m, 1H), 2.03 (dd, 1H), 1.84 (dd, 1H), 1.75 (d, 1H), 1.45-1.65 (m, 5H), 0.9 (d, 3H).

Synthesis of 4-(5-fluoro-benzofuran-3-ylmethoxy)-1H-indole-2-carboxylic acid piperidin-4-ylamide (174)

(1) Step A: 4-{[4-(5-fluoro-benzofuran-3-yl-methoxy)-1H-indole-2-carbonyl]-amino}-piperidine-1-carboxylic acid tert-butyl ester (175)

To a solution of 4-(5-fluoro-benzofuran-3ylmethoxy)-1H-indole-2-carboxylic acid (113, see example 60, 160 mg, 0.49 mmol) is dissolved in 1.5 ml of DMF and cooled to 0° C. After addition of Huenigs base (252 ul, 1.5 mmol) the mixture is stirred for 15 min, then piperidin-4-yl-carbamic acid tert-butyl ester (3, 98.5 mg, 0.49 mmol) is added, followed by PyBOP (269 mg, 0.51 mmol). The mixture is stirred at room temperature for 18 h. Then the mixture is diluted with ethyl acetate, washed 1N sodium hydroxide solution and brine. The organic layers are dried over sodium sulfate and evaporated under reduced pressure. The crude product (581 mg) is purified by flash-chromatography (silica gel, cyclohexane/ethyl acetate 1:1)

Yield: 250 mg (100%). MS (ESI): 506.2 [M–H]$^-$.

(2) Step B: 4-(5-fluoro-benzofuran-3-ylmethoxy)-1H-indole-2-carboxylic acid piperidin-4-ylamide (174)

The tert-butyl ester (175) from above (250 mg, 0.49 mmol) is dissolved in a 4M-solution of HCl in dioxane (4 ml, 16 mmol) and the mixture is stirred for 1 h at room temperature. Evaporation gave the hydrochloride as a yellow solid, which is dissolved in 5 ml of water and the pH is adjusted to 11 by addition of conc sodium hydroxide. The solution is extracted with ethyl acetate, the organic layers are washed with brine and dried over sodium sulphate. Evaporation gave 200 mg (100%) of a white solid. %).

MS (ESI): 408.2 [M+H]$^+$.

Example 138

4-(5-chloro-benzofuran-3-ylmethoxy)-1H-indole-2-carboxylic acid {1-[2-(3,4-dihydroxy-piperidin-1-yl)-propyl]-piperidin-4-yl}-amide

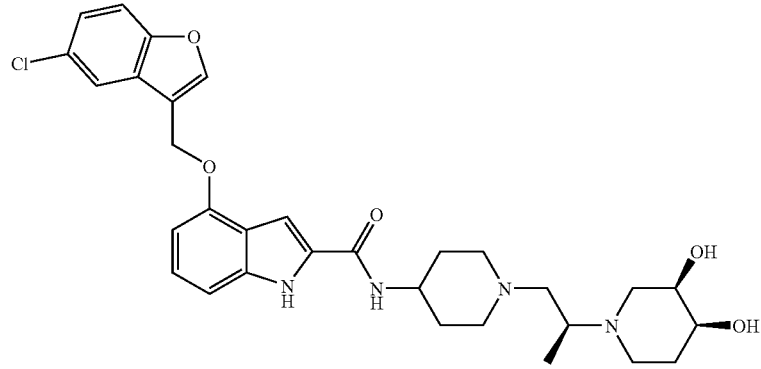

This compound is synthesized from 4-(5-chloro-benzofuran-3-ylmethoxy)-1H-indole-2-carboxylic acid piperidin-4-ylamide, (176, preparation see below) and amine 34 analogously to the method described for 54, followed by cleavage of the protecting group.

MS (ESI): 581 [M+H]$^+$, 1H-NMR (DMSO-d$_6$): δ (ppm) 11.5 (brs, 1H), 8.28 (s, 1H), 8.17 (d, 1H), 7.79 (s, 1H), 7.68 (d, 1H), 7.39 (d, 1H), 7.22 (s, 1H), 7.10 (dd, 1H), 7.03 (d, 1H), 6.7 (d, 1H), 5.36 (s, 2H), 4.18 (m, 1H), 4.12 (d, 1H), 3.72 (m, 1H), 3.52 (m, 1H), 3.45 (m, 1H), 2.45-2.9 (m, 4H), 2.33 (m, 4H), 1.88-2.14 (m, 3H), 1.73 (m, 2H), 1.42-1.65 (m, 4H), 0.89 (d, 3H).

Synthesis of 4-(5-chloro-benzofuran-3-ylmethoxy)-1H-indole-2-carboxylic acid piperidin-4-ylamide (176)

(1) Step A: 4-{[4-(5-chloro-benzofuran-3-yl-methoxy)-1H-indole-2-carbonyl]-amino}-piperidine-1-carboxylic acid tert-butyl ester (177)

This compound is synthesized from 4-(5-chloro-benzofuran-3-ylmethoxy)-1H-indole-2-carboxylic acid (113, see example 60) and amine 3 analogously to the method described for 175.

Yield: 270 mg (60%). MS (ESI): 522 [M−H]$^−$, 1H-NMR (DMSO-d$_6$): δ (ppm) 11.58 (m, 1H), 8.28 (s, 1H), 8.20 (d, 1H), 7.8 (s, 1H), 7.69 (d, 1H), 7.4 (d, 1H), 7.2 (s, 1H), 7.11 (dd, 1H), 7.03 (d, 1H), 6.72 (d, 1H), 5.36 (s, 2H), 3.93 (m, 3H), 2.7-2.9 (m, 2H), 1.76 (d, 2H), 1.4 (s, 9H), 1.29-1.42 (m, 2H).

(2) Step B: 4-(5-chloro-benzofuran-3-ylmethoxy)-1H-indole-2-carboxylic acid piperidin-4-ylamide (176)

This compound is synthesized from 177 analogously to the method described for 175.

MS (ESI): 424.2 [M+H]$^+$, 1H-NMR (DMSO-d$_6$): δ (ppm) 11.38 (s, 1H), 8.14 (s, 1H), 8.02 (d, 1H), 7.66 (s, 1H), 7.55 (d, 1H), 7.27 (d, 1H), 7.09 (s, 1H), 6.98 (dd, 1H), 6.91 (d, 1H), 6.59 (d, 1H), 5.23 (s, 2H), 3.68 (m, 1H), 2.8 (m, 1H), 2.37 (m, 3H), 1.57 (m, 1H), 1.25 (m, 3H).

Example 139

4-(5-Chloro-benzofuran-3-ylmethoxy)-1H-indole-2-carboxylic acid {1-[(9S,9aS)-1-(octahydro-pyrido[2,1-c][1,4]oxazin-9-yl)methyl]-piperidin-4-yl}-amide

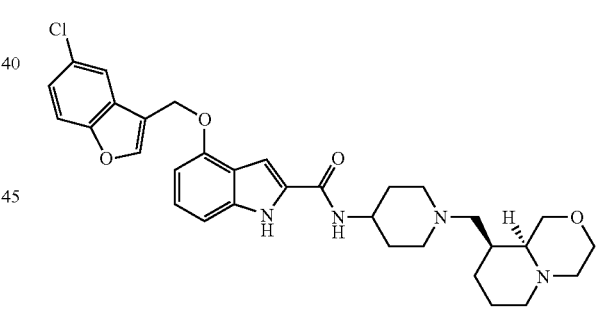

This compound is synthesized from the compound 176 (see example 138) and (9RS,9aSR)-1-(octahydro-pyrido[2,1-c][1,4]oxazin-9-yl)-methanol (63) analogously to the method described in example 127.

Yield: 7.7 mg (12%) of a white solid. MS (ESI): 575/577 [M+H]$^+$, 1H-NMR (DMSO-d$_6$): δ (ppm) 11.5 (s, 1H), 8.11 (d, 1H), 7.78 (d, 1H), 7.67 (d, 1H), 7.38 (dd, 1H), 7.18 (d, 1H), 7.10 (m, 1H), 7.03 (d, 1H), 6.70 (d, 1H), 5.36 (s, 2H), 3.75-3.60 (m, 2H), 3.50-3.30 (m, 4H), 2.80-2.55 (m, 2H), 2.60-2.50 (m, 2H), 2.32 (d, 2H), 2.10-1.65 (m, 9H), 1.60-1.40 (m, 3H), 1.35-1.20 (m, 2H).

Example 140

4-(5-Chloro-benzofuran-3-ylmethoxy)-1H-indole-2-carboxylic acid {1-[(8S,8aS)-1-(hexahydro-pyrrolo[2,1-c][1,4]oxazin-8-yl)methyl]-piperidin-4-yl}-amide

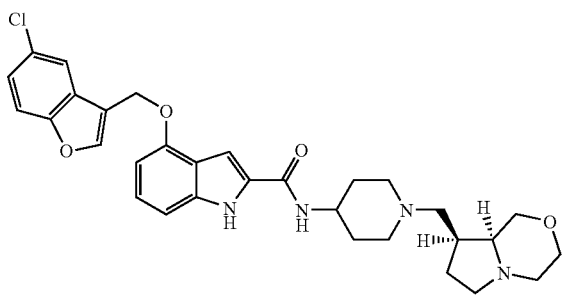

This compound is synthesized from the compound 176 (see example 138) and (9RS,9aSR)-1-(octahydro-pyrido[2,1-c][1,4]oxazin-9-yl)-methanol (67) analogously to the method described in example 127.

Yield: 82 mg (14.6%) of a white solid. MS (ESI): 563/565 [M+H]+, 1H-NMR (DMSO-d6): δ (ppm) 11.5 (s, 1H), 8.25 (s, 1H), 8.10 (d, 1H), 7.78 (d, 1H), 7.67 (d, 1H), 7.38 (bd, 1H), 7.19 (s, 1H), 7.10-7.00 (m, 2H), 6.70 (d, 1H), 5.35 (s, 2H), 4.00 (m, 1H), 3.90 (m, 1H), 3.75-3.60 (m, 2H), 3.40-3.30 (m, 2H), 2.95-2.70 (m, 1H), 2.40-2.20 (m, 2H), 2.10-1.70 (m, 8H), 1.55-1.25 (m, 4H), 1.15 (t, 1H), 1.07 (t, 1H).

Example 141

4-(4-Methoxy-phenyl)-1H-indole-2-carboxylic acid {1-[(1S,9aR)-1-(octahydro-quinolizin-1-yl)methyl]-piperidin-4-yl}-amide

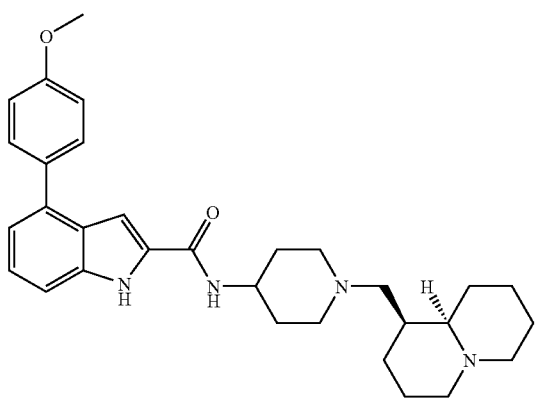

This compound is synthesized from the compound 178 (preparation see below) and octahydro-2H-chinolizin-1-yl-methanol analogously to the method described in example 127.

Yield: 350 mg (33.7%). MS (ESI): 501 [M+H]+, 1H-NMR (DMSO-d6): δ (ppm) 11.6 (s, 1H), 8.22 (d, 1H), 7.56 (d, 2H), 7.37 (d, 1H), 7.31 (m, 1H), 7.20 (dd, 1H), 7.07 (d, 2H), 7.01 (d, 1H), 3.81 (s, 3H), 3.75 (m, 1H), 3.16 (d, 1H), 2.80 (m, 2H), 2.67 (m, 2H), 2.46 (dd, 1H), 2.28 (m, 1H), 1.1-2.1 (m, 19H).

Synthesis of 4-(4-Methoxy-phenyl)-1H-indole-2-carboxylic acid piperidin-4-ylamide (178)

(1) Step A: 4-(4-Methoxy-phenyl)-1H-indole-2-carboxylic acid (128)

4-Bromo-1H-indole-2-carboxylic acid (5 g, 20.8 mmol) and 4-methoxy-phenyl-boronic acid (3.2 g, 20.8 mmol) are dissolved in 1-propanol (100 ml) and the mixture is flushed with argon for 30 min. Then bis(triphenylphosphin)palladium(II)chloride (200 mg, 1 mmol) and Na2CO3 (4.4 g, 40.2 mmol) are added and the reaction mixture is stirred at 85° C. for 3 h. After cooling down to room temperature, ethyl acetate and 2M HCl are added. The organic layers are dried over sodium sulphate. Evaporation gave 6 g of an beige solide, which is further purified by crystallisation from ethyl acetate.

Yield: 4.7 g (84%). MS (ESI): 266 [M−H]−.

(2) Step B: 4-(4-Methoxy-phenyl)-1H-indole-2-carboxylic acid (1-benzyl-piperidin-4-yl)-amide (179)

128 (4.7 g, 17.6 mmol) and 1-benzyl-piperidin-4-ylamine (3.3 g, 17.6 mmol) are dissolved in DMF (70 ml) and after addition of TBTU (6.4 g, 19.4 mmol) and ethyldiisopropylamine (12 ml, 70.4 mmol) the mixture is stirred at room temperature for 2 h. Then the solvent is evaporated at high vacuum. The residue is dissolved in ethyl acetate washed with saturated aqueous sodium hydrogen carbonate and brine. The organic layers are dried over sodium sulfate and evaporated under reduced pressure. The crude mixture is crystallized from methanol.

Yield: 4.1 g (53%). MS (ESI): 440 [M+H]+, 1H-NMR (DMSO-d6): δ (ppm) 11.6 (s, 1H), 8.26 (d, 1H), 7.56 (d, 2H), 7.38 (d, 1H), 7.15-7.35 (m, 7H), 7.08 (d, 2H), 7.01 (d 1H), 4.07 (m, 1H), 3.81 (s, 3H), 3.47 (s, 2H), 2.8 (m, 2H), 2.04 (m, 2H), 1.77 (m, 2H), 1.58 (m, 2H).

(3) Step C: 4-(4-Methoxy-phenyl)-1H-indole-2-carboxylic acid piperidin-4-ylamide (178)

179 (4 g, 9.1 mmol) is dissolved in 100 ml of methanol, flushed with argon and, after addition of Pd—C (100 mg) and 2M HCl (5.5 ml, 11 mmol), the mixture is hydrogenated at room temperature for 3 h. The mixture is filtrated over celite and evaporated.

Yield: 1 g of a white solid (29%). MS (ESI): 350 [M+H]+.

Example 142

4-(4-Ethoxy-phenyl)-1H-indole-2-carboxylic acid {1-[(1S,9aR)-1-(octahydro-quinolizin-1-yl)methyl]-piperidin-4-yl}-amide

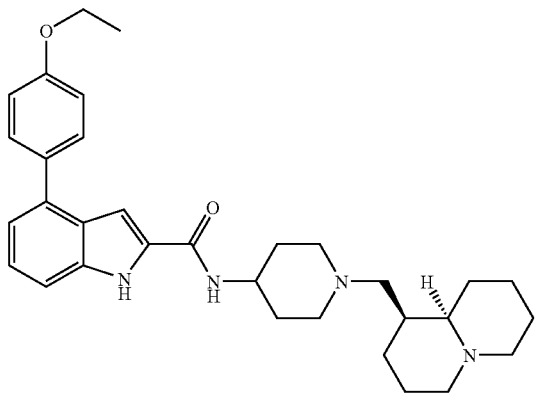

This compound is synthesized from the compound 180 (preparation see below) and octahydro-2H-chinolizin-1-yl-methanol analogously to the method described in example 127.

Yield: 23 mg (16.2%). MS (ESI): 515 [M+H]$^+$, 1H-NMR (DMSO-d$_6$): δ (ppm) 11.67 (s, 1H), 8.28 (d, 1H), 7.56 (d, 2H), 7.33 (d, 1H), 7.3 (m, 1H), 7.20 (dd, 1H), 7.0-7.07 (m, 3H), 4.08 (q, 2H), 3.77 (m, 1H), 2.80 (dd, 2H), 2.67 (m, 2H), 2.46 (dd, 1H), 2.28 (dd, 1H), 2.01 (dd, 1H), 1.36 (t, 3H), 1.1-2.1 (m, 19H).

Synthesis of 4-(4-Ethoxy-phenyl)-1H-indole-2-carboxylic acid piperidin-4-ylamide (180)

This compound has been synthesized from 4-ethoxy-phenyl-boronic acid analogously to the method described in the synthesis of 178 (see example 141).

MS (ESI): 364 [M+H]$^+$, 1H-NMR (DMSO-d$_6$): δ (ppm) 11.64 (s, 1H), 8.28 (d, 1H), 7.55 (d, 2H), 7.35 (d, 1H), 7.31 (s, 1H), 7.19 (dd, 1H), 7.06 (d, 2H), 7.02 (d, 1H), 4.09 (q, 2H), 3.81 (m, 1H), 3.4 (m, 1H), 2.92 (m, 2H), 2.46 (m, 2H), 1.77 (m, 2H), 1.4 (m, 2H), 1.37 (t, 3H).

Example 143

4-(6-Methoxy-pyridin-3-yl)-1H-indole-2-carboxylic acid {1-[(S)-2-((3S,4S)-4-hydroxy-3-methyl-piperidin-1-yl)-propyl]-piperidin-4-yl}-amide

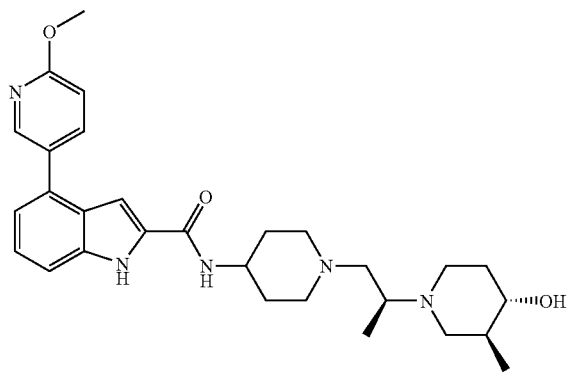

This compound is synthesized from 4-(6-Methoxy-pyridin-3-yl)-1H-indole-2-carboxylic acid piperidin-4-ylamide (181, preparation see below) and amine 164 analogously to the method described for 54, followed by cleavage of the protecting group.

MS (ESI): 504 [M+H]$^+$, 1H-NMR (DMSO-d$_6$): δ (ppm) 11.7 (s, 1H), 8.48 (br s, 1H), 8.28 (d, 1H), 7.97 (d, 1H), 7.41 (d, 1H), 7.36 (s, 1H), 7.24 (dd, 1H), 7.09 (d, 1H), 6.96 (d, 1H), 4.44 (d, 1H), 3.93 (s, 3H), 3.68-3.82 (m, 1H), 2.61-2.96 (m, 6H), 2.04-2.39 (m, 4H), 1.85-1.96 (m, 2H), 1.66-1.82 (m, 3H), 1.45-1.65 (m, 2H), 1.2-1.44 (m, 2H), 0.91 (d, 3H), 0.86 (d, 3H).

Synthesis of 4-(6-Methoxy-pyridin-3-yl)-1H-indole-2-carboxylic acid piperidin-4-ylamide (181)

(1) Step A: 4-[(4-Bromo-1H-indole-2-carbonyl)-amino]-piperidine-1-carboxylic acid tert-butyl ester (182)

4-Bromo-1H-indole-2-carboxylic acid (3 g, 12.5 mmol) is dissolved in 30 ml of DMF and the solution is cooled to 0° C. After addition of Huenigs base (6.4 ml, 37.5 mmol), the mixture is stirred for 15 min. Then piperidin-4-yl-carbamic acid tert-butyl ester 3 (2.5 g, 12.5 mmol) is added, followed by PyBOP (7.2 g, 13.7 mmol). The reaction mixture is stirred for 18 h at room temperature. Then ethyl acetate is added and conc sodium hydroxide until a pH of 11 is reached. The organic layers are washed with brine, dried over sodium sulphate and evaporated. The crude product is further purified by flash-chromatography (silica gel, ethyl acetate/cyclohexane 1:1)

Yield: 5.13 g (97%). MS (ESI): 420, 422 [M−H]$^-$, 1H-NMR (DMSO-d$_6$): δ (ppm) 11.9 (m, 1H), 8.48 (d, 1H), 7.45 (d, 1H), 7.27 (d, 1H), 7.21 (s, 1H), 7.11 (dd, 1H), 2.86 (m, 2H), 1.81 (m, 2H), 1.42 (s, 9H), 1.42 (m, 2H).

(2) Step B: 4-{[4-(6-Methoxy-pyridin-3-yl)-1H-indole-2-carbonyl]-amino}-piperidine-1-carboxylic acid tert-butyl ester (183)

An argon stream is bubbled through a solution of 182 from above (500 mg, 1.2 mmol) and 2-methoxy-5-pyridine boronic acid (181 mg, 1.2 mmol) in 4 ml of 1-propanol for 15 min. Then 2M aqueous sodium carbonate solution (1.2 ml, 2.4 mmol) and bis(triphenylphosphine)palladium-(II)-chloride (50 mg, 0.07 mmol) are added and the reaction mixture is stirred at 85° C. for 3 h. Then the mixture is cooled to 0° C. and ethyl acetate and concentrated sodium hydroxide solution is added until a pH of 11 is reached. The solution is washed with brine and the organic layers are dried over sodium sulfate and evaporated. The crude product is purified by flash-chromatography (silica gel, cyclohexane/ethyl acetate 7:3).

Yield: 290 mg (69%). MS (ESI): 451.2 [M+H]$^+$, 1H-NMR (CDCl$_3$): δ (ppm) 9.3 (s, 1H), 8.53 (s, 1H), 7.96 (d, 1H), 7.46 (d, 1H), 7.38 (dd, 1H), 7.17 (d, 1H), 6.98 (s, 1H), 6.86 (d, 1H), 6.12 (d, 1H), 4.13 (m, 2H), 4.08 (s, 3H), 2.91 (m, 2H), 2.01 (m, 2H), 1.48 (s, 9H) 1.42 (m, 2H), 1.27 (m, 1H).

(3) Step C: 4-(6-Methoxy-pyridin-3-yl)-1H-indole-2-carboxylic acid piperidin-4-ylamide (181)

183 from above (370 mg, 0.82 mmol) is dissolved in a 4M solution of HCl in dioxane (7.5 ml, 30 mmol) and stirred for 1 h at room temperature. Then the reaction mixture is evaporated, dissolved in ethyl acetate and conc sodium hydroxide is added until a pH of 11 is reached. The organic layer is washed with brine, dried over sodium sulphate and evaporated under reduced pressure.

Yield: 300 mg (100%). MS (ESI): 351.2 [M+H]+, 1H-NMR (DMSO-d6): δ (ppm) 11.74 (m, 1H), 8.51 (s, 1H), 8.35 (d, 1H), 8.00 (d, 1H), 7.44 (d, 1H), 7.41 (s, 1H), 7.27 (dd, 1H), 7.11 (d, 1H), 7.00 (d, 1H), 3.95 (s, 3H), 3.84 (m, 1H), 2.96 (m, 2H), 2.31 (m, 1H), 2.01 (m, 2H), 1.75 (m, 2H), 1.4 (m, 2H).

Example 144

4-(6-Methoxy-pyridin-3-yl)-1H-indole-2-carboxylic acid {1-[2-((3S,4S)-4-hydroxy-3-methyl-piperidin-1-yl)-ethyl]-piperidin-4-yl}-amide

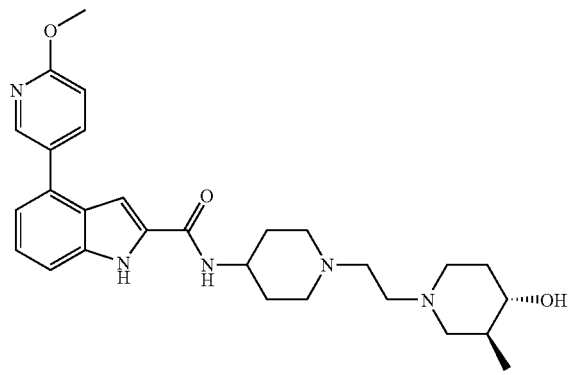

This compound is synthesized from 4-(6-Methoxy-pyridin-3-yl)-1H-indole-2-carboxylic acid [1-(2-hydroxy-ethyl)-piperidin-4-yl]-amide (184, preparation see below) and 2,2-Dimethyl-propionic acid (3S,4S)-3-methyl-piperidin-4-yl ester (17) analogously to the method described in example 150, followed by cleavage of the protecting group.

MS (ESI): 492 [M+H]+, 1H-NMR (DMSO-d6): δ (ppm) 11.70 (s, 1H), 8.48 (br s, 1H), 8.30 (d, 1H), 7.97 (dd, 1H), 7.42 (d, 1H), 7.36 (s, 1H), 7.24 (t, 1H), 7.09 (d, 1H), 6.97 (d, 1H), 4.47 (d, 1H), 3.92 (s, 3H), 3.75 (m, 1H), 2.70-2.90 (m, 5H), 2.31-2.41 (m, 4H), 1.86-2.04 (m, 3H), 1.66-1.82 (m, 3H), 1.46-1.62 (m, 3H), 1.3-1.44 (m, 2H), 0.86 (d, 3H).

Synthesis of 4-(6-Methoxy-pyridin-3-yl)-1H-indole-2-carboxylic acid [1-(2-hydroxy-ethyl)-piperidin-4-yl]-amide (184)

4-(6-Methoxy-pyridin-3-yl)-1H-indole-2-carboxylic acid piperidin-4-ylamide (181), 150 mg, 0.43 mmol) is dissolved in 3 ml of ethanol under argon. After addition of sodium carbonate (182 mg, 1.7 mmol) and 2-bromo-ethanol (61 ul, 0.85 mmol), the reaction mixture is stirred at 80° C. for 13 h. The mixture is diluted with methylene chloride, filtrated and the filtrate is evaporated. Evaporation under reduced pressure gave 128 mg of crude product, which is further purified by Flash-chromatography (dichloro methane/methanol/25% ammonia (90:9:1). Yield: 90 mg (53%). MS (ESI): 395.2 [M+H]+.

Example 145

4-p-Tolyloxy-1H-indole-2-carboxylic acid {1-[(1S, 9aR)-1-(octahydro-quinolizin-1-yl)methyl]-piperidin-4-yl}-amide

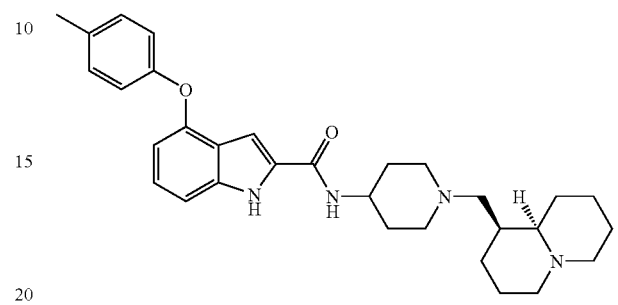

This compound is synthesized from the compound 185 (preparation see below) and octahydro-2H-chinolizin-1-yl-methanol analogously to the method described in example 127.

Yield: 86 mg (34.9%). MS (ESI): 501 [M+H]+, 1H-NMR (DMSO-d6): δ (ppm) 11.7 (s, 1H), 8.2 (d, 1H), 7.2 (d, 2H), 7.15 (d, 2H), 7.1 (s, 1H), 6.85 (d, 2H), 6.47 (d, 1H), 3.72 (m, 1H), 2.8 (dd, 2H), 2.70 (d, 2H), 2.45 (m, 1H), 2.3 (s, 3H), 2.28 (m, 1H), 2.03 (dd, 1H), 1.1-2.1 (m, 19H).

Synthesis of 4-p-tolyloxy-1H-indole-2-carboxylic acid piperidin-4-ylamide (185)

Reaction Scheme 18:

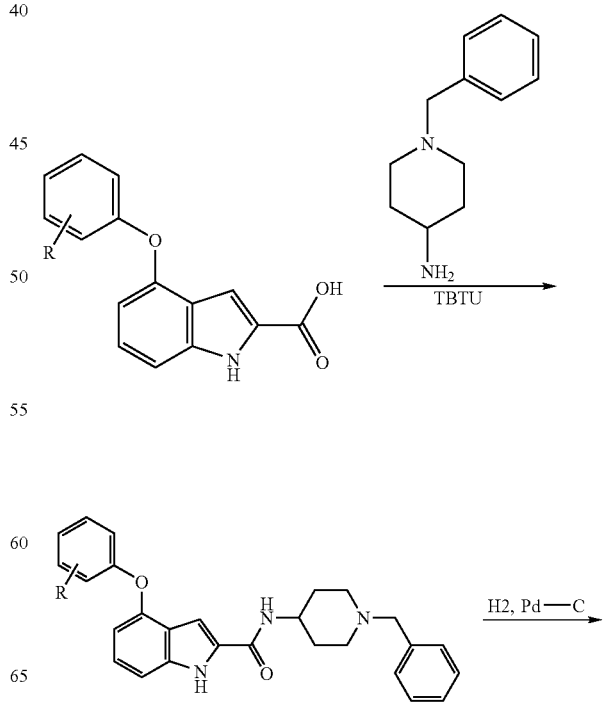

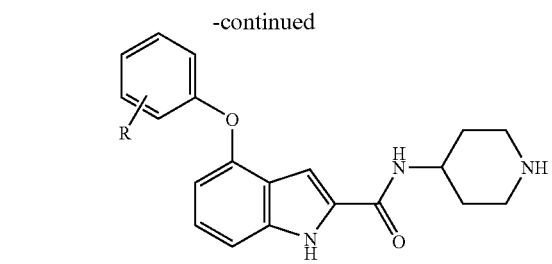

(1) Step A: 4-p-tolyloxy-1H-indole-2-carboxylic acid (1-benzyl-piperidin-4-yl)-amide (186)

4-p-tolyloxy-1H-indole-2-carboxylic acid (137) (850 mg, 3.2 mmol) and 4-amino-N-benzylpiperidine (605 mg, 3.2 mmol) are dissolved in 5 ml of DMF and after addition of TBTU (1.2 g, 3.5 mmol) and ethyldiisopropylamine (2.2 ml, 12.8 mmol) the mixture is stirred at room temperature for 2 h. Then the mixture is evaporated at high vacuum. The residue is dissolved in ethyl acetate and washed with saturated NaHCO3-solution and brine. The organic layers are dried over Na2SO4, filtrated and evaporated under reduced pressure.

Yield: 1.47 g (100%) of a yellow foam. MS (ESI): 438 [M−H]−.

(2) Step B: 4-p-Tolyloxy-1H-indole-2-carboxylic acid piperidin-4-ylamide (185)

Pd—C (1 g) is placed into a flask filled with argon and covered with methanol. 186 (1.4 g, 3.2 mmol) is dissolved in 100 ml of methanol and 1.6 ml of 2M HCl and added. After hydrogenation at room temperature for 5 h the mixture is filtrated over celite and evaporated.

Yield: 1.1 g (96%) of a white foam. MS (ESI): 350 [M+H]+, 1H-NMR (DMSO-$d_6$): δ (ppm) 11.75 (s, 1H), 8.43 (d, 1H), 7.2 (d, 1H), 7.1-7.2 (m, 4H), 6.85 (d, 2H), 6.47 (d, 1H), 4.05 (m, 1H), 3.26 (m, 2H), 2.90 (m, 2H), 2.73 (s, 1H), 2.28 (s, 3H), 1.9 (m, 2H), 1.7 (m, 2H).

Alternatively, the branched indole-2-carboxamides could be prepared as shown in reaction scheme 19.

Reaction Scheme 19:

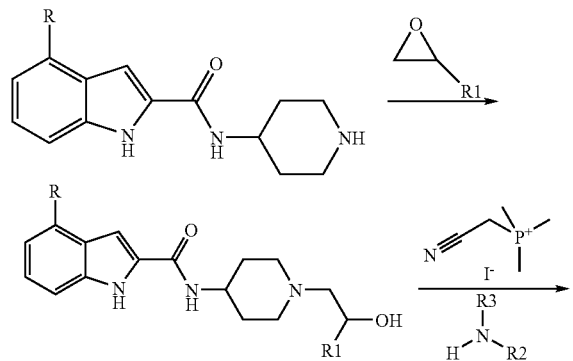

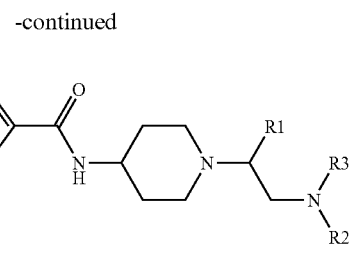

Example 146

4-Isobutoxy-1H-indole-2-carboxylic acid [1-(2-azepan-1-yl-1S-methyl-ethyl)-piperidin-4-yl]-amide

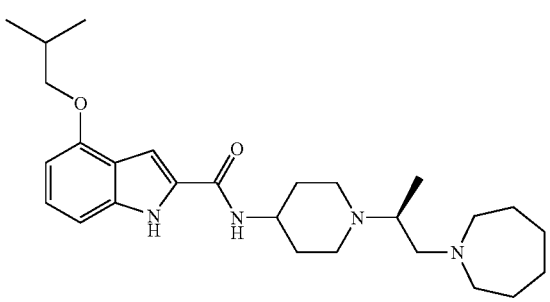

(1) Step A: 4-Isobutoxy-1H-indole-2-carboxylic acid [1-(2R-hydroxy-propyl)-piperidin-4-yl]-amide (187)

A solution of the hydrochloride of 4-isobutoxy-1H-indole-2-carboxylic acid piperidin-4-ylamide (161) from Example 127 (300 mg, 0.85 mmol) in 5 ml of ethanol and triethylamine (0.472 ml, 3.4 mmol) is treated with R(+)-propylene oxide (0.59 ml, 4.25 mmol) and stirred at room temperature in a sealed vessel for 14 hours. Another portion of R(+)-propylene oxide (0.59 ml, 4.25 mmol) is added and stirring continued for 24 hours. The solvents are then evaporated. The crude is re-dissolved in DCM and washed with 2N—NaOH and brine. The organic layer is dried over anhydrous sodium sulphate and evaporated to give a white powder.

Yield: 290 mg (91%). MS (ESI): 374.1 [M+H]$^+$, 1H-NMR (DMSO-d$_6$): δ (ppm) 11.45 (s, 1H), 8.22 (d, 1H), 7.22 (s, 1H), 7.03 (t, 1H), 6.97 (d, 1H), 6.45 (d, 1H), 4.25 (br s, 1H), 3.84 (d, 2H), 3.75 (overlapping m, 2H), 2.87 (m, 2H), 1.98-2.39 (m, 5H), 1.76 (m, 2H) 1.58 (m, 2H), 1.05 (m, 9H).

(2) Step B: 4-Isobutoxy-1H-indole-2-carboxylic acid [1-(2-azepan-1-yl-1S-methyl-ethyl)-piperidin-4-yl]-amide The alcohol (187) from above (100 mg, 0.27 mmol) is mixed with azepane (0.033 ml, 0.297 mmol), DIEA (0.227 ml, 1.35 mmol) and cyanomethyl-triphenyl phosphonium iodide (156 mg, 0.648 mmol) in 2 ml of propionitrile. The suspension is heated at 90° C. for 3 hours. The resulting solution is cooled, diluted with EtOAc, washed with 2N—NaOH and brine, dried over anhydrous sodium sulphate and evaporated. The crude material is purified by chromatography on silicagel using DCM (saturated with ammonia) and MeOH (from 0% to 10%).

Yield: 74 mg (61%). MS (ESI): 455.4 [M+H]$^+$, 1H-NMR (DMSO-d$_6$): δ (ppm) 11.43 (s, 1H), 8.2 (d, 1H), 7.22 (s, 1H), 7.02 (t, 1H), 6.96 (d, 1H), 6.44 (d, 1H), 3.84 (d, 2H), 3.72 (br m, 1H), 2.52-2.95 (m, 8H), 2.15-2.4 (m, 3H), 2.1 (m, 1H), 1.77 (m, 2H), 1.45-1.67 (m, 10H) 1.05 (d, 6H), 0.95 (d, 3H).

Example 147

4-Isobutoxy-1H-indole-2-carboxylic acid [1-(2-azepan-1-yl-1R-methyl-ethyl)-piperidin-4-yl]-amide

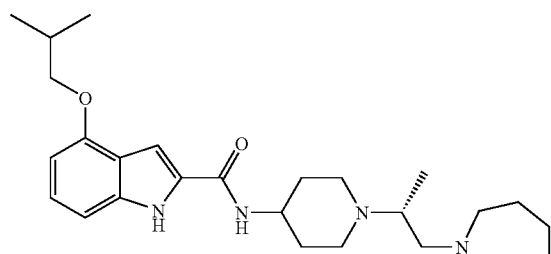

The title compound is prepared as described in Example 83 from 4-isobutoxy-1H-indole-2-carboxylic acid piperidin-4-ylamide (161), S(−)-propylene oxide and azepane. Intermediate 4-Isobutoxy-1H-indole-2-carboxylic acid [1-(2S-hydroxy-propyl)-piperidin-4-yl]-amide (188) and final product had MS and NMR spectra identical to the (R)-enantiomers of Example 146.

Example 148

4-(Furan-3-ylmethoxy)-1H-indole-2-carboxylic acid [1-(2S-azepan-1-yl-propyl)-piperidin-4-yl]-amide

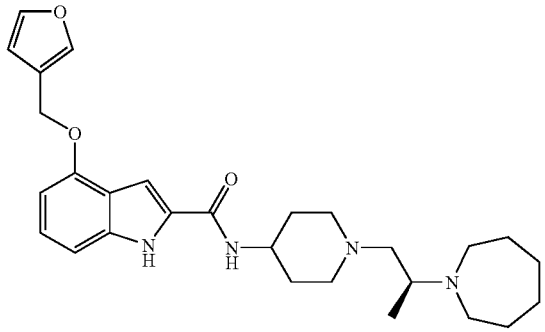

S(−)-propylene oxide (21.2 ml, 302.5 mmol) and azepam (3.41 ml, 30.25 mmol) are mixed in 10 ml of ethanol and stirred in a sealed vessel for 24 hours. The solvents are then evaporated and the crude oil of 1-azepan-1-yl-propan-2S-ol (189) is used as such without further purification. Yield: 2.25 g (47%).

The alcohol (189) from above (63 mg, 0.405 mmol) is mixed with 4-(furan-3-ylmethoxy)-1H-indole-2-carboxylic acid piperidin-4-ylamide (165, see example 133) from step B (100 mg, 0.27 mmol), DIEA (0.227 ml, 1.35 mmol) and cyanomethyl-triphenyl phosphonium iodide (193 mg, 0.81 mmol) in 2 ml of propionitrile. The suspension is heated at 90° C. for 3 hours. The resulting solution is cooled, diluted with EtOAc, washed with 2N—NaOH and brine, dried over anhydrous sodium sulphate and evaporated. The crude material is purified by chromatography on silicagel using DCM (saturated with ammonia) and MeOH (from 0% to 10%).

Yield: 45 mg (35%). MS (ESI): 479.1 [M+H]$^+$, 1H-NMR (DMSO-d$_6$): δ (ppm) 11.46 (s, 1H), 8.14 (d, 1H), 7.82 (s, 1H), 7.68 (s, 1H), 7.22 (s, 1H), 7.05 (t, 1H), 6.99 (d, 1H), 6.62 (s, 1H), 6.59 (d, 1H), 5.03 (d, 2H), 3.72 (m, 1H), 2.75-2.95 (m, 3H), 2.58 (m, 4H), 2.33 (m, 1H), 2.0-2.2 (m, 2H), 1.92 (m, 1H), 1.74 (m, 2H), 1.45-1.6 (m, 10H), 0.91 (d, 3H).

Example 149

4-(Furan-3-ylmethoxy)-1H-indole-2-carboxylic acid [1-(2R-azepan-1-yl-propyl)-piperidin-4-yl]-amide

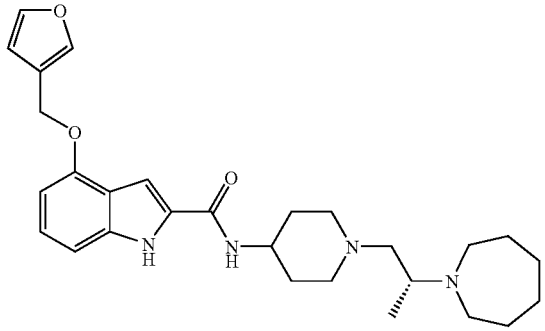

The title compound is prepared from 4-(furan-3-ylmethoxy)-1H-indole-2-carboxylic acid piperidin-4-ylamide (165) as described in Example 133 using R(+)-propylene oxide instead of the (S)-enantiomer.

MS and NMR spectra are identical to its enantiomeric example 148.

Alternatively, the 4-alkoxy-indole-2-carboxamides are prepared as shown in reaction scheme 20.

Reaction Scheme 20:

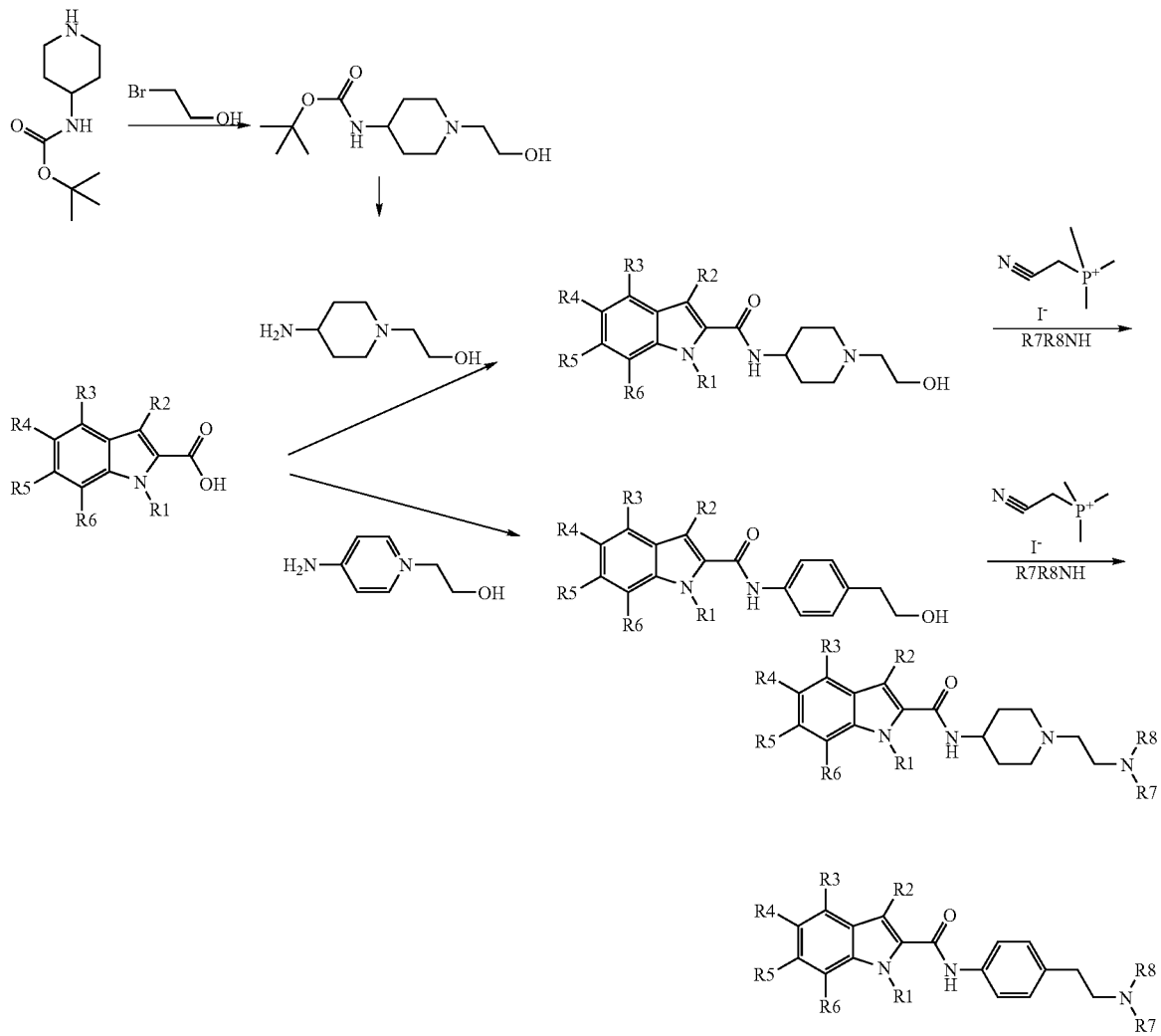

Example 150

4-Isobutoxy-1H-indole-2-carboxylic acid {1-[2-(3,6-dihydro-2H-pyridin-1-yl)-ethyl]-piperidin-4-yl}-amide

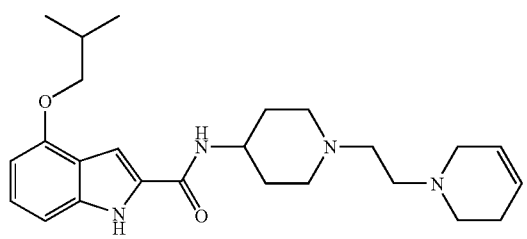

1,2,5,6-Tetrahydropyridine (25.4 µl, 0.279 mmol), cyanomethyl-triphenyl phosphonium iodide (162.5 mg, 0.6686 mmol) and Hünig's base (171 µl, 1 mmol) are added subsequently to a suspension of 190 (preparation see below) (100 mg, 0.279 mmol) in 4 ml of propionitril. The mixture is stirred for 2 h at 100° C., then diluted with ethyl acetate, washed with 1N sodium hydroxide solution and brine and dried over sodium sulfate. Evaporation gave 138 mg of crude product, which is further purified by preparative HPLC (RP, acetonitrile/water).

Yield: 55 mg (47%). MS (ESI): 443.3 [M+H]$^+$, 1H-NMR (DMSO-d$_6$): δ (ppm) 11.45 (s, 1H), 8.2 (d, 1H), 7.23 (d, 1H), 7.04 (t, 1H), 6.97 (d, 1H), 6.45 (d, 1H), 4.5 (d, 1H), 3.85 (d, 2H) 3.74 (m, 1H), 3.41 (m, 1H), 2.88 (m, 2H), 2.71 (m, 2H), 2.38 (m, 4H), 2.1 (m, 1H), 2.0 (m, 4H), 1.76 (m, 2H), 1.68 (m, 2H), 1.55 (m, 2H), 1.35 (m, 2H), 1.06 (d, 6H).

Synthesis of 4-Isobutoxy-1H-indole-2-carboxylic acid [1-(2-hydroxy-ethyl)-piperidin-4-yl]-amide (190)

(1) Step A: [1-(2-Hydroxy-ethyl)-piperidin-4-yl]-carbamic acid tert-butyl ester (191)

Piperidin-4-yl-carbamic acid tert-butyl ester (5 g, 25 mmol) is dissolved in 100 ml of ethanol. After addition of sodium carbonate (10.6 g, 100 mmol), 2-bromo-ethanol (3.55 ml, 50 mmol) is added dropwise. The reaction mixture is refluxed for 16 h and then evaporated. The residue is dissolved in 100 ml of dichloromethane and filtrated. The residue is washed with DCM. The combined filtrates are evaporated, which afforded 10.1 g of a yellow oil, which is further purified by flash chromatography (silicagel, DCM/methanol/conc. ammonia 90:9:1).

Yield: 4.02 g (66%) of a white solid. MS (ESI): 443.3 [M+H]$^+$, 1H-NMR (DMSO-$d_6$): δ (ppm) 11.45 (s, 1H), 8.2 (d, 1H), 7.23 (d, 1H), 7.04 (t, 1H), 6.97 (d, 1H), 6.45 (d, 1H), 4.5 (d, 1H), 3.85 (d, 2H) 3.74 (m, 1H), 3.41 (m, 1H), 2.88 (m, 2H), 2.71 (m, 2H), 2.38 (m, 4H), 2.1 (m, 1H), 2.0 (m, 4H), 1.76 (m, 2H), 1.68 (m, 2H), 1.55 (m, 2H), 1.35 (m, 2H), 1.06 (d, 6H).

(2) Step B: 2-(4-Amino-piperidin-1-yl)-ethanol (192)

Compound 191 (4.02 g, 16.46 mmol) are treated with 4M HCl in dioxane (60 ml, 240 mmol) and the mixture is stirred at room temperature for 1 h. The white precipitate is filtered off, washed with ether and dried under high vacuum. The mother liquor is concentrated and treatred with ether. The white solid is filtered off and dried under high vacuum.

Yield: 3.42 g (95.9%). MS (ESI): 443.3 [M+H]$^+$, 1H-NMR (DMSO-$d_6$): δ (ppm) 11.45 (s, 1H), 8.2 (d, 1H), 7.23 (d, 1H), 7.04 (t, 1H), 6.97 (d, 1H), 6.45 (d, 1H), 4.5 (d, 1H), 3.85 (d, 2H) 3.74 (m, 1H), 3.41 (m, 1H), 2.88 (m, 2H), 2.71 (m, 2H), 2.38 (m, 4H), 2.1 (m, 1H), 2.0 (m, 4H), 1.76 (m, 2H), 1.68 (m, 2H), 1.55 (m, 2H), 1.35 (m, 2H), 1.06 (d, 6H).

(3) Step C: 4-Isobutoxy-1H-indole-2-carboxylic acid [1-(2-hydroxy-ethyl)-piperidin-4-yl]-amide (190)

4-Isobutoxy-1H-indole-2-carboxylic acid 80 (preparation see Example 8, 1 g, 4.29 mmol) is suspended in 5 ml of DMF, cooled to 0° C. and treated with Hünig's Base (1.46 ml, 8.58 mmol). The mixture is stirred for 15 min at 0° C. In a separate reaction flask, compound 192 (931 mg, 4.29 mmol) in 10 ml of DMF is cooled to 0° C., treated with 10M aqueous sodium hydroxide solution (0.858 ml, 8.58 mmol) and stirred for 15 min at this temperature. This solution is added to the above mentioned mixture, followed by benzotriazol-1-yl-oxytripyrrolidinphosphonium hexafluorophosphate (PyBOP, 2.34 g, 4.5 mmol) and stirred for 4 h at room temperature. The reaction mixture is diluted with ethyl acetate and washed with 2N sodium hydroxide solution, water and brine. Evaporation gave a semisolid, yellow crude product, which is treated with ether, filtered of and washed with ether.

Yield: 657 mg (83%). MS (ESI): 443.3 [M+H]$^+$, 1H-NMR (DMSO-$d_6$): δ (ppm) 11.45 (s, 1H), 8.2 (d, 1H), 7.23 (d, 1H), 7.04 (t, 1H), 6.97 (d, 1H), 6.45 (d, 1H), 4.5 (d, 1H), 3.85 (d, 2H) 3.74 (m, 1H), 3.41 (m, 1H), 2.88 (m, 2H), 2.71 (m, 2H), 2.38 (m, 4H), 2.1 (m, 1H), 2.0 (m, 4H), 1.76 (m, 2H), 1.68 (m, 2H), 1.55 (m, 2H), 1.35 (m, 2H), 1.06 (d, 6H).

Example 151

4-Isobutoxy-1H-indole-2-carboxylic acid {1-[2-(4-hydroxy-azepan-1-yl)-ethyl]-piperidin-4-yl}-amide

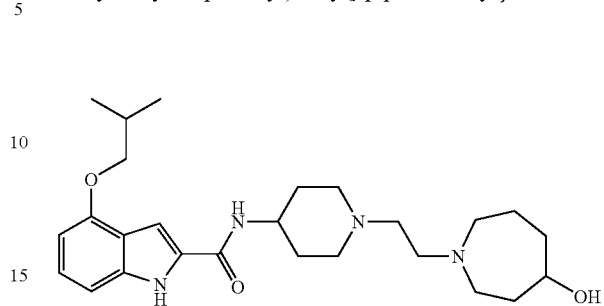

This compound is synthesized analogously to example 150 from 4-isobutoxy-1H-indole-2-carboxylic acid [1-(2-hydroxy-ethyl)-piperidin-4-yl]-amide, 190 and azepan-4-ol.

Yield: 36 mg (80%). MS (ESI): 457 [M+H]$^+$, 1H-NMR (DMSO-$d_6$): δ (ppm) 11.45 (s, 1H), 8.19 (d, 1H), 7.23 (s, 1H), 7.02 (t, 1H), 6.96 (d, 1H), 6.44 (d, 1H), 4.35 (d, 1H), 3.84 (d, 2H) 3.80-3.62 (m, 2H), 3.29 (s, 1H), 2.88 (d, 2H), 2.68-2.30 (m, 8H), 2.14-2.06 (m, 1H), 2.0 (t, 2H), 1.83-1.34 (m, 9H), 1.05 (d, 6H).

Example 152

4-Isobutoxy-1H-indole-2-carboxylic acid {1-[2-(3-amino-azepan-1-yl)-ethyl]-piperidin-4-yl}-amide

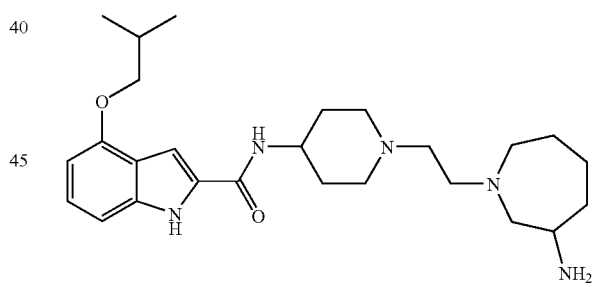

This compound is synthesized analogously to example 150 from 4-isobutoxy-1H-indole-2-carboxylic acid [1-(2-hydroxy-ethyl)-piperidin-4-yl]-amide, 190 and azepan-3-ylamine.

Yield: 48 mg (38%). MS (ESI): 456.3 [M+H]$^+$, 1H-NMR (DMSO-$d_6$): δ (ppm) 11.5 (s, 1H), 8.27 (d, 1H), 7.24 (s, 1H), 7.05 (t, 1H), 6.97 (d, 1H), 6.46 (d, 1H), 3.84 (d, 2H), 3.80-3.70 (m, 1H), 2.89 (m, 2H), 2.79 (m, 1H), 2.68-2.62 (m, 1H), 2.60-2.52 (m, 4H), 2.43-2.27 (m, 3H), 2.15-2.05 (m, 1H), 2.05-1.95 (m, 2H), 1.78-1.72 (m, 2H), 1.70-1.68 (m, 2H), 1.60-1.50 (m, 6H), 1.43-1.35 (m, 1H), 1.32-1.22 (m, 1H), 1.05 (d, 6H).

Example 153

4-Isobutoxy-1H-indole-2-carboxylic acid {1-[2-(3-fluoro-piperidin-1-yl)-ethyl]-piperidin-4-yl}-amide

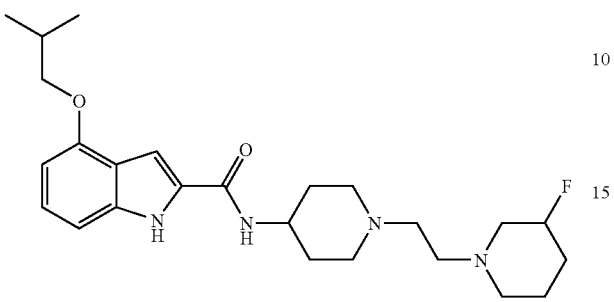

To a suspension of 190 (see example 150) (100 mg, 0.28 mmol), 3-fluoropiperidine hydrochloride (43 mg, 0.208 mmol) and DIEA (0.189 ml, 1.12 mmol) in 0.5 ml of propionitrile is added cyanomethyl-triphenyl phosphonium iodide (81 mg, 0.336 mmol). The mixture is heated at 90° C. for 14 hours. The resulting solution is then diluted with EtOAc (20 ml) and washed twice with saturated sodium bicarbonate, dried over sodium sulfate and evaporated. The crude product is further purified by preparative HPLC.

Yield: 30 mg (24%). MS (ESI): 445.3 [M+H]$^+$, 1H-NMR (DMSO-d$_6$): δ (ppm) 11.43 (s, 1H), 8.19 (d, 1H), 7.22 (s, 1H), 7.02 (t, 1H), 6.96 (d, 1H), 6.45 (d, 1H), 4.45-4.7 (m, 1H), 3.84 (d, 2H), 3.74 (m, 1H), 2.88 (m, 2H), 2.76 (m, 1H), 2.18-2.48 (m, 8H), 2.1 (m, 1H), 2.0 (m, 2H), 1.34-1.9 (m, 7H), 1.05 (d, 6H).

Example 154

4-(5-Chloro-benzofuran-3-ylmethoxy)-1H-indole-2-carboxylic acid [4-(2-piperidin-1-yl-ethyl)-phenyl]-amide

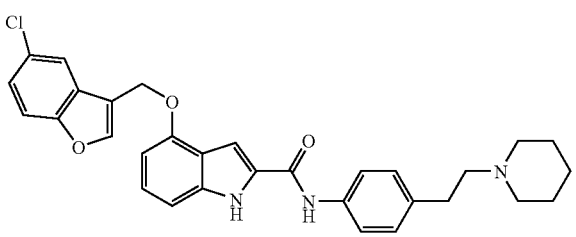

This compound is synthesized analogously to example 150 from 4-(5-Chloro-benzofuran-3-ylmethoxy)-1H-indole-2-carboxylic acid [4-(2-hydroxy-ethyl)-phenyl]-amide (193, preparation see below) and piperidine.

Yield: 140 mg (67%). MS (ESI): 528/530 [M+H]$^+$, 1H-NMR (DMSO-d$_6$): δ (ppm) 11.69 (s, 1H), 10.00 (s, 1H), 8.28 (s, 1H), 7.85-7.35 (m, 6H), 7.25-7.00 (m, 4H), 6.75 (d, 1H), 5.40 (2, 2H), 2.70 (m, 4H), 2.60-2.20 (m, 4H), 1.55-1.40 (m, 6H).

Synthesis of 4-(5-chloro-benzofuran-3-ylmethoxy)-1H-indole-2-carboxylic acid [4-(2-hydroxy-ethyl)-phenyl]-amide (193)

This compound is synthesized analogously to example 42 from 4-(5-Chloro-benzofuran-3-ylmethoxy)-1H-indole-2-carboxylic acid (97) and 2-(4-amino-phenyl)-ethanol.

Yield: 1.59 g (69%) of a white solid. MS (ESI): 461/463 [M+H]$^+$, 1H-NMR (DMSO-d$_6$): δ (ppm) 11.68 (s, 1H), 9.99 (s, 1H), 8.27 (s, 1H), 7.80 (d, 1H), 7.70-7.60 (m, 3H), 7.46 (d, 1H), 7.39 (dd, 1H), 7.20-7.10 (m, 3H), 7.06 (d, 1H), 6.75 (d, 1H), 5.37 (s, 2H) 4.59 (m, 1H), 3.57 (m, 2H), 2.67 (t, 2H).

Example 155

4-(5-Chloro-benzofuran-3-ylmethoxy)-1H-indole-2-carboxylic acid {4-[2-(4-hydroxy-piperidin-1-yl)-ethyl]-phenyl}-amide

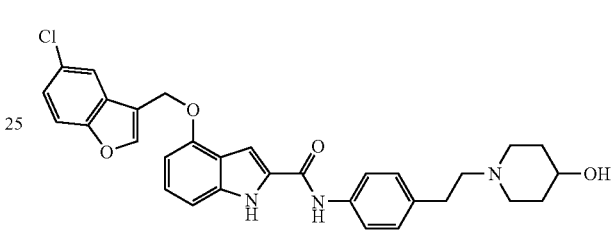

This compound is synthesized analogously to example 154 from 4-(5-Chloro-benzofuran-3-ylmethoxy)-1H-indole-2-carboxylic acid [4-(2-hydroxy-ethyl)-phenyl]-amide (193) and 2,2-dimethyl-propionic acid piperidin-4-yl ester, followed by removal of the protective group by sodium methylate.

Yield: 38 mg (34.9%). MS (ESI): 528/530 [M+H]$^+$, 1H-NMR (DMSO-d$_6$): δ (ppm) 11.68 (s, 1H), 8.27 (s, 1H), 7.63 (d, 1H), 7.70-7.60 (m, 3H), 7.45 (d, 1H), 7.38 (dd, 1H) (s, 1H), 7.20-7.00 (m, 4H), 6.75 (d, 1H), 5.37 (s, 2H), 4.49 (d, 1H), 3.42 (m, 1H), 2.80-2.60 (m, 4H), 2.45-2.40 (m, 1H), 2.10-1.95 (m, 3H), 1.75-1.65 (m, 2H), 1.45-1.30 (m, 2H).

The 4-aryl-indole-2-carboxamides are generally prepared by a Suzuki coupling of the 4-bromo-indole-2-carboxamides with the corresponding aryl-boronic acids (reaction scheme 15).

Reaction Scheme 21:

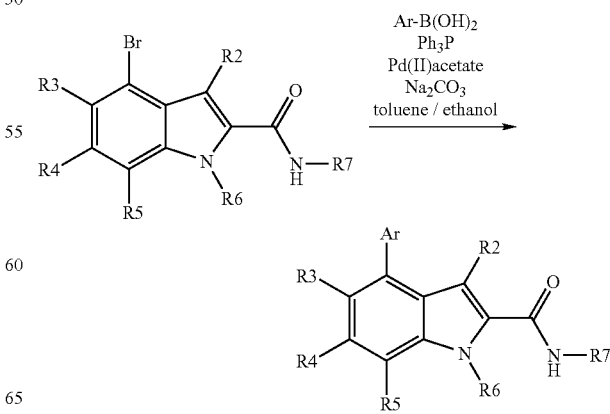

Example 156

4-Phenyl-1H-indole-2-carboxylic acid [1-(2-azepan-1-yl-ethyl)-piperidin-4-yl]-amide

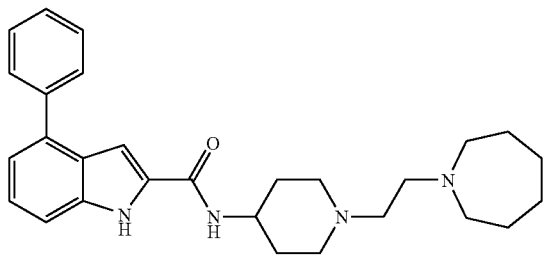

Bromindole 194 (preparation see below) 150 mg, 0.335 mmol), Phenyl-boronic acid (82 mg, 0.67 mmol) and triphenylphosphine (26.4 mg, 0.112 mmol) are dissolved in 10 ml of toluene. After addition of 1 ml of ethanol, argon is flushed through the mixture for 30 min. Then Pd(II)acetate (3 mg, 13.4 µmol) and 2M aqueous sodiumcarbonate (0.67 ml, 1.34 mmol) are added. The mixture is stirred under reflux for 3 h. After cooling down to r.t., the mixture is treated with 30 ml of ethyl acetate and 5% aqueous NaHCO3 solution and filtrated over celite. The organic layer is separated and evaporation under reduced pressure gave 170 mg of crude product, which is further purified by flash chromatography (silica gel, ethyl acetate/methanol conc. NH3 90:10:2) and crystallization from ethyl acetate.

Yield: 45 mg (30%) of a white solid; MS (ESI): 445.4 [M+H]$^+$, 1H-NMR (DMSO-d$_6$): δ (ppm) 11.64 (s, 1H), 8.25 (d, 1H), 7.63 (d, 2H), 7.50 (dd, 2H), 7.40 (m, 2H), 7.31 (s, 1H), 7.23 (dd, 1H), 7.08 (d, 1H), 3.73 (m, 1H), 2.85 (m, 2H), 2.57 (m, 6H), 2.36 (m, 2H), 1.99 (m, 2H), 1.74 (m, 2H), 1.52 (m, 10H).

(1) 4-Bromo-1H-indole-2-carboxylic acid [1-(2-azepan-1-yl-ethyl)-piperidin-4-yl]-amide (194)

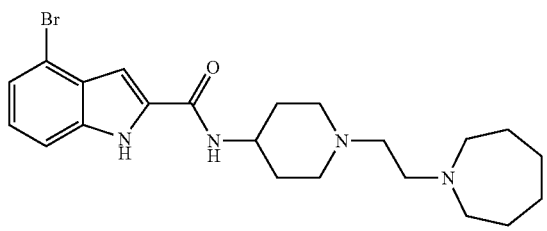

4-Bromo-1H-indole-2-carboxylic acid (1.5 g, 3.1 mmol), 1-(2-azepan-1-yl-ethyl)-piperidin-4-ylamine tri-hydrochloride (5) (2.1 g, 3.1 mmol) and DIEA (4.3 ml, 12.4 mmol) are dissolved under argon atmosphere in DMF (25 ml). TBTU (2.3 g, 3.4 mmol) is added at room temperature. The reaction mixture is stirred for 2 h at r.t., evaporated under high vacuum, dissolved in ethyl acetate and washed twice with 5% aqueous NaHCO3 solution. The organic layers are dried over sodium sulfate. Evaporation under reduced pressure gave 1.3 g (93%) of a beige solid.

MS (ESI): 447.1, 449.1 [M+H]$^+$, 1H-NMR (DMSO-d$_6$): δ (ppm) 11.9 (s, 1H), 8.4 (d, 1H), 7.4 (d, 1H), 7.25 (d, 1H), 7.2 (s, 1H), 7.08 (dd, 1H), 3.76 (m, 1H), 2.88 (m, 2H), 2.55-2.68 (m, 6H), 2.4 (m, 2H), 2.05 (m, 2H), 1.78 (m, 2H), 1.5-1.62 (m, 10H).

Example 157

4-(4-Trifluoromethyl-phenyl)-1H-indole-2-carboxylic acid [1-(2-azepan-1-yl-ethyl)-piperidin-4-yl]-amide

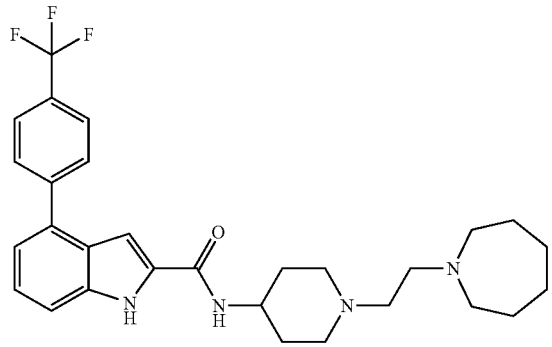

This compound is synthesized from compound 194 (see example 156) and 4-trifluoromethyl-phenyl boronic acid analogously to the method described in Example 156.

Yield: 35 mg (20%) of a white crystals; MS (ESI): 513 [M+H]$^+$, 1H-NMR (DMSO-d$_6$): δ (ppm) 11.75 (s, 1H), 8.25 (d, 1H), 7.85 (s, 4H), 7.48 (d, 1H), 7.32 (s, 1H), 7.28 (dd, 1H), 7.15 (d, 1H), 3.75 (m, 1H), 2.87 (m, 2H), 2.5-2.6 (m, 6H), 2.38 (m, 2H), 2.0 (m, 2H), 1.78 (m, 2H), 1.48-1.55 (m, 10H).

Example 158

4-p-Tolyl-1H-indole-2-carboxylic acid [1-(2-azepan-1-yl-ethyl)-piperidin-4-yl]-amide

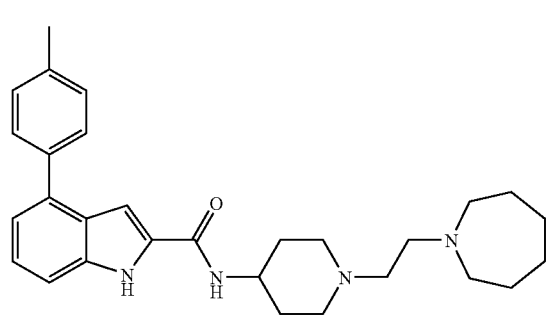

This compound is synthesized from compound 194 (see example 156) and 4-p-tolyl boronic acid analogously to the method described in Example 156.

Yield: 40 mg (26%) of a white foam; MS (ESI): 459 [M+H]$^+$, 1H-NMR (DMSO-d$_6$): δ (ppm) 11.6 (s, 1H), 8.25 (d, 1H), 7.53 (d, 2H), 7.48 (d, 1H), 7.32 (d, 2H), 7.3 (s, 1H), 7.2 (dd, 1H), 7.05 (d, 1H), 3.75 (m, 1H), 2.5-2.6 (m, 8H), 2.38 (s, 3H), 2.33-2.4 (m, 2H), 2.0 (m, 2H), 1.75 (m, 2H), 1.48-1.55 (m, 10H).

Example 159

4-(4-Dimethylamino-phenyl)-1H-indole-2-carboxylic acid [1-(2-azepan-1-yl-ethyl)-piperidin-4-yl]-amide

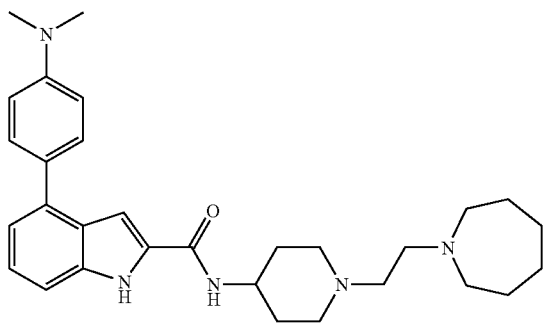

This compound is synthesized from compound 194 (see example 156) and (4-dimethylamino-phenyl)-boronic acid analogously to the method described in Example 156.

Yield: 45 mg (28%) of a white foam; MS (ESI): 488.2 [M+H]$^+$, 1H-NMR (DMSO-d$_6$): δ (ppm) 11.55 (s, 1H), 8.25 (d, 1H), 7.3-7.4 (m, 2H), 7.15-7.25 (m, 3H), 7.07 (m, 2H), 3.8 (s, 3H), 3.78 (s, 3H), 3.75 (m, 1H), 2.88 (m, 2H), 2.57 (m, 6H), 2.38 (m, 2H), 2.0 (m, 2H), 1.75 (m, 2H), 1.5 (m, 4H), 1.75 (m, 10H).

Example 160

4-Benzo[1,2,5]oxadiazol-5-yl-1H-indole-2-carboxylic acid [1-(2-azepan-1-yl-ethyl)-piperidin-4-yl]-amide

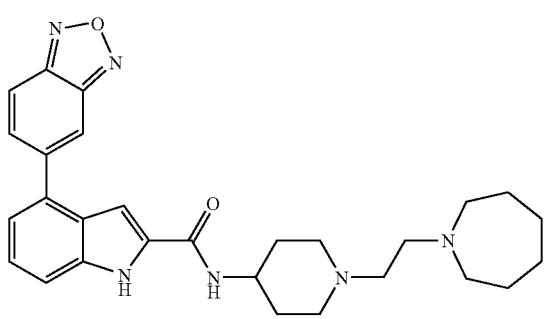

This compound is synthesized from compound 194 (see example 156) and benzo[1,2,5]oxadiazol-5-yl-boronic acid analogously to the method described in Example 156.

Yield: 85 mg (39%) of a white crystals; MS (ESI): 487.1 [M+H]$^+$, 1H-NMR (DMSO-d$_6$): δ (ppm) 11.8 (s, 1H), 8.3 (d, 1H), 8.2 (s, 1H), 8.18 (d, 1H), 7.95 (d, 1H), 7.52 (m, 1H), 7.38 (s, 1H), 7.3 (d, 1H), 3.75 (m, 1H), 2.87 (m, 2H), 2.5-2.6 (m, 6H), 2.36 (m, 2H), 2.0 (m, 2H), 1.75 (m, 2H), 1.47-1.58 (m, 10H).

Example 161

4-(4-Methoxy-phenyl)-1H-indole-2-carboxylic acid [1-(2-azepan-1-yl-ethyl)-piperidin-4-yl]-amide

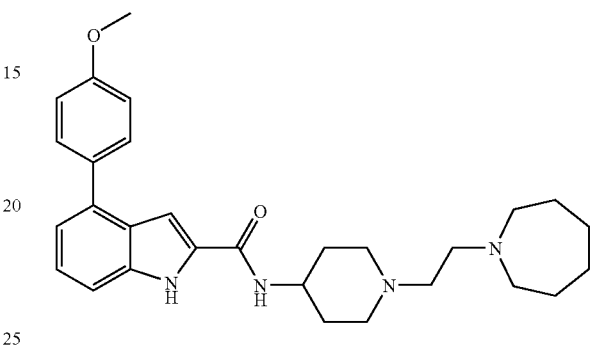

This compound is synthesized from compound 194 (see example 156) and (4-methoxy-phenyl)-boronic acid analogously to the method described in Example 156.

Yield: 22 mg (38%) of a white foam; MS (ESI): 475.4 [M+H]$^+$, 1H-NMR (DMSO-d$_6$): δ (ppm) 11.59 (s, 1H), 8.23 (d, 1H), 7.49 (d, 2H), 7.32 (m, 2H), 7.18 (dd, 1H), 7.0 (d, 1H), 6.85 (d, 2H), 3.75 (m, 1H), 2.97 (s, 6H), 2.87 (m, 2H), 2.56 (m, 6H), 2.48 (m, 2H), 2.0 (m, 2H), 1.77 (m, 2H), 1.52 (m, 10H).

Example 162

4-(3-Cyano-phenyl)-1H-indole-2-carboxylic acid [1-(2-azepan-1-yl-ethyl)-piperidin-4-yl]-amide

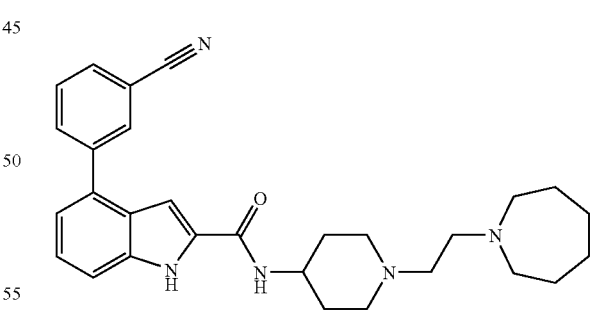

This compound is synthesized from compound 194 (see example 156) and 3-cyano-phenyl boronic acid analogously to the method described in Example 156.

Yield: 115 mg (55%) of a white crystals; MS (ESI): 470.1 [M+H]$^+$, 1H-NMR (DMSO-d$_6$): δ (ppm) 11.75 (s, 1H), 8.38 (d, 1H), 8.05 (s, 1H), 7.98 (dd, 1H), 7.88 (m, 1H), 7.72 (dd, 1H), 7.47 (d, 1H), 7.3 (d, 1H), 7.25 (d, 1H), 7.15 (d, 1H), 3.75 (m, 1H), 2.87 (m, 2H), 2.48-2.6 (m, 6H), 2.37 (m, 2H), 2.0 (m, 2H), 1.75 (m, 2H), 1.47-1.58 (m, 10H).

Example 163

4-(4-Ethoxy-phenyl)-1H-indole-2-carboxylic acid [1-(2-azepan-1-yl-ethyl)-piperidin-4-yl]-amide

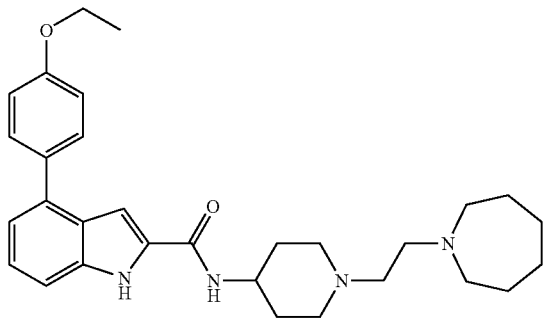

This compound is synthesized from compound 194 (see example 156) and (4-ethoxy-phenyl)-boronic acid analogously to the method described in Example 156.

Yield: 40 mg (24%) of beige crystals; MS (ESI): 487 [M−H]$^−$, 1H-NMR (DMSO-d$_6$): δ (ppm) 11.6 (s, 1H), 8.25 (d, 1H), 7.57 (d, 2H), 7.38 (d, 1H), 7.32 (s, 1H), 7.2 (dd, 1H), 7.05 (d, 2H), 7.02 (d, 1H), 4.07 (q, 2H), 3.75 (m, 1H), 2.85 (m, 2H), 2.50-2.58 (m, 6H), 2.38 (m, 2H), 2.0 (m, 2H), 1.75 (m, 2H), 1.48-1.58 (m, 8H), 1.38 (t, 3H).

Example 164

4-[3-(3-Methoxy-propoxy)-phenyl]-1H-indole-2-carboxylic acid [1-(2-azepan-1-yl-ethyl)-piperidin-4-yl]-amide

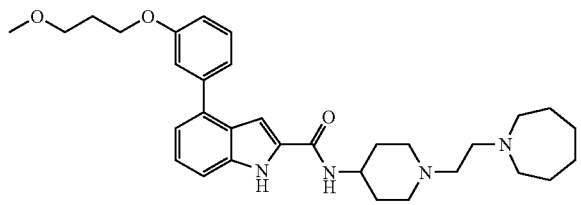

This compound is synthesized from compound 194 (see example 156) and [3-(3-methoxy-propoxy)-phenyl]-boronic acid analogously to the method described in Example 156.

Yield: 160 mg (67%) of beige foam; MS (ESI): 533.2 [M+H]$^+$, 1H-NMR (DMSO-d$_6$): δ (ppm) 11.65 (s, 1H), 8.28 (d, 1H), 7.38-7.43 (m, 2H), 7.32 (s, 1H), 7.2-7.25 (m, 2H), 7.15 (m, 1H), 7.08 (d, 1H), 6.95 (dd, 1H), 4.1 (t, 2H), 3.75 (m, 1H), 3.48 (t, 2H), 3.25 (s, 3H), 2.85 (m, 2H), 2.48-2.58 (m, 8H), 2.35 (m, 2H), 1.95-2.04 (m, 4H), 1.75 (m, 2H), 1.48-1.6 (m, 10H).

Example 165

4-(4-Trifluoromethoxy-phenyl)-1H-indole-2-carboxylic acid [1-(2-azepan-1-yl-ethyl)-piperidin-4-yl]-amide

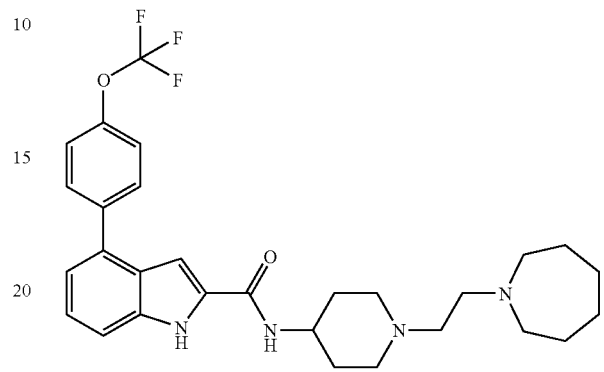

This compound is synthesized from compound 194 (see example 156) and 4-Trifluoromethoxy-phenyl boronic acid analogously to the method described in Example 156.

Yield: 75 mg (42%) of white foam; MS (ESI): 529 [M+H]$^+$, 1H-NMR (DMSO-d$_6$): δ (ppm) 11.7 (s, 1H), 8.28 (d, 1H), 7.78 (d, 2H), 7.50 (d, 2H), 7.44 (d, 1H), 7.3 (s, 1H), 7.25 (dd, 1H), 7.08 (d, 1H), 3.75 (m, 1H), 2.87 (m, 2H), 2.5-2.6 (m, 6H), 2.38 (m, 2H), 2.0 (m, 2H), 1.75 (m, 2H), 1.48-1.6 (m, 10H).

Example 166

4-(2,4-Dimethoxy-phenyl)-1H-indole-2-carboxylic acid [1-(2-azepan-1-yl-ethyl)-piperidin-4-yl]-amide

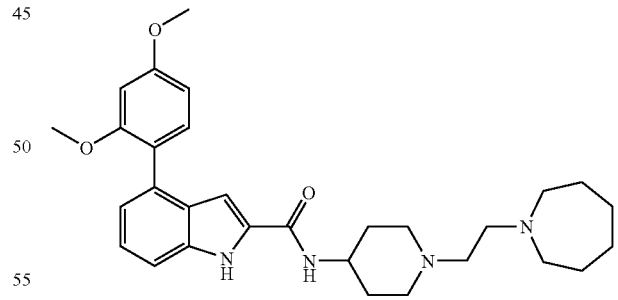

This compound is synthesized from compound 194 (see example 156) and (2,4-dimethoxy-phenyl)-boronic acid analogously to the method described in Example 156.

Yield: 120 mg (53%) of a beige foam; MS (ESI): 505.2 [M+H]$^+$, 1H-NMR (DMSO-d$_6$): δ (ppm) 11.45 (s, 1H), 8.15 (d, 1H), 7.34 (d, 1H), 7.2 (d, 1H), 7.15 (dd, 1H), 6.93 (d, 1H), 6.9 (d, 1H), 6.7 (d, 1H), 6.65 (dd, 1H), 3.84 (s, 3H), 3.73 (m, 1H), 3.68 (s, 3H), 2.85 (m, 2H), 2.47-2.58 (m, 8H), 2.35 (m, 2H), 1.98 (m, 2H), 1.75 (m, 2H), 1.47-1.58 (m, 8H).

Example 167

4-(3,4-Dimethoxy-phenyl)-1H-indole-2-carboxylic acid [1-(2-azepan-1-yl-ethyl)-piperidin-4-yl]-amide

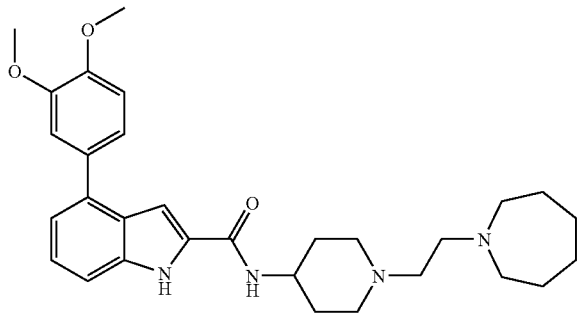

This compound is synthesized from compound 194 (see example 156) and (3,4-dimethoxy-phenyl)-boronic acid analogously to the method described in Example 156.

Yield: 65 mg (29%) of white crystals; MS (ESI): 505.2 [M+H]$^+$, 1H-NMR (DMSO-d$_6$): δ (ppm) 11.6 (s, 1H), 8.25 (d, 1H), 7.3-7.4 (m, 2H), 7.15-7.25 (m, 3H), 7.07 (m, 2H), 3.8 (s, 3H), 3.78 (s, 3H), 3.75 (m, 1H), 2.88 (m, 2H), 2.57 (m, 6H), 2.38 (m, 2H), 2.0 (m, 2H), 1.75 (m, 2H), 1.5 (m, 4H), 1.75 (m, 10H).

Example 168

4-Benzo[1,3]dioxol-5-yl-1H-indole-2-carboxylic acid [1-(2-azepan-1-yl-ethyl)-piperidin-4-yl]-amide

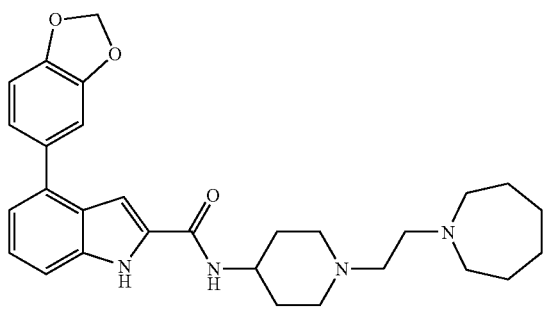

This compound is synthesized from compound 194 (see example 156) and benzo[1,3]dioxol-5-yl-boronic acid analogously to the method described in Example 156.

Yield: 75 mg (34%) of a white crystals; MS (ESI): 489.1 [M+H]$^+$, 1H-NMR (DMSO-d$_6$): δ (ppm) 11.6 (s, 1H), 8.28 (d, 1H), 7.38 (d, 1H), 7.3 (m, 1H), 7.2 (d, 1H), 7.18 (m, 1H), 7.1 (dd, 1H), 7.04 (dd, 1H), 6.08 (s, 2H), 3.75 (m, 1H), 2.87 (m, 2H), 2.48-2.6 (m, 6H), 2.37 (m, 2H), 2.0 (m, 2H), 1.75 (m, 2H), 1.47-1.58 (m, 10H).

Example 169

4-Pyridin-4-yl-1H-indole-2-carboxylic acid [1-(2-azepan-1-yl-ethyl)-piperidin-4-yl]-amide

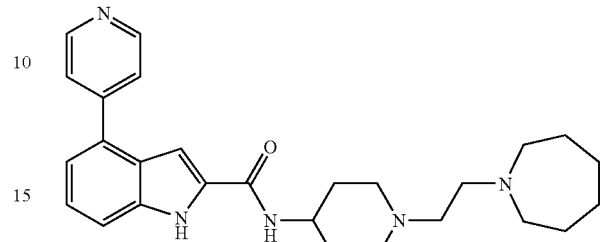

This compound is synthesized from compound 194 (see example 156) and pyridin-4-yl-boronic acid analogously to the method described in Example 156.

Yield: 35 mg (53%) of beige crystals; MS (ESI): 446.2 [M+H]$^+$, 1H-NMR (DMSO-d$_6$): δ (ppm) 11.8 (s, 1H), 8.68 (d, 2H), 8.3 (d, 1H), 7.68 (d, 1H), 7.5 (d, 1H), 7.38 (s, 1H), 7.3 (m, 1H), 7.2 (d, 1H), 3.75 (m, 1H), 2.88 (m, 2H), 2.45-2.6 (m, 6H), 2.38 (m, 2H), 2.0 (m, 2H), 1.75 (m, 2H), 1.48-1.6 (m, 10H).

Example 170

4-(6-Methoxy-pyridin-3-yl)-1H-indole-2-carboxylic acid [1-(2-azepan-1-yl-ethyl)-piperidin-4-yl]-amide

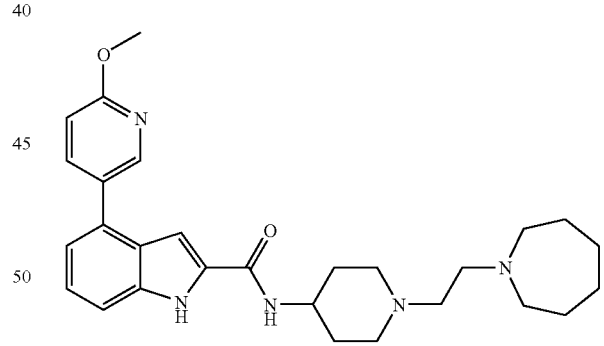

This compound is synthesized from compound 194 (see example 156) and (6-methoxy-pyridin-3-yl)-boronic acid analogously to the method described in Example 156.

Yield: 125 mg (59%) of a white crystals; MS (ESI): 476.4 [M+H]$^+$, 1H-NMR (DMSO-d$_6$): δ (ppm) 11.65 (s, 1H), 8.48 (d, 1H), 8.3 (d, 1H), 7.98 (dd, 1H), 7.42 (d, 1H), 7.35 (s, 1H), 7.24 (dd, 1H), 7.08 (d, 1H), 6.97 (d, 1H), 3.93 (s, 3H), 3.75 (m, 1H), 2.87 (m, 2H), 2.48-2.6 (m, 6H), 2.35 (m, 2H), 2.0 (m, 2H), 1.75 (m, 2H), 1.47-1.58 (m, 10H).

Example 171

4-(4-Ethoxy-phenyl)-1H-indole-2-carboxylic acid [1-(2-piperidin-1-yl-ethyl)-piperidin-4-yl]-amide

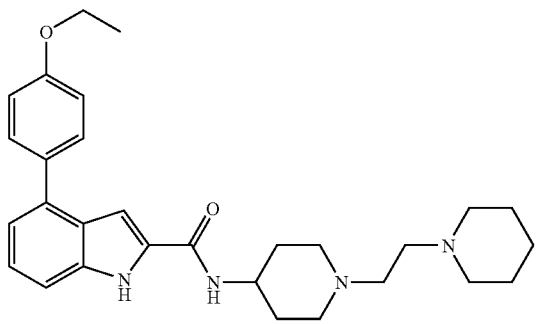

This compound is synthesized from compound 195 (preparation see below) and (4-ethoxy-phenyl)-boronic acid analogously to the method described in Example 156.

Yield: 100 mg (46%) of yellow crystals; MS (ESI): 475 [M+H]$^+$, 1H-NMR (DMSO-d$_6$): δ (ppm) 11.6 (s, 1H), 8.25 (d, 1H), 7.55 (d, 2H), 7.35 (d, 1H), 7.3 (s, 1H), 7.2 (dd, 1H), 7.05 (d, 2H), 7.02 (d, 1H), 4.08 (q, 2H), 3.73 (m, 1H), 2.87 (m, 2H), 2.25-2.4 (m, 8H), 2.0 (m, 2H), 1.75 (m, 2H), 1.3-1.57 (m, 8H), 1.38 (t, 3H).

(1) 4-Bromo-1H-indole-2-carboxylic acid [1-(2-piperidin-1-yl-ethyl)-piperidin-4-yl]-amide (195)

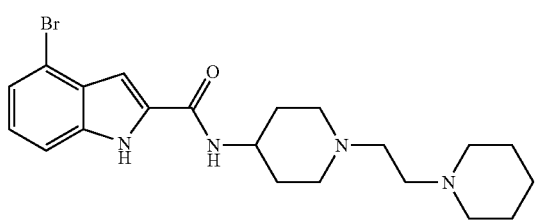

This compound is synthesized from 4-bromo-1H-indole-2-carboxylic acid and amine 4 analogously to the method described above for the synthesis of 194 (see example 156).

MS (ESI): 433, 435 [M+H]$^+$, 1H-NMR (DMSO-d$_6$): δ (ppm) 11.9 (s, 1H), 8.4 (d, 1H), 7.4 (d, 1H), 7.23 (d, 1H), 7.19 (s, 1H), 7.08 (dd, 1H), 3.76 (m, 1H), 2.88 (m, 2H), 2.3-2.4 (m, 8H), 2.0 (m, 2H), 1.78 (m, 2H), 1.3-1.6 (m, 8H).

Example 172

4-(4-Methoxy-phenyl)-1H-indole-2-carboxylic acid {1-[2-(4-hydroxy-piperidin-1-yl)-ethyl]-piperidin-4-yl}-amide

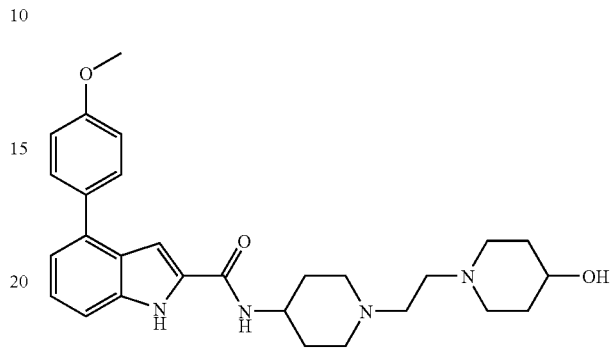

This compound is synthesized from compound 196 (preparation see below) and (4-methoxy-phenyl)-boronic acid analogously to the method described in Example 156.

Yield: 55 mg (35%) of white foam; MS (ESI): 477.2 [M+H]$^+$, 1H-NMR (DMSO-d$_6$): δ (ppm) 11.6 (s, 1H), 8.25 (d, 1H), 7.58 (d, 2H), 7.36 (d, 1H), 7.3 (s, 1H), 7.2 (dd, 1H), 7.05 (d, 2H), 7.02 (d, 1H), 4.55 (br, 1H), 3.85 (s, 3H), 3.78 (m, 1H), 3.45 (m, 1H), 2.9 (m, 2H), 2.78 (m, 2H), 2.45 (m, 4H), 2.15 (m, 2H), 2.05 (m, 2H), 1.3-1.8 (m, 8H).

(1) 4-Bromo-1H-indole-2-carboxylic acid {1-[2-(4-hydroxy-piperidin-1-yl)-ethyl]-piperidin-4-yl}-amide (196)

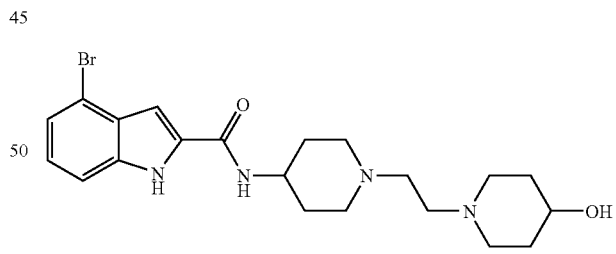

This compound is synthesized from 4-Bromo-1H-indole-2-carboxylic acid and amine 21 analogously to the method described for 194 (see example 156).

MS (ESI): 449, 451.2 [M+H]$^+$, 1H-NMR (DMSO-d$_6$): δ (ppm) 11.9 (s, 1H), 8.42 (d, 1H), 7.4 (d, 1H), 7.23 (d, 1H), 7.2 (s, 1H), 7.08 (dd, 1H), 3.8 (m, 1H), 3.5 (m, 1H), 2.88 (m, 2H), 2.95 (m, 2H), 2.86 (m, 2H), 2.6 (m, 2H), 2.52 (m, 2H), 2.3 (m, 2H), 2.12 (m, 2H), 1.8 (m, 2H), 1.75 (m, 2H), 1.58 (m, 2H), 1.43 (m, 2H).

Example 173

4-(4-Ethoxy-phenyl)-1H-indole-2-carboxylic acid {1-[2-(4-hydroxy-piperidin-1-yl)-ethyl]-piperidin-4-yl}-amide

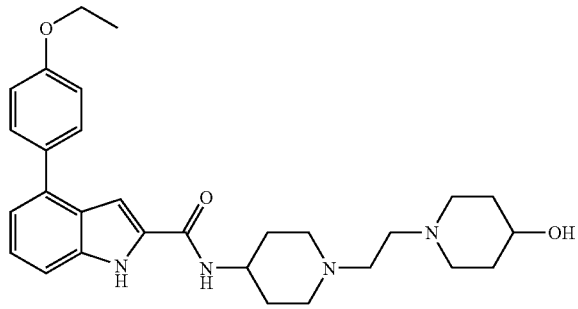

This compound is synthesized from compound 196 (see example 172) and (4-ethoxy-phenyl)-boronic acid analogously to the method described in Example 156.

Yield: 45 mg (21%) of white crystals; MS (ESI): 491 [M+H]+, 1H-NMR (DMSO-d6): δ (ppm) 11.6 (s, 1H), 8.24 (d, 1H), 7.54 (d, 2H), 7.34 (d, 1H), 7.3 (s, 1H), 7.19 (dd, 1H), 7.06 (d, 2H), 7.0 (d, 1H), 4.47 (d, 1H), 4.08 (q, 2H), 3.73 (m, 1H), 3.40 (m, 1H), 2.85 (m, 2H), 2.68 (m, 2H), 2.36 (m, 4H), 1.98 (m, 4H), 1.74 (m, 2H), 1.65 (m, 2H), 1.51 (m, 2H), 1.37 (t, 3H), 1.32 (m, 2H).

Example 174

4-(6-Methoxy-pyridin-3-yl)-1H-indole-2-carboxylic acid {1-[2-(4-hydroxy-piperidin-1-yl)-ethyl]-piperidin-4-yl}-amide

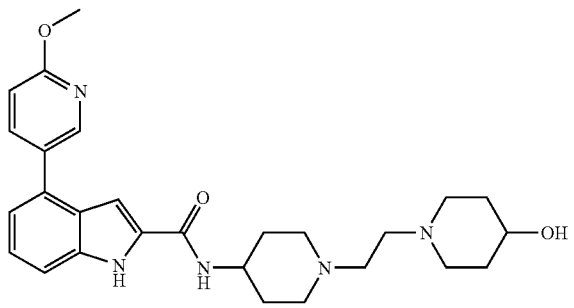

This compound is synthesized from compound 196 (see example 172) and (6-methoxy-pyridin-3-yl)-boronic acid analogously to the method described in Example 156.

Yield: 28 mg (18%) of white crystals; MS (ESI): 478.1 [M+H]+, 1H-NMR (DMSO-d6): δ (ppm) 11.68 (s, 1H), 8.47 (d, 1H), 8.27 (d, 1H), 7.95 (dd, 1H), 7.40 (d, 1H), 7.35 (s, 1H), 7.23 (dd, 1H), 7.09 (d, 1H), 6.97 (d, 1H), 4.48 (d, 1H), 3.92 (s, 3H), 3.75 (m, 1H), 3.39 (m, 1H), 2.85 (m, 2H), 2.68 (m, 2H), 2.36 (m, 4H), 1.99 (m, 4H), 1.75 (m, 2H), 1.65 (m, 2H), 1.54 (m, 2H), 1.35 (m, 2H).

Example 175

4-(4-Methoxy-phenyl)-1H-indole-2-carboxylic acid {1-[2-(3-hydroxy-8-aza-bicyclo[3.2.1]oct-8-yl)-ethyl]-piperidin-4-yl}-amide

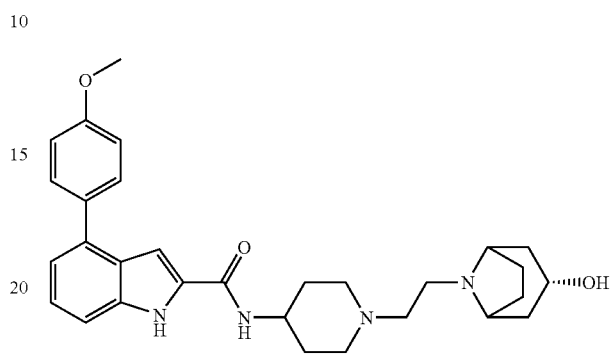

This compound is synthesized from compound 197 (preparation see below) and (4-methoxy-phenyl)-boronic acid analogously to the method described in Example 156.

Yield: 90 mg (57%) of white foam; MS (ESI): 503.2 [M+H]+, 1H-NMR (DMSO-d6): δ (ppm) 11.6 (s, 1H), 8.25 (d, 1H), 7.55 (d, 2H), 7.35 (d, 1H), 7.3 (m, 1H), 7.2 (dd, 1H), 7.05 (d, 2H), 7.02 (d, 1H), 4.25 (br s, 1H), 3.82 (s, 3H), 3.78 (m, 1H), 3.75 (m, 1H), 3.1 (m, 2H), 2.88 (m, 2H), 2.38 (m, 4H), 2.0 (m, 4H), 1.85 (m, 2H), 1.77 (m, 4H), 1.55 (m, 4H).

(1) 4-Bromo-1H-indole-2-carboxylic acid {1-[2-(3-hydroxy-8-aza-bicyclo[3.2.1]oct-8-yl)-ethyl]-piperidin-4-yl}-amide (197)

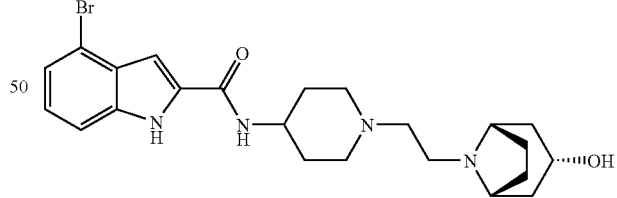

This compound is synthesized from 4-Bromo-1H-indole-2-carboxylic acid and amine 24 analogously to the method described for 194 (see example 156).

MS (ESI): 475.3, 477 [M+H]+, 1H-NMR (DMSO-d6, 150° C.): δ (ppm) 11.7 (br s, 1H), 8.28 (br s, 1H), 7.49 (d, 1H), 7.25 (d, 1H), 7.15 (s, 1H), 7.1 (dd, 1H), 4.1 (br s, 1H), 3.97 (m, 3H), 3.5 (m, 2H), 3.0 (m, 2H), 2.5 (m, 6H), 1.9-2.2 (m, 10H).

Example 176

4-(6-Methoxy-pyridin-3-yl)-1H-indole-2-carboxylic acid {1-[2-(3-hydroxy-8-aza-bicyclo[3.2.1]oct-8-yl)-ethyl]-piperidin-4-yl}-amide

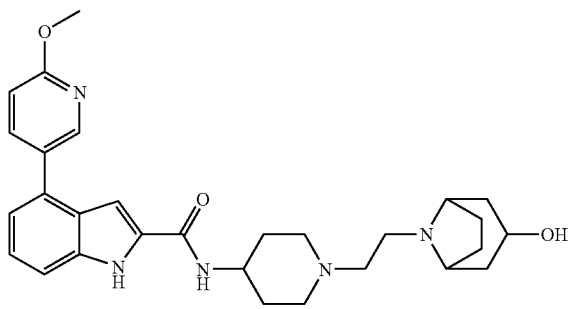

This compound is synthesized from compound 197 (see example 175) and (6-methoxy-pyridin-3-yl)-boronic acid analogously to the method described in Example 156.

Yield: 90 mg (57%) of white foam; MS (ESI): 504.2 [M+H]$^+$, 1H-NMR (DMSO-d$_6$): δ (ppm) 11.6 (s, 1H), 8.48 (d, 1H), 8.28 (d, 1H), 7.97 (dd, 1H), 7.4 (d, 1H), 7.35 (m, 1H), 7.23 (dd, 1H), 7.08 (d, 1H), 6.95 (d, 1H), 4.23 (br, 1H), 3.93 (s, 3H), 3.78 (m, 1H), 3.75 (m, 1H), 3.1 (m, 2H), 2.88 (m, 2H), 2.38 (m, 4H), 2.0 (m, 4H), 1.8 (m, 6H), 1.53 (m, 4H).

Alternatively, the 4-alkoxy-indole-2-carboxamides are prepared as shown in reaction scheme 22.

Reaction Scheme 22:

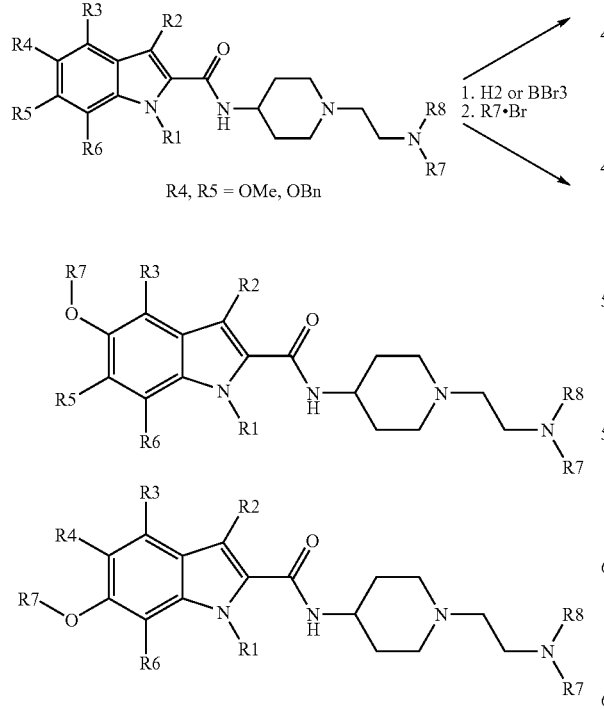

R4, R5 = OMe, OBn

Example 177

4-Hydroxy-1H-indole-2-carboxylic acid [1-(2-azepan-1-yl-ethyl)-piperidin-4-yl]-amide

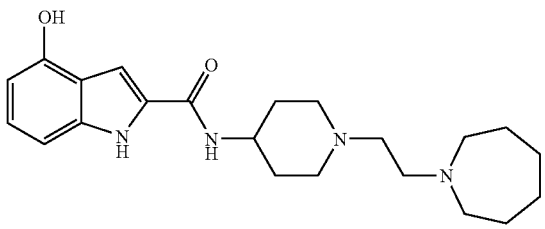

The methoxy derivative from example 1 (100 mg, 0.25 mmol) is dissolved in 5 ml of DCM. A solution of BBr3 (1M in DCM, 2.5 ml, 2.5 mmol) is added and the mixture is stirred for 18 hours. It is then poured onto ice and washed with EtOAc (30 ml). The pH of the water layer is adjusted to 9 and extracted twice with EtOAc. The organic layers are combined washed with brine, dried over anhydrous sodium sulfate and evaporated.

Yield: 24 mg (25%). MS (ESI): 385.3 [M+H]$^+$, 1H-NMR (DMSO-d$_6$): δ (ppm) 9.62 (s, 1H), 8.14 (d, 1H), 7.2 (d, 1H), 6.94 (t, 1H), 6.86 (d, 1H), 6.37 (d, 1H), 3.75 (m, 1H), 2.89 (m, 2H), 2.53-2.65 (m, 6H), 2.39 (m, 2H), 2.03 (m, 2H), 1.78 (m, 2H), 1.47-1.68 (m, 10H), 1.25 (m, 1H).

Synthesis of the benzthiophene-2-carboxamides

The 4-alkoxy-benzthiophene-2-carboxylates are synthesized starting from 4-thiophen-2-yl-butyric acid (reaction scheme 23).

Reaction Scheme 2312:

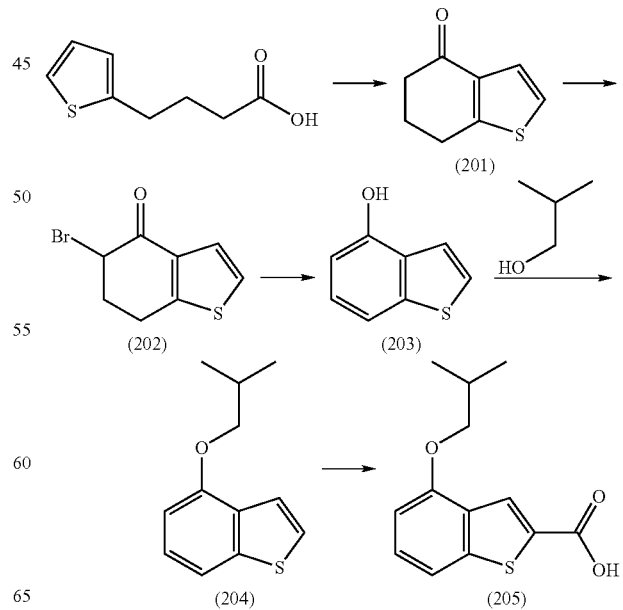

(1) 6,7-Dihydro-5H-benzo[b]thiophen-4-one (198)

Ortho-phosphoric acid (85%, 0.27 ml, 3.7 mmol) is dissolved in acetic acid anhydride (13 ml) and after addition of 4-thiophen-2-yl-butyric acid (9 g, 52.9 mmol) the mixture is stirred at 120° C. for 2.5 h. The brown solution is cooled down using an ice bath, water is added and the reaction mixture is extracted with dichloromethane. The organic layers are washed with 2M NaOH solution and twice with water until a neutral pH is reached. The solution is dried over Na2SO4 and evaporated under reduced pressure. The crude product is obtained as a brown oil (7.84 g), which is further purified by flash-chromatography (silica gel, ethyl acetate/hexane 9:1).

Yield: 5.83 g (72%) of a slightly yellow solid. MS (ESI): 152 [M]$^+$, 1H-NMR (DMSO-d$_6$): δ (ppm) 7.38 (d, 1H), 7.25 (d, 1H), 3.03 (t, 2H), 2.48 (m, 2H), 2.12 (t, 2H).

(2) 5-Bromo-6,7-dihydro-5H-benzo[b]thiophen-4-one (199)

6,7-Dihydro-5H-benzo[b]thiophen-4-one (198, 5.8 g, 38.3 mmol) is dissolved in 200 ml of dry diethyl ether and cooled down to −10° C. A solution of bromine (6.1 g, 38.3 mmol) in 30 ml of tetrachloromethane and 2-3 drops of diethyl ether is slowly added. The mixture is stirred for 15 min at −10° C., 15 min at 0° C. and 18 h at room temperature. Then water and diethyl ether is added slowly. The organic layers are washed with water, dried over Na2SO4 and evaporated.

Yield: 8.7 g of a yellow solid (containing 23% of starting material). MS (ESI): 230, 232 [M]+, 1H-NMR (DMSO-d$_6$): δ (ppm) 7.46 (d, 1H), 7.3 (d, 1H), 4.87 (dt, 1H), 3.1 (m, 2H), 2.45 (m, 2H).

(3) Benzo[b]thiophen-4-ol (200)

5-Bromo-6,7-dihydro-5H-benzo[b]thiophen-4-one (199, 77% pure, 8.7 g, 28.9 mmol), LiBr (5.7 g, 65.1 mmol) and Li2CO3 (4.3 g, 57.8 mmol) are placed under argon in 300 ml of DMF and refluxed for 3 h. The reaction mixture is allowed to cool down to room temperature and evaporated under high vacuum. After addition of ice water and cold 2M aqueous HCl solution the mixture is extracted with diethyl ether. The organic layers are extracted with 2M NaOH and the combined aqueous layers are acidified with concentrated HCl. The product is extracted twice with ethyl acetate and the organic layers are washed with saturated NaCl solution, dried over Na2SO4 and evaporated under reduced pressure.

Yield: 4.7 g of a brown solid, which is used without further purification. MS (ESI): 149.0 [M−H]$^−$, 1H-NMR (DMSO-d$_6$): δ (ppm) 9.95 (br s, 1H), 7.55 (d, 1H), 7.45 (d, 1H), 7.38 (d, 1H), 7.15 (dd, 1H), 6.72 (d, 1H).

(4) 4-Isobutoxy-benzo[b]thiophene (201)

Benzo[b]thiophen-4-ol (200, 4.3 g, 28.9 mmol) and isobutanol (3.2 ml, 34.7 mmol) are dissolved under argon in 150 ml of toluene. After addition of triphenylphosphine (9.1 g, 34.7 mmol) and a 40% solution of DEAD in toluene (16.8 ml, 34.7 mmol), the mixture is stirred at 120° C. over night. After cooling down, the reaction mixture is subsequently washed with saturated aqueous NaHCO3 solution and NaCl solution, dried over Na2SO4 and evaporated under reduced pressure. Triphenylphosphinoxid is removed by crystallization from ethyl acetate and hexane and the crude product is further purified by flash chromatography (silica gel, hexane/ethyl acetate 9:1).

Yield: 5.4 g (91%) of a yellow oil. MS (ESI): 206 [M]$^+$, 1H-NMR (DMSO-d$_6$): δ (ppm) 7.62 (d, 1H), 7.5 (d, 1H), 7.44 (d, 1H), 7.27 (dd, 1H), 6.85 (d, 1H), 3.88 (d, 2H), 2.12 (m, 1H), 1.05 (d, 6H).

(5) 4-Isobutoxy-benzo[b]thiophene-2-carboxylic acid (202)

A 1.6 M solution of n-butyl lithium in hexane (18 ml, 28.8 mmol) is dissolved under an argon atmosphere in 100 ml of dry diethyl ether, followed by dropwise addition of a solution of 4-Isobutoxy-benzo[b]thiophene (201, 5.4 g, 26.1 mmol) in 40 ml of diethyl ether. The reaction mixture is refluxed for 45 min, then cooled down and transferred via syringe to a mixture of excess dry ice (115 g, 2.61 mol) in diethyl ether (the dry ice is washed before twice with diethyl ether). The mixture is allowed to stir overnight at room temperature, then distributed between diethyl ether and water. The ether layers are reextracted with water. The aqueous layers are acidified with 2M aqueous HCl solution, and the precipitate is filtered off, washed with water and dried under high vacuum.

Yield: 3.72 g (57%) of a white solid. MS (ESI): 250 [M]$^+$, 1H-NMR (DMSO-d$_6$): δ (ppm) 13.4 (brs, 1H), 7.98 (s, 1H), 7.55 (d, 1H), 7.43 (dd, 1H), 6.9 (d, 1H), 3.9 (d, 2H), 2.14 (m, 1H), 1.05 (d, 6H).

Example 178

4-Methoxy-benzo[b]thiophene-2-carboxylic acid [1-(2-azepan-1-yl-ethyl)-piperidin-4-yl]-amide

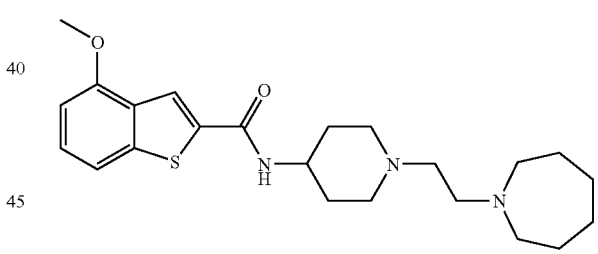

A solution of a mixture of 4- and 6-methoxy-benzo[b] thiophene-2-carboxylic acid (*C. R. Hebd. Seances Acad. Sci.* 1965, 261, 705) (440 mg, 1.05 mmol), amine 5 (357 mg, 1.051) in 10 ml of DMF is treated with EDC (178 mg, 1.05 mmol), HOBT hydrate (178 mg, 1.15 mmol) and triethylamine (0.44 ml, 3.15 mmol). The mixture is stirred overnight and then evaporated under high vacuum. The crude residue is dissolved in ethyl acetate and washed twice with sodium bicarbonate (10%), brine and dried over sodium sulfate. The crude product is then purified by flash chromatography (ethyl acetate/methanol/ammonia 90:10:1).

Yield: 45 mg (10%) of a yellow solid (and 84 mg of the 6-substituted isomer). MS (ESI): 416.1 [M+H]$^+$, 1H-NMR (DMSO-d$_6$): δ (ppm) 8.53 (d, 1H), 8.2 (s, 1H), 7.5 (d, 1H), 7.37 (dd, 1H), 6.9 (d, 1H), 3.94 (s, 3H), 3.7 (br m, 1H), 2.88 (m, 2H), 2.6 (m, 6H), 2.4 (m, 2H), 2.0 (m, 2H), 1.75 (m, 2H), 1.47-1.6 (m, 10H).

Example 179

4-Isobutoxy-benzo[b]thiophene-2-carboxylic acid [1-(2-azepan-1-yl-ethyl)-piperidin-4-yl]-amide

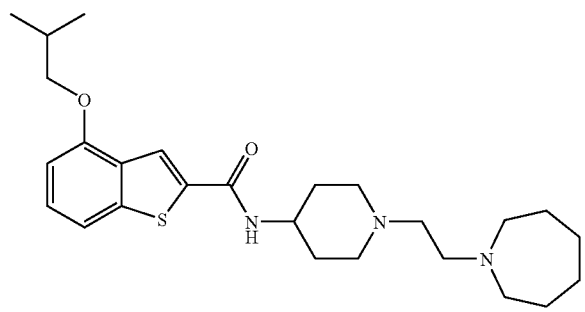

This compound is synthesized from compound 202 and amine 5 analogously to the method described in Example 178.

Yield: 340 mg (53%) of beige powder. MS (ESI): 458.4 [M+H]$^+$, 1H-NMR (DMSO-d$_6$): δ (ppm) 8.58 (d, 1H), 8.15 (s, 1H), 7.5 (d, 1H), 7.35 (dd, 1H), 6.88 (d, 1H), 3.9 (d, 2H), 3.7 (br m, 1H), 2.9 (m, 2H), 2.6 (m, 6H), 2.4 (m, 2H), 2.15 (m, 1H), 2.0 (m, 2H), 1.78 (m, 2H), 1.5-1.65 (m, 10H), 1.05 (d, 6H).

Example 180

4-Isobutoxy-benzo[b]thiophene-2-carboxylic acid [1-(2-piperidin-1-yl-ethyl)-piperidin-4-yl]-amide

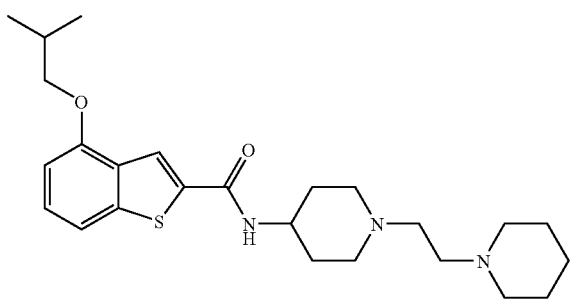

This compound is synthesized from compound 202 and amine 1 analogously to the method described in Example 178.

Yield: 93 mg (26%) of beige powder. MS (ESI): 444.3 [M+H]$^+$, 1H-NMR (DMSO-d$_6$): δ (ppm) 8.58 (d, 1H), 8.15 (s, 1H), 7.48 (d, 1H), 7.35 (dd, 1H), 6.88 (d, 1H), 3.9 (d, 2H), 3.7 (br m, 1H), 2.88 (m, 2H), 2.3-2.4 (m, 8H), 2.15 (m, 1H), 1.98 (m, 2H), 1.78 (m, 2H), 1.58 (m, 2H), 1.47 (m, 4H), 1.35 (m, 2H), 1.05 (d, 6H).

Synthesis of the benzofuran-2-carboxamides

Example 181

4-Methoxy-benzofuran-2-carboxylic acid [1-(2-azepan-1-yl-ethyl)-piperidin-4-yl]-amide

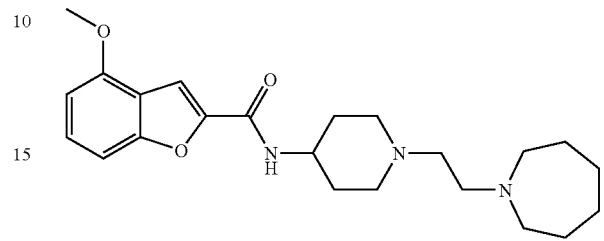

This compound is synthesized analogously to Example 1 from 4-Methoxy-benzofuran-2-carboxylic acid and amine 5.
MS (ESI): 400.2 [M+H]$^+$, 1H-NMR (DMSO-d$_6$): δ (ppm) 8.42 (d, 1H), 7.5 (s, 1H), 7.37 (t, 1H), 7.21 (d, 1H), 6.84 (d, 1H), 3.92 (s, 3H), 3.72 (m, 1H), 2.88 (m, 2H), 2.35-2.68 (m, 8H), 2.02 (m, 2H), 1.76 (m, 2H), 1.48-1.67 (m, 10H).

The compounds of formula I in free form or in pharmaceutically acceptable salt form exhibit valuable pharmacological properties, e.g. as CCR2 and CCR5 antagonists as indicated in in vitro tests as described below.

a) CCR2 Membrane Binding Assay

The SPA (Scintillation Proximity Assay) technology is used to show that the test compounds prevent MCP-1 from binding to cell membranes expressing the CCR2 receptor. Transfected CHO-dukX cells stably expressing the hCCR2b gene are grown in MEM alpha medium to a confluency of between 70 and 80%. After discarding the medium, 30 ml ice-cold physiological buffer solution containing 1 mM EDTA are added and the cells removed from the plate using a scraper. The cell suspension is centrifuged at 800 g for 10' at 4° C. and the cell pellet resuspended in buffer. Cell lysis is done using a Polytron PTI300D instrument at 28 000 RPM for 2 times 30 seconds on ice. Membranes are collected by centrifugation at 42 000 g for 20 minutes at 4° C. and subjected to a second round of lysis (Polytron, 28 000 RPM, 2×30 seconds on ice). Following centrifugation at 42 000 g for 20 minutes at 4° C. the membranes are resuspended in buffer at a protein concentration of 2 mg/ml and stored at −80° C. Ten millimolar stock solutions of test compounds in 100% DMSO are prepared. Test compounds are further diluted in buffer to yield the four-fold concentrated solutions for the tests that assayed a range of 10$^{-10}$ to 10$^{-5}$ M. The SPA assay is performed in a final volume of 200 μl per well in 96 well plates. The components are added per well in the following order:

| | |
|---|---|
| 50 μl | Buffer (+/−test compound) |
| 50 μl | Wheat germ agglutinin-SPA beads (1.25 mg/well) in buffer |
| 50 μl | CCR2B membrane suspension diluted with buffer to 0.04 mg/ml (2 μg/well), alternatively 50'000 cells per well |
| 50 μl | [$^{125}$I] MCP-1 in buffer (60 pM final concentration, 2.5 μCi/plate) |

After addition of all components the plate is sealed and incubated for 90 minutes at room temperature with constant shaking. Following incubation the plate is centrifuged at 1000 RPM in a Sorvall RC3B centrifuge for 4 minutes at room temperature and counted for 3 minutes per well in a TOP COUNT instrument (Packard). The quench-corrected counts are used for the analysis of radioligand binding.

Compounds of formula I have an $IC_{50}$ between 0.0003 and 10 μM.

In a similar manner, binding assays for the rat, mouse and rhesus monkey CCR2 receptors have been established. Due to the species specificity of the CCR2 antagonists, the compounds of formula I have an $IC_{50}$ between 0.015 and 10 μM on mouse CCR2 and between 0.020 and 10 μM on rat CCR2.

b) CCR2 Functional Assay—Ca2+ Mobilization hCCR2b-CHO#84 Cells:

CHOdukX cell line stably expressing the hCCR2 gene is grown in MEMα up to a confluence of 80%. The day before the experiment, cells are harvested from the tissue culture flask by trypsinization, washed, plated in a black/clear bottom 96-well plate at $5 \times 10^4$ cells per well and cultured overnight at 37° C. in a humid atmosphere enriched with 5% $CO_2$. On the next day, cells are washed twice and loaded for 1 hour at RT in the dark with 2 μM Fluo-4 in buffer C. After two further washes, the cells are resuspended in buffer D. Serial dilutions of the compounds, in buffer D, are mixed with the cells and incubated for half an hour at RT in the dark. Cells are then stimulated by the injection of MCP-1 and calcium fluxes are monitored using the Flexstation™, a benchtop scanning fluorometer with and integrated fluid transfer workstation.

|  | HBSS* 1× | 20 mM Hepes | 0.1% BSA | 625 μM Probenecid | 0.5% BSA |
|---|---|---|---|---|---|
| Buffer A | X | X |  |  |  |
| Buffer B | X | X | X |  |  |
| Buffer C | X | X |  | X |  |
| Buffer D | X | X |  | X | X |

*Hank's balanced alt Solution (10×) without phenol red (#14065-049, Gibco BRL).

hCCR2b-300.19 Cells:

Pre-B cell line 300-19 stably expressing the hCCR2 gene (Loetscher et al., J. Biol. Chem. 276 (5), 2986-91 (2001)) is grown in RPMI 1640 with glutamax-I supplemented with 1×MEM non essential amino-acid, 1 mM sodium pyruvate, $5 \times 10^{-5}$ M β-mercaptoethanol and 10% FCS. For the experiment, the cells are used in the exponential growing phase, at a maximal concentration of $1.5 \times 10^6$ cells per ml. Cells are washed in buffer A and loaded at about $2.10^6$ cells per ml in 2 μM fluo-4 in buffer B for 30 min. in the dark, at 37° C. in a waterbath. After two washes with buffer A, cells are plated in black/clear bottom 96-well plate at $2 \times 10^5$ cells per well in buffer B. All following steps, including the compound and the chemokine dilutions, are performed as described above for the hCCR2b-CHO#84 cells, except that buffer B is used instead of buffer D.

In this assay, compounds of formula I have an $IC_{50}$ between 0.0005 and 10 μM.

c) CCR2 Functional Assay—Chemotaxis

An in vitro cell migration assay for CCR2-dependent chemotaxis based on Transwell™ membrane inserts is used to profile the compounds. The assay is performed with the human monocytic THP-1 cell line and activated peripheral blood lymphocytes (PBL). THP-1 cells are cultured in RPMI1640 supplemented with 10% heat-inactivated FCS. Activated PBL are prepared from human blood by elutriation and then activated by culture on anti-human CD3-coated culture plates and expanded by subsequent culture in medium supplemented with IL-2. Aliquots of activated PBL are frozen in liquid nitrogen and used in migration experiments after thawing and overnight culture. Cells from cultures at a density of less than $1.2 \times 10^6$ cells/ml are counted, washed and resuspended at an appropriate density in RPMI1640 containing 0.5% BSA. Transwell™ membrane inserts of 6.5 mm diameter, 3 or 8 μm pore size and tissue culture treated polycarbonate membrane are used for the migration assays. The transwell inserts are loaded with cells and compounds in a final volume of 100 μl in RPMI1640/0.5% BSA. For THP-1 cells, 8 μm pore size inserts are used. For PBLs the use of 3 μm pore size inserts resulted in lower non-specific counts. The inserts are placed in a 24-well tissue culture plate containing recombinant human MCP-1 and compounds in a final volume of 600 μl. After allowing the cells to migrate to the bottom compartment, the assay is stopped by removing and discarding the transwell inserts. Cells in the bottom compartment are collected and counted on a FACScan flow cytometer by acquiring all events for 30 s with settings established for each cell type. Migration is expressed as absolute cell counts/30 s relative to the input cell number measured under the same conditions.

In this assay, compounds of formula I have an $IC_{50}$ between 0.0012 and 10 μM.

d) CCR5 Membrane Binding Assay

Human CCR5 is used to generate stable transfectants in CHO K1 cells. Membranes prepared from these CCR5 transfectants are used in a radioligand binding assay using 125-I-MIP-1α as a ligand and the compounds of formula I are tested for inhibitory activity. The data are reported as $IC_{50}$, i.e. the concentration of compound required to achieve 50% inhibition of [I-125]MIP-1α binding. In this assay, compounds of formula I have an $IC_{50}$ between 0.004 and 10 μM.

The Agents of the invention are effective as dual CCR-2 and CCR-5 antagonists. Thus the Agents of the invention are useful for the prophylaxis and treatment of CCR-2 and CCR-5 mediated diseases or medical conditions. CCR-2 and CCR-5 play an important role in leukocyte trafficking, in particular in monocyte migration to inflammatory sites and thus the agents of the invention may be used to inhibit monocyte migration e.g. in the treatment of inflammatory conditions, allergies and allergic conditions, autoimmune diseases, chronic pain, graft rejection, cancers which involve leukocyte filtration, stenosis or restenosis, atherosclerosis, rheumatoid arthritis, osteoarthritis and chronic pain.

Diseases or conditions which may be treated with the Agents of the Invention include: Inflammatory or allergic conditions, including respiratory allergic diseases such as asthma, allergic rhinitis, COPD, hypersensitivity lung diseases, hypersensitivity pneumonitis, interstitial lung disease (ILD), (e.g. idiopathic pulmonary fibrosis, or ILD associated with autoimmune diseases such as RA, SLE, etc.); chronic obstructive pulmonary disease, anaphylaxis or hypersensitivity responses, drug allergies (e.g. to penicillins or cephalosporins), and insect sting allergies; inflammatory bowel diseases, such as Crohn's disease and ulcerative colitis; spondyloarthropathies, sclerodoma; psoriasis and inflammatory dermatoses such as dermatitis, eczema, atopic dermatitis, allergic contact dermatitis, urticaria; vasculitis;

Autoimmune diseases, in particular autoimmune diseases with an aetiology including an inflammatory component such as arthritis (for example rheumatoid arthritis, arthritis chronica progrediente, psoriatic arthritis and arthritis deformans) and rheumatic diseases, including inflammatory conditions and rheumatic diseases involving bone loss, inflammatory pain, hypersensitivity (including both airways hypersensitivity and dermal hypersensitivity) and allergies. Specific auto-immune diseases for which Antibodies of the Invention may be employed include autoimmune haematological disorders (including e.g. hemolytic anaemia, aplastic anaemia, pure red cell anaemia and idiopathic thrombocytopenia), systemic lupus erythematosus, polychondritis, sclerodoma, Wegener granulomatosis, dermatomyositis, chronic active hepatitis, myasthenia gravis, psoriasis, Steven-Johnson syndrome, idiopathic sprue, autoimmune inflammatory bowel disease (including e.g. ulcerative colitis, Crohn's disease and Irritable Bowel Syndrome), autoimmune thyroiditis, Behcet's disease, endocrine ophthalmopathy, Graves disease, sarcoidosis, multiple sclerosis, primary biliary cirrhosis, juvenile diabetes (diabetes mellitus type 1), uveitis (anterior and posterior), keratoconjunctivitis sicca and vernal keratoconjunctivitis, interstitial lung fibrosis, and glomerulonephritis (with and without nephrotic syndrome, e.g. including idiopathic nephrotic syndrome or minimal change nephropathy);

graft rejection (e.g. in transplantation including heart, lung, combined heart-lung, liver, kidney, pancreatic, skin, or corneal transplants) including allograft rejection or xenograft rejection or graft-versus-host disease, and organ transplant associated arteriosclerosis; atherosclerosis;

cancer with leukocyte infiltration of the skin or organs; breast cancer; stenosis or restenosis of the vasculature, particularly of the arteries, e.g. the coronary artery, including stenosis or restenosis which results from vascular intervention, as well as neointimal hyperplasia;

stroke;

and other diseases or conditions involving inflammatory responses including reperfusion injury, hematologic malignancies, cytokine induced toxicity (e.g. septic shock or endotoxic shock), polymyositis, dermatomyositis, and granulomatous diseases including sarcoidosis; infectious diseases, including HIV and AIDS.

The term "treatment" as used herein is to be understood as including both therapeutic and prophylactic modes of therapy e.g. in relation to the treatment of neoplasia, therapy to prevent the onset of clinically or preclinically evident neoplasia, or for the prevention of initiation of malignant cells or to arrest or reverse the progression of premalignant to malignant cells, as well as the prevention or inhibition of neoplasia growth or metastasis. In this context, the present invention is, in particular, to be understood as embracing the use of compounds of the present invention to inhibit or prevent development of skin cancer, e.g. squamus or basal cell carcinoma consequential to UV light exposure, e.g. resultant from chronic exposure to the sun.

Agents of the Invention are particularly useful for treating diseases of bone and cartilage metabolism including osteoarthritis, osteoporosis and other inflammatory arthritides, e.g. rheumatoid arthritis, and bone loss in general, including age-related bone loss, and in particular periodontal disease.

The Agents of the Invention may also be used in ocular applications which include the treatment of ocular disorders, in particular of ocular inflammatory disorders, of ocular pain including pain associated with ocular surgery such as PRK or cataract surgery, of ocular allergy, of photophobia of various etiology, of elevated intraocular pressure (in glaucoma) by inhibiting the production of trabecular meshwork inducible glucocorticoid response (TIGR) protein, and of dry eye disease.

For the above indications, the appropriate dosage will, of course, vary depending upon, for example, the particular Agent of the Invention to be employed, the subject to be treated, the mode of administration and the nature and severity of the condition being treated. However, in prophylactic use, satisfactory results are generally indicated to be obtained at dosages from about 0.05 mg to about 10 mg per kilogram body weight, more usually from about 0.1 mg to about 5 mg per kilogram body weight. The frequency of dosing for prophylactic use will normally be in the range from about once per week up to about once every 3 months, more usually in the range from about once every 2 weeks up to about once every 10 weeks, e.g. once every 4 or 8 weeks. Agent of the Invention is conveniently administered parenterally, intravenously, e.g. into the antecubital or other peripheral vein, intramuscularly, or subcutaneously. For example, a prophylactic treatment typically comprises administering the Agent of the Invention once per month to once every 2 to 3 months, or less frequently.

The Agents of the invention may be administered in combination with another active agent. Suitable active agents include antimetabolites (e.g. methotrexate), anti-TNF agents (e.g. Remicade® (infliximab), Enbrel® (Etanercept), Humira® (adalumimab)), anti-IL-1 agents (e.g. pralnacasan, ACZ885), nucleoside and non-nucleoside revers transcriptase inhibitors, HIV protease inhibitors, fusion inhibitors and other antiretroviral agents. The active agent or agents may be administered simultaneously, separately or sequentially with the Agent of the invention.

Pharmaceutical compositions of the invention may be manufactured in conventional manner. A composition according to the invention is preferably provided in lyophilized form. For immediate administration it is dissolved in a suitable aqueous carrier, for example sterile water for injection or sterile buffered physiological saline. If it is considered desirable to make up a solution of larger volume for administration by infusion rather as a bolus injection, it is advantageous to incorporate human serum albumin or the patient's own heparinised blood into the saline at the time of formulation. The presence of an excess of such physiologically inert protein prevents loss of antibody by adsorption onto the walls of the container and tubing used with the infusion solution. If albumin is used, a suitable concentration is from 0.5 to 4.5% by weight of the saline solution.

The Agents of the Invention may be administered by any conventional route, e.g. orally, for example in the form of solutions for drinking, tablets or capsules or parenterally, for example in the form of injectable solutions or suspensions. Normally for systemic administration oral dosage forms are preferred, although for some indications the Agents of the Invention may also be administered topically or dermally, e.g. in the form of a dermal cream or gel or like preparation or, for the purposes of application to the eye, in the form of an ocular cream, gel or eye-drop preparation; or may be administered by inhalation, e.g., for treating asthma. Suitable unit dosage forms for oral administration comprise e.g. from 25 to 250 mg of Agent of the Invention per unit dosage.

The invention claimed is:

1. A compound of formula (I), or a pharmaceutically acceptable salt:

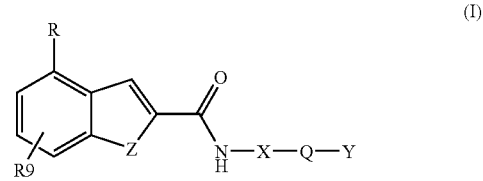

(I)

Wherein:

Z is $NR_3$;

R is $C_1$-$C_7$ alkoxy, optionally substituted with a furyl, benzofuryl, phenyl or thiazolyl; each of which is optionally substituted with halo; linear, branched or cyclic lower alkyl; or with a linear, branched or cyclic lower alkoxy;

$R_9$ is H;

$R_3$ is selected from the group consisting of H and $C_1$-$C_7$ alkyl;

X is a $C_3$-$C_{18}$ cycloalkyl or phenyl; each of which may be optionally substituted with halogen hydroxyl, $C_1$-$C_7$ alkyl;

Q is selected from the group consisting of: —$CH_2$—, —$CH_2$—$CH_2$—, —$CH_2$—$CH_2$—$CH_2$—, —$CH(CH_3)$—$CH_2$—, —$CH_2$—$CH(CH_3)$—, —$CH_2$—NH—, —$CH(CH_3)$—NH—, —$CH_2$—$N(CH_3)$—, —$CH_2$—$CH(CH_2OH)$— or —$CH(CH_3)$—$NH(CH_3)$—;

Y is piperidinyl, azepanyl, azocanyl, tetrahydropyranyl or 8-aza-bicyclo[3.2.1]oct-8-yl, each of which is optionally substituted with hydroxy, amino, halo, $C_1$-$C_7$ alkyl.

2. A compound of formula (II), or a pharmaceutically acceptable salt;

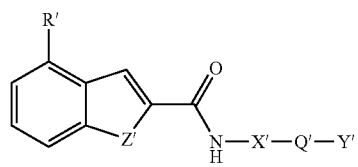

(II)

wherein:

Z' is NH;

R' is $C_1$-$C_7$ alkoxy, optionally substituted with a furyl, benzofuryl, phenyl or thiazolyl; each of which is optionally substituted with halo; linear, branched or cyclic lower alkyl; or with a linear, branched or cyclic lower alkoxy;

X' is selected from the group consisting of:

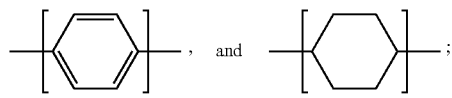, and

Q' is selected from the group consisting of: —$CH_2$—, —$CH_2$—$CH_2$—, —$CH(CH_3)$—$CH_2$—, —$CH_2$—$CH(CH_3)$—, —$CH(CH_3)$—NH—, —$CH_2$—$N(CH_3)$—, —$CH_2$—$CH(CH_2OH)$— or —$CH(CH_3)$—$NH(CH_3)$—;

Y' is piperidinyl, azepanyl, azocanyl, tetrahydropyranyl, 8-aza-bicyclo[3.2.1]oct-8-yl, each of which is optionally substituted with hydroxy, amino, halo, $C_1$-$C_7$alkyl.

3. A compound according to claim 1 or 2 selected from:

4-Isobutoxy-1H-indole-2-carboxylic acid [4-(2-azepan-1-yl-ethyl)-phenyl]-amide

4-Isobutoxy-1H-indole-2-carboxylic acid (4-{[methyl-(tetrahydro-pyran-4-yl)-amino]-methyl}-cyclohexyl)-amide 4-Isobutoxy-1H-indole-2-carboxylic acid (4-{[methyl-(tetrahydro-pyran-4-yl)-amino]-methyl}-phenyl)-amide 4-Isobutoxy-1H-indole-2-carboxylic acid (4-{(R)-1-[methyl-(tetrahydro-pyran-4-yl)-amino]-ethyl}-phenyl)-amide.

4. A process for the preparation of a compound of formula (I) comprising:

(a) reacting a compound of formula (III):

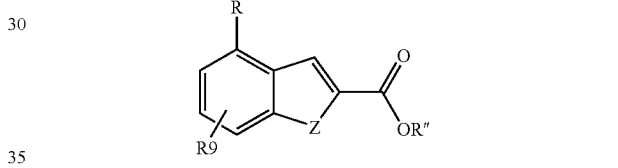

(III)

wherein R" is H or a lower alkyl group, with a compound of formula $NH_2$—X-Q-Y, the groups R, R9, Z, X, Q and Y being as defined in claim 1 and recovering the resultant compounds of formula (I) in free or salt form.

5. A compound obtainable by the process of claim 4.

6. A pharmaceutical composition comprising a compound according to claim 1 in association with a pharmaceutically acceptable diluent or carrier.

* * * * *